United States Patent
Yokokawa et al.

(10) Patent No.: US 9,527,809 B2
(45) Date of Patent: Dec. 27, 2016

(54) COMPOUND, ACTINIC RAY-SENSITIVE OR RADIATION-SENSITIVE RESIN COMPOSITION, RESIST FILM, AND PATTERN FORMATION METHOD, AND METHOD FOR MANUFACTURING ELECTRONIC DEVICE USING SAME, AND ELECTRONIC DEVICE

(71) Applicant: FUJIFILM Corporation, Tokyo (JP)

(72) Inventors: Natsumi Yokokawa, Shizuoka (JP); Hiroo Takizawa, Shizuoka (JP); Shuji Hirano, Shizuoka (JP); Wataru Nihashi, Shizuoka (JP); Hideaki Tsubaki, Shizuoka (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

(21) Appl. No.: 14/868,408

(22) Filed: Sep. 29, 2015

(65) Prior Publication Data

US 2016/0024005 A1    Jan. 28, 2016

Related U.S. Application Data

(63) Continuation of application No. PCT/JP2014/055678, filed on Mar. 5, 2014.

(30) Foreign Application Priority Data

Mar. 29, 2013  (JP) .................... 2013-075196

(51) Int. Cl.
| | | |
|---|---|---|
| G03F 7/004 | (2006.01) |
| C07C 381/12 | (2006.01) |
| H01L 21/027 | (2006.01) |
| G03F 7/039 | (2006.01) |
| G03F 7/20 | (2006.01) |
| G03F 7/32 | (2006.01) |
| C07D 309/12 | (2006.01) |
| C07D 317/22 | (2006.01) |
| G03F 7/038 | (2006.01) |

(52) U.S. Cl.
CPC .......... *C07C 381/12* (2013.01); *C07D 309/12* (2013.01); *C07D 317/22* (2013.01); *G03F 7/0045* (2013.01); *G03F 7/0046* (2013.01); *G03F 7/038* (2013.01); *G03F 7/039* (2013.01); *G03F 7/0392* (2013.01); *G03F 7/0397* (2013.01); *G03F 7/20* (2013.01); *G03F 7/2004* (2013.01); *G03F 7/2041* (2013.01); *G03F 7/2059* (2013.01); *G03F 7/325* (2013.01); *H01L 21/0275* (2013.01)

(58) Field of Classification Search
CPC .... G03F 7/00475; G03F 7/0046; G03F 7/038; G03F 7/39; G03F 7/0392; G03F 7/0397; G03F 7/20; G03F 7/2041; G03F 7/2059; G03F 7/325; C07C 381/12; H01L 21/0275

USPC ..... 430/322, 325, 296, 270.1, 913; 549/415, 549/453; 560/9; 568/18
See application file for complete search history.

(56) References Cited

U.S. PATENT DOCUMENTS

| | | | | |
|---|---|---|---|---|
| 7,776,510 B2 * | 8/2010 | Iwai | ....................... | C07C 309/04 430/270.1 |
| 8,206,890 B2 * | 6/2012 | Kawaue | ................ | C07C 309/09 430/270.1 |
| 8,338,076 B2 * | 12/2012 | Kawaue | ................ | C07D 307/33 430/270.1 |
| 8,765,352 B2 * | 7/2014 | Utsumi | ................ | C07D 327/04 430/270.1 |
| 8,945,814 B2 * | 2/2015 | Cameron | ................ | G03F 7/027 430/270.1 |
| 9,005,874 B2 * | 4/2015 | Komuro | ................ | C07C 309/12 430/270.1 |
| 9,029,065 B2 * | 5/2015 | Aqad | ..................... | C07C 303/32 430/270.1 |
| 9,046,767 B2 * | 6/2015 | Aqad | ..................... | C07C 381/12 |
| 9,052,592 B2 * | 6/2015 | Nakamura | | |

(Continued)

FOREIGN PATENT DOCUMENTS

| | | |
|---|---|---|
| JP | H07179511 | 7/1995 |
| JP | 09-015848 | 1/1997 |

(Continued)

OTHER PUBLICATIONS

Machine translation of JP 2012-123189 (no. date).*

(Continued)

*Primary Examiner* — Amanda C Walke
(74) *Attorney, Agent, or Firm* — Jianq Chyun IP Office

(57) ABSTRACT

There is provided an actinic ray-sensitive or radiation-sensitive resin composition containing a compound represented by the following formula (1) or (2), and the formula (1) and (2) are defined as herein,

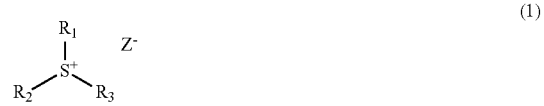

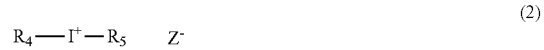

and a resist film comprising the actinic ray-sensitive or radiation-sensitive resin composition, and a pattern forming method comprising a step of exposing the resist film, and a step of developing the exposed film, and a method for manufacturing an electronic device, comprising the pattern forming method, and an electronic device manufactured by the manufacturing method of an electronic device.

12 Claims, 4 Drawing Sheets

(56) References Cited

U.S. PATENT DOCUMENTS

| | | | |
|---|---|---|---|
| 9,063,416 B2* | 6/2015 | Komuro | |
| 9,081,277 B2* | 7/2015 | Matsuda | C07C 381/12 |
| 2005/0053861 A1 | 3/2005 | Yoneda et al. | |
| 2008/0311522 A1 | 12/2008 | Iwai et al. | |
| 2010/0304296 A1 | 12/2010 | Ichikawa et al. | |
| 2012/0301829 A1 | 11/2012 | Kawaue et al. | |
| 2013/0122427 A1 | 5/2013 | Kataoka et al. | |
| 2016/0002199 A1* | 1/2016 | Cameron | G03F 7/027 430/270.1 |

FOREIGN PATENT DOCUMENTS

| | | | | |
|---|---|---|---|---|
| JP | 2004-250427 | | 9/2004 | |
| JP | 2006-241384 | | 9/2006 | |
| JP | 2009-019028 | | 1/2009 | |
| JP | 2011-006400 | | 1/2011 | |
| JP | 2011053560 | | 3/2011 | |
| JP | 2012-027436 | | 2/2012 | |
| JP | 2012123189 A * | | 6/2012 | G03F 7/004 |
| JP | 2012-237983 | | 12/2012 | |
| JP | 2012-242657 | | 12/2012 | |
| JP | 2012-247502 | | 12/2012 | |
| JP | 2013-033229 | | 2/2013 | |
| JP | 2013040164 A * | | 2/2013 | C07C 309/17 |
| JP | 2013047209 A * | | 3/2013 | C07C 381/12 |
| JP | 2013-182023 | | 9/2013 | |

OTHER PUBLICATIONS

Machine translation of JP 2013-047209 (no. date).*

"Office Action of Japan Counterpart Application", issued on Mar. 22, 2016, with English translation thereof, p. 1-6, in which the listed references were cited.

"International Search Report of PCT/JP2014/055678 (Form PCT/ISA/210)", mailed on Apr. 8, 2014, with English translation thereof, pp. 1-4, in which eight of the listed references (JP2012-237983, JP2011-006400 JP2013-033229, JP2012-242657, JP2012-247502, JP2006-241384, JP2004-250427 and JP2013-182023 were cited.

"Written Opinion of the International Searching Authority of PCT/JP2014/055678 , this report contains the following items: Form PCT/ISA237(cover sheet), PCT/ISA237(Box No. 1) and PCT/1SA237(Box No. V)", mailed on Apr. 8, 2014, which is English translation of "Written Opinion of the International Searching Authority", pp. 1-9.

* cited by examiner

COMPOUND, ACTINIC RAY-SENSITIVE OR RADIATION-SENSITIVE RESIN COMPOSITION, RESIST FILM, AND PATTERN FORMATION METHOD, AND METHOD FOR MANUFACTURING ELECTRONIC DEVICE USING SAME, AND ELECTRONIC DEVICE

CROSS REFERENCE TO RELATED APPLICATION

This is a continuation of International Application No. PCT/JP2014/055678 filed on Mar. 5, 2014, and claims priority from Japanese Patent Application No. 2013-075196 filed on Mar. 29, 2013, the entire disclosures of which are incorporated therein by reference.

TECHNICAL FIELD

The present invention relates to a compound, an actinic ray-sensitive or radiation-sensitive resin composition, a resist film, a pattern forming method, which are suitably used for the ultramicrolithography process such as production of VLSI or high-capacity microchip or in other photofabrication processes, a manufacturing method of an electronic device using the same, and an electronic device. More specifically, the present invention relates to a compound, an actinic ray-sensitive or radiation-sensitive resin composition, a resist film, a pattern forming method, which are suitably usable for semiconductor microfabrication employing an electron beam or EUV light (wavelength: near 13 nm), a manufacturing method of an electronic device using the same, and an electronic device.

BACKGROUND ART

In the process of producing a semiconductor device such as IC and LSI, microfabrication by lithography using a photoresist composition has been conventionally performed. Recently, with the increase in integration degree of an integrated circuit, formation of an ultrafine pattern in the sub-micron or quarter-micron region is required. To cope with this requirement, the exposure wavelength also tends to become shorter, for example, from g line to i line or further to KrF excimer laser light. In addition to the excimer laser light, development of lithography using electron beam, X-ray or EUV light is also being pursued at present.

In the photoresist composition, a compound capable of generating an acid upon irradiation with an actinic ray or radiation (hereinafter, sometimes referred to as "acid generator") is used, and as for the acid generator, a wide variety of compounds have been heretofore proposed. For example, an onium salt-based acid generator such as iodonium salt and sulfonium salt, an oxime sulfonate-based acid generator, a diazomethane-based acid generator, a nitrobenzyl sulfonate-based acid generator, an iminosulfonate-based acid generator, and a disulfone-based acid generator are known (Patent Documents 1 to 3).

RELATED ART

Patent Document

Patent Document 1: JP-A-9-15848 (the term "JP-A" as used herein means an "unexamined published Japanese patent application")
Patent Document 2: JP-A-2009-19028
Patent Document 3: JP-A-2012-027436

SUMMARY OF THE INVENTION

Problems that the Invention is to Solve

Meanwhile, in recent years, a resist pattern is increasingly subdivided and as the demand for high resolution further grows, it is required to enhance various lithography properties.

The patent documents above are silent on a photoresist composition realizing high resolution, high exposure latitude and good pattern profile particularly in the region of fine (for example, a line width or space width of 50 nm or less) pattern formation, and more improvements of the photoresist composition are demanded.

Considering the problems above, an object of the present invention is to provide a compound, an actinic ray-sensitive or radiation-sensitive resin composition, a resist film, a pattern forming method, which are capable of realizing high resolution, high exposure latitude and good pattern profile in the region of fine (for example, a line width or space width of 50 nm or less) pattern formation, a manufacturing method of an electronic device using the same, and an electronic device.

Means for Solving the Problems

As a result of intensive studies, the present inventors have found that the above-described object can be achieved by an actinic ray-sensitive or radiation-sensitive resin composition containing an acid generator having a specific structure.

That is, the present invention is as follows.

[1] An actinic ray-sensitive or radiation-sensitive resin composition containing a compound represented by the following formula (1) or (2):

[Chem. 1]

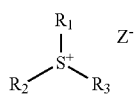
(1)

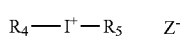
(2)

wherein each of $R_1$ to $R_5$ independently represents an organic group having a carbon number of 30 or less, at least two members out of $R_1$ to $R_3$ may combine with each other to form a ring, each of at least one of $R_1$ to $R_3$ and at least one of $R_4$ and $R_5$ has at least one group selected from the group consisting of groups represented by the following formulae (I) to (IV), and $Z^-$ represents a non-nucleophilic anion:

[Chem. 2]

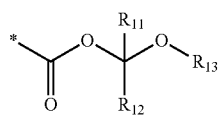
(I)

-continued

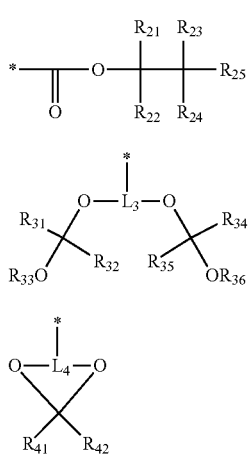

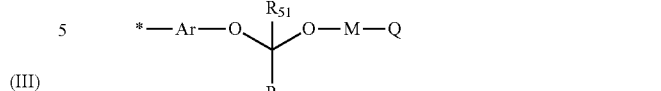

wherein in formulae (I) to (IV), $R_{11}$ represents a hydrogen atom or an alkyl group, $R_{12}$ represents a hydrogen atom, an alkyl group, a cycloalkyl group or an aryl group, $R_{13}$ represents an alkyl group, a cycloalkyl group or an aryl group, $R_{12}$ and $R_{13}$ may combine with each other to form a ring, each of $R_{21}$ to $R_{24}$ independently represents an alkyl group, $R_{25}$ represents a hydrogen atom or an alkyl group, at least two members out of $R_{23}$ to $R_{25}$ may combine with each other to form a ring, provided that $R_{21}$ and $R_{22}$ do not combine with each other to form a ring and at least one of $R_{21}$ and $R_{22}$ does not combine with at least one of $R_{23}$ to $R_{25}$ to form a ring, $L_3$ represents a trivalent linking group, each of $R_{31}$ and $R_{34}$ independently represents a hydrogen atom or an alkyl group, each of $R_{32}$ and $R_{35}$ independently represents a hydrogen atom, an alkyl group, a cycloalkyl group or an aryl group, each of $R_{33}$ and $R_{36}$ independently represents an alkyl group, a cycloalkyl group or an aryl group, $R_{32}$ and $R_{33}$ may combine with each other to form a ring, $R_{35}$ and $R_{36}$ may combine with each other to form a ring, $L_4$ represents a trivalent linking group, each of $R_{41}$ and $R_{42}$ independently represents a hydrogen atom or an alkyl group, $R_{41}$ and $R_{42}$ may combine with each other to form a ring, and

* represents a bond.

[2] The actinic ray-sensitive or radiation-sensitive resin composition as described in [1], wherein in formulae (1) and (2), $Z^-$ represents a sulfonate anion.

[3] The actinic ray-sensitive or radiation-sensitive resin composition as described in [2], wherein in formulae (1) and (2), $Z^-$ represents a benzenesulfonate anion.

[4] The actinic ray-sensitive or radiation-sensitive resin composition as described in any one of [1] to [3], further containing a resin having a group represented by any one of formulae (I) to (IV) and the following formula (V):

[Chem. 3]

wherein in formula (V),

Ar represents a divalent aromatic ring group, each of $R_{51}$ and $R_{52}$ independently represents a hydrogen atom, an alkyl group, a cycloalkyl group, a monovalent aromatic ring group, or a group formed by combining an alkylene group and a monovalent aromatic ring group, M represents a single bond or a divalent linking group, Q represents an alkyl group, a cycloalkyl group that may contain a heteroatom, a monovalent aromatic ring group that may contain a heteroatom, an amino group, an ammonium group, a mercapto group, a cyano group or an aldehyde group, two members out of Q, M and $R_{51}$ may combine to form a ring, and

* represents a bond.

[5] The actinic ray-sensitive or radiation-sensitive resin composition as described in [4], wherein the resin is a resin having a group represented by formula (I) or (II).

[6] The actinic ray-sensitive or radiation-sensitive resin composition as described in any one of [1] to [5], containing a compound represented by formula (1).

[7] The actinic ray-sensitive or radiation-sensitive resin composition as described in any one of [1] to [6], which is used for X-ray, electron beam or extreme-ultraviolet ray exposure.

[8] A resist film comprising the actinic ray-sensitive or radiation-sensitive resin composition described in any one of [1] to [7].

[9] A pattern forming method comprising a step of exposing the resist film of [8], and a step of developing the exposed film.

[10] The pattern forming method as described in [9], wherein the exposure is performed using an electron beam or an extreme-ultraviolet ray.

[11] The pattern forming method as described in [9] or [10], wherein the development is performed using a developer containing an organic solvent.

[12] A method for manufacturing an electronic device, comprising the pattern forming method described in any one of [9] to [11].

[13] An electronic device manufactured by the manufacturing method of an electronic device described in [12].

[14] A compound represented by formula (1):

[Chem. 4]

$$\underset{R_2}{\overset{R_1}{\underset{|}{\vphantom{|}}}}\!\!\!\overset{}{\underset{}{S^+}}\!\!-R_3 \quad Z^-  \qquad (1)$$

wherein each of $R_1$ to $R_3$ independently represents an aryl group having a carbon number of 30 to less, at least two members out of $R_1$ to $R_3$ may combine with each other to form a ring, at least one of $R_1$ to $R_3$ has at least one group selected from the group consisting of groups represented by the following formula (I) to (IV), $Z^-$ represents a sulfonate anion:

[Chem. 5]

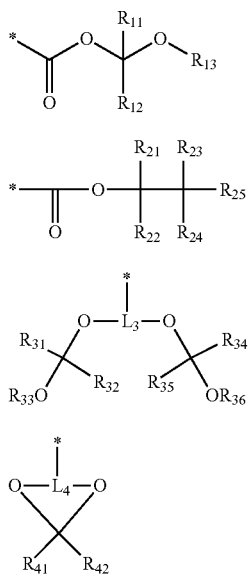

wherein in formulae (I) to (IV), $R_{11}$ represents a hydrogen atom or an alkyl group, $R_{12}$ represents a hydrogen atom, an alkyl group, a cycloalkyl group or an aryl group, $R_{13}$ represents an alkyl group, a cycloalkyl group or an aryl group, $R_{12}$ and $R_{13}$ may combine with each other to form a ring, each of $R_{21}$ to $R_{24}$ independently represents an alkyl group, $R_{25}$ represents a hydrogen atom or an alkyl group, at least two members out of $R_{23}$ to $R_{25}$ may combine with each other to form a ring, provided that $R_{21}$ and $R_{22}$ do not combine with each other to form a ring and at least one of $R_{21}$ and $R_{22}$ does not combine with at least one of $R_{23}$ to $R_{25}$ to form a ring, $L_3$ represents a trivalent linking group, each of $R_{31}$ and $R_{34}$ independently represents a hydrogen atom or an alkyl group, each of $R_{32}$ and $R_{35}$ independently represents a hydrogen atom, an alkyl group, a cycloalkyl group or an aryl group, each of $R_{33}$ and $R_{36}$ independently represents an alkyl group, a cycloalkyl group or an aryl group, $R_{32}$ and $R_{33}$ may combine with each other to form a ring, $R_{35}$ and $R_{36}$ may combine with each other to form a ring, $L_4$ represents a trivalent linking group, each of $R_{41}$ and $R_{42}$ independently represents a hydrogen atom or an alkyl group, $R_{41}$ and $R_{42}$ may combine with each other to form a ring, and

* represents a bond.

Advantage of the Invention

According to the present invention, a compound, an actinic ray-sensitive or radiation-sensitive resin composition, a resist film, a pattern forming method, which are capable of realizing high resolution, high exposure latitude and good pattern profile in the region of fine (for example, a line width or space width of 50 nm or less) pattern formation, a manufacturing method of an electronic device using the same, and an electronic device can be provided.

MODE FOR CARRYING OUT THE INVENTION

Figure 1:
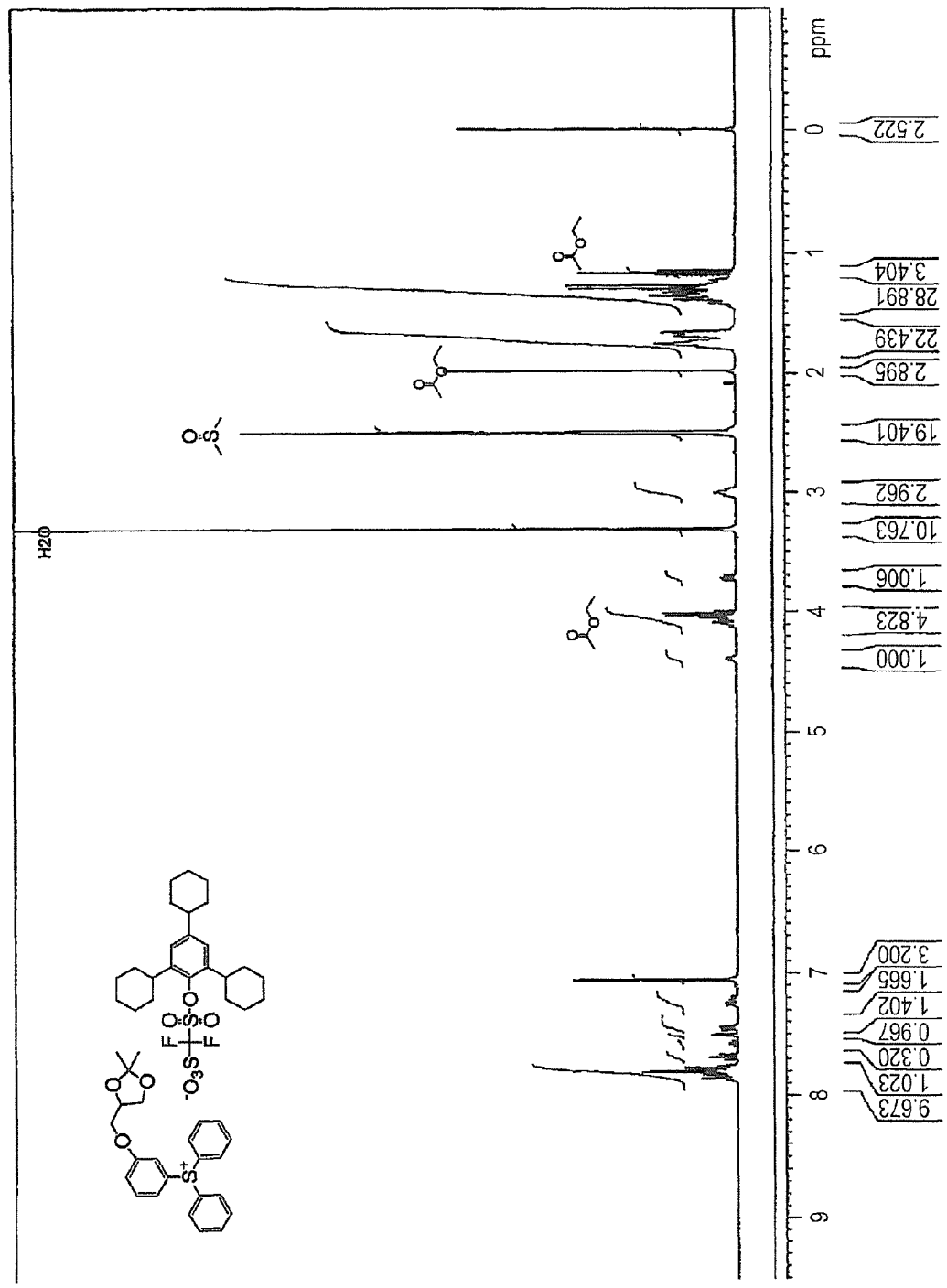
FIG. 1 is a view illustrating $^1$H-NMR chart of Compound (b-47).

The mode for carrying out the present invention is described in detail below.

In the description of the present invention, when a group (atomic group) is denoted without specifying whether substituted or unsubstituted, the group encompasses both a group having no substituent and a group having a substituent. For example, "an alkyl group" encompasses not only an alkyl group having no substituent (unsubstituted alkyl group) but also an alkyl group having a substituent (substituted alkyl group).

The "actinic ray" or "radiation" as used in the description of the present invention means, for example, a bright line spectrum of mercury lamp, a far ultraviolet ray typified by excimer laser, an extreme-ultraviolet ray (EUV light), an X-ray or an electron beam (EB). In addition, in the present invention, the "light" means an actinic ray or radiation.

Unless otherwise indicated, the "exposure" as used in the present invention encompasses not only exposure to a mercury lamp, a far ultraviolet ray typified by excimer laser, X-ray, EUV light, etc. but also lithography with a particle beam such as electron beam and ion beam.

The actinic ray-sensitive or radiation-sensitive resin composition of the present invention is preferably used for X-ray, electron beam, extreme-ultraviolet ray or ArF exposure, more preferably for X-ray, electron beam or extreme-ultraviolet ray exposure.

The actinic ray-sensitive or radiation-sensitive resin composition of the present invention contains a compound represented by the following formula (1) or (2):

[Chem. 6]

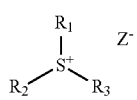 (1)

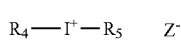 (2)

In the formulae, each of $R_1$ to $R_5$ independently represents an organic group having a carbon number of 30 or less, and at least two members of $R_1$ to $R_3$ may combine with each other to form a ring.

Each of at least one of $R_1$ to $R_3$ and at least one of $R_4$ and $R_5$ has at least one group selected from the group consisting of groups represented by the following formulae (I) to (IV).

$Z^-$ represents a non-nucleophilic anion.

[Chem. 7]

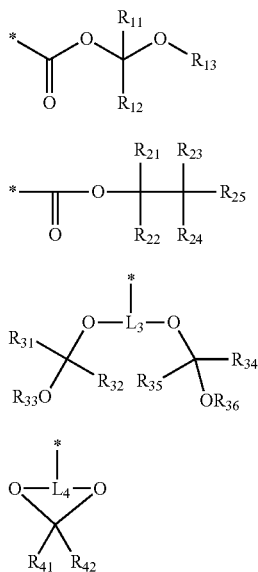

In formulae (I) to (IV), $R_{11}$ represents a hydrogen atom or an alkyl group.

$R_{12}$ represents a hydrogen atom, an alkyl group, a cycloalkyl group or an aryl group.

$R_{13}$ represents an alkyl group, a cycloalkyl group or an aryl group.

$R_{12}$ and $R_{13}$ may combine with each other to form a ring.

Each of $R_{21}$ to $R_{24}$ independently represents an alkyl group.

$R_{25}$ represents a hydrogen atom or an alkyl group. At least two members out of $R_{23}$ to $R_{25}$ may combine with each other to form a ring.

$R_{21}$ and $R_{22}$ do not combine with each other to form a ring and at least one of $R_{21}$ and $R_{22}$ does not combine with at least one of $R_{23}$ to $R_{25}$ to form a ring.

$L_3$ represents a trivalent linking group.

Each of $R_{31}$ and $R_{34}$ independently represents a hydrogen atom or an alkyl group.

Each of $R_{32}$ and $R_{35}$ independently represents a hydrogen atom, an alkyl group, a cycloalkyl group or an aryl group.

Each of $R_{33}$ and $R_{36}$ independently represents an alkyl group, a cycloalkyl group or an aryl group.

$R_{32}$ and $R_{33}$ may combine with each other to form a ring.

$R_{35}$ and $R_{36}$ may combine with each other to form a ring.

$L_4$ represents a trivalent linking group.

Each of $R_{41}$ and $R_{42}$ independently represents a hydrogen atom or an alkyl group.

$R_{41}$ and $R_{42}$ may combine with each other to form a ring.

* represents a bond.

The actinic ray-sensitive or radiation-sensitive resin composition according to the present invention may be used for negative development (development where the exposed area remains as a pattern and the unexposed area is removed) or may be used for positive development (development where the exposed area is removed and the unexposed area remains as a pattern). That is, the actinic ray-sensitive or radiation-sensitive resin composition according to the present invention may be an actinic ray-sensitive or radiation-sensitive resin composition for organic solvent development, which is used for development employing an organic solvent-containing developer, or may be an actinic ray-sensitive or radiation-sensitive resin composition for alkali development, which is used for development employing an alkali developer. Here, the term "for organic solvent development" means usage where the composition is subjected to at least a step of performing development by using an organic solvent-containing developer, and the term "for alkali development" means usage where the composition is subjected to at least a step of performing development by using an alkali developer.

The actinic ray-sensitive or radiation-sensitive resin composition of the present invention is typically a resist composition and is preferably a negative resist composition (that is, a resist composition for organic solvent development), because high effects can be obtained in particular. In addition, the composition according to the present invention is typically a chemical amplification resist composition.

The actinic ray-sensitive or radiation-sensitive resin composition of the present invention can realize high resolution, high exposure latitude and good pattern profile in the region of fine (for example, a line width or space width of 50 nm or less) pattern formation. The reason therefor is not clearly known but is presumed as follows.

The actinic ray-sensitive or radiation-sensitive resin composition of the present invention contains a compound represented by formula (1) or (2).

Here, the compound represented by formula (1) or (2) has a group represented by formulae (I) to (IV) capable of decomposing by an action of an acid to generate an acid group and therefore, is a compound that decomposes by an action of an acid to cause a change in solubility for a developer.

The group represented by formula (I) to (IV) has low activation energy and high reactivity with an acid generated at the time of exposure and in turn, the reactivity of a compound represented by formula (1) or (2) with the acid is also high.

Accordingly, when a resist film is formed using the actinic ray-sensitive or radiation-sensitive resin composition and subjected to pattern formation, the difference in the dissolution rate between exposed area and unexposed area of the resist film is increased, as a result, the resolution and the profile of the pattern obtained are considered to be improved.

In addition, the reactivity of the compound represented by formula (1) or (2) with an acid is high as described above and therefore, at the time of formation of a pattern having a desired profile, the dependency of the reaction amount on the exposure dose can be decreased, as a result, the exposure latitude is considered to be enhanced.

The components of the actinic ray-sensitive or radiation-sensitive resin composition of the present invention are described in detail below.

[1] Compound Represented by Formula (1) or (2)

The actinic ray-sensitive or radiation-sensitive resin composition of the present invention contains a compound represented by formula (1) or (2) (hereinafter, sometimes referred to as "acid generator"). The actinic ray-sensitive or radiation-sensitive resin composition of the present invention preferably contains a compound represented by formula (1).

Formulae (1) and (2) are described in detail below.

In formula (1) or (2), each of at least one of $R_1$ to $R_3$ and at least one of $R_4$ and $R_5$ has at least one group (hereinafter, sometimes referred to as "substituent (P)") selected from the group consisting of groups represented by formulae (I) to (IV).

Formula (I) is described in detail below.

The alkyl group of $R_{11}$ is preferably an alkyl group having a carbon number of 1 to 5 and is preferably a methyl group.

$R_{11}$ is preferably a hydrogen atom.

The alkyl group of $R_{12}$ is preferably an alkyl group having a carbon number of 1 to 20 and specifically includes a methyl group, an ethyl group, a propyl group, an n-butyl group, a sec-butyl group, a tert-butyl group, a hexyl group, and an octyl group. The alkyl group of $R_{12}$ may contain —O— or —CO—.

The cycloalkyl group of $R_{12}$ is preferably a cycloalkyl group having a carbon number of 3 to 20 and specifically, preferable examples thereof include a cyclopentyl group, a cyclohexyl group, a norbornyl group, and an adamantyl group. The cycloalkyl group of $R_{12}$ may contain —O— or —CO—.

The aryl group of $R_{12}$ is preferably an aryl group having a carbon number of 6 to 15 and specifically includes a phenyl group, a tolyl group, a naphthyl group, an anthryl group, etc.

$R_{12}$ is preferably a hydrogen atom, an alkyl group having a carbon number of 1 to 15, or a cycloalkyl group having a carbon number of 3 to 20, more preferably a hydrogen atom, an alkyl group having a carbon number of 1 to 11, or a cycloalkyl group having a carbon number of 3 to 20, and in view of thermal stability, still more preferably a hydrogen atom, a tertiary alkyl group having a carbon number of 1 to 11, or a tertiary cycloalkyl group having a carbon number of 3 to 20.

The alkyl group of $R_{13}$ may contain an oxygen atom or may be substituted with a fluorine atom. The alkyl group of $R_{13}$ is preferably an alkyl group having a carbon number of 1 to 15 and specifically includes a methyl group, an ethyl group, a propyl group, an n-butyl group, a sec-butyl group, a tert-butyl group, a hexyl group, an octyl group, etc.

The cycloalkyl group of $R_{13}$ may contain an oxygen atom or a fluorine atom and is preferably a cycloalkyl group having a carbon number of 3 to 15. The cycloalkyl group of $R_{13}$ specifically includes a cyclopentyl group, a cyclohexyl group, a norbornyl group, an adamantyl group, etc.

Specific examples and preferable range of the aryl group of $R_{13}$ are the same as those of the aryl group of $R_{12}$.

$R_{13}$ is preferably an alkyl group having a carbon number of 1 to 15 or a cycloalkyl group having a carbon number of 3 to 15.

As for the ring that may be formed by combining $R_{12}$ and $R_{13}$ with each other, for example, there is a case of forming a propylene group or a butylene group to form a 5- or 6-membered ring (preferably a 6-membered ring) containing an oxygen atom.

$R_{11}$, $R_{12}$ and $R_{13}$ in formula (1) may have a substituent, and the substituent includes, for example, an alkyl group, a cycloalkyl group, an aryl group, an amino group, an amido group, a ureido group, a urethane group, a hydroxyl group, a carboxyl group, a halogen atom, an alkoxy group, a thioether group, an acyl group, an acyloxy group, an alkoxycarbonyl group, a cyano group, and a nitro group. The carbon number of the substituent is preferably 10 or less. The substituent above is preferably a cyclohexyl group or an adamantyl group.

Specific examples of the group represented by formula (I) are illustrated below, but the present invention is not limited thereto.

[Chem. 8]

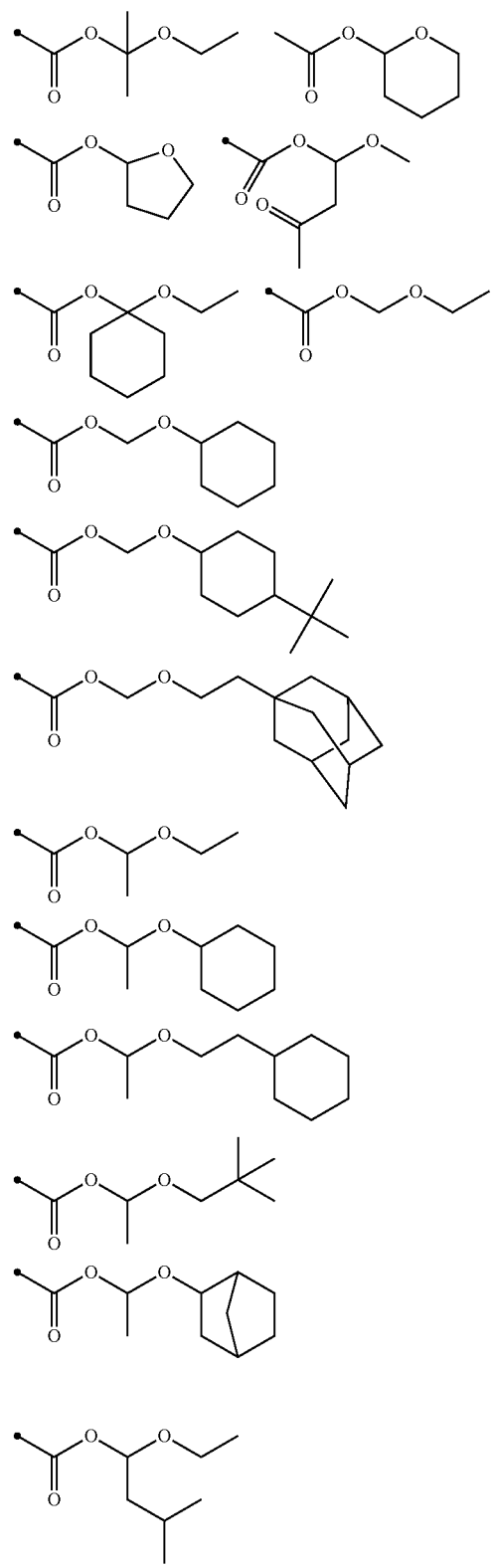

-continued

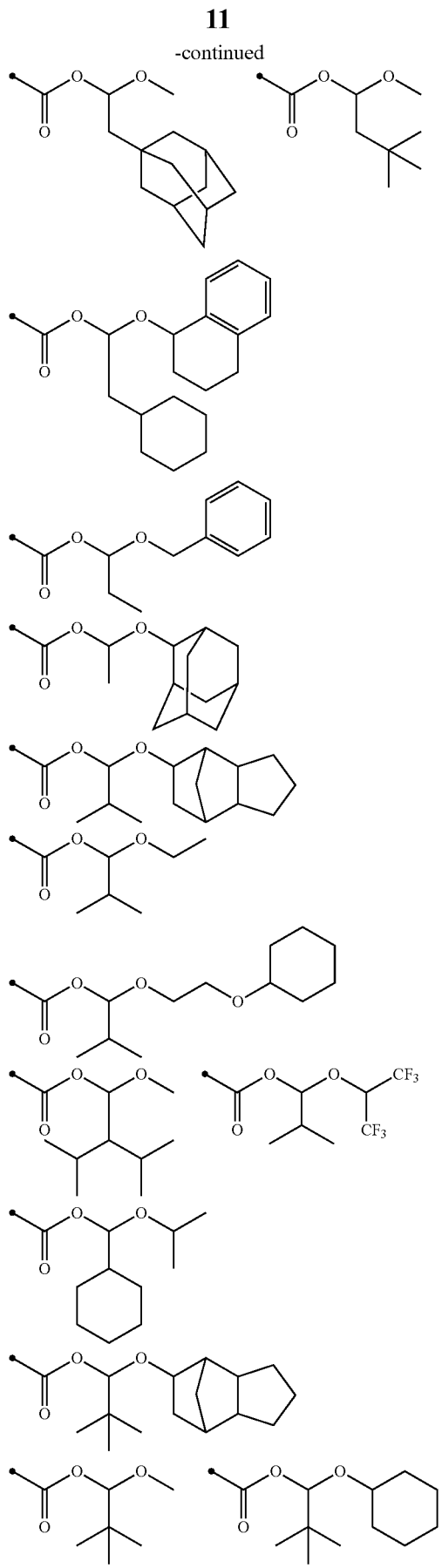

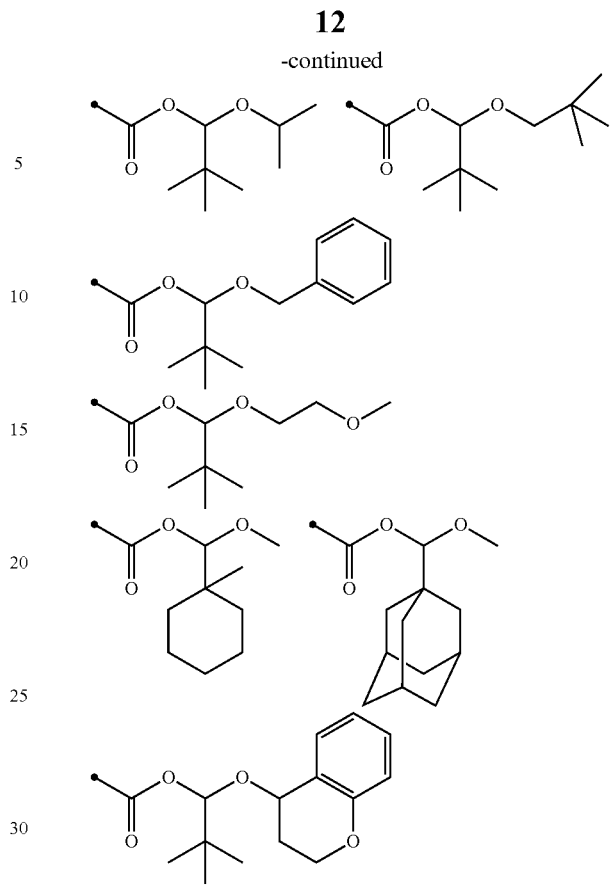

Formula (II) is described in detail below.

The alkyl group of $R_{21}$ to $R_{25}$ is preferably an alkyl group having a carbon number of 1 to 10 and specifically includes a methyl group, an ethyl group, a propyl group, an isopropyl group, an n-butyl group, a sec-butyl group, a tert-butyl group, a neopentyl group, a hexyl group, a 2-ethylhexyl group, an octyl group, a dodecyl group, etc.

$R_{21}$ and $R_{22}$ are preferably an alkyl group having a carbon number of 1 to 4, more preferably a methyl group or an ethyl group, still more preferably an ethyl group.

In view of reactivity of the acid generator, $R_{21}$ and $R_{22}$ do not combine with each other to form a ring and at least one of $R_{21}$ and $R_{22}$ does not combine with at least one of $R_{23}$ to $R_{25}$ to form a ring.

When $R_{21}$ and $R_{22}$ form a ring, compared with a case where $R_{21}$ and $R_{22}$ do not form a ring, the bulk of an oxonium ion generated by acid coordination is decreased and since an elimination reaction becomes more difficult to proceed, the acid decomposition reactivity is reduced, which is considered to make it impossible to obtain the effects of the present invention.

$R_{23}$ and $R_{24}$ are preferably an alkyl group having a carbon number of 1 to 4, more preferably a methyl group or an ethyl group, still more preferably a methyl group.

$R_{25}$ is preferably a hydrogen atom or an alkyl group having a carbon number of 1 to 4, more preferably a hydrogen atom or a methyl group, still more preferably a hydrogen atom.

In the case where a ring is not formed by combining at least two members out of $R_{23}$ to $R_{25}$ do not combine with each other, it is particularly preferred that $R_{23}$ and $R_{24}$ represent a methyl group and $R_{25}$ represents a hydrogen atom.

In the case where at least two members out of $R_{23}$ to $R_{25}$ combine with each other to form a ring, the ring that may be formed is preferably a ring having a carbon number of 3 to 12 and may be a monocyclic ring such as cyclopentyl group and cyclohexyl group, or a polycyclic group such as norbornyl group, adamantyl group, tetracyclodecanyl group and tetracyclododecanyl group. The ring that is formed by combining at least two members out of $R_{23}$ to $R_{25}$ is more preferably a ring having a carbon number of 6 to 12, still more preferably a cyclohexane ring, a cycloheptane ring, a cyclooctane ring, a cyclononane ring, a norbornane ring or an adamantane ring, yet still more preferably a cyclohexane ring or an adamantane ring.

The ring that may be formed by combining at least two members out of $R_{23}$ to $R_{25}$ may further have a substituent, and specific examples and preferable range of the substituent are the same as those of the substituent that may be substituted on $R_{11}$, $R_{12}$ and $R_{13}$ in formula (I).

Specific examples of the group represented by formula (II) are illustrated below, but the present invention is not limited thereto.

[Chem. 9]

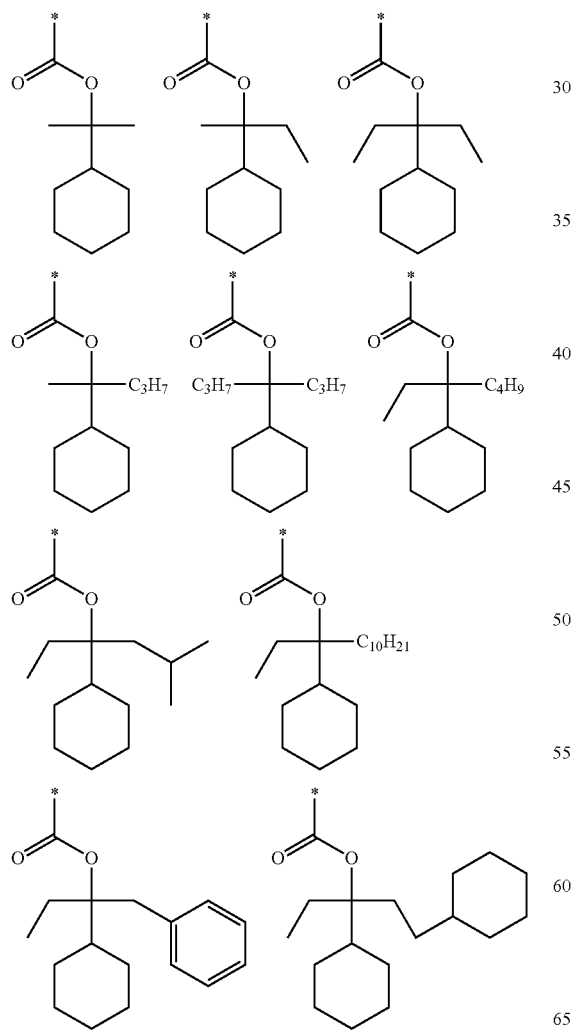

[Chem. 10]

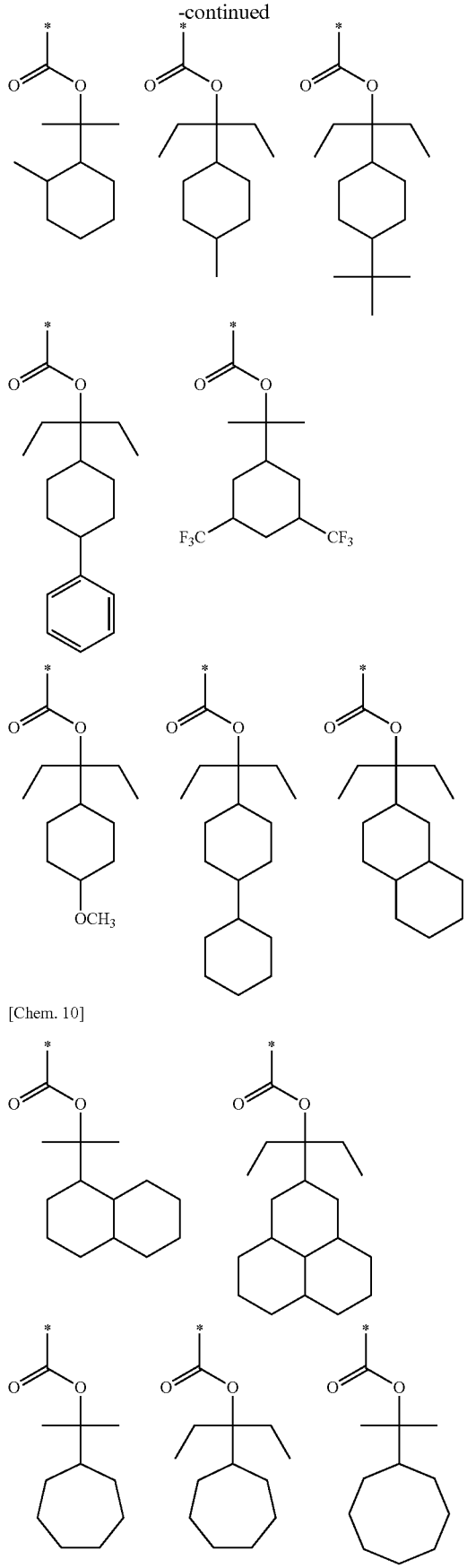

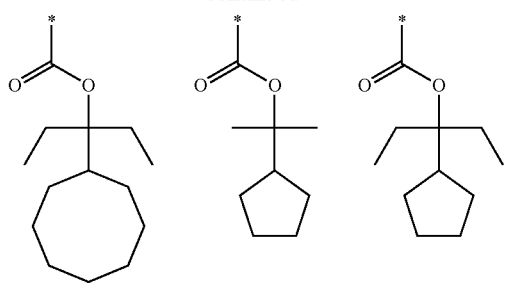
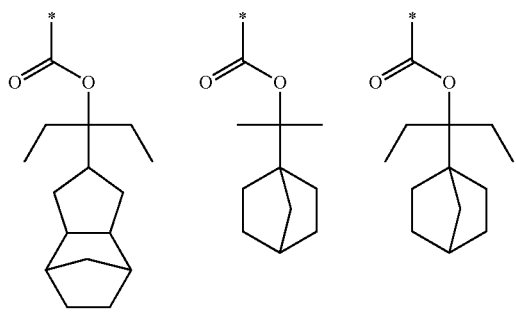
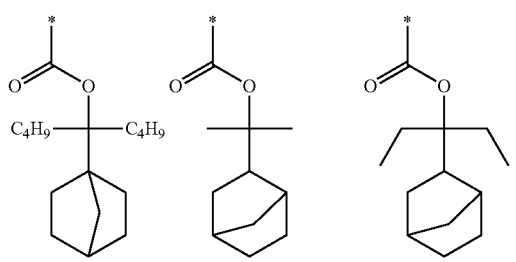
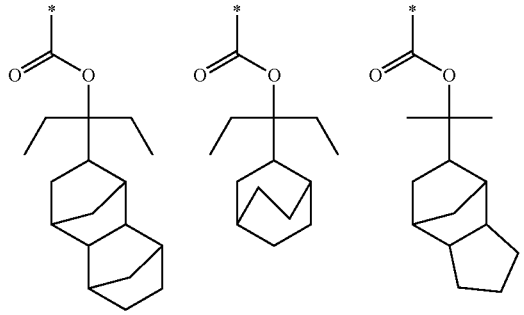
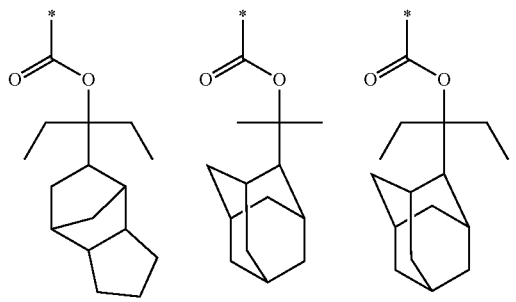
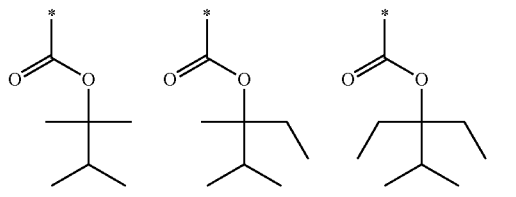

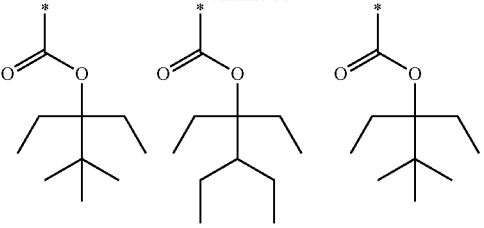

Formula (III) is described in detail below.

Specific examples and preferable ranges of $R_{31}$ and $R_{33}$ are the same as those of $R_{11}$ in formula (I).

Specific examples and preferable ranges of $R_{32}$ and $R_{34}$ are the same as those of $R_{12}$ in formula (I).

Specific examples and preferable ranges of $R_{33}$ and $R_{36}$ are the same as those of $R_{13}$ in formula (I).

The ring that may be formed by combining $R_{32}$ and $R_{33}$ with each other is the same as the ring that may be formed by combining $R_{12}$ and $R_{13}$ with each other.

The ring that may be formed by combining $R_{35}$ and $R_{36}$ with each other is the same as the ring that may be formed by combining $R_{12}$ and $R_{13}$ with each other.

The trivalent linking group of $L_3$ includes those formed by removing arbitrary two hydrogen atoms from an aryl group, an alkyl group and a cycloalkyl group.

The alkyl group above is preferably an alkyl group having a carbon number of 1 to 15 and specifically includes a methyl group, an ethyl group, a propyl group, an n-butyl group, a sec-butyl group, a tert-butyl group, a hexyl group, and an octyl group.

The cycloalkyl group above is preferably a cycloalkyl group having a carbon number of 3 to 15 and specifically, preferable examples thereof include a cyclopentyl group, a cyclohexyl group, a norbornyl group, an adamantyl group, and a diadamantyl group.

The aryl group above is preferably an aryl group having a carbon number of 6 to 15 and specifically includes a phenyl group, a tolyl group, a naphthyl group, an anthryl group, etc.

$L_3$ is preferably a group formed by removing arbitrary two hydrogen atoms from an alkyl group having a carbon number of 1 to 15, or a group formed by removing arbitrary two hydrogen atoms from a cycloalkyl group having a carbon number of 3 to 15, more preferably a group formed by removing arbitrary two hydrogen atoms from an alkyl group having a carbon number of 1 to 10, or a group formed by removing arbitrary two hydrogen atoms from a cycloalkyl group having a carbon number of 3 to 10.

$R_{31}$ to $R_{36}$ and $L_3$ may further have a substituent, and specific examples and preferable range of the substituent are the same as those of the substituent that may be substituted on $R_{11}$, $R_{12}$ and $R_{13}$ in formula (I).

Specific examples of the trivalent linking group represented by $L_3$ are illustrated below, but the present invention is not limited thereto. * indicates a bond connected to the oxygen atom in the group represented by formula (III), and ** indicates the same bond as the bond * in formula (III).

[Chem. 11]
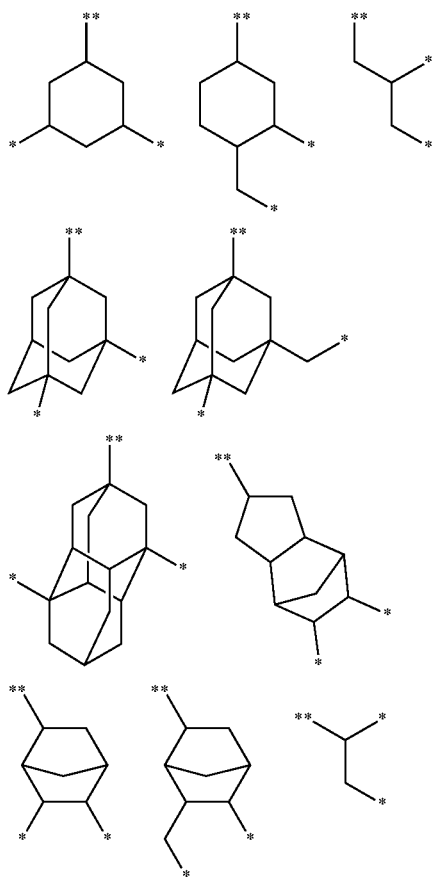
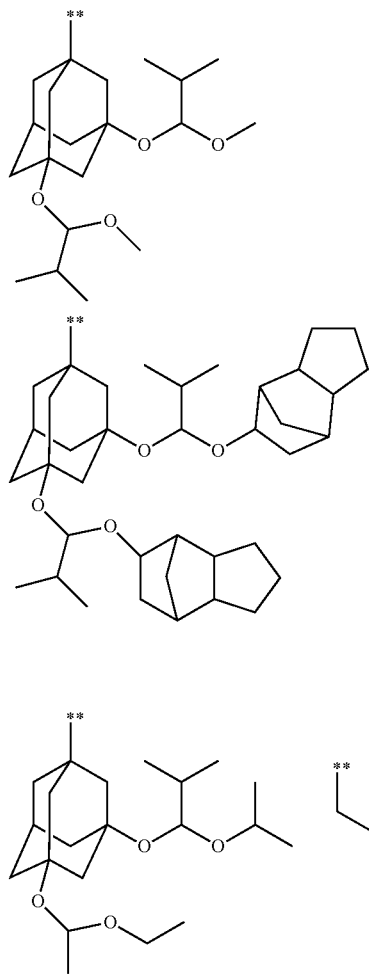
Specific examples of the group represented by formula (III) are illustrated below, but the present invention is not limited thereto.
[Chem. 12]
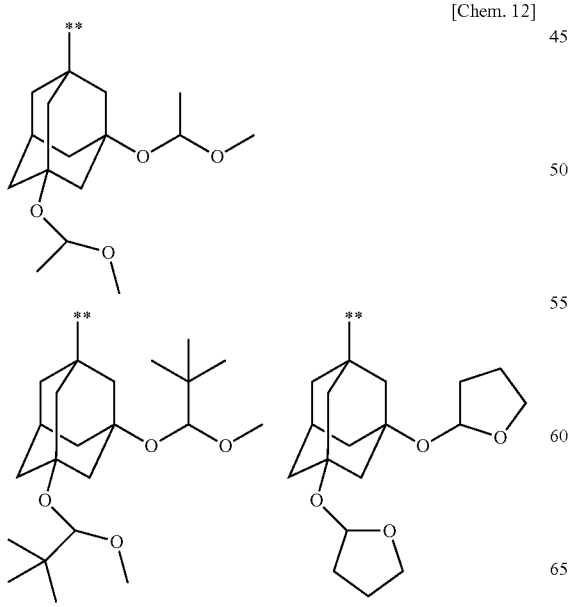
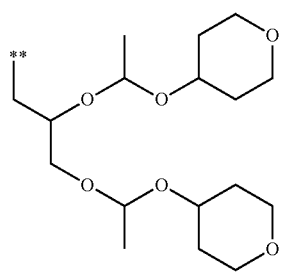
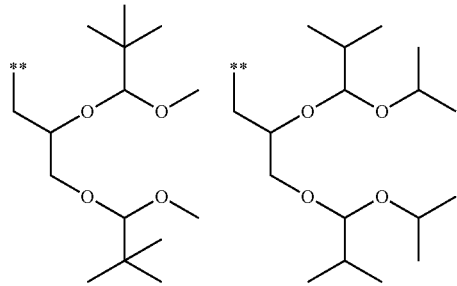

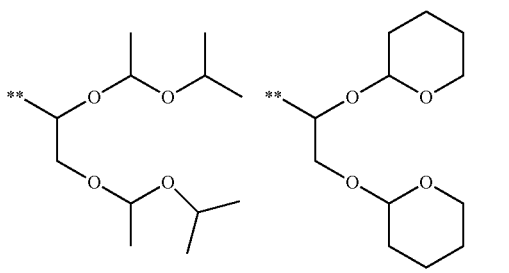
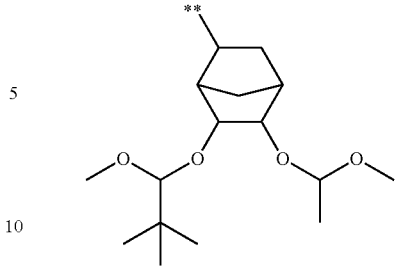

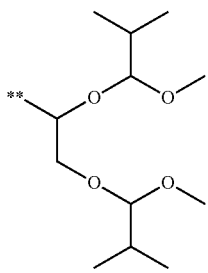

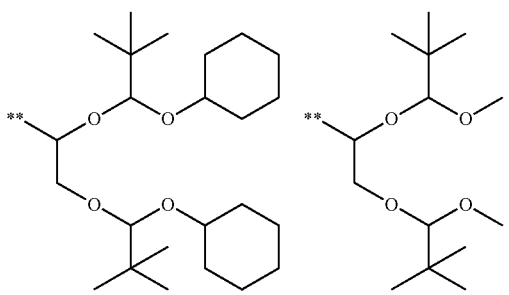

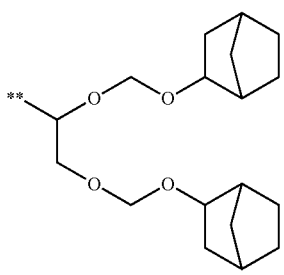

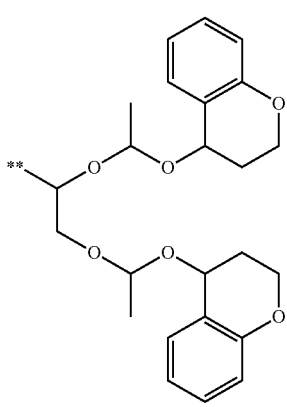

Formula (IV) is described in detail below.

The alkyl group of $R_{41}$ and $R_{42}$ is preferably an alkyl group having a carbon number of 1 to 20 and specifically includes a methyl group, an ethyl group, a propyl group, an n-butyl group, a sec-butyl group, a tert-butyl group, a hexyl group, and an octyl group.

$R_{31}$ and $R_{42}$ may combine with each other to form a ring, and the ring formed includes an alicyclic ring or a heterocyclic ring.

The alicyclic group may be monocyclic or polycyclic and is preferably a monocyclic cycloalkyl group such as cyclopentyl group, cyclohexyl group and cyclooctyl group, or a polycyclic cycloalkyl group such as norbornyl group, tricyclodecanyl group, tetracyclodecanyl group, tetracyclododecanyl group and adamantyl group. Among others, a cyclopentyl group or a cyclohexyl group is preferred.

The heterocyclic group includes those derived from a furan ring, a pyran ring, a thiophene ring, a benzofuran ring, a benzopyran ring, a benzothiophene ring, a dibenzofuran ring, a dibenzothiophene ring and a pyridine ring. Among these, a heterocyclic group derived from a pyrane ring is preferred.

$R_{41}$ and $R_{42}$ are preferably a hydrogen atom or an alkyl group.

Specific examples and preferable range of the trivalent linking group represented by $L_4$ are the same as those of $L_3$ in formula (III).

$R_{41}$, $R_{42}$ and $L_4$ may further have a substituent, and specific examples and preferable range of the substituent are the same as those of the substituent that may be substituted on $R_{11}$, $R_{12}$ and $R_{13}$ in formula (I).

Specific examples of the trivalent linking group represented by $L_4$ are illustrated below, but the present invention is not limited thereto. * indicates a bond connected to the oxygen atom in the group represented by formula (IV), and ** indicates the same bond as the bond * in the group represented by formula (IV).

[Chem. 13]

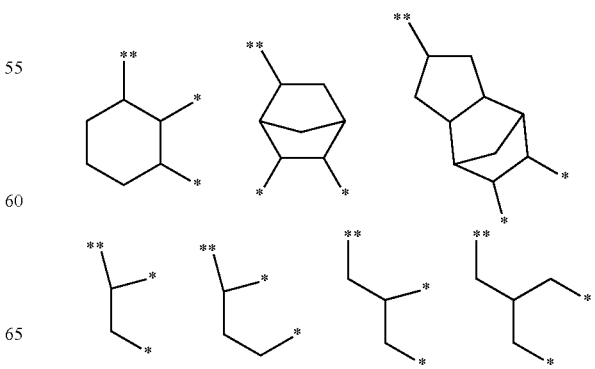

-continued

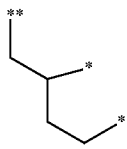

Specific examples of the group represented by formula (IV) are illustrated below, but the present invention is not limited thereto.

[Chem. 14]

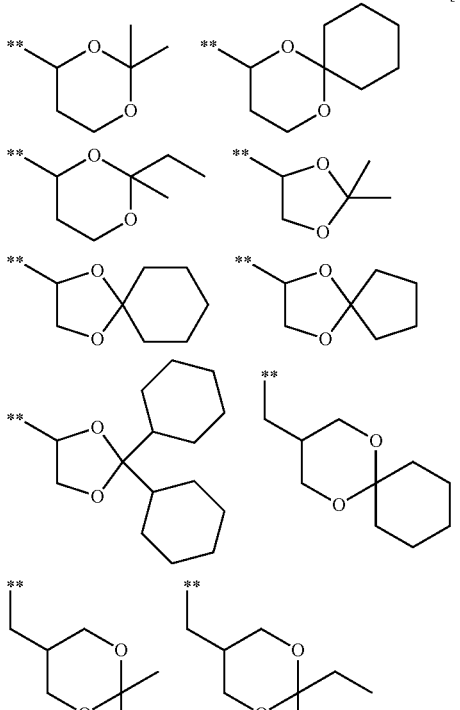

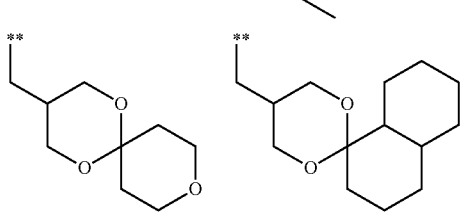

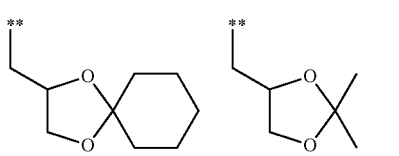

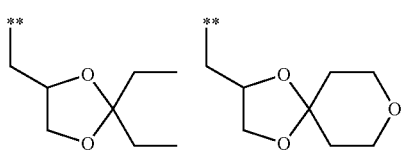

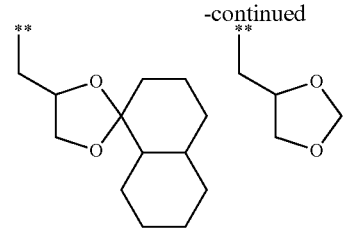

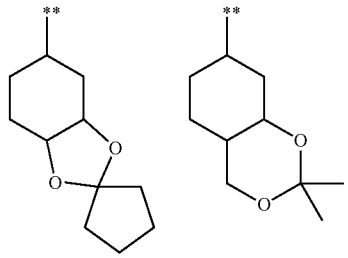

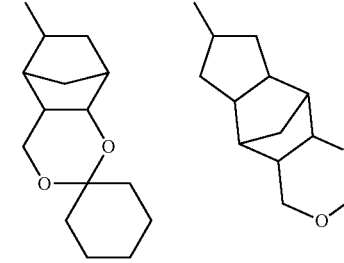

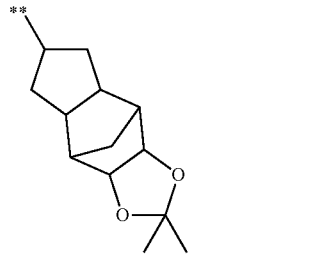

In formulae (1) and (2), at least one of $R_1$ to $R_3$ and at least one of $R_4$ and $R_5$ are not particularly limited as long as each has a substituent (P), but it is preferable to have a group represented by the following formula (P).

[Chem. 15]

$$*\text{-L-P} \tag{P}$$

In formula (P), L represents a single bond or a divalent linking group.

P represents the substituent (P) above.

* is a bond connected to at least one of $R_1$ to $R_3$ or at least one of $R_4$ and $R_5$ in the compound represented by formula (1) or (2).

The divalent linking group of L is preferably —O—, a divalent organic group having a carbon number of 1 to 8, or a divalent linking group formed by combining a plurality thereof and includes, for example, —O—, an alkylene group (e.g., methylene, ethylene, propylene, butylene), an arylene group (phenylene group), and a divalent linking group formed by combining a plurality thereof.

L is preferably —O— or a divalent linking group formed by combining —O— and an alkylene group (preferably a methyl group).

In the pattern formation, from the standpoint of more increasing the difference in the dissolution rate between exposed area and unexposed area, the substituent (P) of the present invention is preferably a group represented by formula (I) or (II), more preferably a group represented by formula (I).

The organic group having a carbon number of 30 or less of $R_1$ to $R_5$ includes an aryl group, an alkyl group, a cycloalkyl group, etc.

At least one of $R_1$ to $R_5$ is preferably an aryl group, and it is more preferred that all of these three members are an aryl group. The aryl group may be a heteroaryl group such as indole residue and pyrrole residue, other than a phenyl group, a naphthyl group, etc. The alkyl group and cycloalkyl group of $R_1$ to $R_5$ are preferably a linear or branched alkyl group having a carbon number of 1 to 10 and a cycloalkyl group having a carbon number of 3 to 10. The alkyl group is more preferably a methyl group, an ethyl group, an n-propyl group, an i-propyl group, an n-butyl group, etc. The cycloalkyl group is more preferably a cyclopropyl group, a cyclobutyl group, a cyclopentyl group, a cyclohexyl group, a cycloheptyl group, etc. These groups may further have a substituent, and the substituent includes, but is not limited to, a nitro group, a halogen atom such as fluorine atom, a carboxyl group, a hydroxyl group, an amino group, a cyano group, an alkoxy group (preferably having a carbon number of 1 to 15), a cycloalkyl group (preferably having a carbon number of 3 to 15), an aryl group (preferably having a carbon number of 6 to 14), an alkoxycarbonyl group (preferably having a carbon number of 2 to 7), an acyl group (preferably having a carbon number of 2 to 12), an alkoxycarbonyloxy group (preferably having a carbon number of 2 to 7), etc.

In the case where the substituent (P) is contained in $R_1$, $R_2$ or $R_3$ of formula (1), the compound (B) is preferably a compound represented by any one of the following formulae (2-1) to (2-3):

[Chem. 16]

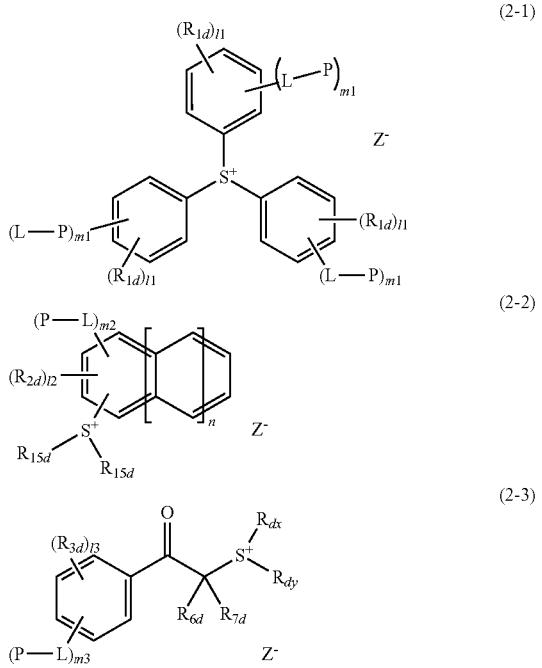

(2-1)

(2-2)

(2-3)

In formula (2-1), each $R_{1d}$ independently represents a hydrogen atom or a monovalent organic group. Two Rid may combine with each other to form a ring. In other words, two $R_{1d}$ may combine with each other to form a single bond or a divalent linking group. The divalent linking group is preferably a linking group having a carbon number of 4 or less and includes, for example, a methylene group, an ethylene group, an ether bond, a carbonyl group, and an ester group.

L represents a single bond or a divalent linking group.
P represents a group represented by formulae (I) to (IV).
$Z^-$ represents a non-nucleophilic counter anion.
Each l1 independently represents an integer of 0 to 5.
Each m independently represents an integer of 0 to 5.
However, any one of the plurality of m1 represents an integer of 1 or more.

In formula (2-2), each $R_{2d}$ independently represents a hydrogen atom or a monovalent organic group. Two $R_{2d}$ may combine with each other to form a ring.

Each $R_{15d}$ independently represents an alkyl group that may have a substituent. Two $R_{15d}$ may combine with each other to form a ring. Two $R_{15d}$ may combine with each other to form a ring.

Each of the group represented by —$S^+(R_{15d})(R_{15d})$, m pieces of (P-L), and 1 pieces of $R_4$ may be substituted on an arbitrary position of any aromatic ring in formula (2-2).

L represents a single bond or a divalent linking group.
P represents a group represented by formulae (I) to (IV).
$Z^-$ represents a non-nucleophilic counter anion.
n represents 0 or 1.
Each l2 independently represents an integer of 0 to 5.
m2 represents an integer of 1 to 5.

In formula (2-3), each $R_{3d}$ independently represents a hydrogen atom or a monovalent organic group. Two $R_{3d}$ may combine with each other to form a ring.

Each $R_{6d}$ and $R_{7d}$ independently represents a hydrogen atom or a monovalent organic group. $R_{6d}$ and $R_{7d}$ may combine with each other to form a ring.

Each of $R_{dx}$ and $R_{dy}$ independently represents an alkyl group that may have a substituent. $R_{dx}$ and $R_{dy}$ may combine with each other to form a ring.

L represents a single bond or a divalent linking group.
P represents a group represented by formulae (I) to (IV).
$Z^-$ represents a non-nucleophilic counter anion.
Each l3 independently represents an integer of 0 to 5.
m3 represents an integer of 1 to 5.

The organic group of $R_{1d}$, $R_{2d}$ and $R_{3d}$ is preferably an alkyl group, a cycloalkyl group, an alkoxy group or a halogen atom. Two or more $R_4$ may combine to form a ring structure, and the ring structure may contain an oxygen atom, a sulfur atom, an ester bond, or an amido bond. The group formed by combining two or more $R_4$ includes a butylene group, a pentylene group, etc.

The alkyl group, cycloalkyl group and alkoxy group of $R_{1d}$, $R_{2d}$ and $R_{3d}$ include the same alkyl groups, cycloalkyl groups and alkoxy groups as those of $R_{1C}$ to $R_{5C}$ in formula (1-3).

The alkyl group of $R_{15d}$, $R_{dx}$ and $R_{dy}$ is linear or branched and is preferably an alkyl group having a carbon number of 1 to 10, and examples thereof include a methyl group, an ethyl group, an n-propyl group, an i-propyl group, an n-butyl group, a 2-methylpropyl group, a 1-methylpropyl group, a tert-butyl group, an n-pentyl group, a neopentyl group, an n-hexyl group, an n-heptyl group, an n-octyl group, a 2-ethylhexyl group, an n-nonyl group, and an n-decyl group. Among these alkyl groups, a methyl group, an ethyl group, an n-butyl group, a tert-butyl group, etc. are preferred, and, for example, a methyl group, an ethyl group, an n-propyl group, an n-butyl group, and a divalent linking group in which two $R_{15d}$ combine with each other (or $R_{dx}$ and $R_{dy}$ combine with each other) to form a tetrahydrothiophene ring structure together with the sulfur atom, are more preferred.

The organic group of $R_{6d}$ and $R_{7d}$ is preferably an alkyl group or a cycloalkyl group. $R_{6d}$ and $R_{7d}$ may combine to form a ring structure, and the ring structure may contain an oxygen atom, a sulfur atom, an ester bond, or an amido bond. The group formed by combining $R_{6d}$ and $R_{7d}$ includes a butylene group, a pentylene group, etc.

The alkyl group and cycloalkyl group of $R_{6d}$ and $R_{7d}$ include the same alkyl groups and cycloalkyl groups as those of $R_{6C}$ and $R_{7C}$ in formula (1-3), and a 2-oxoalkyl group, a 2-oxocycloalkyl group, and an alkoxycarbonyl methyl group are preferred.

The 2-oxoalkyl group and 2-oxocycloalkyl group include groups having >C=O at the 2-position of the alkyl group and cycloalkyl group of $R_{1c}$ to $R_{7c}$.

The alkoxy group in the alkoxycarbonylmethyl group include the same alkoxy groups as in $R_{1c}$ to $R_{5c}$.

$R_{6d}$ and $R_{7d}$ are preferably a hydrogen atom or an alkyl or cycloalkyl group having a carbon number of 4 or more, more preferably an alkyl or cycloalkyl group having a carbon number of 6 or more, still more preferably 8 or more.

The divalent linking group of L has the same meaning as that in formula (P), and specific examples and preferable range thereof are also the same.

Specific examples and preferable range of $Z^-$ are the same as those of $Z^-$ in the later-described formulae (1) and (2).

Specific examples of the cation in the acid generator are illustrated below, but the present invention is not limited thereto.

[Chem. 17]

A-1
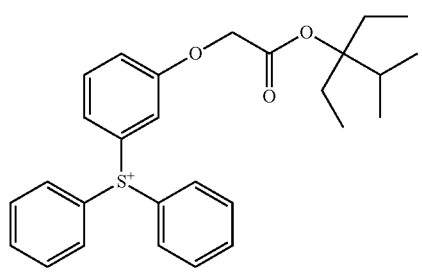

A-2
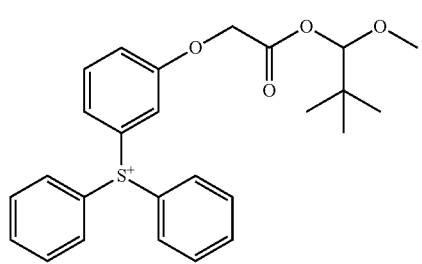

-continued

A-3
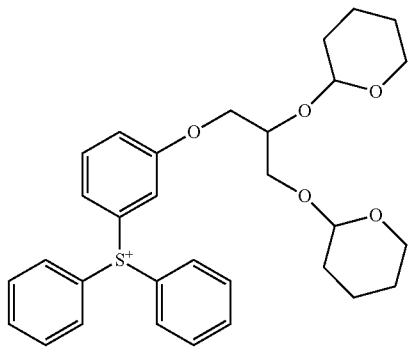

A-4
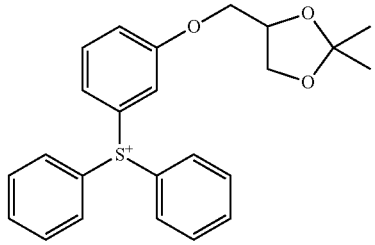

A-5
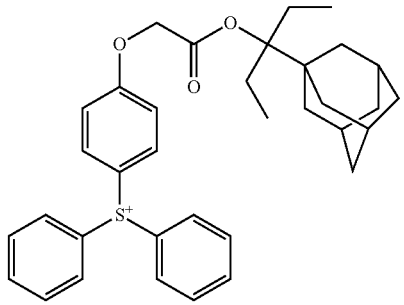

A-6
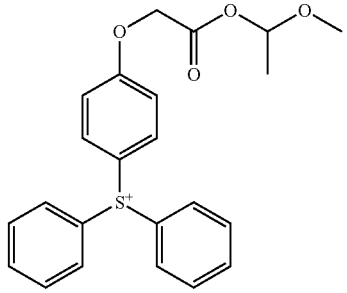

A-7
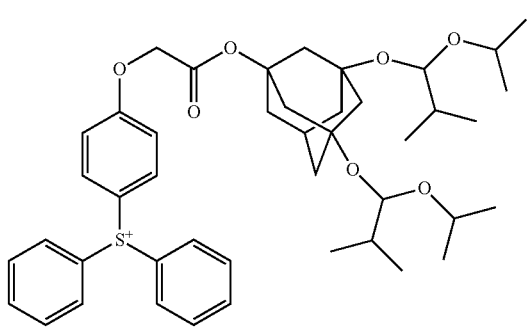

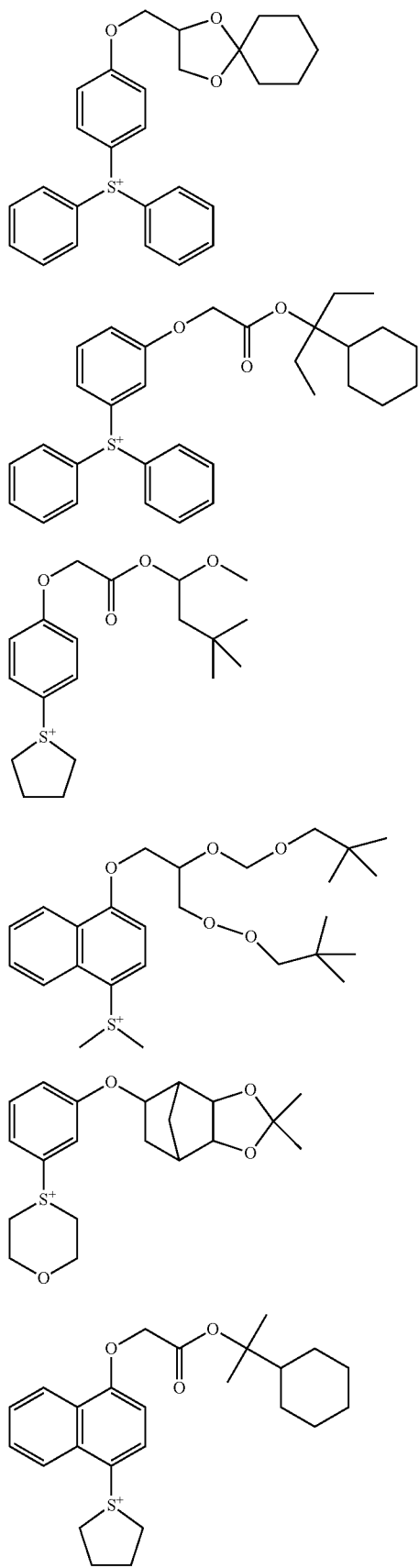
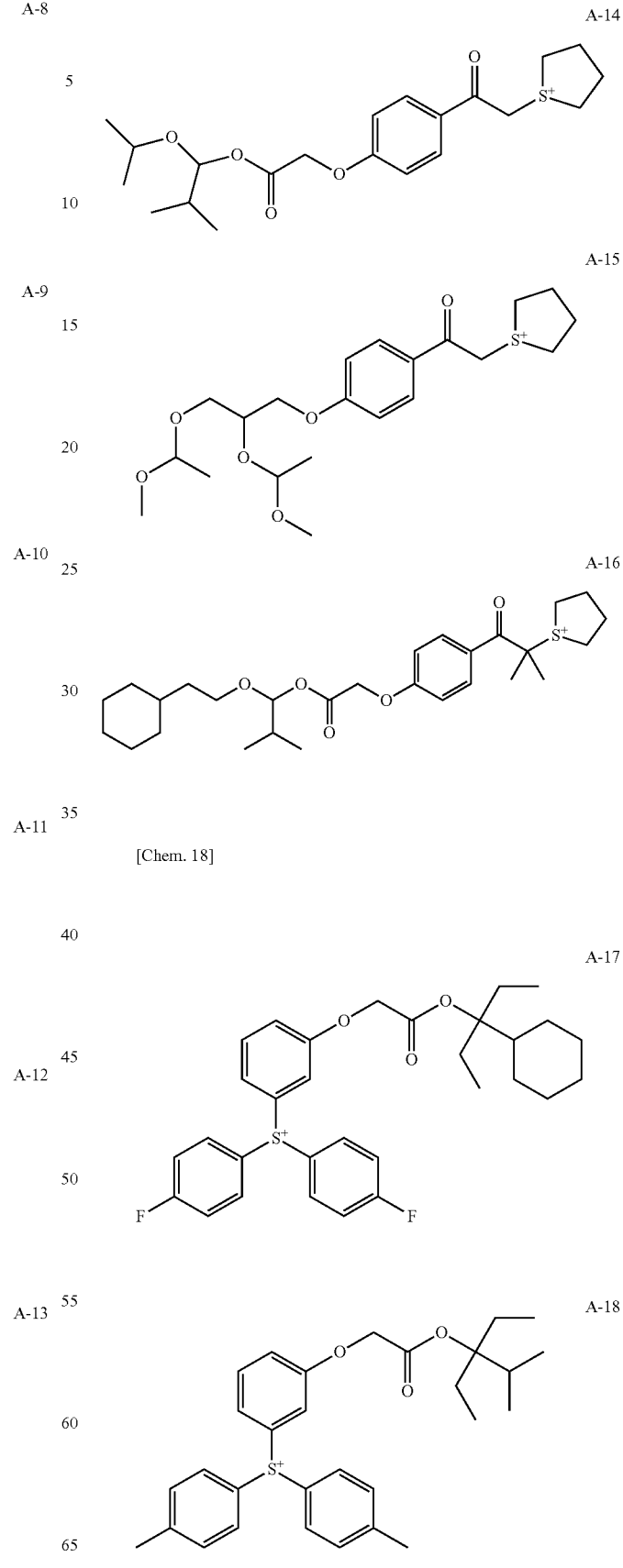

A-19
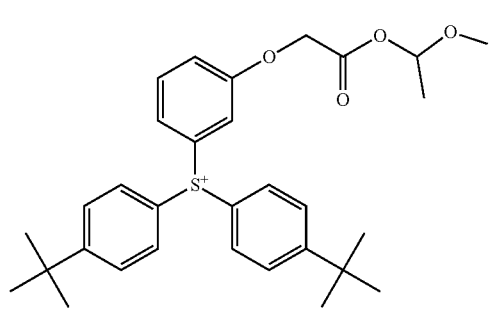
A-20
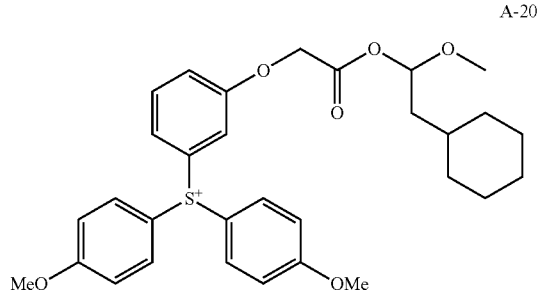
A-21
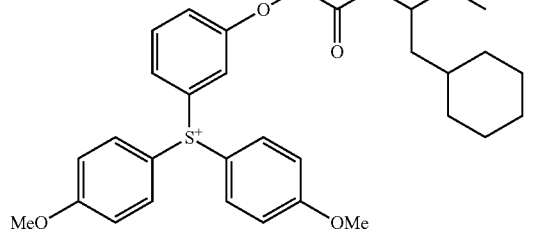
A-22
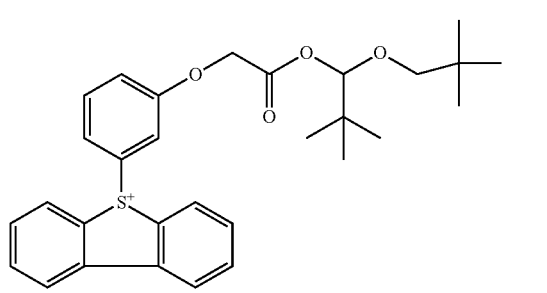
A-23
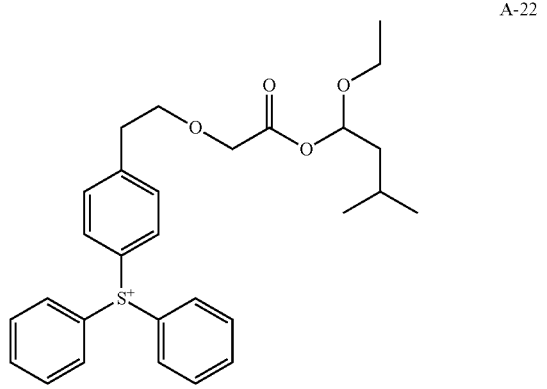
A-24
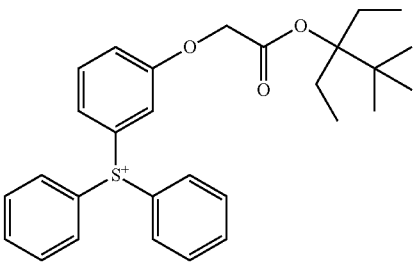
A-25
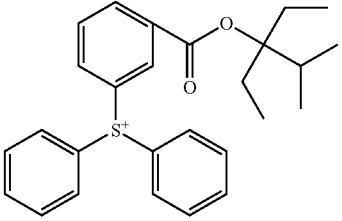
A-26
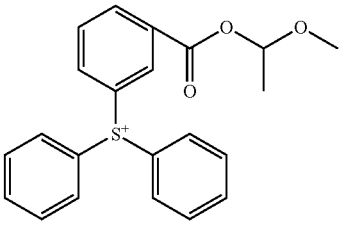
A-27
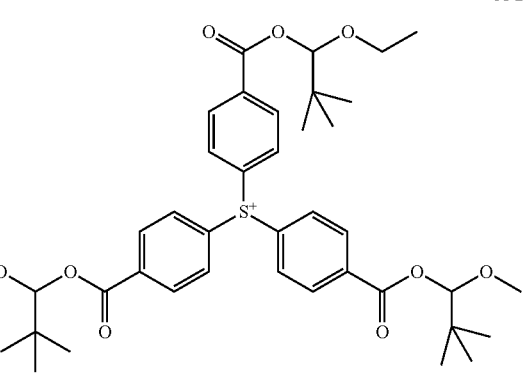
A-28
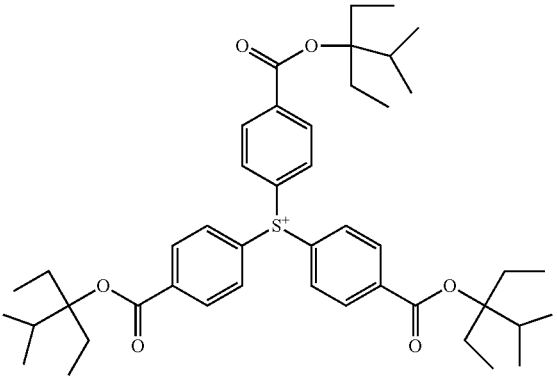

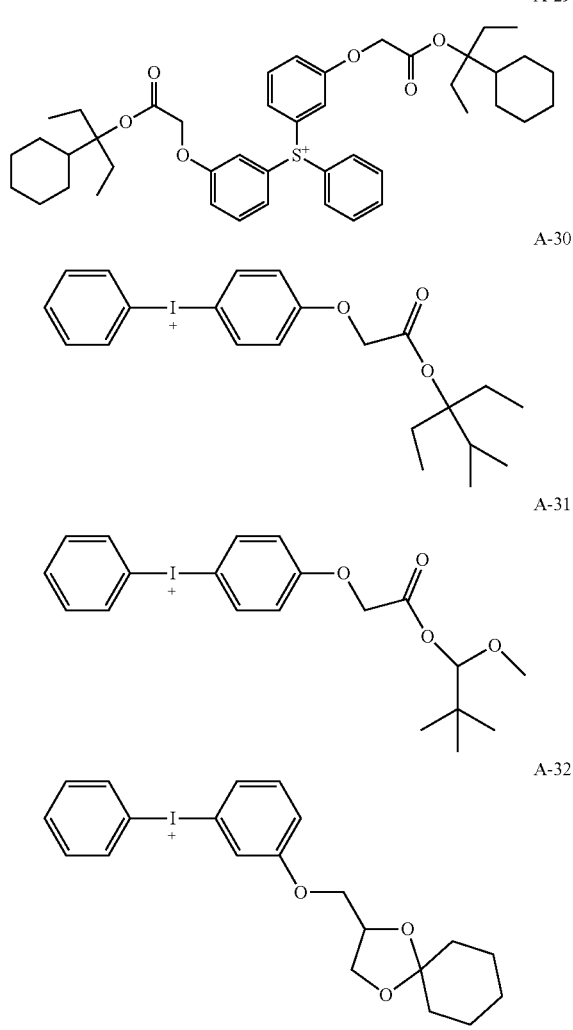

A-29

A-30

A-31

A-32

The non-nucleophilic anion (an anion having an extremely low ability of causing a nucleophilic reaction) of $Z^-$ includes, for example, a sulfonate anion (such as aliphatic sulfonate anion, aromatic sulfonate anion and camphorsulfonate anion), a carboxylate anion (such as aliphatic carboxylate anion, aromatic carboxylate anion and aralkylcarboxylate anion), a sulfonylimide anion, a bis(alkylsulfonyl)imide anion, and a tris(alkylsulfonyl)methide anion.

The aliphatic moiety in the aliphatic sulfonate anion and aliphatic carboxylate anion may be an alkyl group or a cycloalkyl group but is preferably a linear or branched alkyl group having a carbon number of 1 to 30 or a cycloalkyl group having a carbon number of 3 to 30.

The aromatic group in the aromatic sulfonate anion and aromatic carboxylate anion is preferably an aryl group having a carbon number of 6 to 14 and includes, for example, a phenyl group, a tolyl group and a naphthyl group.

The above-described alkyl group, cycloalkyl group and aryl group may have a substituent. Specific examples of the substituent include a nitro group, a halogen atom such as fluorine atom, a carboxyl group, a hydroxyl group, an amino group, a cyano group, an alkoxy group (preferably having a carbon number of 1 to 15), a cycloalkyl group (preferably having a carbon number of 3 to 15), an aryl group (preferably having a carbon number of 6 to 14), an alkoxycarbonyl group (preferably having a carbon number of 2 to 7), an acyl group (preferably having a carbon number of 2 to 12), an alkoxycarbonyloxy group (preferably having a carbon number of 2 to 7), an alkylthio group (preferably having a carbon number of 1 to 15), an alkylsulfonyl group (preferably having a carbon number of 1 to 15), an alkyliminosulfonyl group (preferably having a carbon number of 2 to 15), an aryloxysulfonyl group (preferably having a carbon number of 6 to 20), an alkylaryloxysulfonyl group (preferably having a carbon number of 7 to 20), a cycloalkylaryloxysulfonyl group (preferably having a carbon number of 10 to 20), an alkyloxyalkyloxy group (preferably having a carbon number of 5 to 20), and a cycloalkylalkyloxyalkyloxy group (preferably having a carbon number of 8 to 20). As for the aryl group or ring structure, which is contained in each group, the substituent further includes an alkyl group (preferably having a carbon number of 1 to 15).

The aralkyl group in the aralkylcarboxylate anion is preferably an aralkyl group having a carbon number of 7 to 12 and includes, for example, a benzyl group, a phenethyl group, a naphthylmethyl group, a naphthylethyl group, and a naphthylbutyl group.

The sulfonylimide anion includes, for example, saccharin anion.

The alkyl group in the bis(alkylsulfonyl)imide anion and tris(alkylsulfonyl)methide anion is preferably an alkyl group having a carbon number of 1 to 5, and the substituent on this alkyl group includes a halogen atom, a halogen atom-substituted alkyl group, an alkoxy group, an alkylthio group, an alkyloxysulfonyl group, an aryloxysulfonyl group, a cycloalkylaryloxysulfonyl group, etc., with a fluorine atom and a fluorine atom-substituted alkyl group being preferred.

In addition, the alkyl groups in the bis(alkylsulfonyl)imide anion may combine with each other to form a ring structure. Thanks to this configuration, the acid strength is increased.

Other non-nucleophilic anions include, for example, a fluorinated phosphorus (e.g., $PF_6^-$), fluorinated boron (e.g., $BF_4^-$), and fluorinated antimony (e.g., $SbF_6^-$).

The non-nucleophilic anion is preferably a sulfonate anion, more preferably an aliphatic sulfonate anion substituted with a fluorine atom at least at the α-position of the sulfonic acid, an aromatic sulfonate anion substituted with a fluorine atom or a fluorine atom-containing group, a bis(alkylsulfonyl)imide anion in which the alkyl group is substituted with a fluorine atom, or a tris(alkylsulfonyl)methide anion in which the alkyl group is substituted with a fluorine atom. The non-nucleophilic anion is more preferably a benzenesulfonate anion, still more preferably a fluorine atom-containing benzenesulfonate anion, and most preferably pentafluorobenzenesulfonate anion or 3,5-bis(trifluoromethyl)benzenesulfonate anion.

An anion represented by the following formula (AN1) is also a preferred embodiment of the non-nucleophilic anion:

[Chem. 19]

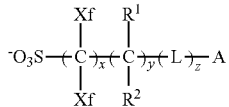

(AN1)

In the formula, each Xf independently represents a fluorine atom or an alkyl group substituted with at least one fluorine atom.

Each of $R^1$ and $R^2$ independently represents a hydrogen atom, a fluorine atom or an alkyl group, and when a plurality of $R^1$ or $R^2$ are present, each $R^1$ or $R^2$ may be the same as or different from every other $R^1$ or $R^2$.

L represents a divalent linking group, and when a plurality of L are present, each L may be the same as or different from every other L.

A represents a cyclic organic group.

x represents an integer of 1 to 20, y represents an integer of 0 to 10, and z represents an integer of 0 to 10.

Formula (AN1) is described in more detail.

The alkyl group in the fluorine atom-substituted alkyl group of Xf is preferably an alkyl group having a carbon number of 1 to 10, more preferably a carbon number of 1 to 4. In addition, the fluorine atom-substituted alkyl group of Xf is preferably a perfluoroalkyl group.

Xf is preferably a fluorine atom or a perfluoroalkyl group having a carbon number of 1 to 4. Specific examples of Xf include a fluorine atom, $CF_3$, $C_2F_5$, $C_3F_7$, $C_4F_9$, $CH_2CF_3$, $CH_2CH_2CF_3$, $CH_2C_2F_5$, $CH_2CH_2C_2F_5$, $CH_2C_3F_7$, $CH_2CH_2C_3F_7$, $CH_2C_4F_9$ and $CH_2CH_2C_4F_9$, with a fluorine atom and $CF_3$ being preferred. In particular, it is preferred that both Xf are a fluorine atom.

The alkyl group of $R^1$ and $R^2$ may have a substituent (preferably a fluorine atom) and is preferably an alkyl group having a carbon number of 1 to 4, more preferably a perfluoroalkyl group having a carbon number of 1 to 4. Specific examples of the alkyl group having a substituent of $R^1$ and $R^2$ include $CF_3$, $C_2F_5$, $C_3F_7$, $C_4F_9$, $C_5F_{11}$, $C_6F_{13}$, $C_7F_{15}$, $C_8F_{17}$, $CH_2CF_3$, $CH_2CH_2CF_3$, $CH_2C_2F_5$, $CH_2CH_2C_2F_5$, $CH_2C_3F_7$, $CH_2CH_2C_3F_7$, $CH_2C_4F_9$ and $CH_2CH_2C_4F_9$, with $CF_3$ being preferred.

$R^1$ and $R^2$ are preferably a fluorine atom or $CF_3$.

x is preferably from 1 to 10, more preferably from 1 to 5.

y is preferably from 0 to 4, more preferably 0.

z is preferably from 0 to 5, more preferably from 0 to 3.

The divalent linking group of L is not particularly limited and includes, for example, —COO—, —OCO—, —CO—, —O—, —S—, —SO—, —SO$_2$—, an alkylene group, a cycloalkylene group, an alkenylene group, and a linking group formed by combining a plurality thereof. A linking group having a total carbon number of 12 or less is preferred. Among these, —COO—, —OCO—, —CO— and —O— are preferred, and —COO—, —OCO— are more preferred.

The cyclic organic group of A is not particularly limited as long as it has a cyclic structure, and examples thereof include an alicyclic group, an aryl group, and a heterocyclic group (including not only those having aromaticity but also those having no aromaticity).

The alicyclic group may be monocyclic or polycyclic and is preferably a monocyclic cycloalkyl group such as cyclopentyl group, cyclohexyl group and cyclooctyl group, or a polycyclic cycloalkyl group such as norbornyl group, tricyclodecanyl group, tetracyclodecanyl group, tetracyclododecanyl group and adamantyl group. Above all, an alicyclic group having a bulky structure with a carbon number of 7 or more, such as norbornyl group, tricyclodecanyl group, tetracyclodecanyl group, tetracyclododecanyl group and adamantyl group, is preferred from the standpoint that the diffusion in the film during heating after exposure can be suppressed and MEEF can be improved.

The aryl group includes a benzene ring, a naphthalene ring, a phenanthrene ring, and an anthracene ring.

The heterocyclic group includes those derived from a furan ring, a thiophene ring, a benzofuran ring, a benzothiophene ring, a dibenzofuran ring, a dibenzothiophene ring and a pyridine ring. Among these, heterocyclic groups derived from a furan ring, a thiophene ring and a pyridine ring are preferred.

The cyclic organic group also includes a lactone structure. Specific examples thereof include lactone structures represented by formulae (LC1-1) to (LC1-17) which may be contained in the later-described resin (P).

The cyclic organic group may have a substituent, and the substituent includes an alkyl group (may be any of linear, branched or cyclic; preferably having a carbon number of 1 to 12), a cycloalkyl group (may be any of monocyclic, polycyclic or spirocyclic; preferably having a carbon number of 3 to 20), an aryl group (preferably having a carbon number of 6 to 14), a hydroxy group, an alkoxy group, an ester group, an amido group, a urethane group, a ureido group, a thioether group, a sulfonamido group, a sulfonic acid ester group, etc. Incidentally, the carbon constituting the cyclic organic group (the carbon contributing to ring formation) may be a carbonyl carbon.

From the standpoint of realizing a better pattern profile at the time of pattern formation in the fine region, $Z^-$ is preferably an aromatic sulfonate anion, more preferably an aromatic sulfonate anion having a structure where a benzene ring is substituted with a fluorine atom or a fluorinated substituent.

From the standpoint of increasing the exposure margin at the time of formation of a finer pattern, the total carbon number in the anion above is preferably 15 or more so as to prevent the diffusion of acid generated.

Specific examples of the non-nucleophilic anion of $Z^-$ are illustrated below, but the present invention is not limited thereto.

[Chem. 20]

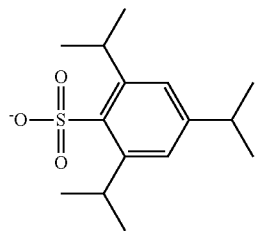

Z-1

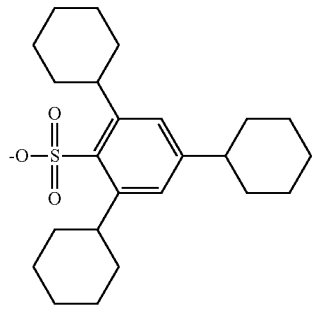

Z-2

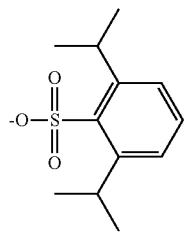

Z-3

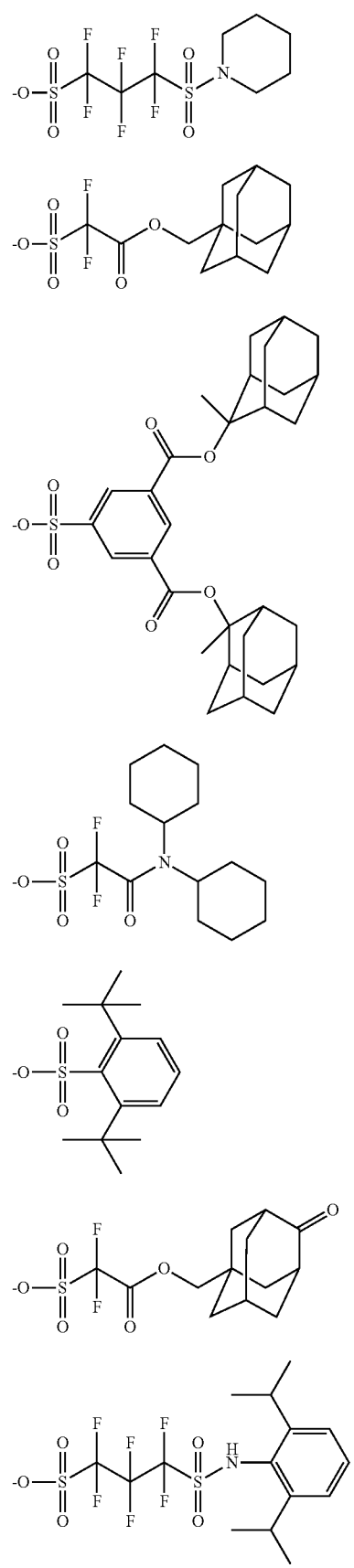
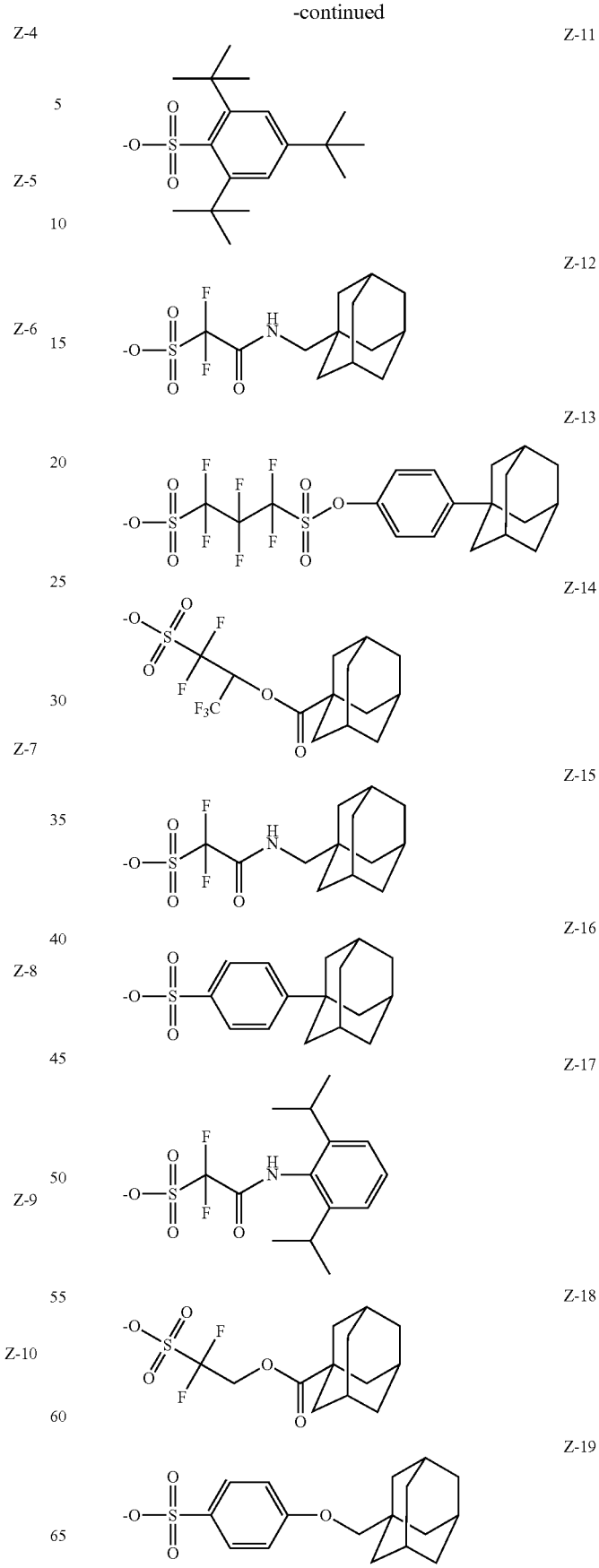

[Chem. 21]

Z-34 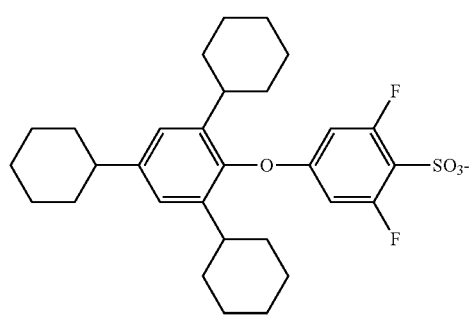
Z-35 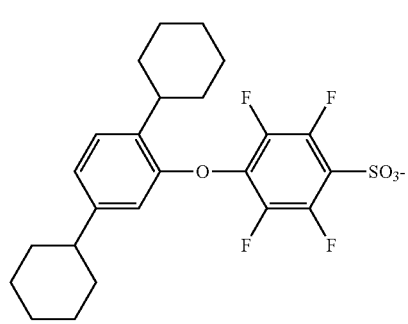
Z-36 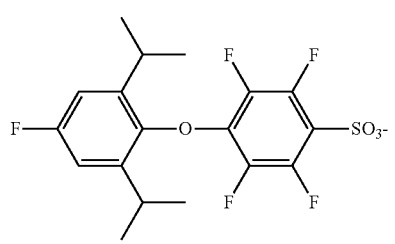
Z-37 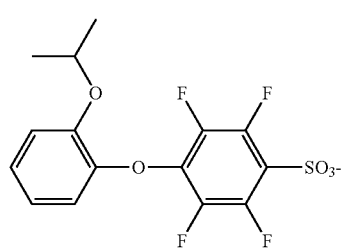
Z-38 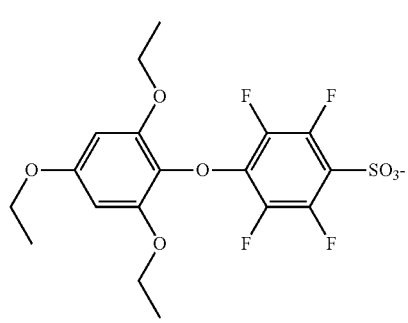
Z-39 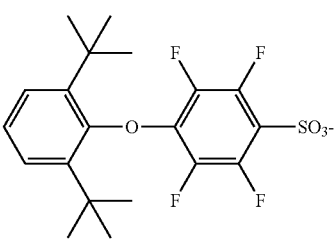
Z-40 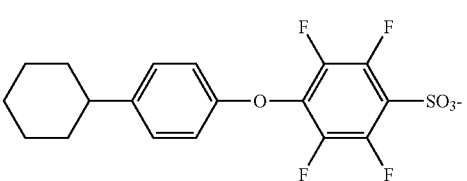
Z-41 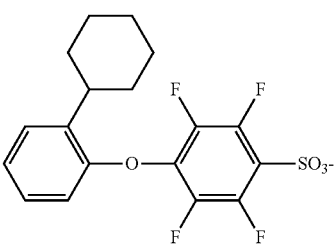
Z-42 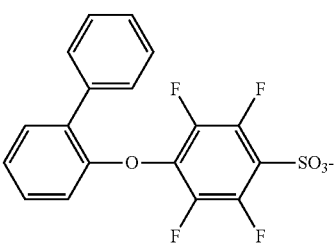
Z-43 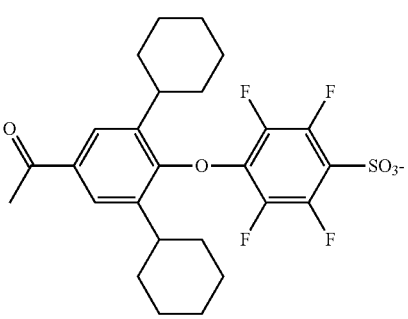
Z-44 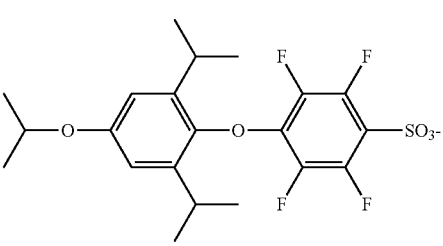

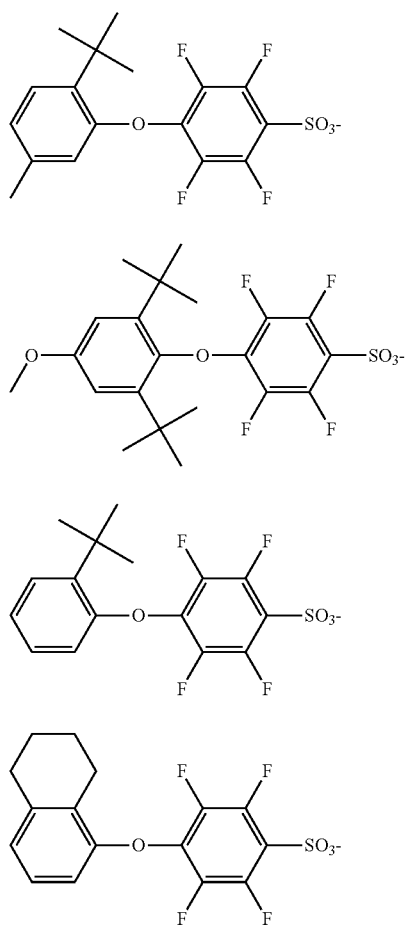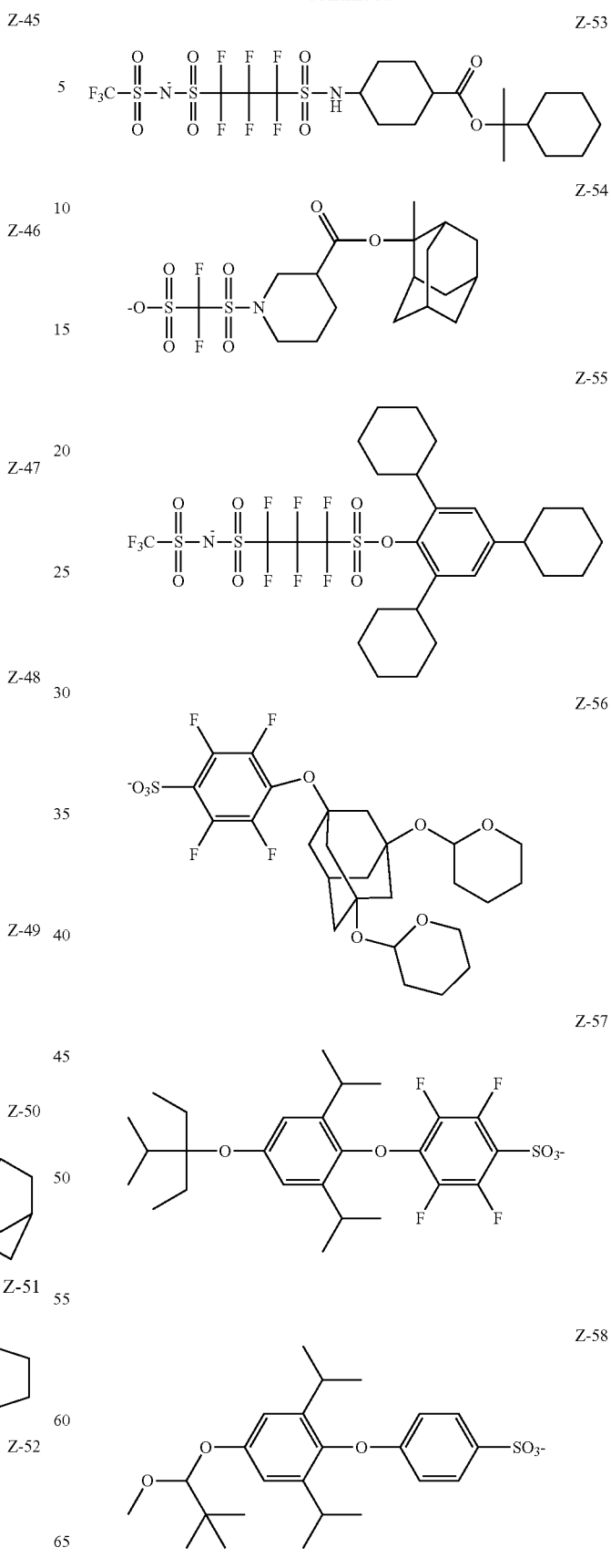

Z-59
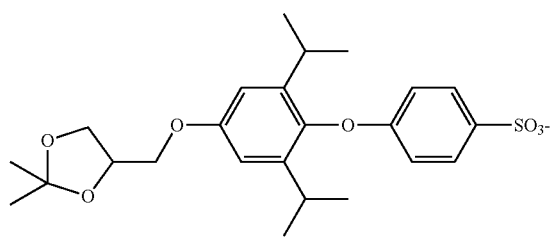
Z-60
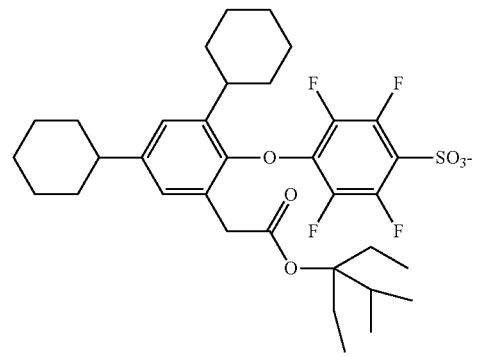
[Chem. 23]
Z-61
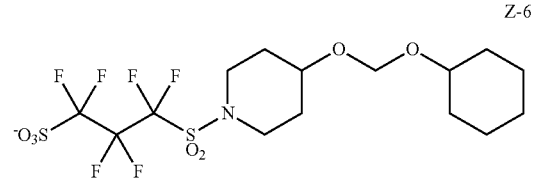
Z-62
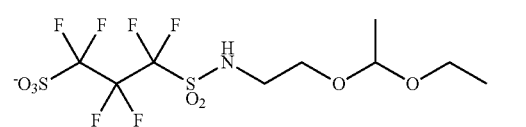
Z-63
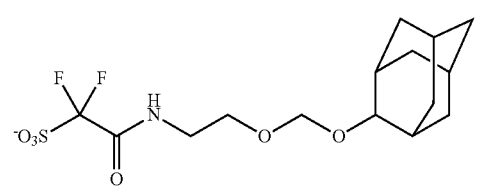
Z-64
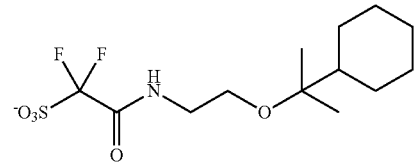
Z-65
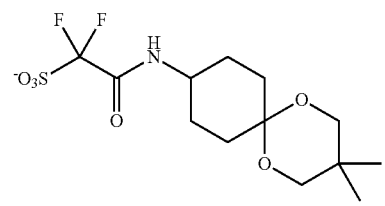
Z-66
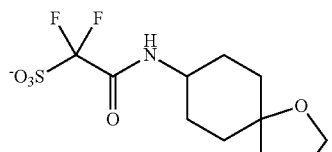
Z-67
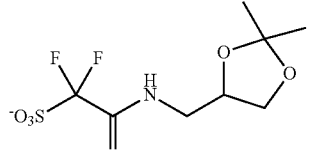
Z-68
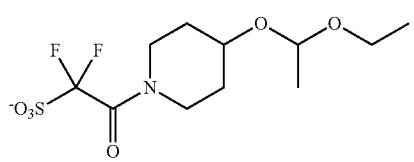
Z-69
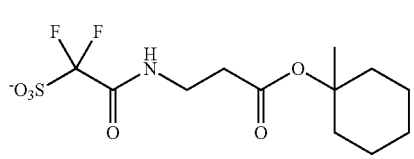
Z-70
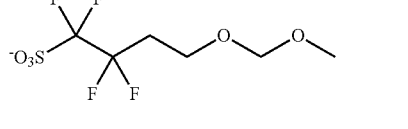
Z-71
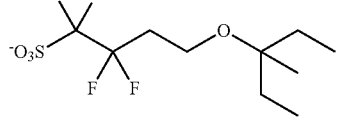
Z-72
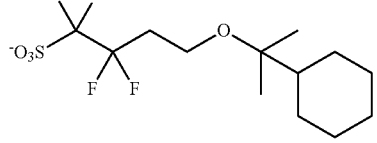
Z-73
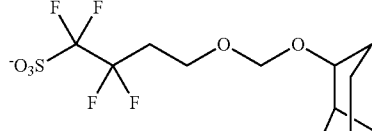
Z-74
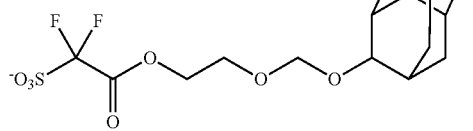

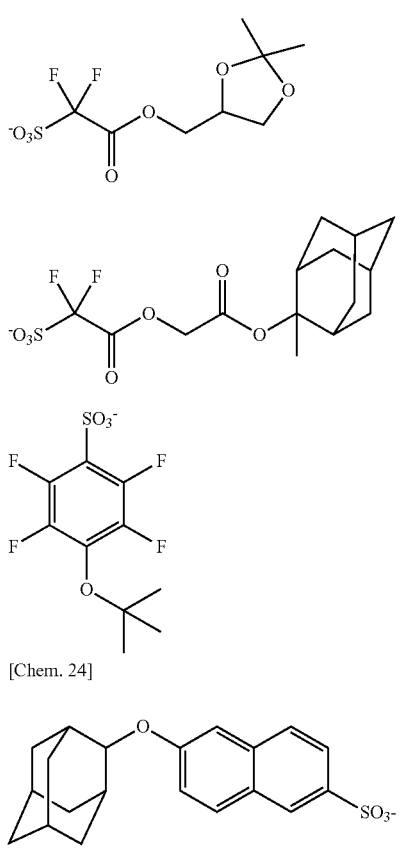

Structures of the acid generator are shown below, but the present invention is not limited thereto.

TABLE 1

| Cation | Anion | PAG |
|---|---|---|
| A-1 | Z-1 | b-1 |
| A-2 | Z-1 | b-2 |
| A-3 | Z-1 | b-3 |
| A-4 | Z-1 | b-4 |
| A-1 | Z-2 | b-5 |
| A-2 | Z-2 | b-6 |
| A-3 | Z-2 | b-7 |
| A-4 | Z-2 | b-8 |
| A-25 | Z-2 | b-9 |
| A-26 | Z-2 | b-10 |
| A-27 | Z-2 | b-11 |
| A-28 | Z-2 | b-12 |
| A-1 | Z-3 | b-13 |
| A-2 | Z-3 | b-14 |
| A-1 | Z-4 | b-15 |
| A-2 | Z-4 | b-16 |
| A-1 | Z-5 | b-17 |
| A-2 | Z-5 | b-18 |
| A-11 | Z-5 | b-19 |
| A-13 | Z-5 | b-20 |
| A-14 | Z-5 | b-21 |
| A-15 | Z-5 | b-22 |
| A-16 | Z-5 | b-23 |
| A-1 | Z-6 | b-24 |
| A-1 | Z-7 | b-25 |
| A-1 | Z-8 | b-26 |
| A-1 | Z-9 | b-27 |
| A-1 | Z-10 | b-28 |
| A-1 | Z-11 | b-29 |
| A-1 | Z-12 | b-30 |
| A-1 | Z-13 | b-31 |
| A-1 | Z-14 | b-32 |
| A-1 | Z-15 | b-33 |
| A-1 | Z-16 | b-34 |
| A-1 | Z-17 | b-35 |
| A-1 | Z-18 | b-36 |
| A-2 | Z-18 | b-37 |
| A-11 | Z-18 | b-38 |
| A-13 | Z-18 | b-39 |
| A-14 | Z-18 | b-40 |
| A-15 | Z-18 | b-41 |
| A-16 | Z-18 | b-42 |
| A-2 | Z-19 | b-43 |
| A-2 | Z-20 | b-44 |
| A-1 | Z-21 | b-45 |
| A-2 | Z-21 | b-46 |
| A-4 | Z-21 | b-47 |
| A-25 | Z-21 | b-48 |
| A-26 | Z-21 | b-49 |
| A-25 | Z-22 | b-50 |
| A-25 | Z-23 | b-51 |
| A-25 | Z-24 | b-52 |
| A-1 | Z-25 | b-53 |
| A-2 | Z-25 | b-54 |
| A-1 | Z-26 | b-55 |
| A-1 | Z-27 | b-56 |
| A-1 | Z-28 | b-57 |
| A-1 | Z-30 | b-58 |
| A-2 | Z-30 | b-59 |
| A-3 | Z-30 | b-60 |
| A-4 | Z-30 | b-61 |
| A-5 | Z-30 | b-62 |
| A-6 | Z-30 | b-63 |
| A-7 | Z-30 | b-64 |
| A-8 | Z-30 | b-65 |
| A-9 | Z-25 | b-66 |
| A-10 | Z-30 | b-67 |
| A-11 | Z-30 | b-68 |
| A-12 | Z-30 | b-69 |
| A-13 | Z-30 | b-70 |
| A-14 | Z-30 | b-71 |
| A-15 | Z-30 | b-72 |
| A-16 | Z-30 | b-73 |
| A-17 | Z-30 | b-74 |
| A-18 | Z-30 | b-75 |
| A-19 | Z-30 | b-76 |
| A-20 | Z-30 | b-77 |
| A-21 | Z-30 | b-78 |
| A-22 | Z-30 | b-79 |
| A-23 | Z-30 | b-80 |
| A-24 | Z-30 | b-81 |
| A-25 | Z-30 | b-82 |
| A-26 | Z-30 | b-83 |
| A-27 | Z-30 | b-84 |
| A-28 | Z-30 | b-85 |
| A-29 | Z-30 | b-86 |
| A-30 | Z-30 | b-87 |
| A-31 | Z-30 | b-88 |
| A-32 | Z-30 | b-89 |
| A-2 | Z-31 | b-90 |
| A-2 | Z-32 | b-91 |
| A-2 | Z-33 | b-92 |
| A-2 | Z-34 | b-93 |
| A-2 | Z-35 | b-94 |
| A-2 | Z-36 | b-95 |
| A-2 | Z-37 | b-96 |
| A-2 | Z-38 | b-97 |
| A-2 | Z-39 | b-98 |
| A-2 | Z-40 | b-99 |
| A-2 | Z-41 | b-100 |
| A-2 | Z-42 | b-101 |
| A-2 | Z-43 | b-102 |
| A-2 | Z-44 | b-103 |
| A-2 | Z-45 | b-104 |
| A-2 | Z-46 | b-105 |
| A-2 | Z-47 | b-106 |
| A-2 | Z-48 | b-107 |
| A-2 | Z-49 | b-108 |
| A-2 | Z-50 | b-109 |

TABLE 1-continued

| Cation | Anion | PAG |
|---|---|---|
| A-2 | Z-51 | b-110 |
| A-2 | Z-52 | b-111 |
| A-2 | Z-53 | b-112 |
| A-2 | Z-54 | b-113 |
| A-2 | Z-55 | b-114 |
| A-2 | Z-56 | b-115 |
| A-2 | Z-57 | b-116 |
| A-2 | Z-58 | b-117 |
| A-2 | Z-59 | b-118 |
| A-2 | Z-60 | b-119 |
| A-2 | Z-61 | b-120 |
| A-2 | Z-62 | b-121 |
| A-2 | Z-63 | b-122 |
| A-2 | Z-64 | b-123 |
| A-2 | Z-65 | b-124 |
| A-2 | Z-66 | b-125 |
| A-2 | Z-67 | b-126 |
| A-2 | Z-68 | b-127 |
| A-2 | Z-69 | b-128 |
| A-2 | Z-70 | b-129 |
| A-2 | Z-71 | b-130 |
| A-2 | Z-72 | b-131 |
| A-2 | Z-73 | b-132 |
| A-2 | Z-74 | b-133 |
| A-2 | Z-75 | b-134 |
| A-2 | Z-76 | b-135 |
| A-2 | Z-77 | b-136 |
| A-2 | Z-78 | b-137 |

The acid generator of the present invention can be generally synthesized by the same method as the method for introducing an acid-decomposable group into an acid-decomposable resin, for example, by a method of protecting a hydroxyl group-containing sulfonium cation with a general protecting agent, a method of protecting a tertiary alcohol with an acyl group-containing sulfonium cation, or a method of protecting a carboxylic acid-containing sulfonium cation by using a chloroacetic acid ester.

The compound (1) or (2) may be a resin.

The compound (1) or (2) may be a resin that is the same as or different from the later-described resin (A) having a group capable of decomposing by an action of an acid to produce a polar group (hereinafter, sometimes referred to as "resin (A)").

In the case where the compound (1) or (2) is a resin, the non-nucleophilic anion of $Z^-$ is preferably a non-nucleophilic anion having a polymer chain.

In the case where the compound (1) or (2) is the same as the resin (A), the non-nucleophilic anion of $Z^-$ is preferably an anion having a polymer chain containing a group capable of decomposing by an action of an acid to produce a polar group, and a resin having a nucleophilic anion structure in a repeating unit of the resin is more preferred.

Specific examples of the anion structure-containing repeating unit contained in the non-nucleophilic anion of $Z^-$ are illustrated below, but the present invention is not limited thereto.

[Chem. 25]

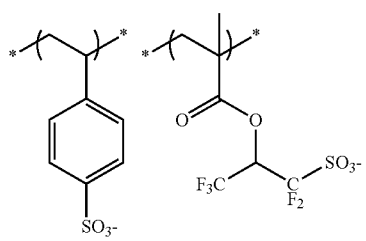

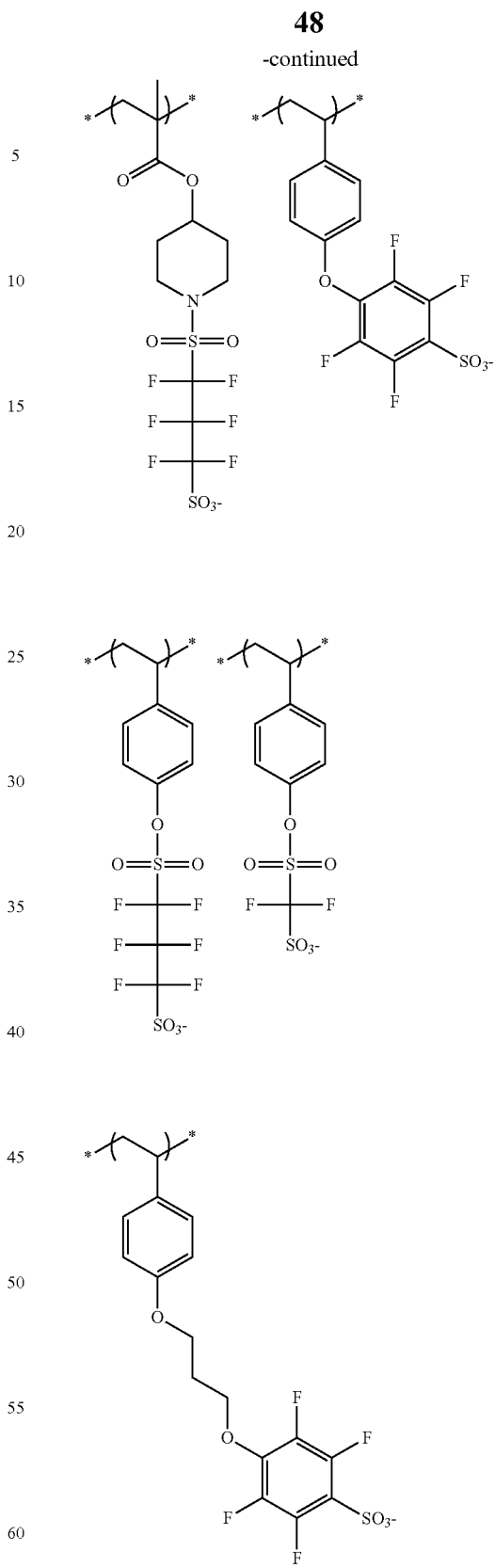

In the case where the compound (1) or (2) is the same as the resin (A), specific examples of the compound (1) or (2) are illustrated below, but the present invention is not limited thereto.

[Chem. 26]
Z-79 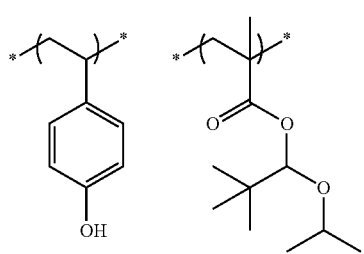
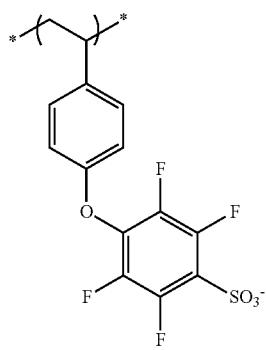
Z-80 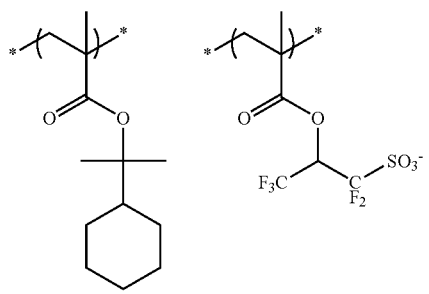
Z-81 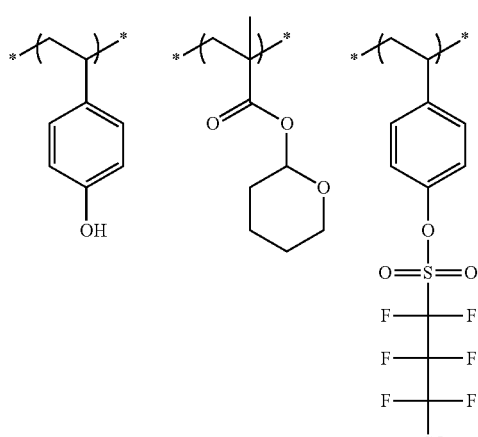
Z-82 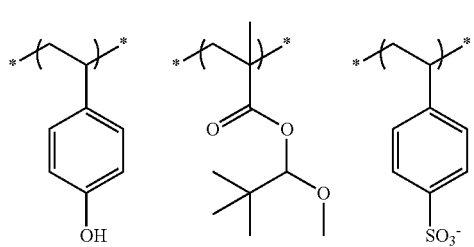
Z-83 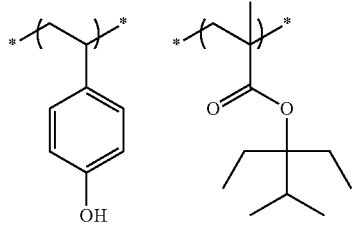
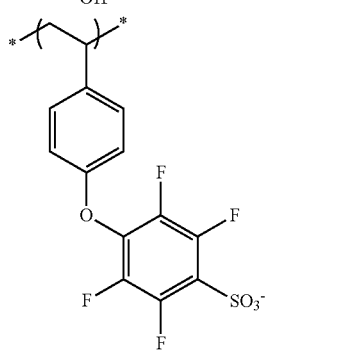
Z-84 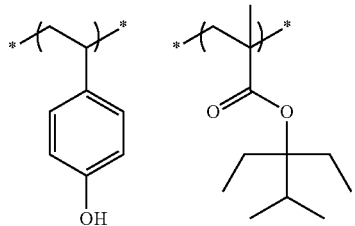
Z-85 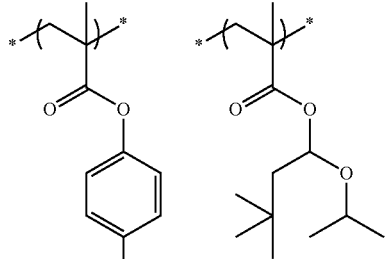
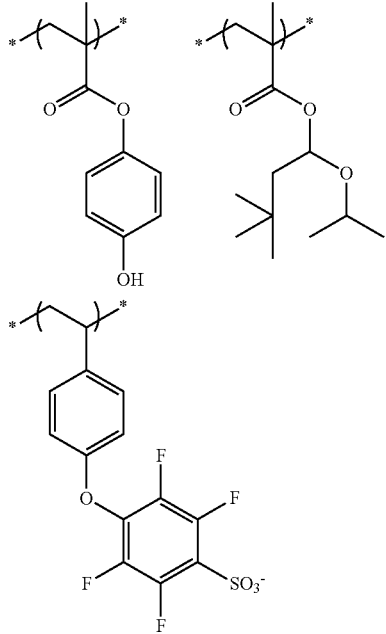

-continued

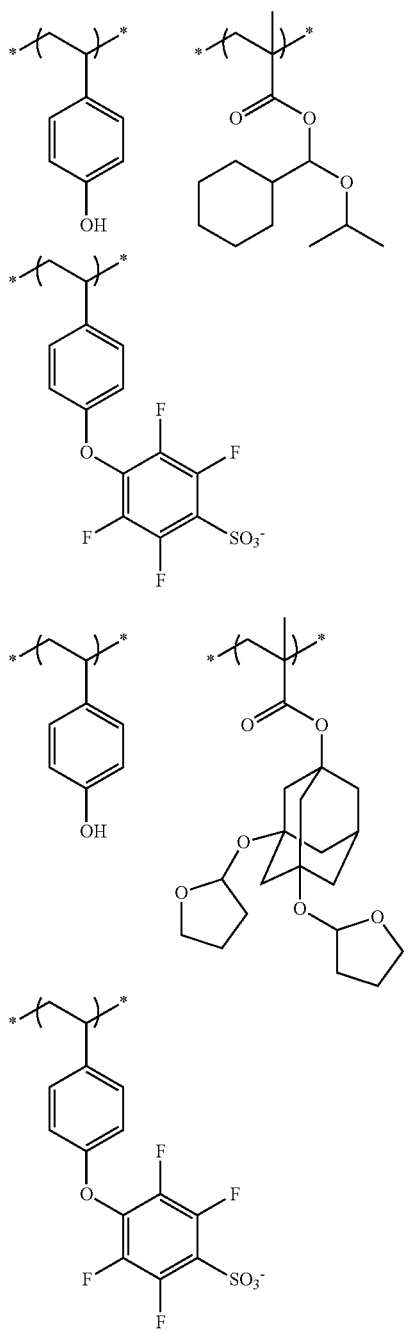

Z-86

Z-87

[Chem. 27]

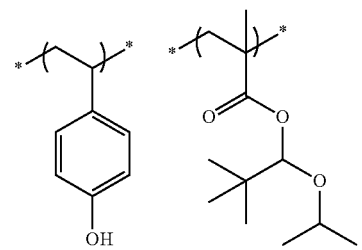

b-138

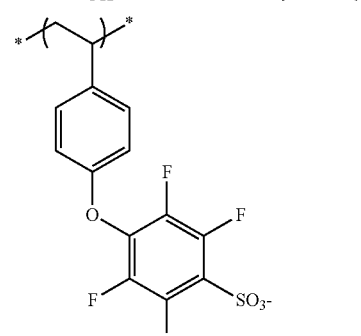

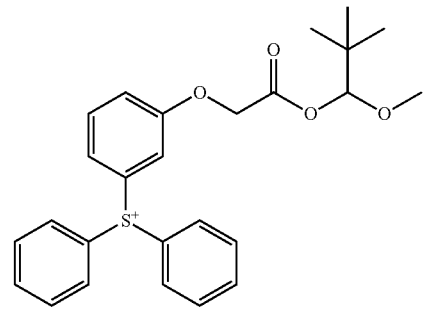

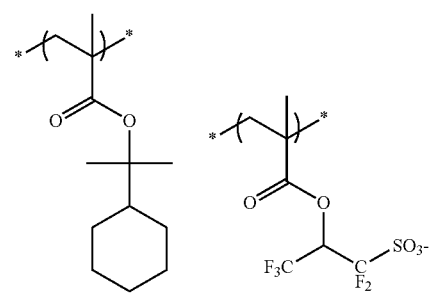

b-139

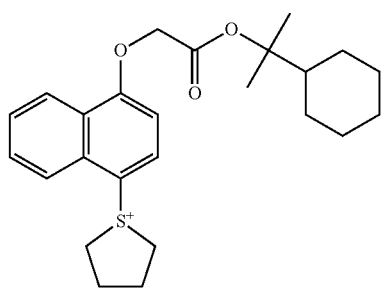

In the case where the compound (1) or (2) is a resin, preferable ranges of the weight average molecular weight and polydispersity of the compound (1) or (2) are the same as those in the later-described resin (A).

In the case where the compound (1) or (2) is the same as the resin (A), specific structures of the compound (1) or (2) are illustrated below, but the present invention is not limited thereto.

b-140
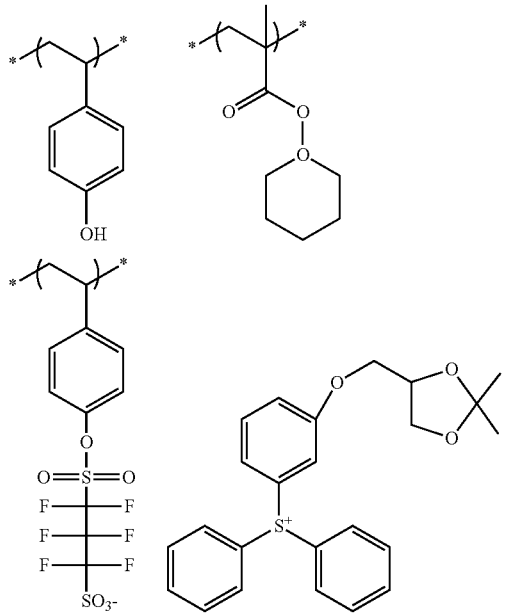
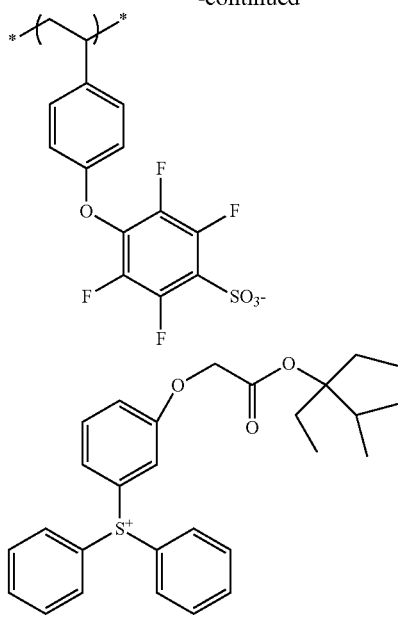
b-141
b-143
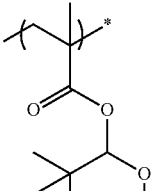
[Chem. 28]
b-144
b-142
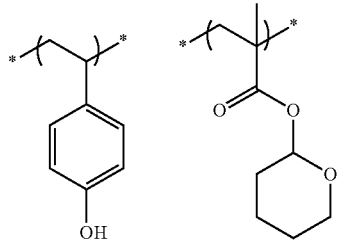
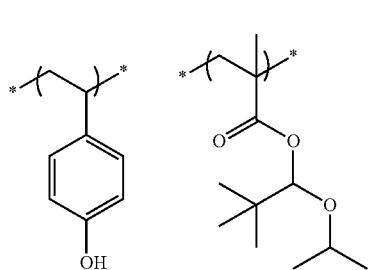
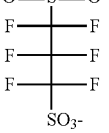

55
-continued
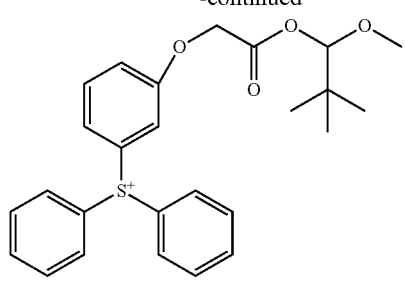
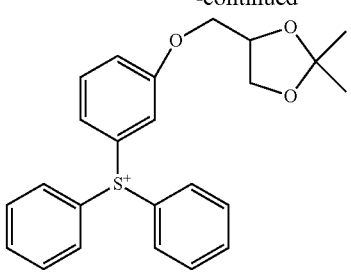
b-145
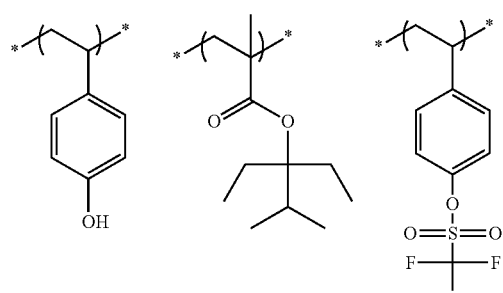
b-147
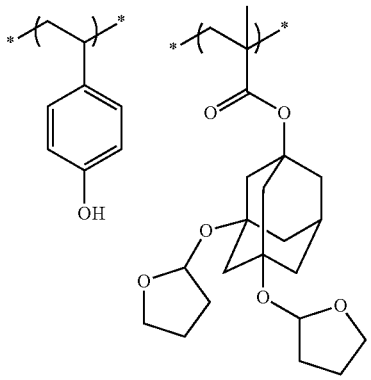
b-146
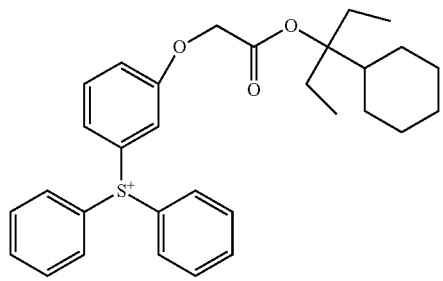
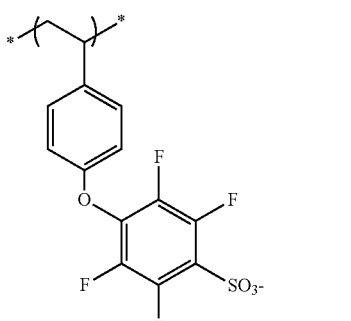
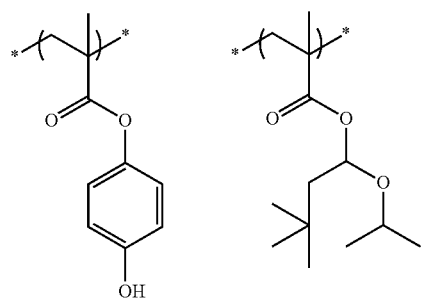
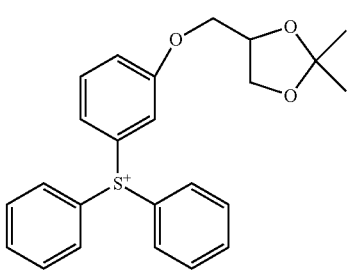
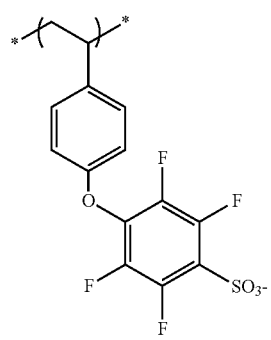
b-148
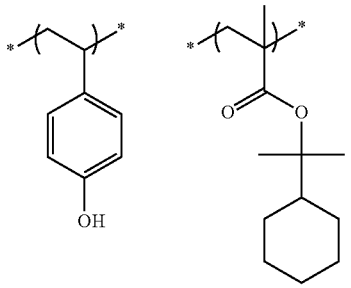

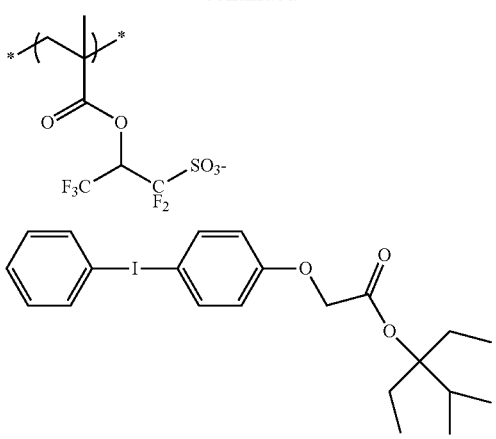
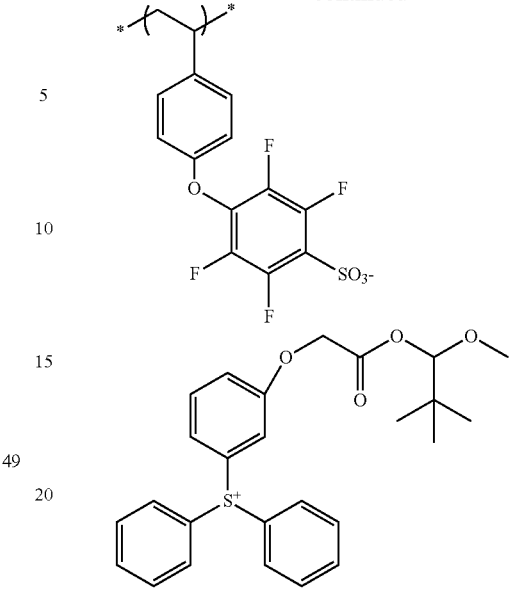

b-149

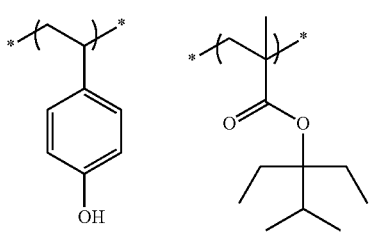

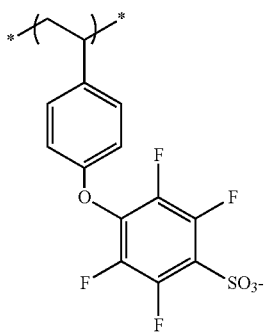

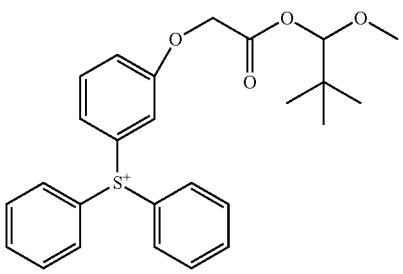

b-150

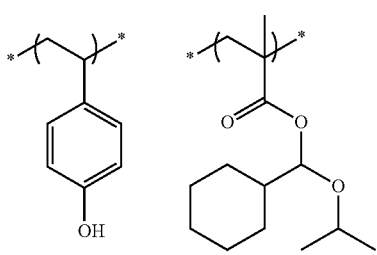

In the actinic ray-sensitive or radiation-sensitive resin composition of the present invention, one of the compounds represented by formula (1) or (2) may be used alone, or two or more thereof may be used in combination. The content thereof is preferably from 0.05 to 60 mass %, more preferably from 1 to 55 mass %, still more preferably from 2 to 50 mass %, based on the total solid content of the actinic ray-sensitive or radiation-sensitive resin composition.

[2](B') Jointly-Used Acid Generator

The actinic ray-sensitive or radiation-sensitive resin composition of the present invention may further contain (B') a compound capable of generating an acid upon irradiation with an actinic ray or radiation (hereinafter, sometimes referred to as "jointly-used acid generator (B')"), in addition to the compound represented by formula (1) or (2).

The jointly-used acid generator (B') is described below.

The jointly-used acid generator (B') which can be used may be appropriately selected from a photo-initiator for cationic photopolymerization, a photo-initiator for radical photopolymerization, a photodecoloring agent for dyes, a photodiscoloring agent, a known compound that generates an acid upon irradiation with an electron beam or extreme-ultraviolet ray and is used for microresist, etc., and a mixture thereof.

The jointly-used acid generator (B') may be in the form of a low molecular compound or in the form of being incorporated into part of a polymer. In addition, the form of a low molecular compound and the form of being incorporated into part of a polymer may also be used in combination.

In the case where the jointly-used acid generator (B') is in the form of a low molecular compound, the molecular weight is preferably 3,000 or less, more preferably 2,000 or less, still more preferably 1,000 or less.

In the case where the jointly-used acid generator (B') is in the form of being incorporated into part of a polymer, the acid generator may be incorporated into part of the above-described acid-decomposable resin or may be incorporated into a resin different from the acid-decomposable resin.

The jointly-used acid generator includes, for example, a diazonium salt, a phosphonium salt, a sulfonium salt, an iodonium salt, imidosulfonate, oxime sulfonate, diazodisulfone, disulfone, and o-nitrobenzyl sulfonate.

Among the jointly-used acid generators, the preferable compound is not particularly limited as long as it is a known compound, but preferred are compounds represented by the following formulae (ZI'), (ZII') and (ZIII'):

[Chem. 29]

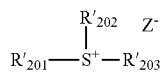

(ZI')

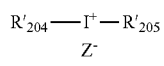

(ZII')

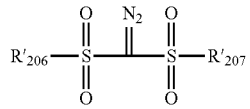

(ZIII')

In formulae (ZI') (ZII') and (ZIII'), $R'_{201}$ to $R'_{207}$ have the same meanings as $R_1$ to $R_5$ in formulae (1), (2) and (3), respectively, and specific examples and preferable examples are also the same. However, $R'_{201}$ to $R'_{205}$ in formulae (ZI') and (ZII') do not contain a group represented by formula (I) to (IV).

In addition, in formulae (ZI') and (ZII'), $Z^-$ represents a non-nucleophilic anion (an anion having an extremely low ability of causing a nucleophilic reaction) and is the same as that described in $Z^-$ of formulae (1) and (2).

As the component (ZI'), the below-described compounds (ZI'-1), (ZI'-2), (ZI'-3) and (ZI'-4) are more preferred.

The compound (ZI'-1) is an arylsulfonium compound where at least one of $R'_{201}$ to $R'_{203}$ in formula (ZI) is an aryl group, that is, a compound having an arylsulfonium as the cation.

In the arylsulfonium compound, all of $R'_{201}$ to $R'_{203}$ may be an aryl group or part of $R_{201}$ to $R_{203}$ may be an aryl group, with the remaining being an alkyl group or a cycloalkyl group.

Specific examples and preferable examples of the aryl-sulfonium compound are the same as those described for the compound (ZI-1) except for not having the above-described acid-decomposable group.

The compound (ZI'-2) is a compound where each of $R'_{201}$ to $R'_{203}$ in formula (ZI') independently represents an aromatic ring-free organic group.

Examples of the aromatic ring-free organic group of $R'_{201}$ to $R'_{203}$ are the same as those described for the compound (ZI-2) except for not having the above-described acid-decomposable group.

The compound (ZI'-3) is a compound represented by the following formula (ZI'-3), and this is a compound having a phenacylsulfonium salt structure.

[Chem. 30]

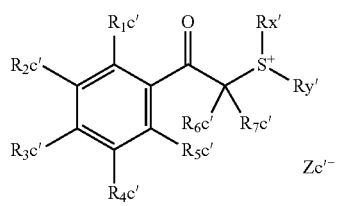

(ZI'-3)

In formula (ZI'-3), each of $R_{1c}'$ to $R_{7c}'$, $R_x'$ and $R_y'$ independently has the same meaning as $R_{1c}$ to $R_{7c}$, $R_x$ and $R_y$ described above in formula (ZI-3). However, all of $R_{1c}'$ to $R_{7c}'$, $Rx'$ and $Ry'$ do not contain a group represented by formulae (I) to (IV).

$Zc'^-$ represents a non-nucleophilic anion, and examples thereof are the same as those of the non-nucleophilic anion of $Z^-$ in formula (ZI).

Specific examples of the cation of the compound represented by formula (ZI'-2) or (ZI'-3) are illustrated below.

[Chem. 31]

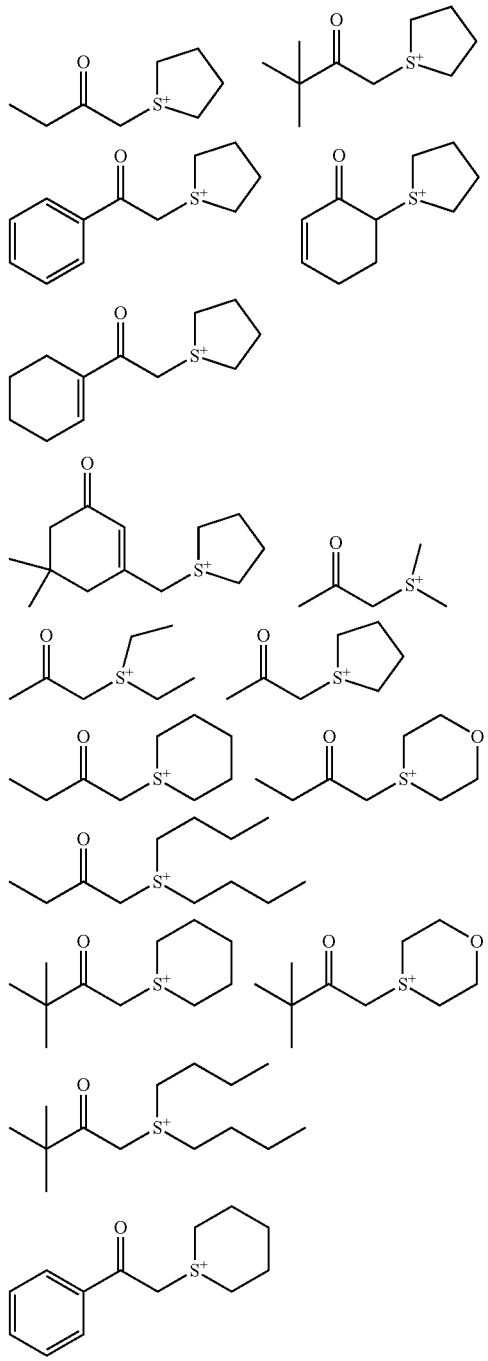

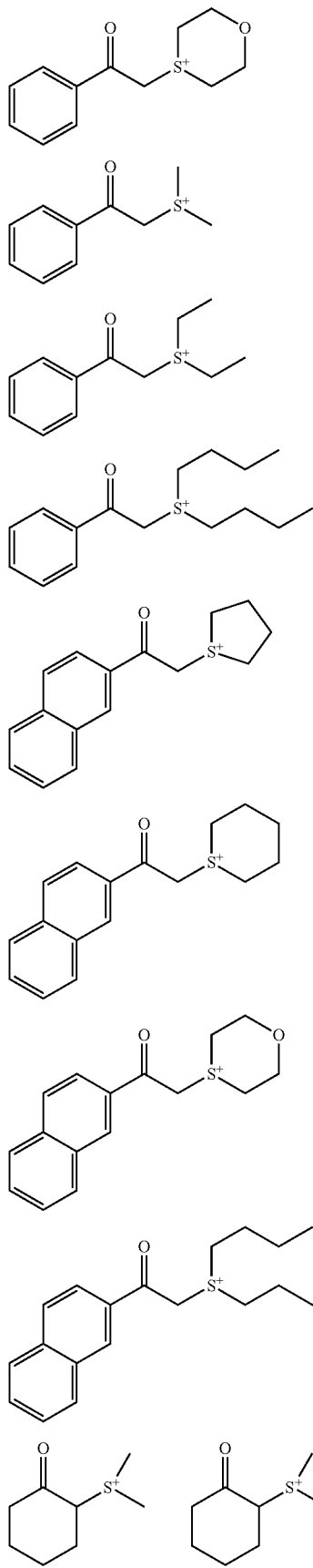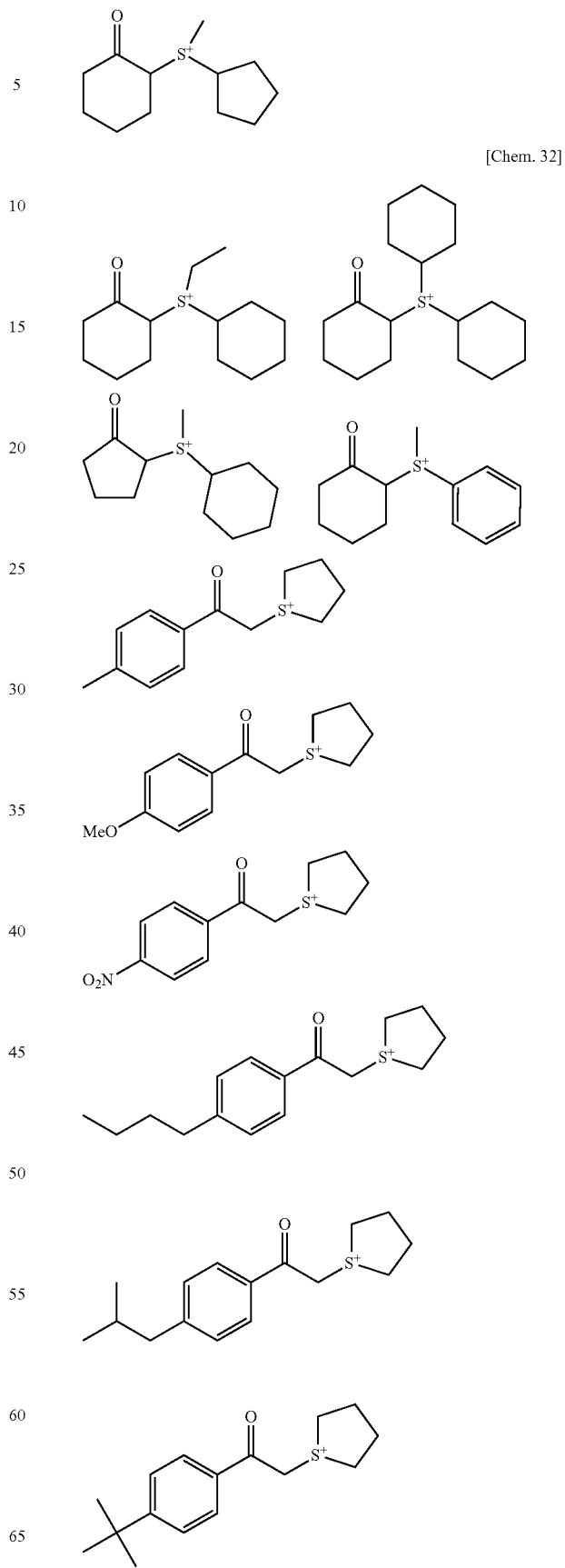

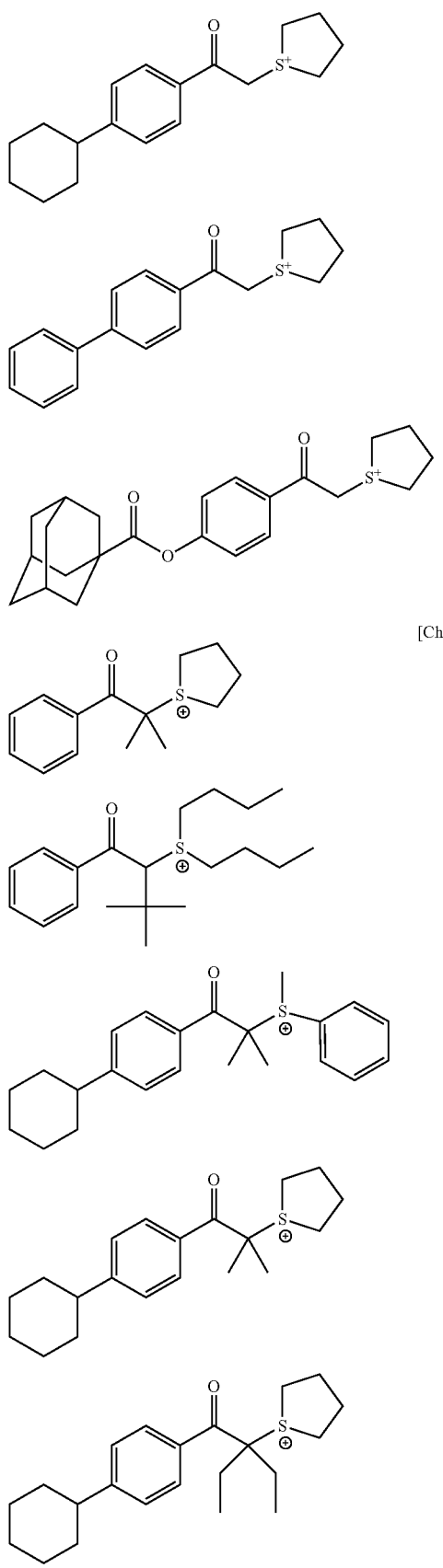
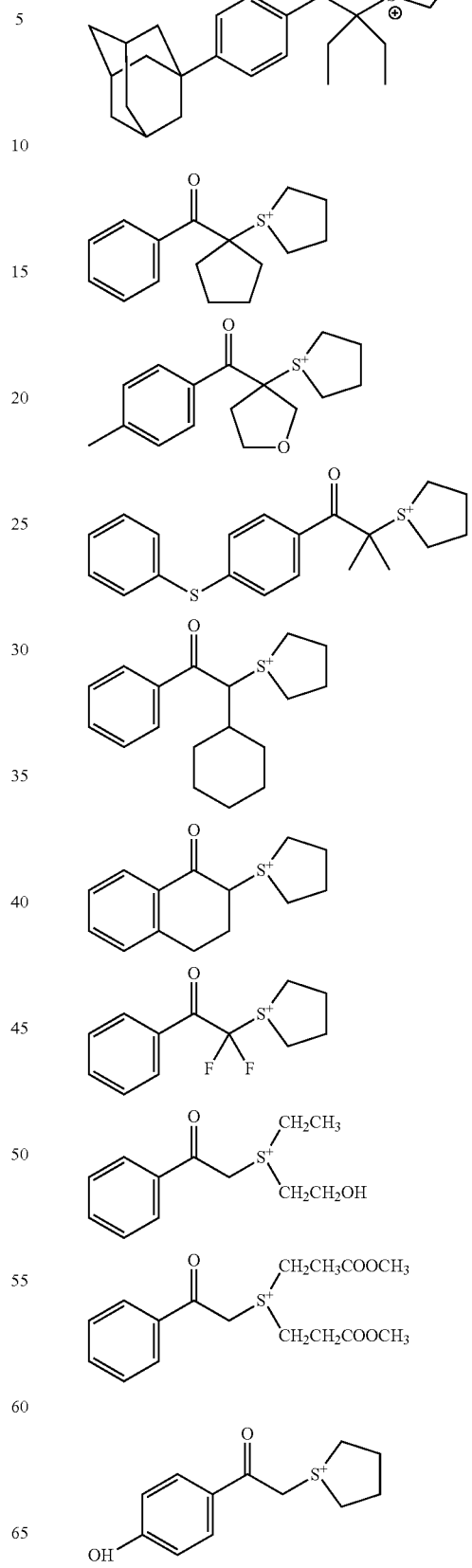
[Chem. 33]
[Chem. 34]

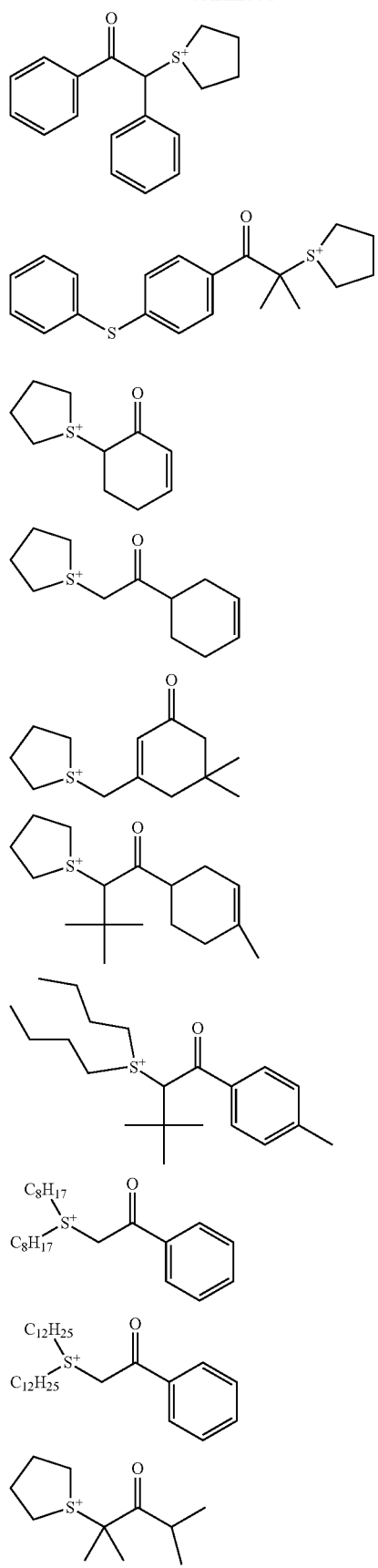
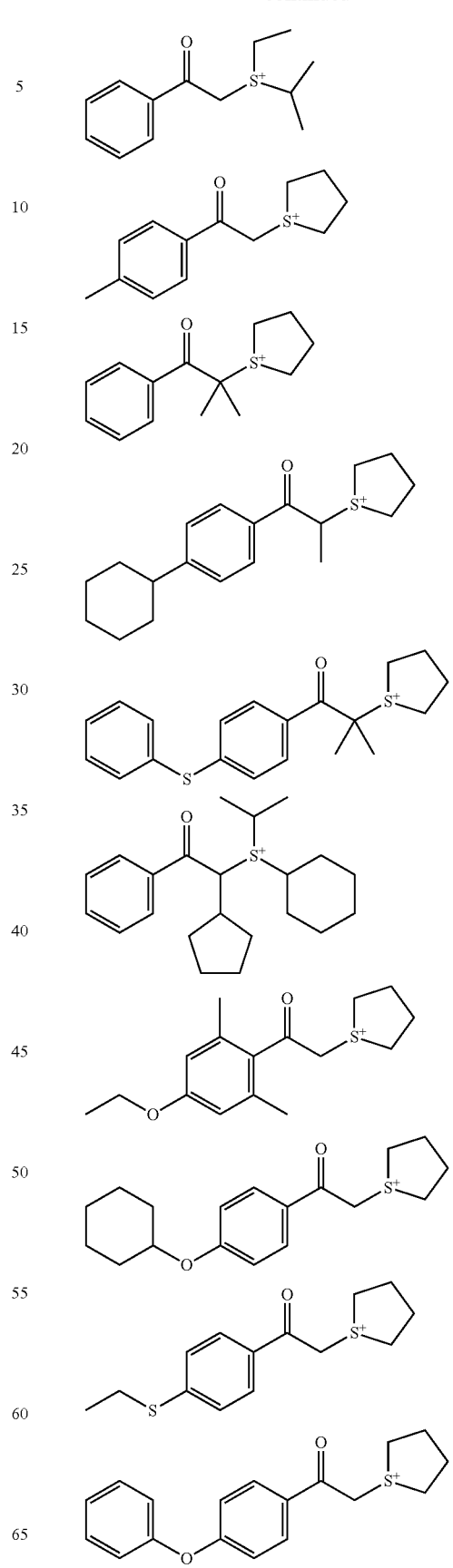
[Chem. 35]
[Chem. 36]

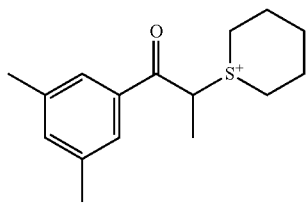

The compound (ZI'-4) is represented by the following formula (ZI'-4):

[Chem. 37]

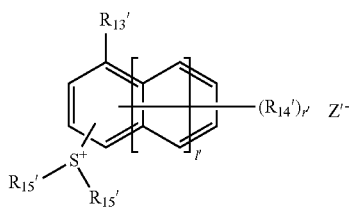

(ZI'-4)

In formula (ZI'-4), each of $R_{13}'$ to $R_{15}'$ independently has the same meaning as $R_{13}$ to $R_{15}$ described above in formula (ZI-4). However, all of $R_{13}'$ to $R_{15}'$ do not contain the above-described acid-decomposable group.

l' and r' have the same meanings as l and r, respectively, described above in formula (ZI-4).

$Z'^-$ represents a non-nucleophilic anion, and examples thereof are the same as those of the non-nucleophilic anion of $Z^-$ in formula (ZI). However, here, the non-nucleophilic anion does not contain the above-described acid-decomposable group.

Specific examples of the cation of the compound represented by formula (ZI'-4) are illustrated, below.

[Chem. 38]

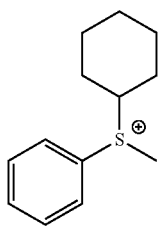

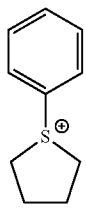

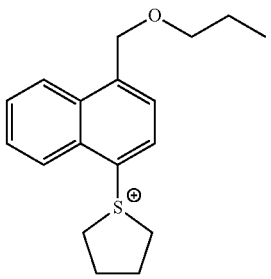

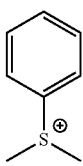

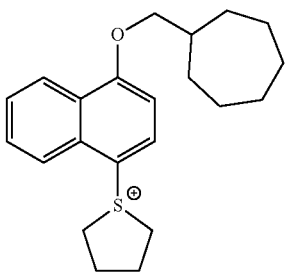

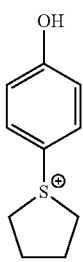

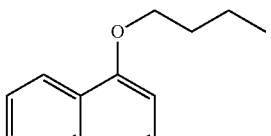

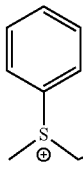
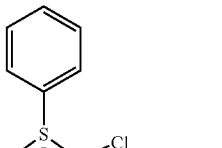

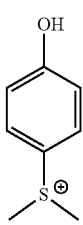

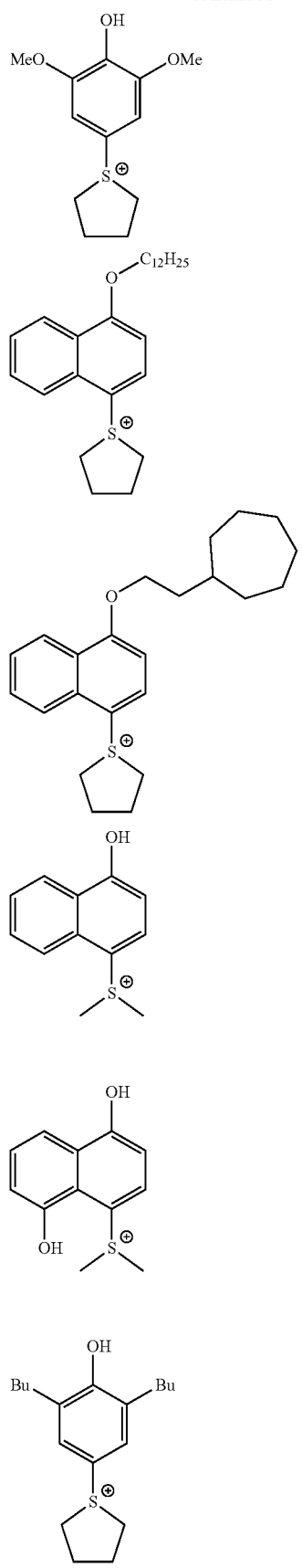
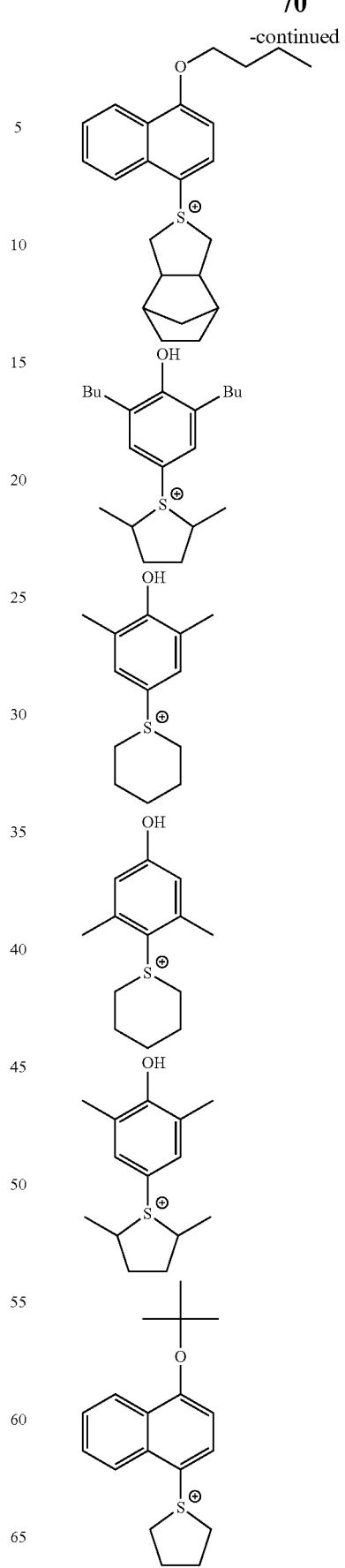

[Chem. 39]
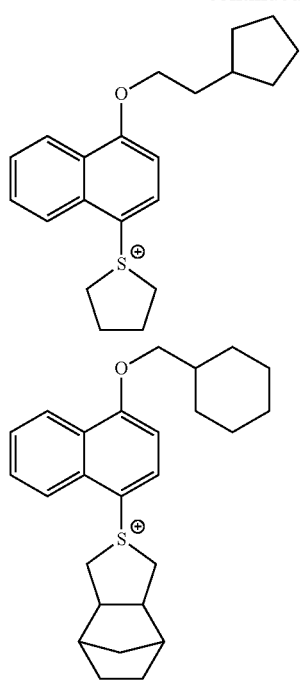
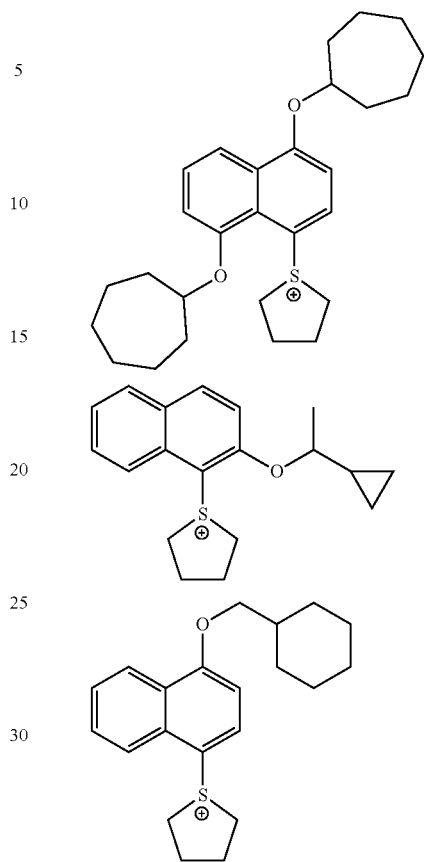
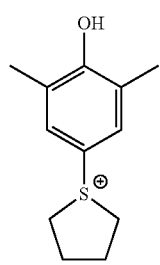
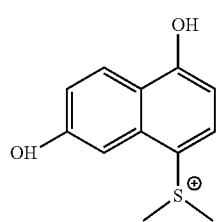
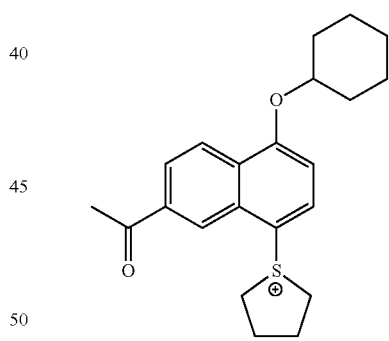
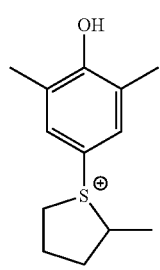
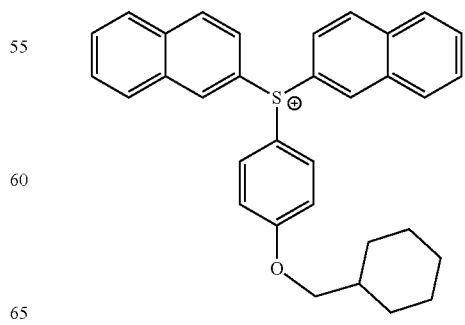

73
-continued
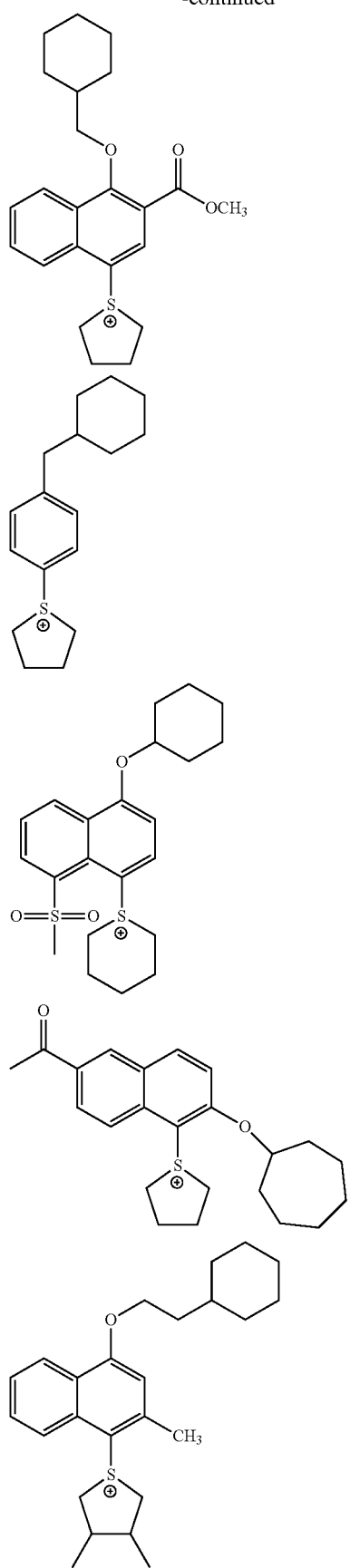
74
-continued
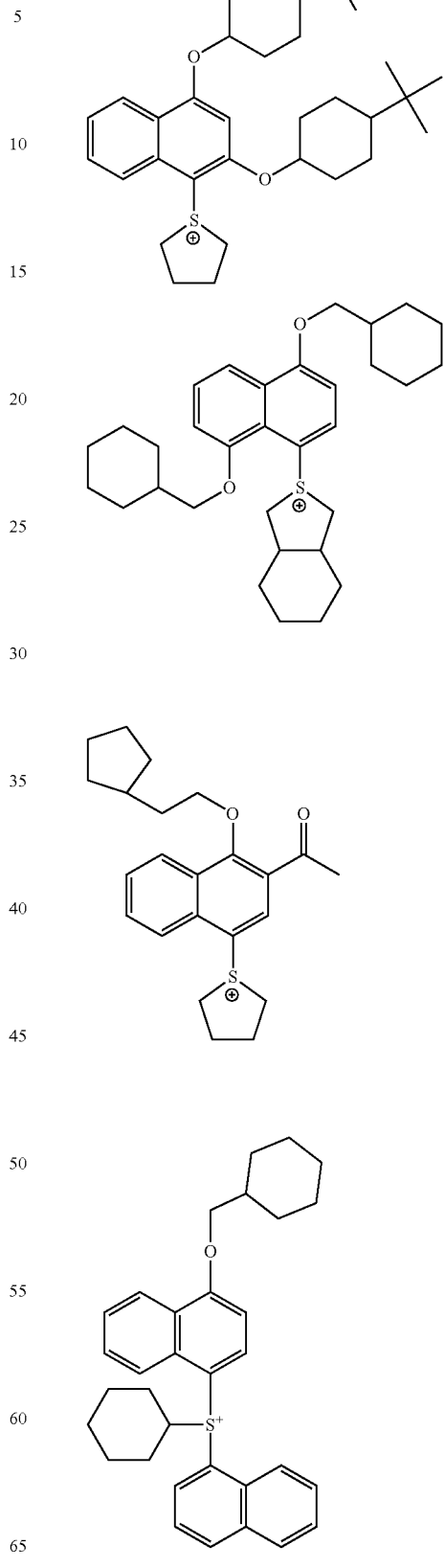

-continued

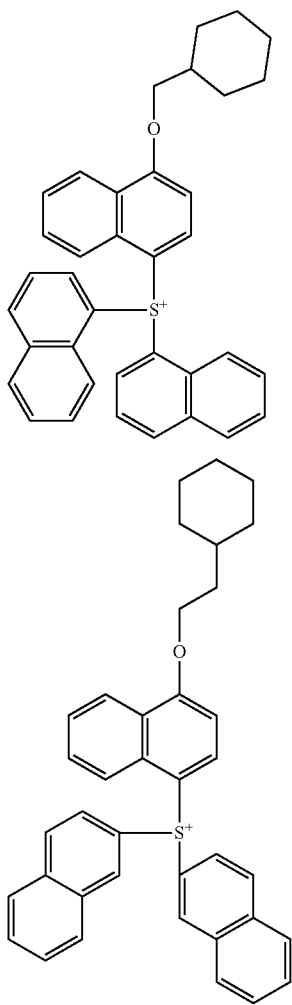

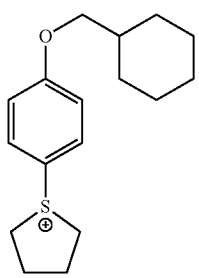

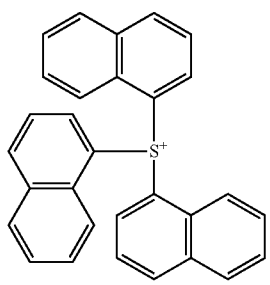

-continued

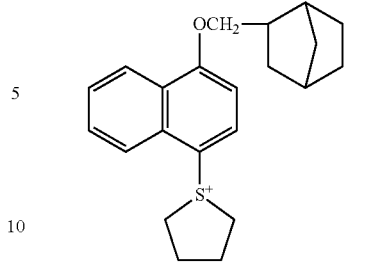

The jointly-used acid generator (B') further includes compounds represented by the following formulae (ZIV'), (ZV') and (ZVI'):

[Chem. 40]

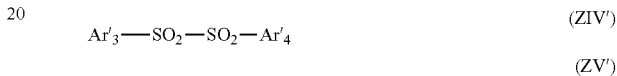  (ZIV')

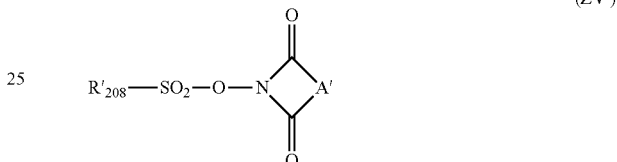  (ZV')

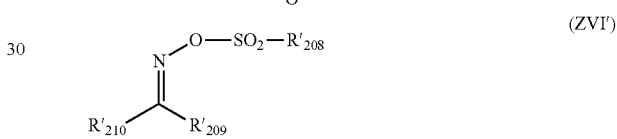  (ZVI')

In formulae (ZV') and (ZVI'), $Ar'_3$ and $Ar'_4$ respectively have the same meanings as $Ar_3$ and $Ar_4$ in formula (ZIV), and specific examples are also the same. However, $Ar'_3$ and $Ar'_4$ in formula (ZIV') doe not contain the above-described acid-decomposable group.

In formulae (ZV') and (ZVI'), A', $R'_{208}$, $R'_{209}$ and $R'_{210}$ respectively have the same meanings as A, $R_{208}$, $R_{209}$ and $R_{210}$ in formulae (ZV) and (ZVI), and specific examples are also the same. However, A', $R'_{208}$, $R'_{209}$ and $R'_{210}$ in formulae (ZV') and (ZVI') do not contain a group represented by formulae (I) to (IV).

Among the jointly-used acid generators (B'), more preferred are the compounds represented by formulae (ZI') to (ZIII').

In addition, the jointly-used acid generator (B') is preferably a compound capable of generating an acid having one sulfonic acid group or imide group, more preferably a compound capable of generating a monovalent perfluoroalkanesulfonic acid, a compound capable of generating an aromatic sulfonic acid substituted with a monovalent fluorine atom or a fluorine atom-containing group, or a compound capable of generating an imide acid substituted with a monovalent fluorine atom or a fluorine atom-containing group, still more preferably a sulfonium salt of fluoro-substituted alkanesulfonic acid, fluorine-substituted benzenesulfonic acid, fluorine-substituted imide acid or fluorine-substituted methide acid. In particular, the acid generator that can be used is preferably a compound capable of generating a fluoro-substituted alkanesulfonic acid, a fluoro-substituted benzenesulfonic acid or a fluoro-substituted imide acid, where pKa of the acid generated is −1 or less, and in this case, the sensitivity is enhanced.

Specific examples of the jointly-used acid generator (B') are illustrated below.
[Chem. 41]
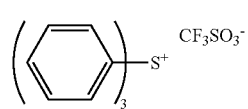 (z1)
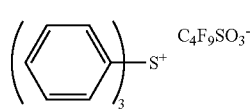 (z2)
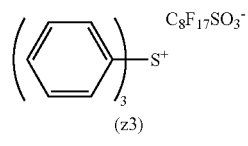 (z3)
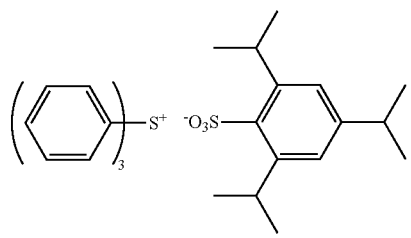 (z4)
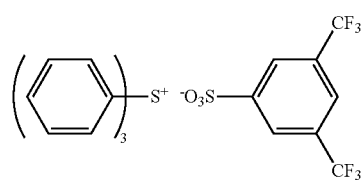 (z5)
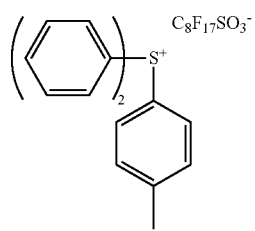 (z6)
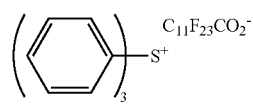 (z7)
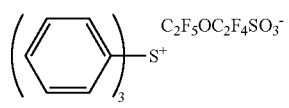 (z8)
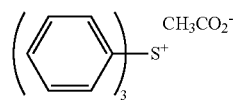 (z9)
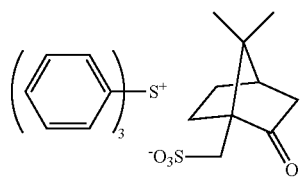 (z10)
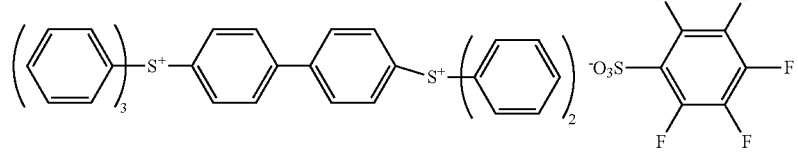 (z11)
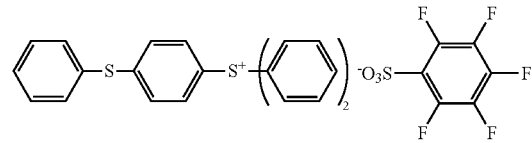 (z12)
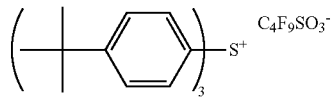 (z13)
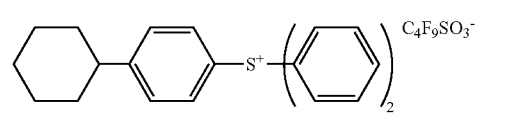 (z14)
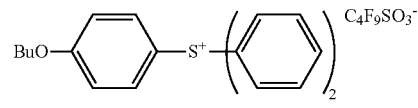 (z15)
 (z16)
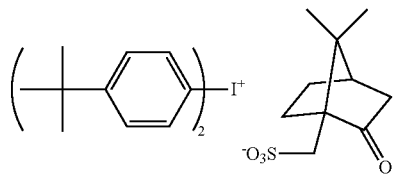 (z17)

-continued
(z18) 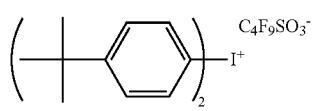
(z19) 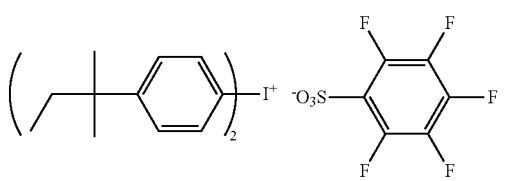
(z20) 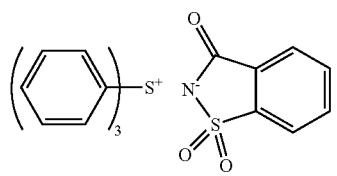
(z21) 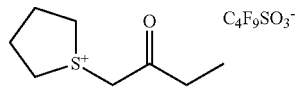
(z22) 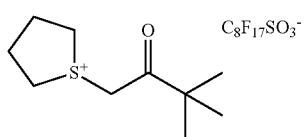
(z23) 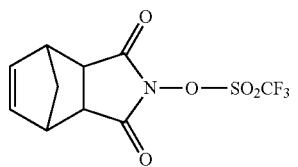
(z24) 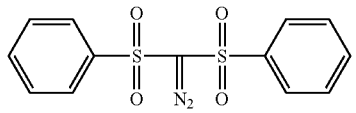
(z25) 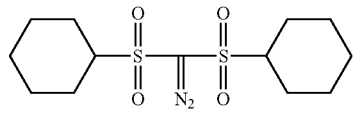
(z26) 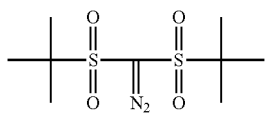
(z27) 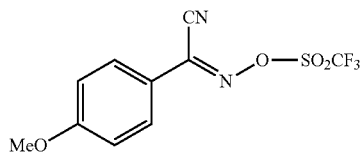
(z28) 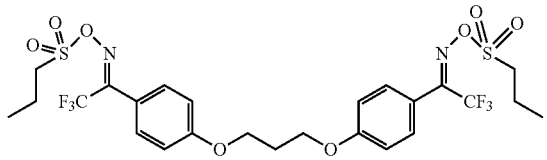
(z29) 
(z30) 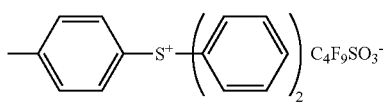
(z31) 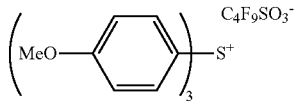
(z32) 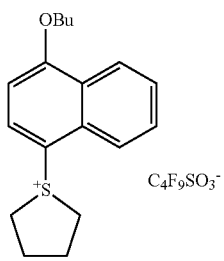
(z33) 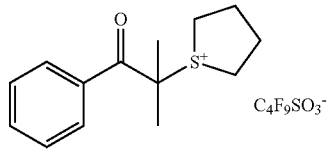
(z34) 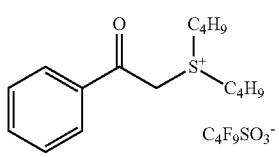
(z35) 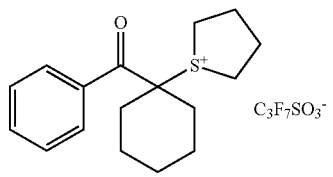

-continued
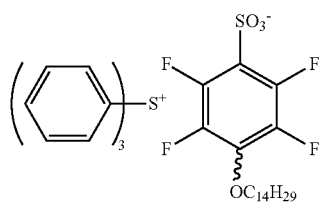 (z36)
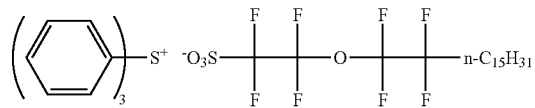 (z37)
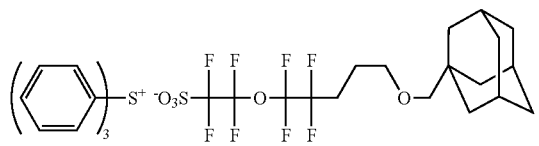 (z38)
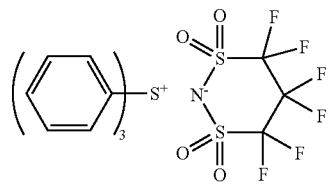 (z39)
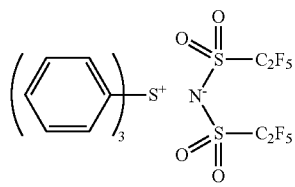 (z40)
[Chem. 42]
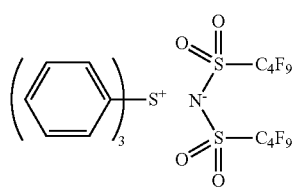 (z41)
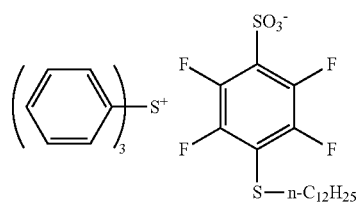 (z42)
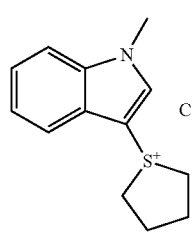 (z43)
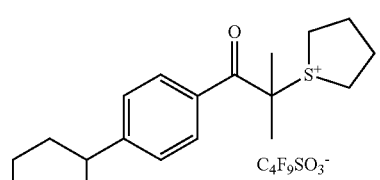 (z44)
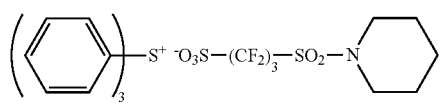 (z45)
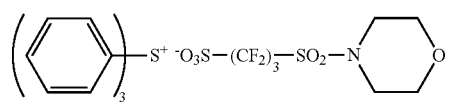 (z46)
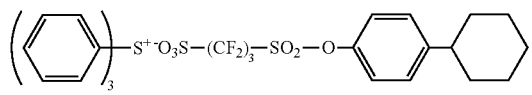 (z47)
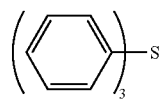 (z48)
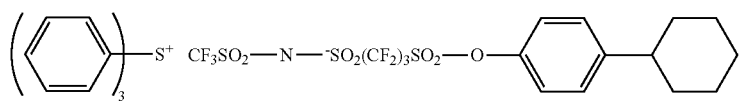 (z49)

-continued
(z50) 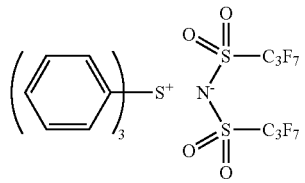
(z51) 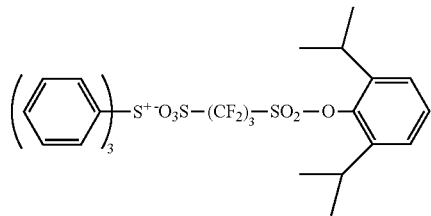
(z52) 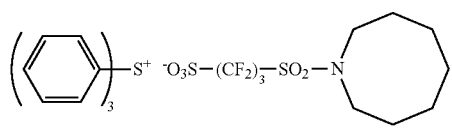
(z53) 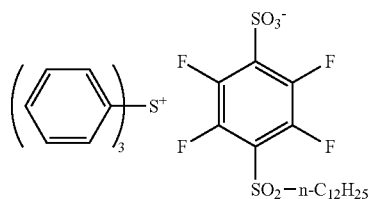
(z54) 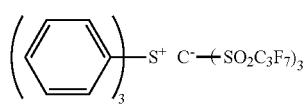
(z55) 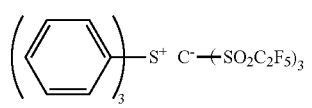
(z56) 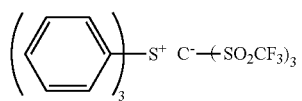
(z57) 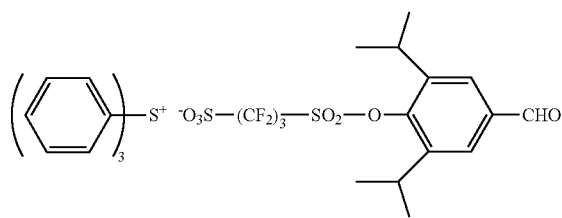
(z58) 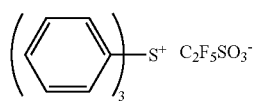
(z59) 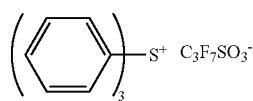
(z60) 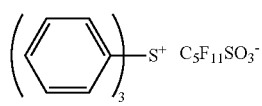
(z61) 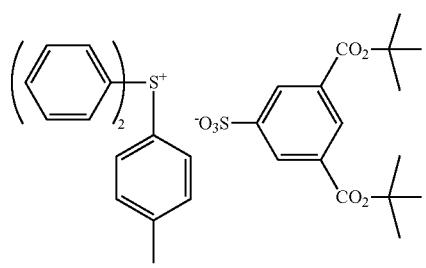
(z62) 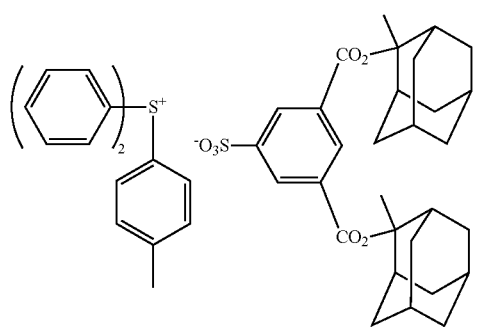
(z63) 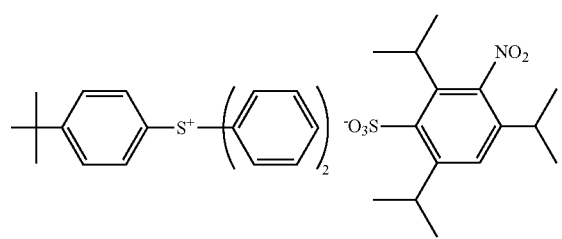

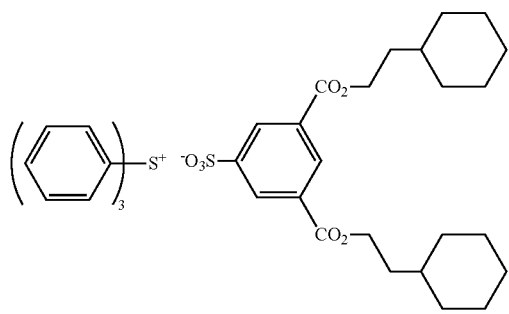
(z65)
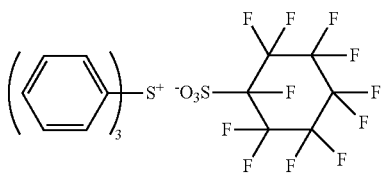
(z66)
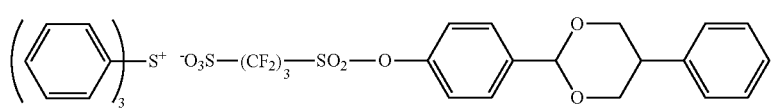
(z67)
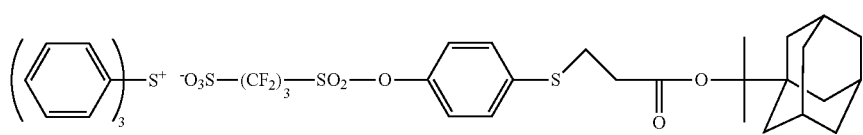
(z68)
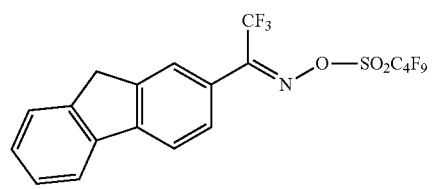
(z69)
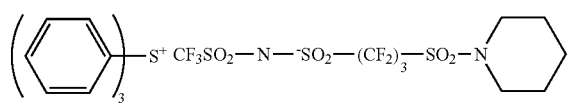
(z70)
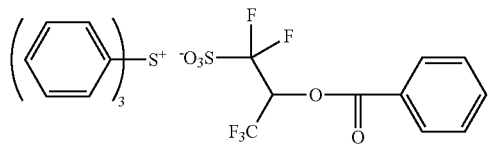
[Chem. 43]
(z71)
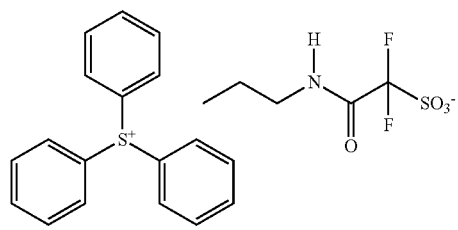
(z72)
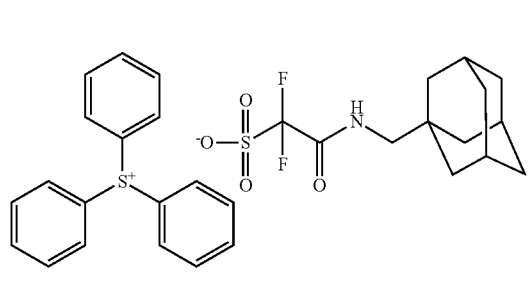
(z73)
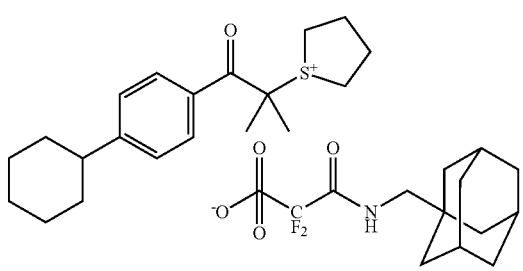

-continued
(z74)
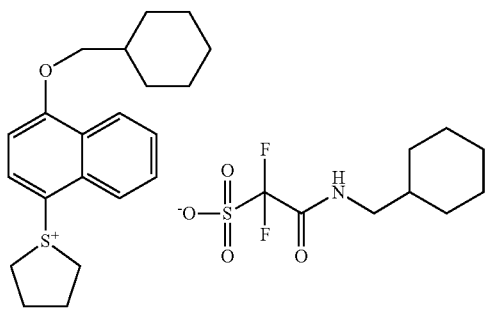
(z75)
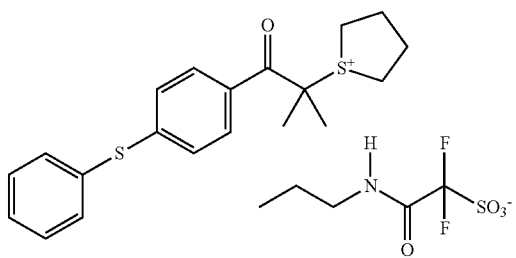
(z76)
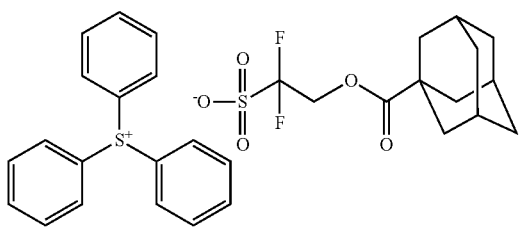
(z77)
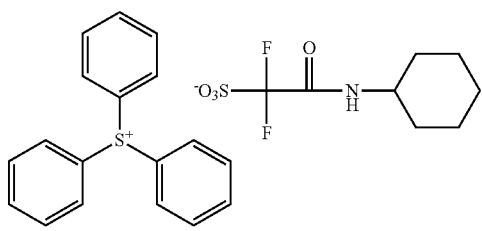
(z78)
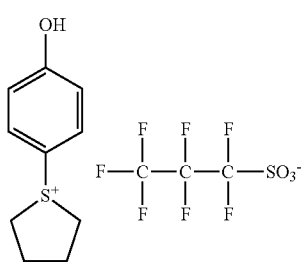
(z79)
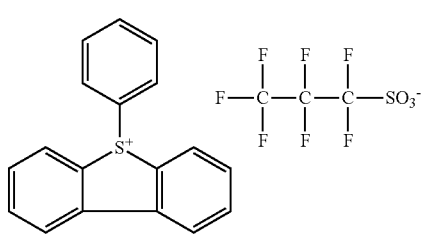
(z80)
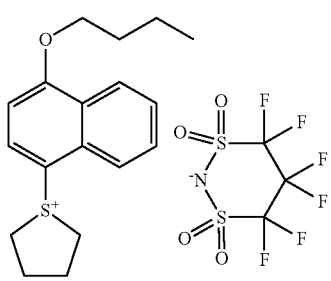
(z81)
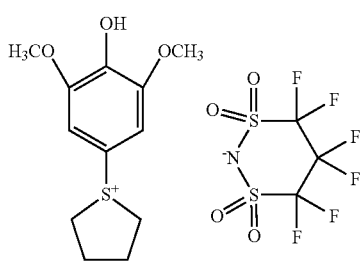
(z82)
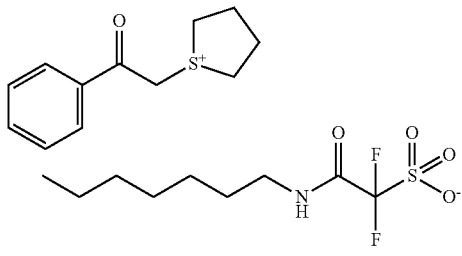
(z83)
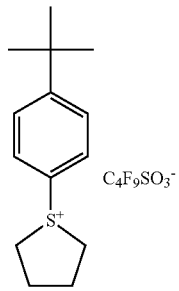
$C_4F_9SO_3^-$ -continued (z84) 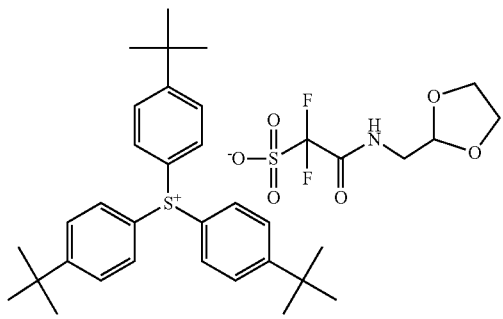

(z85) 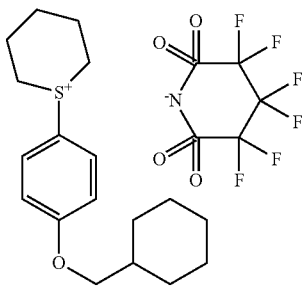

(z86) 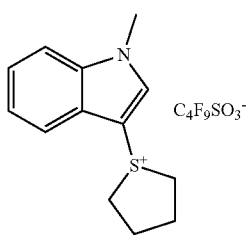

(z87) 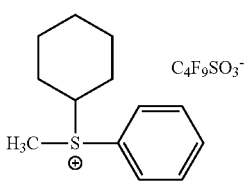

(z88) 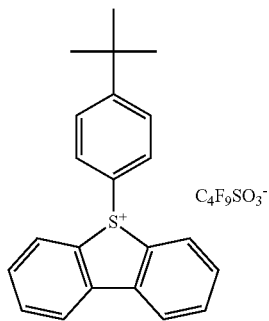

(z89) 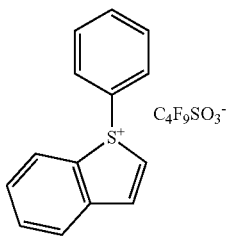

(z90) 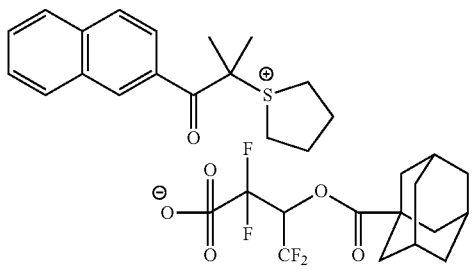

(z91) 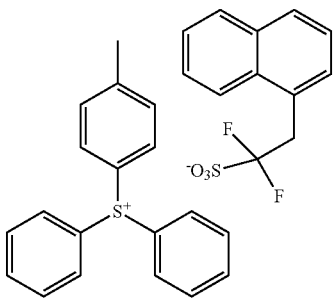

The jointly-used acid generator (B') can be synthesized by a known method, for example, can be synthesized in conformity with the method described in JP-A-2007-161707.

As for the jointly-used acid generator (B'), one kind may be used, or two or more kinds may be used in combination.

The actinic ray-sensitive or radiation-sensitive resin composition of the present invention may or may not contain the jointly-used acid generator (B'), but in the case of containing the jointly-used acid generator (B'), the content thereof in the composition is preferably from 0.05 to 15 mass %, more preferably from 0.1 to 10 mass %, still more preferably from 1 to 6 mass %, based on the total solid content of the actinic ray-sensitive or radiation-sensitive resin composition.

[3](A) Resin Having a Group Capable of Decomposing by an Action of an Acid to Produce a Polar Group The resin (A) contained in the actinic ray-sensitive or radiation-sensitive resin composition of the present invention is, for example, a resin (hereinafter, sometimes referred to as "acid-decomposable resin" or "resin (A)") having a group (hereinafter, sometimes referred to as an "acid-decomposable group") capable of decomposing by an action of an acid to produce a polar group, in the main chain or side chain of the resin or in both the main chain and the side chain. The acid-decomposable resin is preferably a resin containing (a) a repeating unit having an acid-decomposable group.

Here, the resin (A) is a resin capable of increasing the polarity by an action of an acid to decrease the solubility in an organic solvent-containing developer. In addition, the resin (A) is also a resin capable of increasing the polarity by an action of an acid to increase the solubility in an alkali developer.

The polar group that is produced resulting from the decomposition of an acid-decomposable group is preferably an acidic group.

The acidic group is not particularly limited as long as it is a group insolubilized in an organic solvent-containing developer, but the acidic group is preferably a phenolic hydroxyl group, a carboxylic acid group, a sulfonic acid group, a fluorinated alcohol group, a sulfonamide group, a sulfonylimide group, an (alkylsulfonyl)(alkylcarbonyl)methylene group, an (alkylsulfonyl)(alkylcarbonyl)imide group, a bis(alkylcarbonyl)methylene group, a bis(alkylcarbonyl)imide group, a bis(alkylsulfonyl)methylene group, a bis(alkylsulfonyl)imide group, a tris(alkylcarbonyl)methylene group, or a tris(alkylsulfonyl)methylene group, more preferably an acidic group (a group capable of dissociating in an aqueous 2.38 mass % tetramethylammonium hydroxide solution that has been conventionally used as a developer for a resist) such as carboxylic acid group, fluorinated alcohol group (preferably hexafluoroisopropanol), phenolic hydroxyl group and sulfonic acid group.

The group preferred as the acid-decomposable group is a group in which a hydrogen atom of the group above is substituted with a group capable of leaving by an action of an acid.

The group capable of leaving by an action of an acid includes, for example, —C($R_{36}$)($R_{37}$)($R_{38}$), —C($R_{36}$)($R_{37}$)(O$R_{39}$), and —C($R_{01}$)($R_{02}$)(O$R_{39}$).

In the formulae, each of $R_{36}$ to $R_{39}$ independently represents an alkyl group, a cycloalkyl group, a monovalent aromatic ring group, a group formed by combining an alkylene group with a monovalent aromatic ring group, or an alkenyl group. $R_{36}$ and $R_{37}$ may combine with each other to form a ring.

Each of $R_{01}$ and $R_{02}$ independently represents a hydrogen atom, an alkyl group, a cycloalkyl group, a monovalent aromatic ring group, a group formed by combining an alkylene group with a monovalent aromatic ring group, or an alkenyl group.

The acid-decomposable group is preferably a cumyl ester group, an enol ester group, an acetal ester group, a tertiary alkyl ester group, etc., more preferably a tertiary alkyl ester group.

From the standpoint of more remarkably exerting the effects of the present invention, the acid-decomposable group is, among others, preferably at least one group selected from the group consisting of groups represented by formula (1) to (IV) contained in the compound represented by formula (1) or (2), or a group represented by the following formula (V):

[Chem. 44]

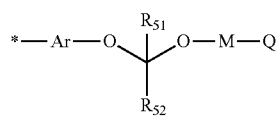

(V)

In formula (V), Ar represents a divalent aromatic ring group.

Each of $R_{51}$ and $R_{52}$ independently represents a hydrogen atom, an alkyl group, a cycloalkyl group, a monovalent aromatic ring group, or a group formed by combining an alkylene group with a monovalent aromatic ring group.

M represents a single bond or a divalent linking group.

Q represents an alkyl group, a cycloalkyl group that may contain a heteroatom, a monovalent aromatic ring group that may contain a heteroatom, an amino group, an ammonium group, a mercapto group, a cyano group or an aldehyde group.

Two members out of Q, M and $R_{51}$ may combine to form a ring.

* represents a bond.

Q represents an alkyl group, a cycloalkyl group that may contain a heteroatom, a monovalent aromatic ring group that may contain a heteroatom, an amino group, an ammonium group, a mercapto group, a cyano group or an aldehyde group.

At least two members out of Q, M and $R_{51}$ may combine to form a ring (preferably a 5- or 6-membered ring).

The alkyl group of $R_{51}$ and $R_{52}$ is, for example, an alkyl group having a carbon number of 1 to 8, and specifically, the alkyl group is preferably a methyl group, an ethyl group, a propyl group, an n-butyl group, a sec-butyl group, a hexyl group, or an octyl group.

The cycloalkyl group of $R_{51}$ and $R_{52}$ is, for example, a cycloalkyl group having a carbon number of 3 to 15, and specifically, preferable examples thereof include a cyclopentyl group, a cyclohexyl group, a norbornyl group, and an adamantyl group.

The monovalent aromatic ring group of $R_{51}$ and $R_{52}$ is, for example, an aryl group having a carbon number of 6 to 15, and specifically, preferable examples thereof include a phenyl group, a tolyl group, a naphthyl group, and an anthryl group.

The group of $R_{51}$ and $R_{52}$ formed by combining an alkylene group with a monovalent aromatic ring group is, for example, a group having a carbon number of 6 to 20 and includes an aralkyl group such as benzyl group and phenethyl group.

The divalent linking group of M includes, for example, an alkylene group (e.g., methylene, ethylene, propylene, butylene, hexylene, octylene), a cycloalkylene group (e.g., cyclopentylene, cyclohexylene, adamantylene), an alkenylene group (e.g., ethenylene, propenylene, butenylene), a divalent aromatic ring group (e.g., phenylene, tolylene, naphthylene), —S—, —O—, —CO—, —SO$_2$—, —N($R_0$)—, and a divalent linking group formed by combining a plurality of these members. $R_0$ is a hydrogen atom or an alkyl group (for example, an alkyl group having a carbon number of 1 to 8, and specifically, a methyl group, an ethyl group, a propyl group, an n-butyl group, a sec-butyl group, a hexyl group, an octyl group, etc.).

The alkyl group of Q is the same as each group of $R_{51}$ and $R_{52}$ above.

The heteroatom-free aliphatic hydrocarbon ring group and heteroatom-free monovalent aromatic ring group in the cycloalkyl group that may contain a heteroatom and the monovalent aromatic ring group that may contain a heteroatom, as Q, include, for example, the above-described cycloalkyl group and monovalent aromatic ring group as $R_{S5}$ and $R_{52}$ and preferably have a carbon number of 3 to 15.

The heteroatom-containing cycloalkyl group and the heteroatom-containing monovalent aromatic ring group include, for example, a group having a heterocyclic structure such as thiirane, cyclothiolane, thiophene, furan, pyrrole, benzothiophene, benzofuran, benzopyrrole, triazine, imidazole, benzimidazole, triazole, thiadiazole, thiazole and pyrrolidone, but the groups are not limited thereto as long as the group has a structure generally called a heterocyclic ring (a ring formed of carbon and a heteroatom or a ring formed of a heteroatom).

The ring that may be formed by combining at least two members of Q, M and $R_{51}$ includes, for example, a case where at least two members of Q, M and $R_{51}$ combine to form, for example, a propylene group or a butylene group and thereby form a 5- or 6-membered ring containing an oxygen atom.

Each of the groups represented by $R_{51}$, $R_{52}$, M and Q in formula (V) may have a substituent, and the substituent includes, for example, those recited above as the substituent that may be substituted on $R_{11}$, $R_{12}$ and $R_{13}$ in formula (I). The carbon number of the substituent is preferably 8 or less.

The group represented by -M-Q is preferably a group composed of 1 to 30 carbons, more preferably a group composed of 5 to 20 carbons.

Specific examples of the repeating unit (a) are illustrated below, but the present invention is not limited thereto.

[Chem. 45]

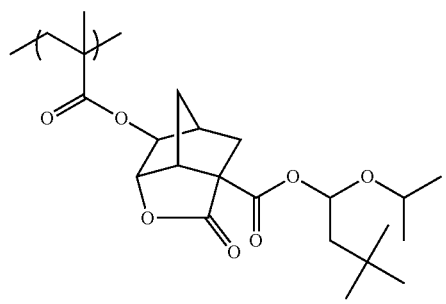

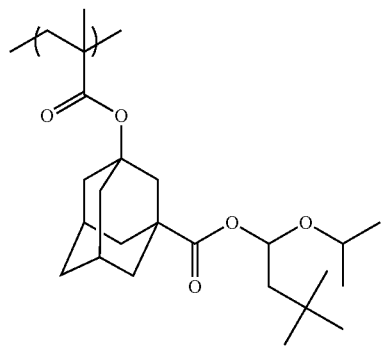

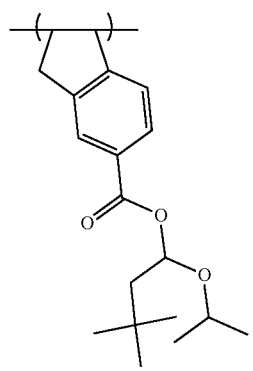 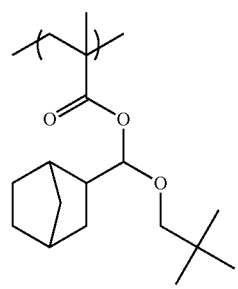

-continued

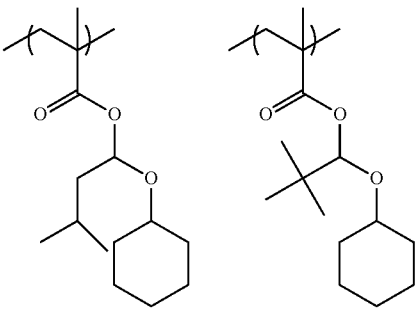

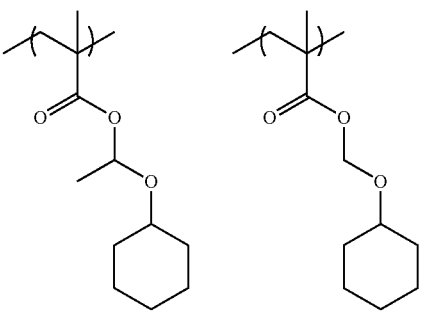

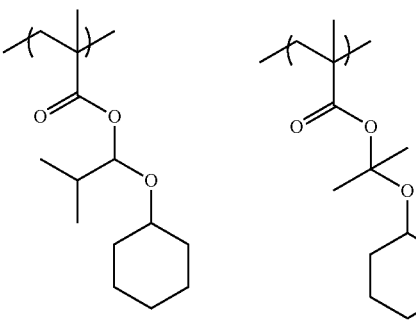

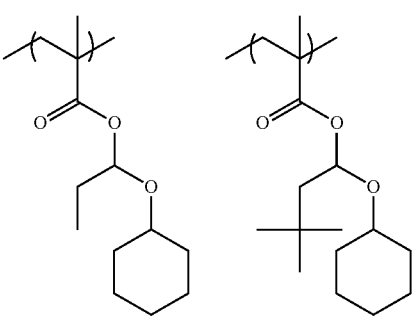

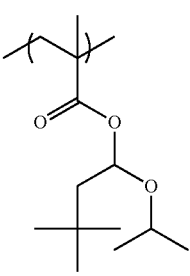

95
-continued
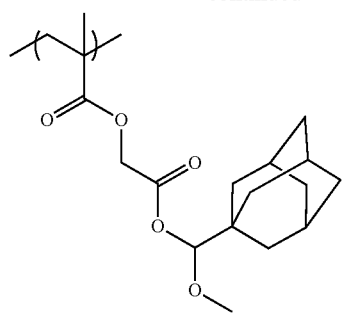
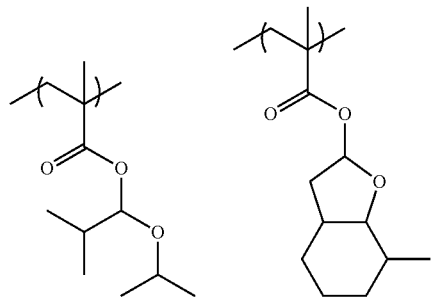
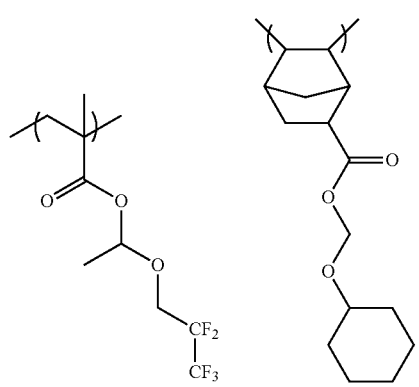
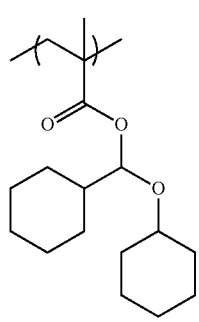
96
-continued
[Chem. 46]
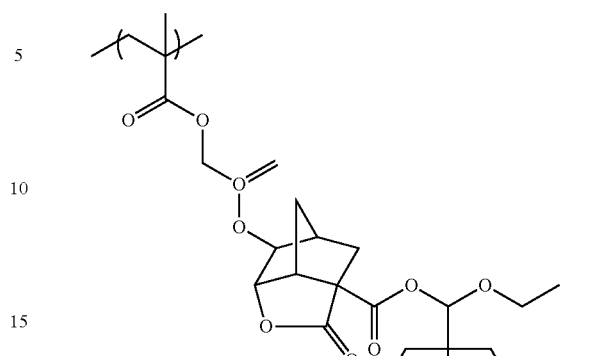
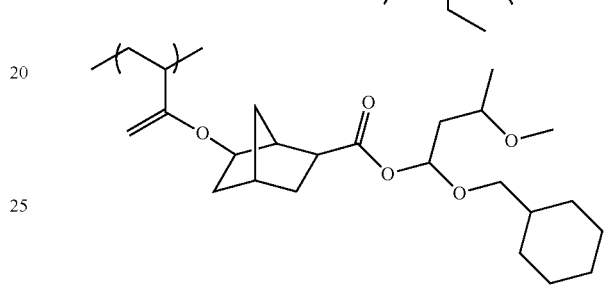
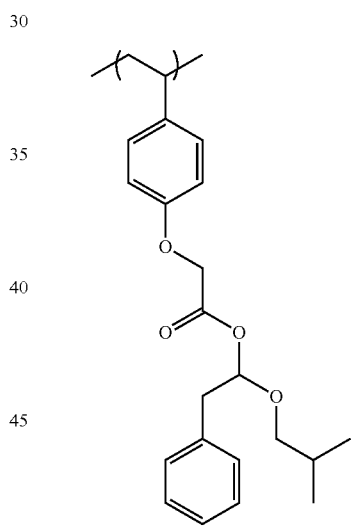
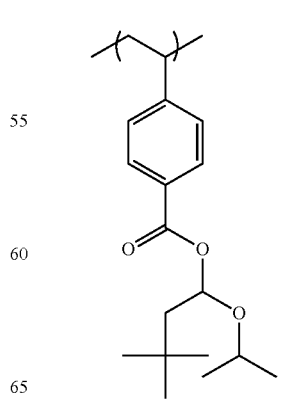

[Chem. 47]
(VI-1) 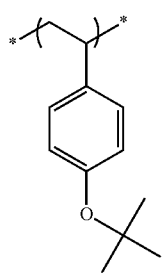
(VI-2) 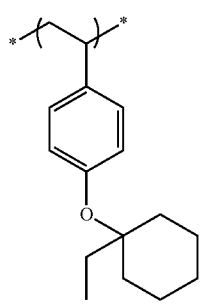
(VI-3) 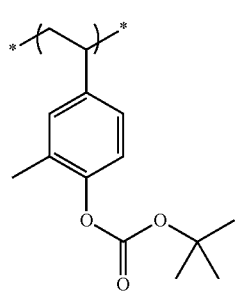
(VI-4) 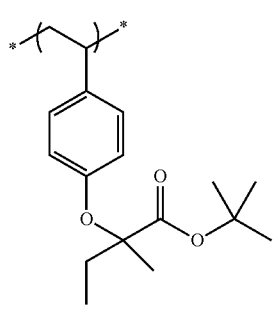
(VI-5) 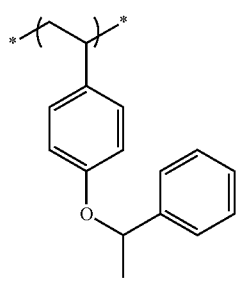
(VI-6) 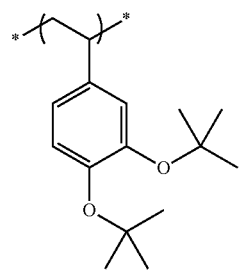
(VI-7) 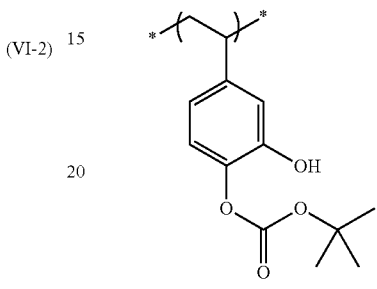
(VI-8) 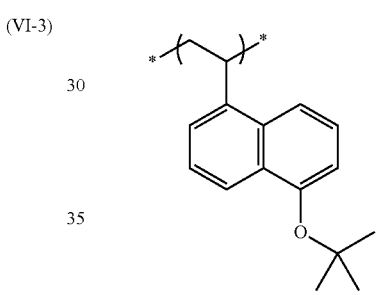
(VI-9) 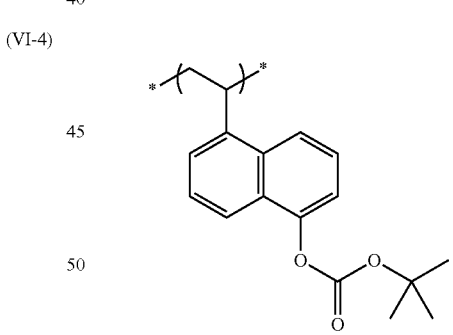
(VI-10) 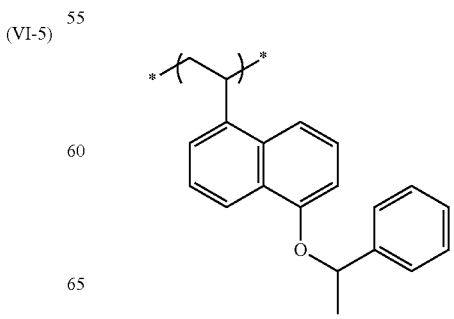

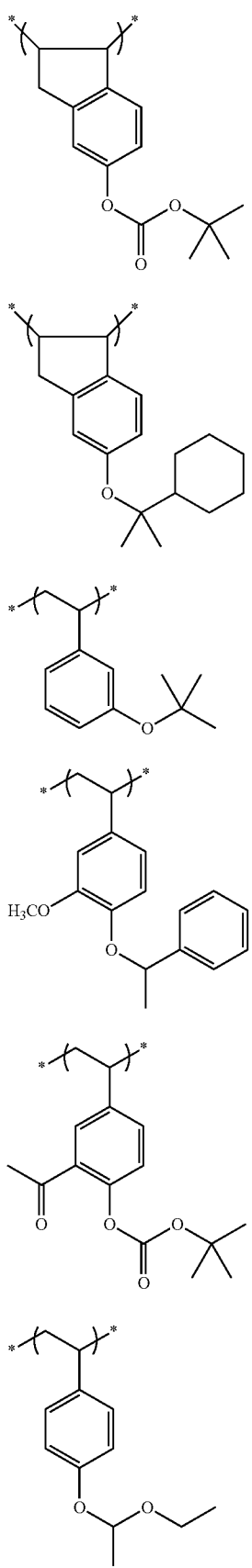
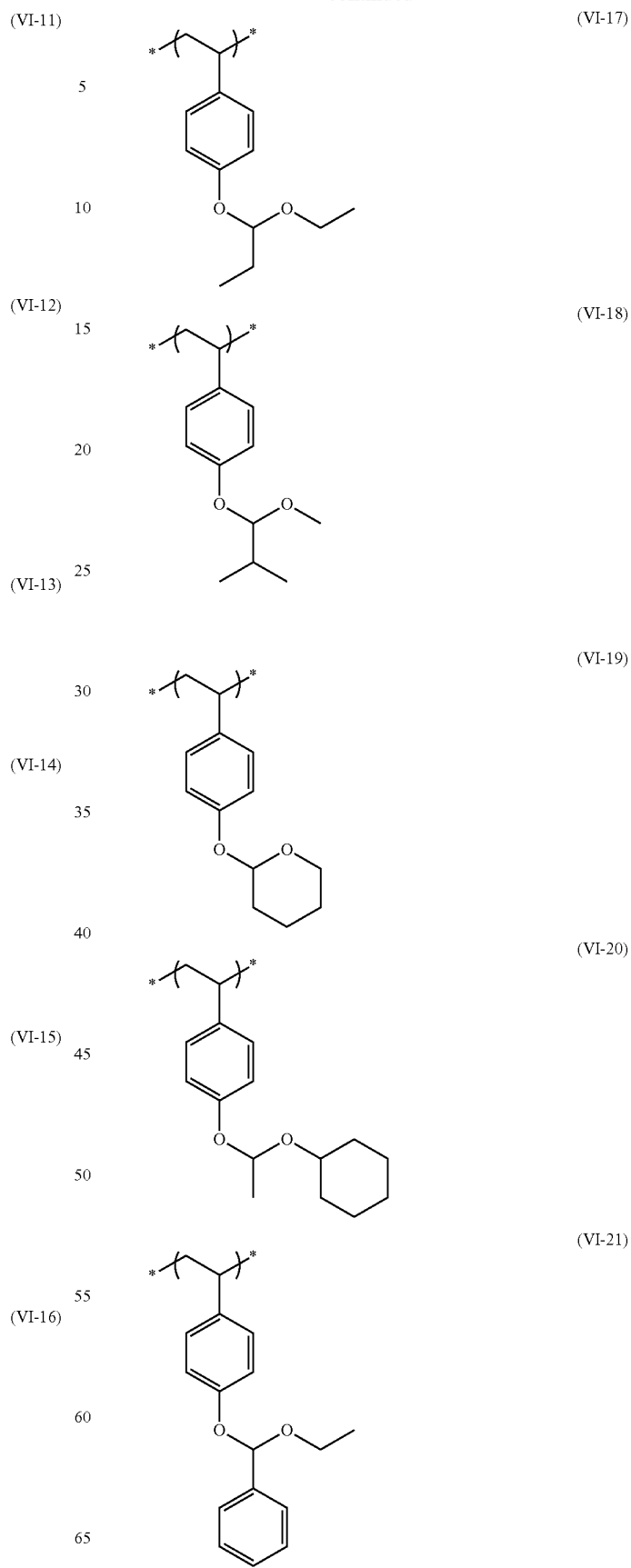

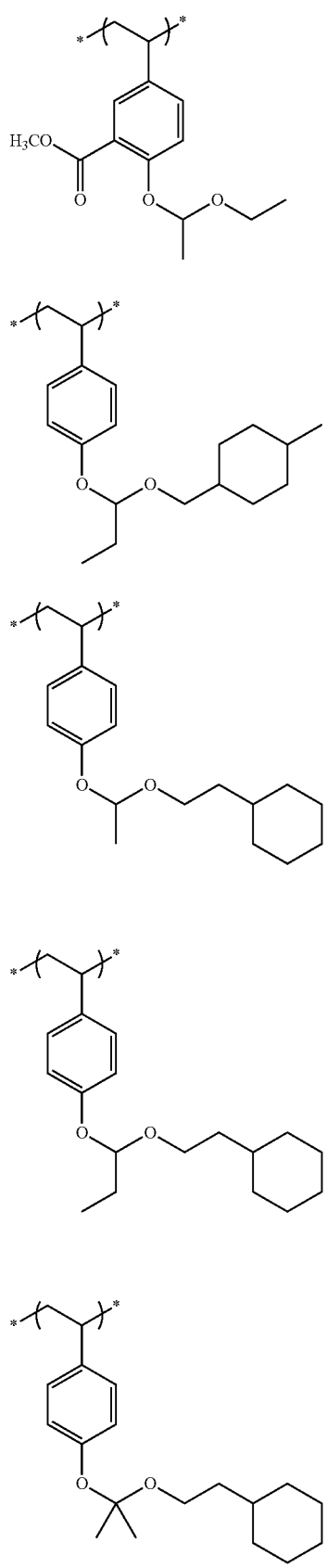
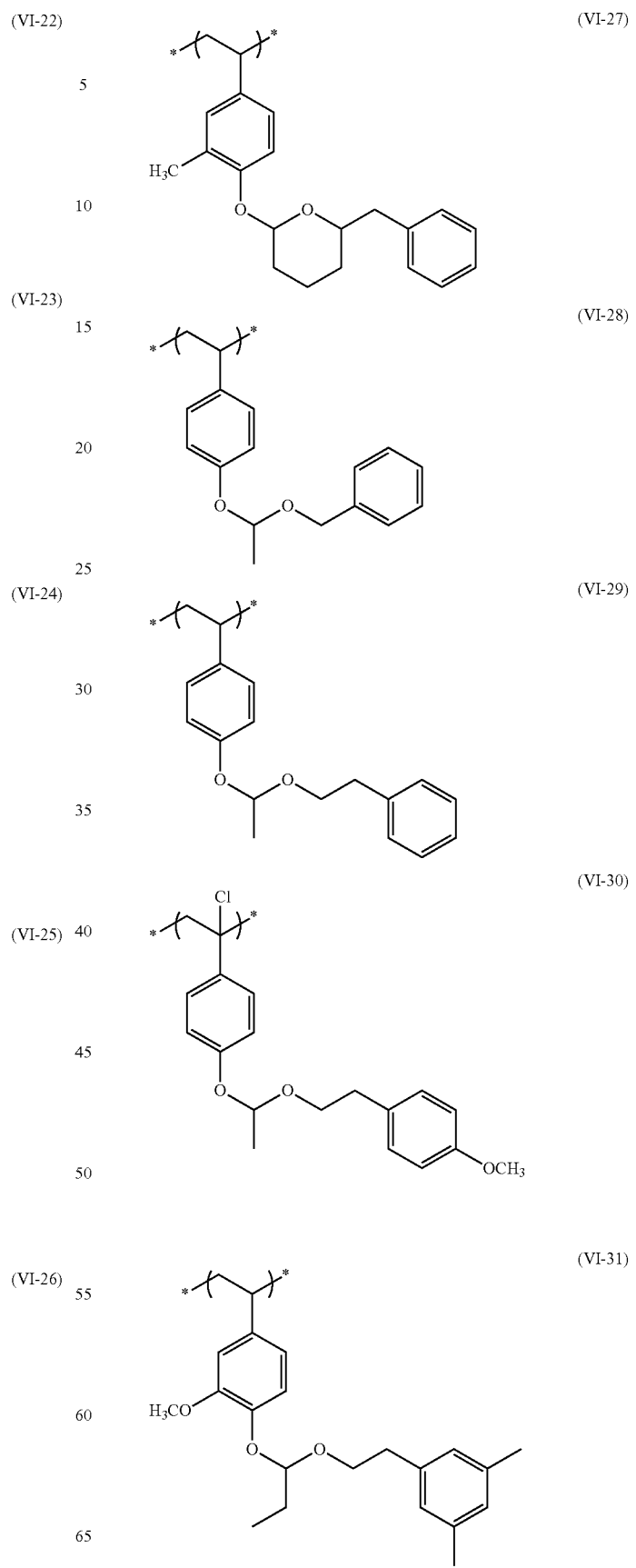

(VI-32) 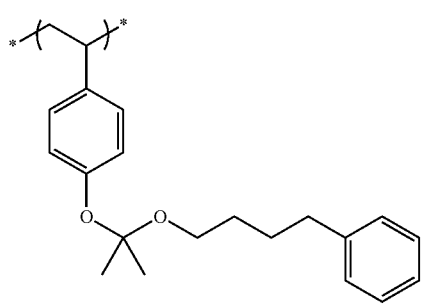
(VI-33) 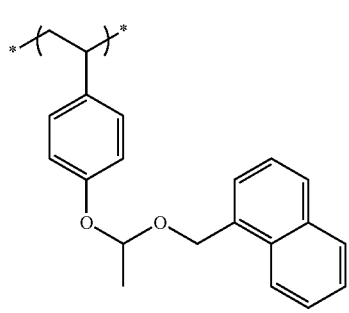
(VI-34) 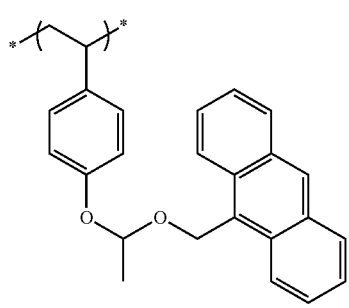
(VI-35) 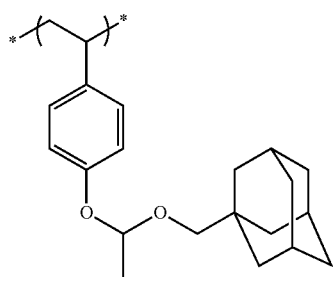
[Chem. 48]
(VI-36) 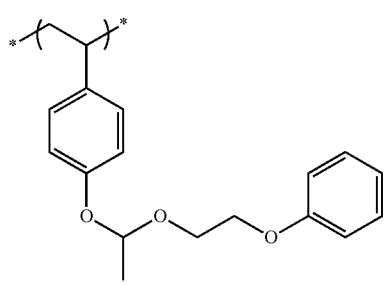
(VI-37) 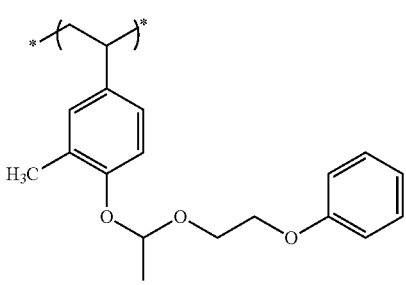
(VI-38) 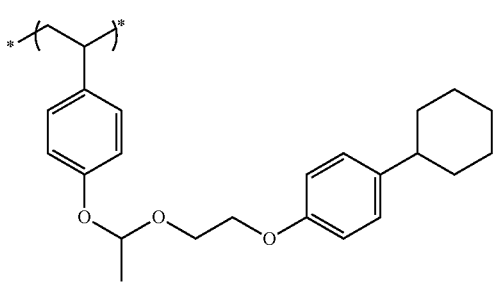
(VI-39) 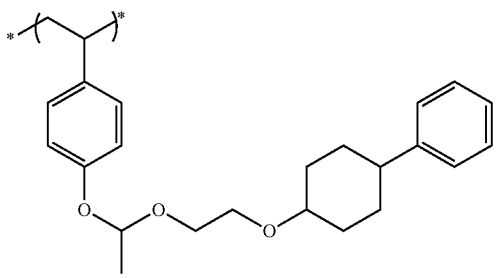
(VI-40) 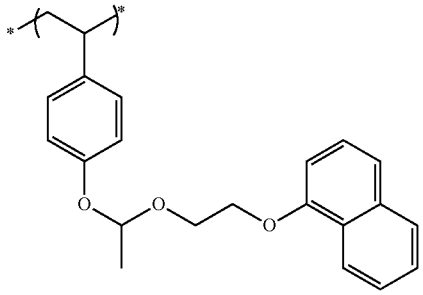
(VI-41) 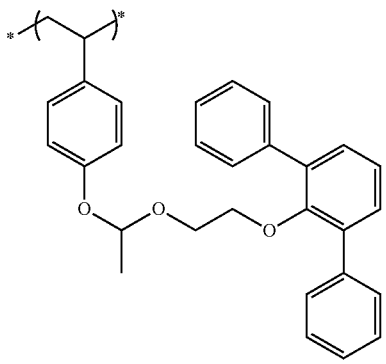

(VI-42)
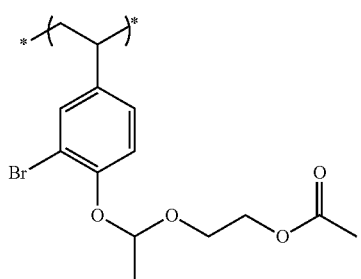
(VI-43)
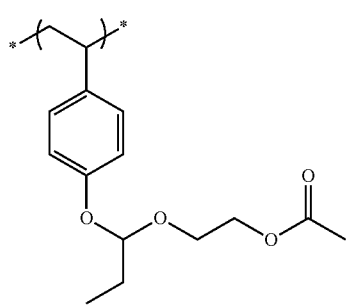
(VI-44)
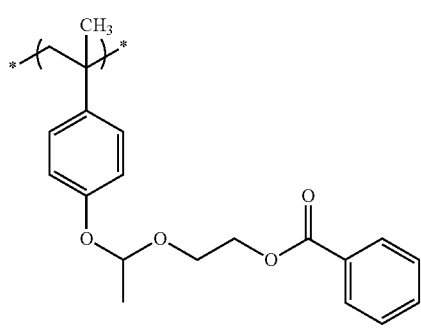
(VI-45)
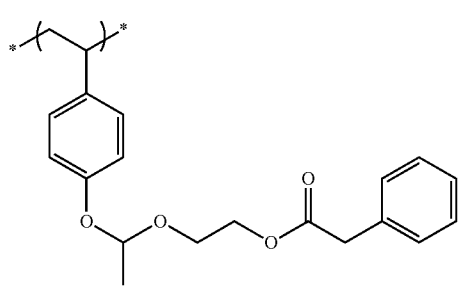
(VI-46)
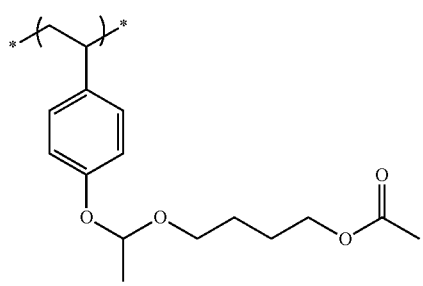
(VI-47)
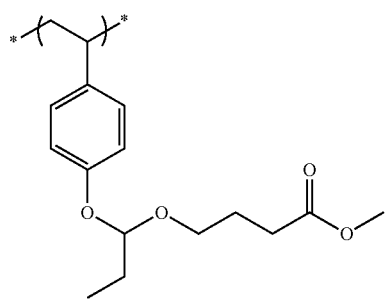
(VI-48)
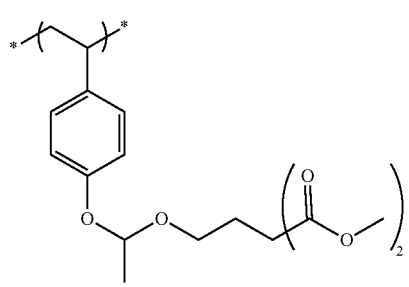
(VI-49)
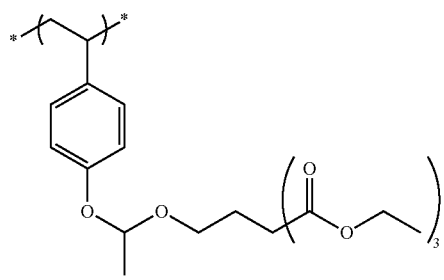
(VI-50)
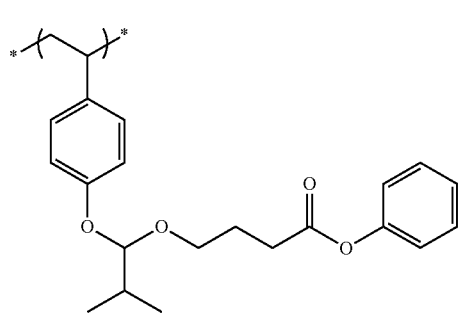
(VI-51)
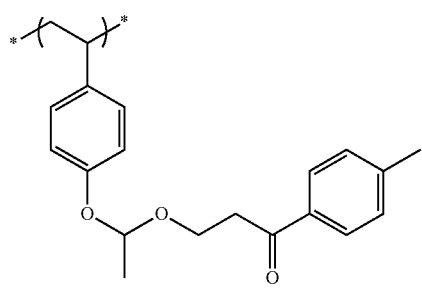

(VI-52)
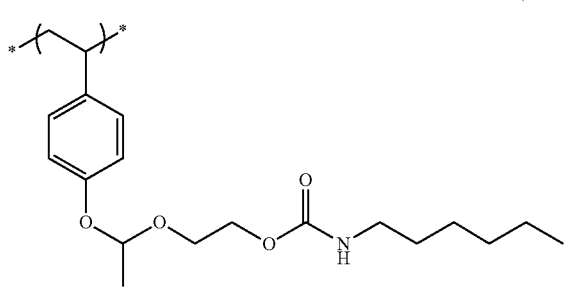
(VI-53)
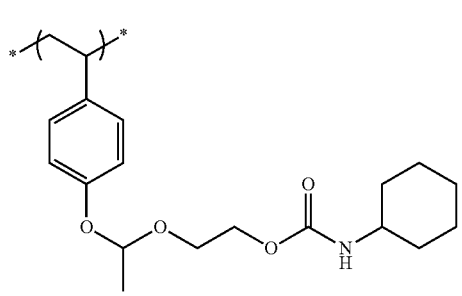
(VI-54)
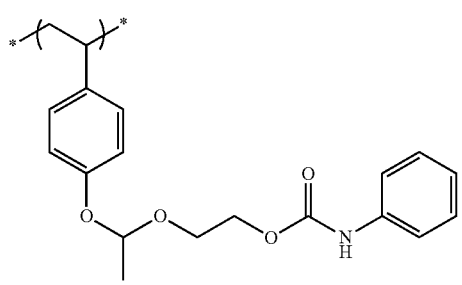
(VI-55)
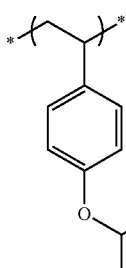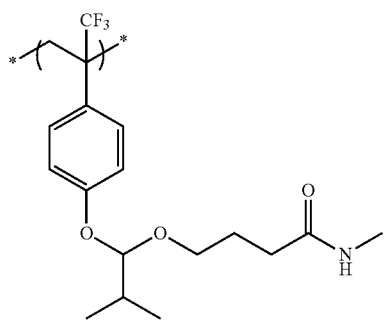
(VI-56)
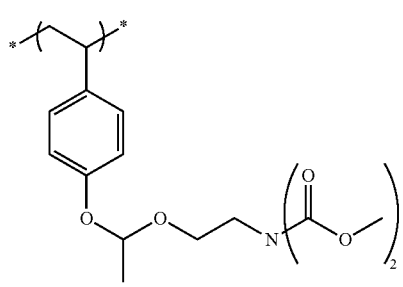
(VI-57)
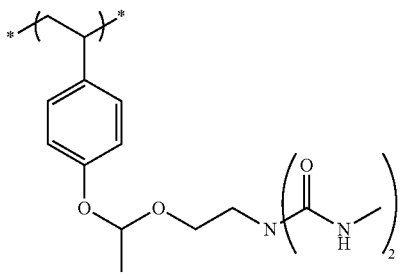
(VI-58)
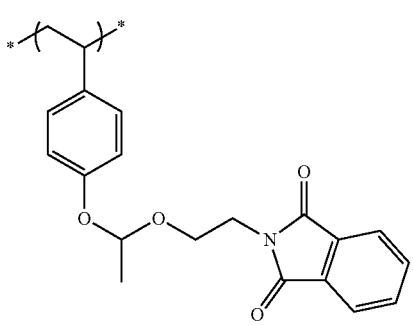
(VI-59)
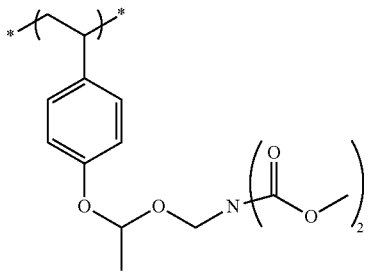
[Chem. 49]
(VI-60)
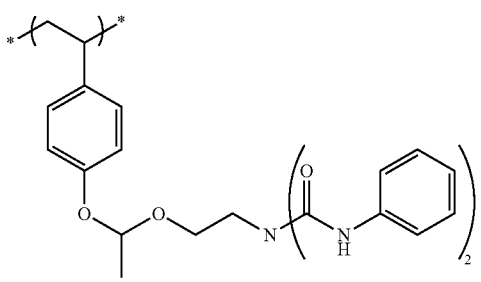
(VI-61)
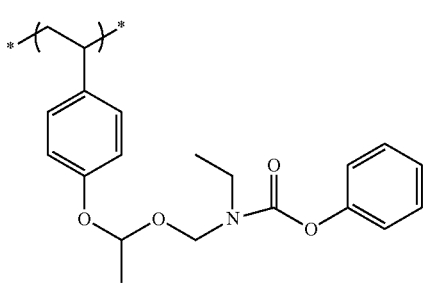

(VI-62)
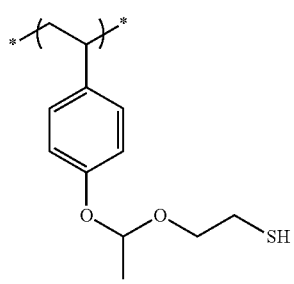
(VI-63)
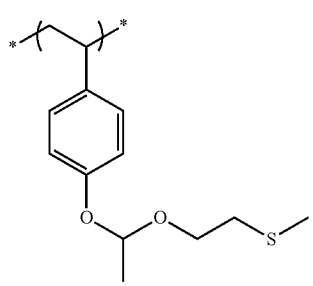
(VI-64)
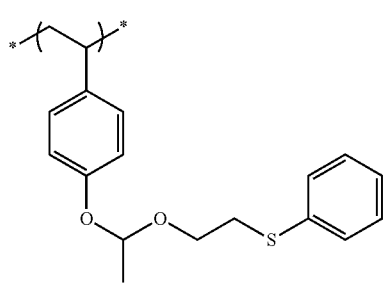
(VI-65)
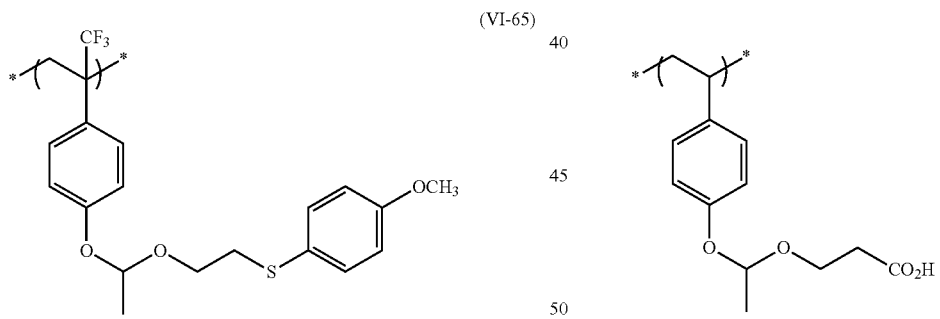
(VI-66)
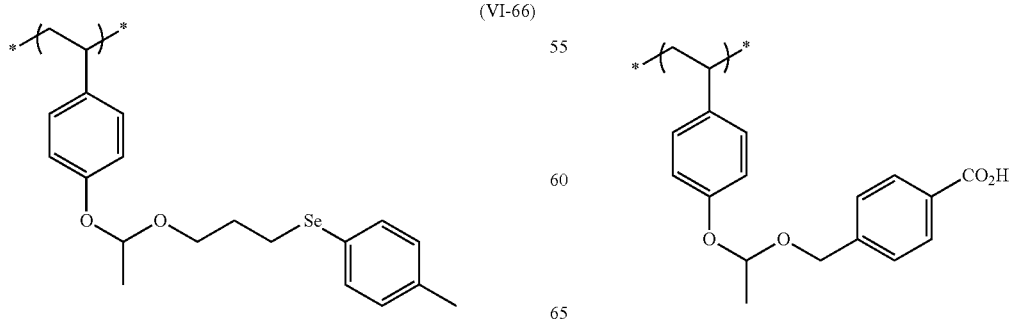
(VI-67)
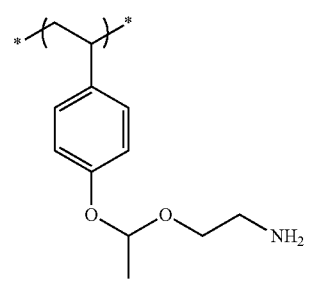
(VI-68)
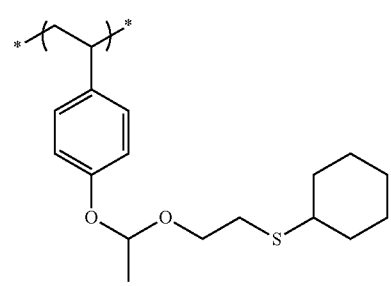
(VI-69)
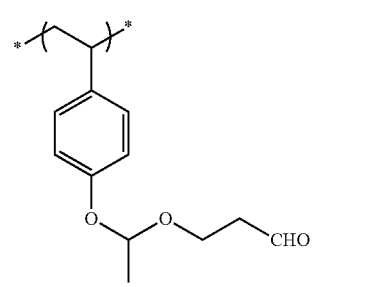
(VI-70)
(VI-71)

(VI-72) 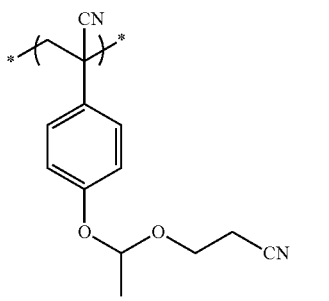
(VI-73) 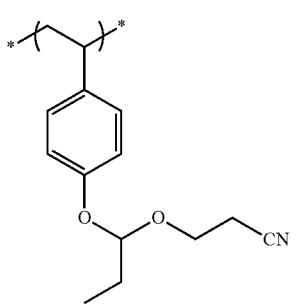
(VI-74) 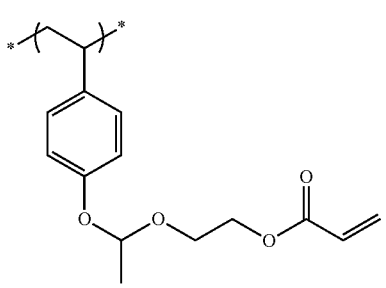
(VI-75) 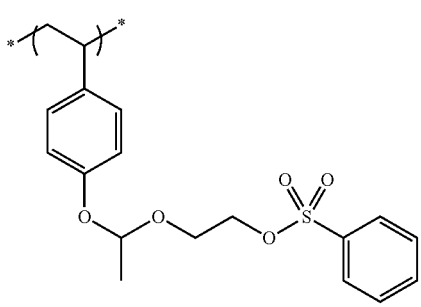
(VI-76) 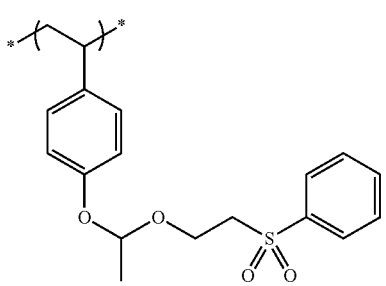
(VI-77) 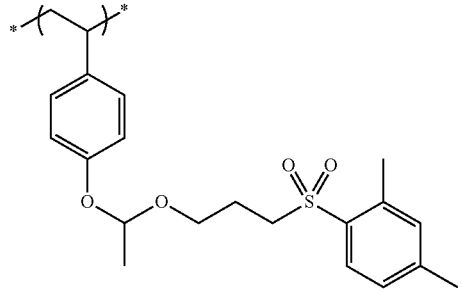
(VI-78) 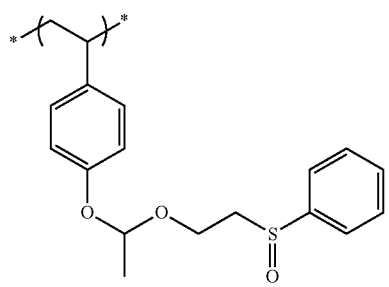
(VI-79) 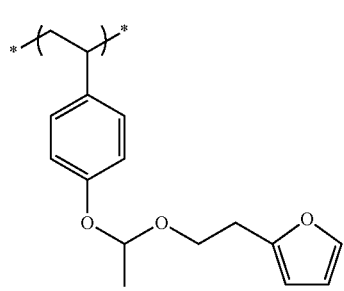
(VI-80) 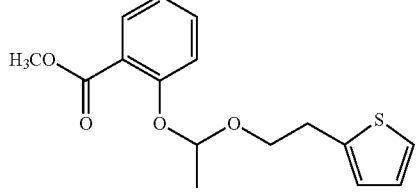
(VI-81) 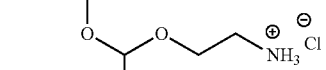
(VI-82) 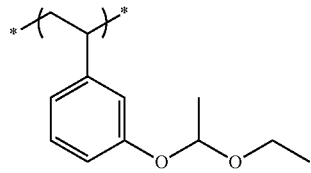

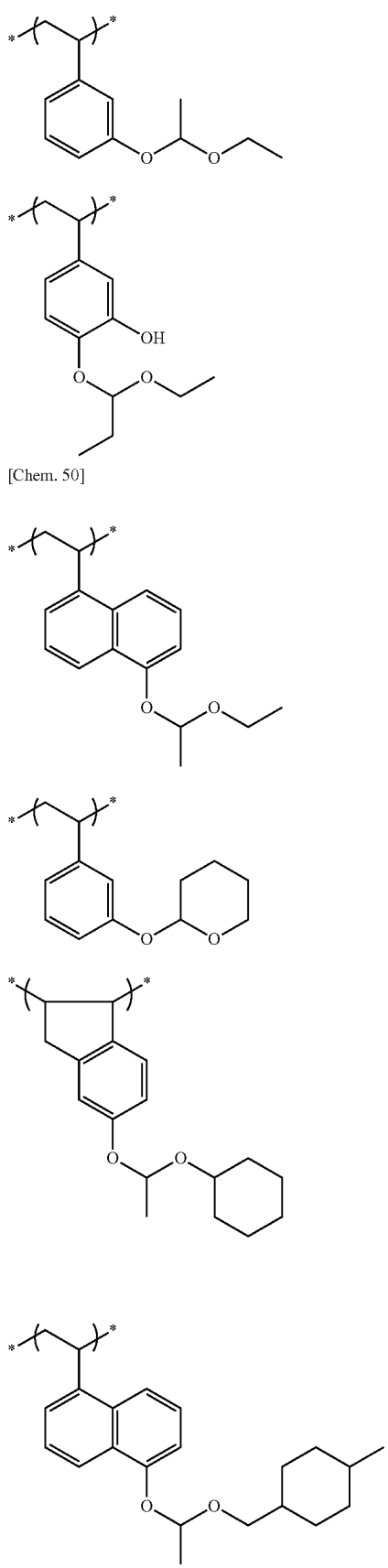
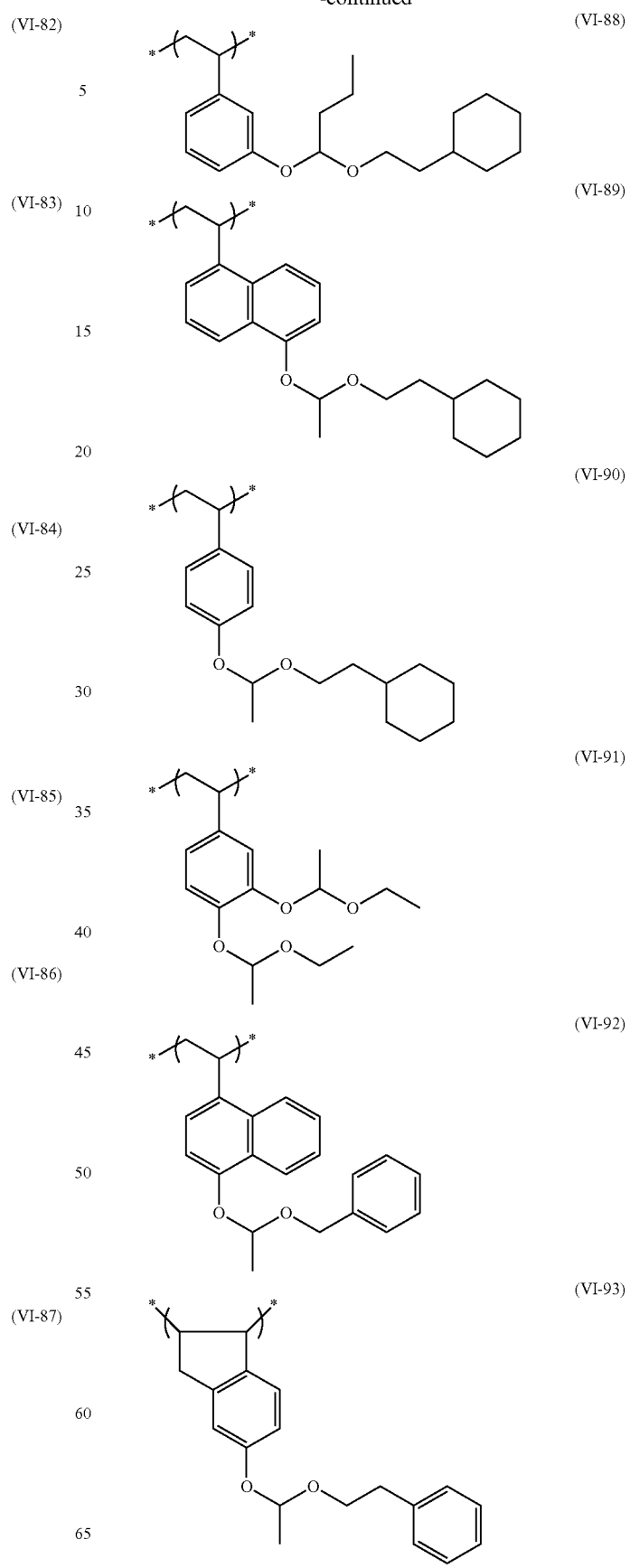

(VI-94) 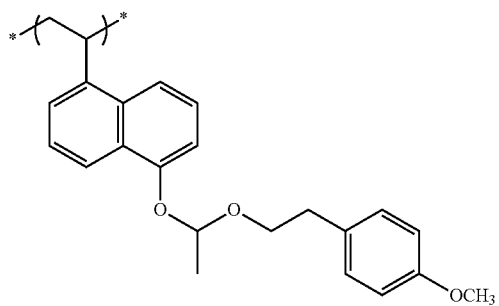
(VI-95) 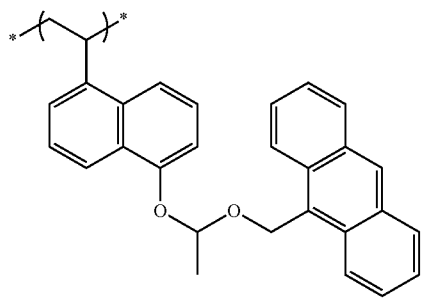
(VI-96) 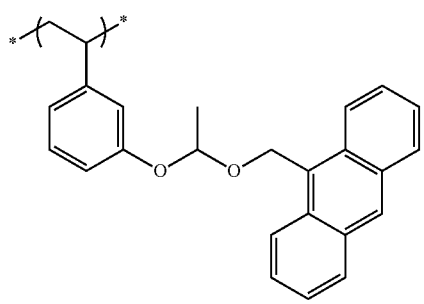
(VI-97) 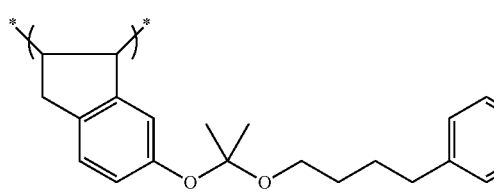
(VI-98) 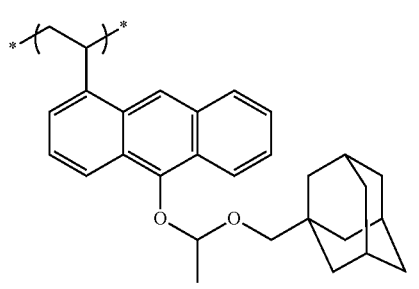
(VI-99) 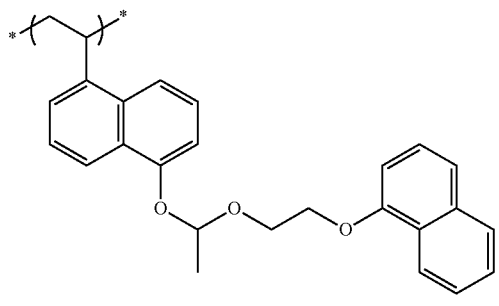
(VI-100) 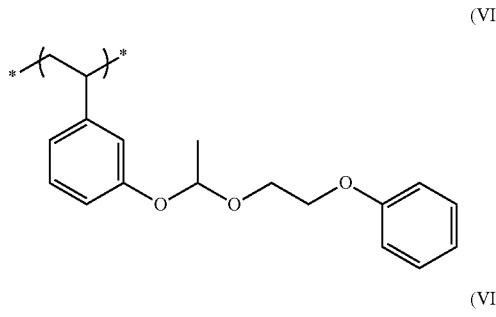
(VI-101) 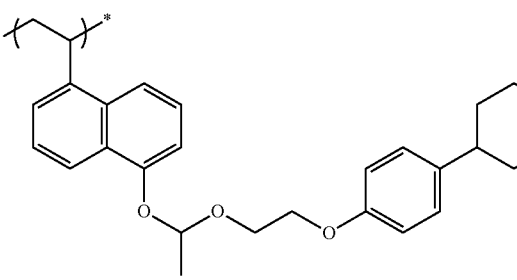
(VI-102) 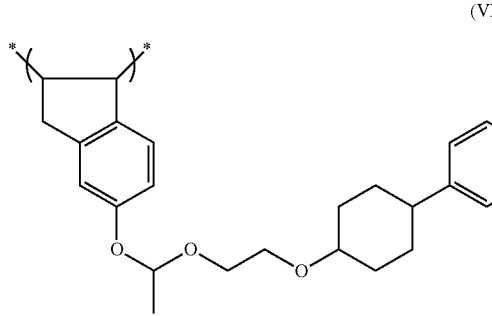
(VI-103) 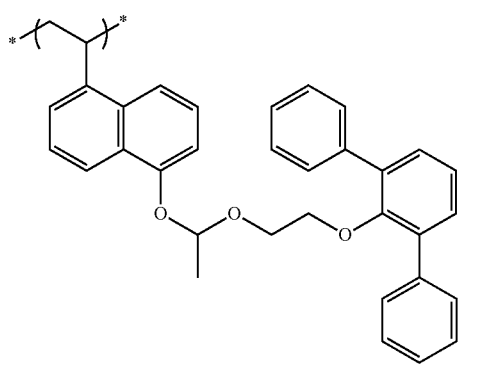

(VI-104)
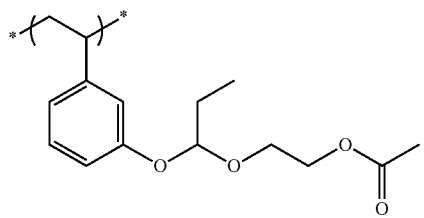
(VI-105)
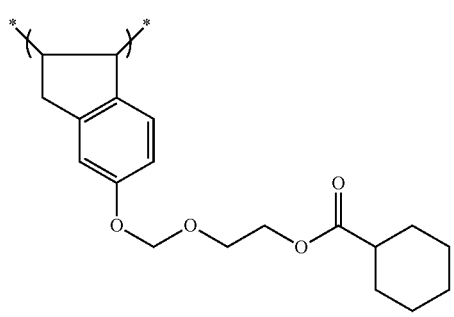
(VI-106)
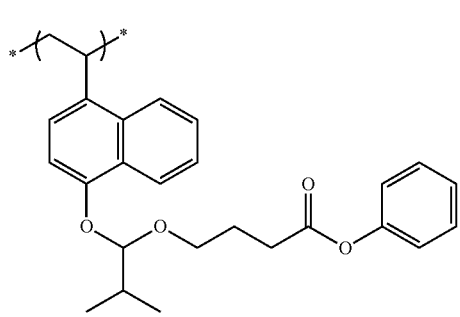
(VI-107)
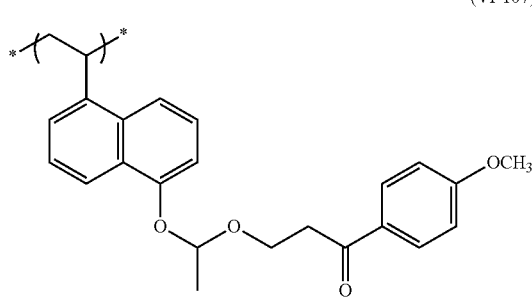
(VI-108)
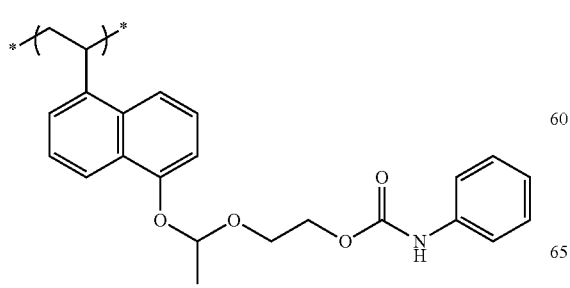
(VI-109)
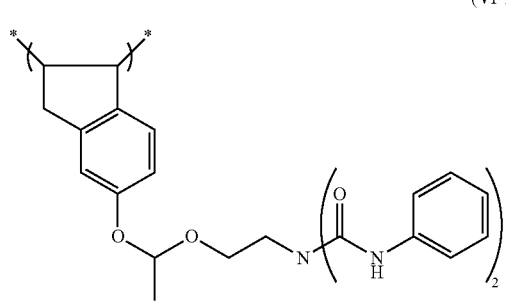
(VI-110)
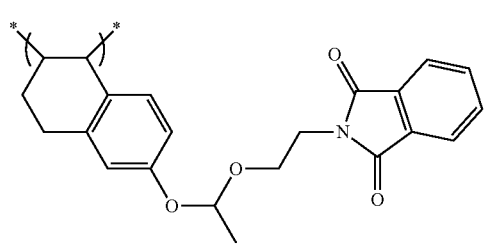
(VI-111)
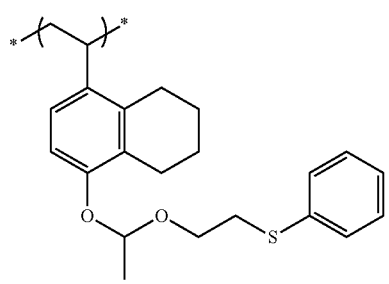
(VI-112)
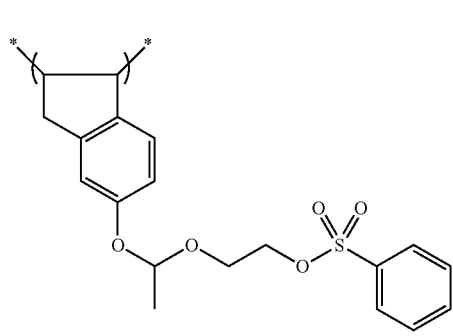
[Chem. 51]
(VI-113)
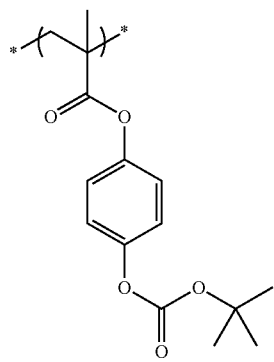

(VI-114)
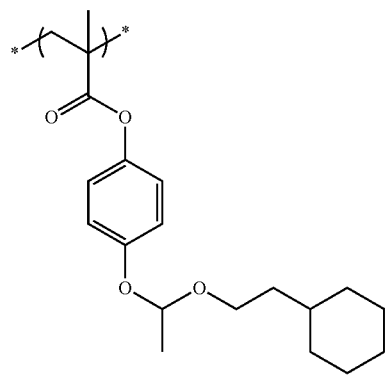
(VI-115)
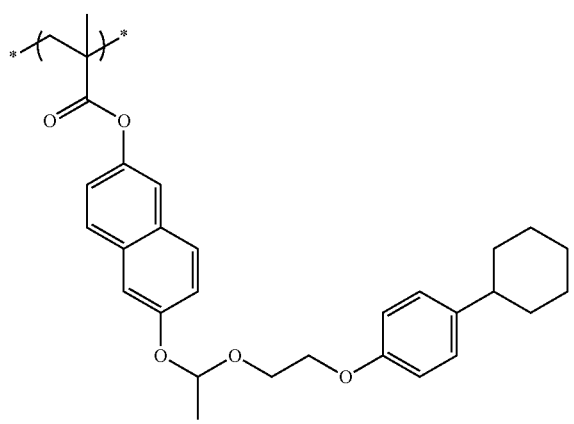
(VI-116)
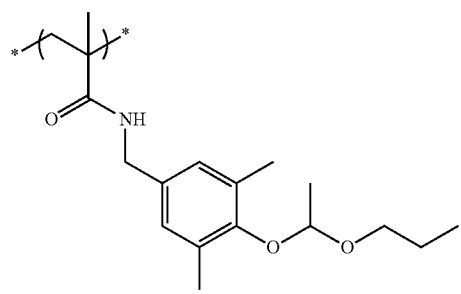
[Chem. 52]
(VI-117)
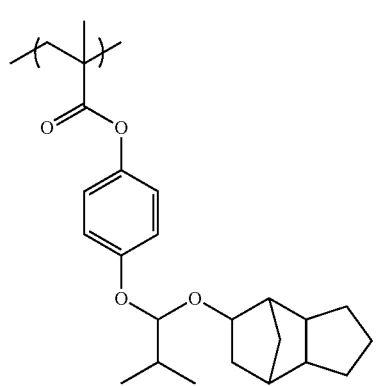
(VI-118)
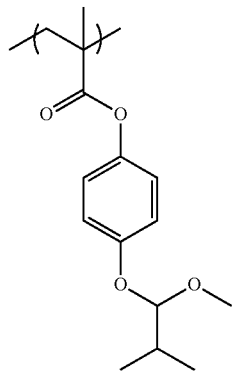
(VI-119)
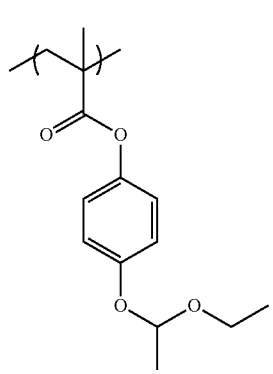
(VI-120)
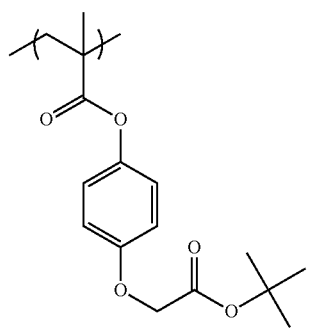
(VI-121)
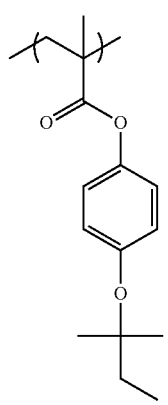

(VI-122) 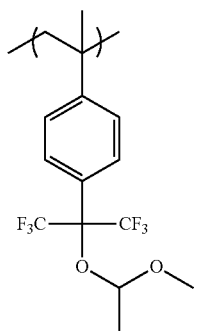
(VI-123) 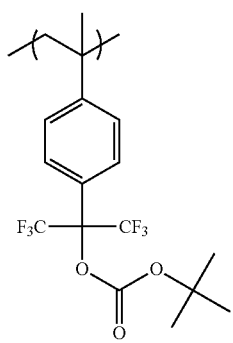
(VI-124) 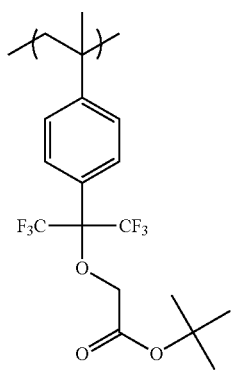
(VI-125) 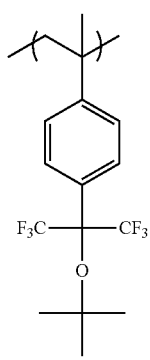
(VI-126) 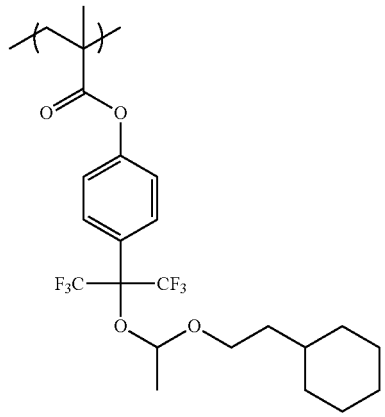
(VI-127) 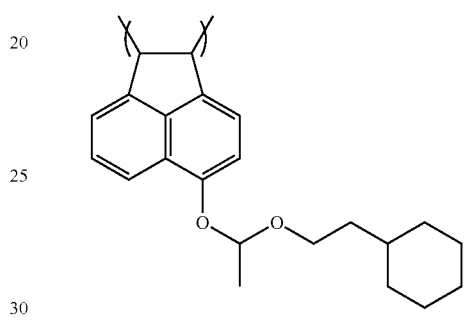
(VI-128) 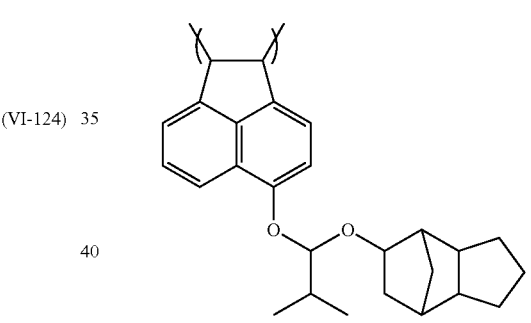
(VI-129) 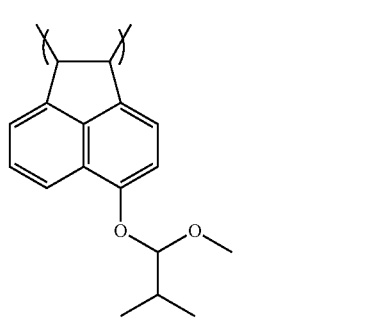
(VI-130) 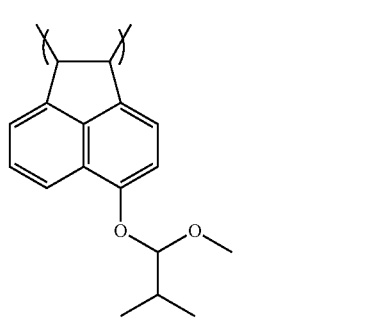

(VI-131) 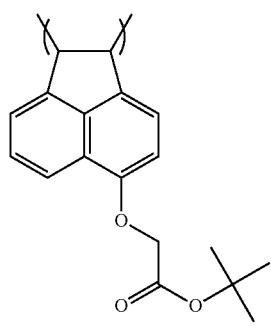
(VI-132) 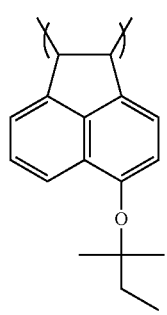
(VI-133) 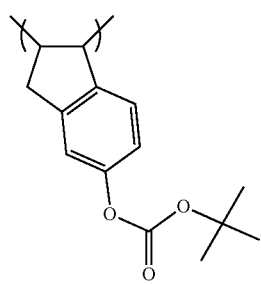
(VI-134) 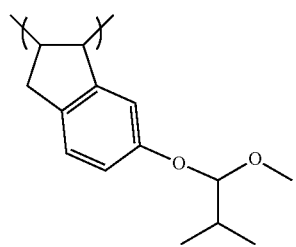
(VI-135) 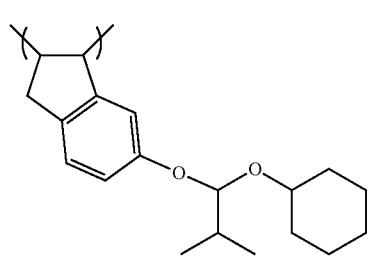
(VI-136) 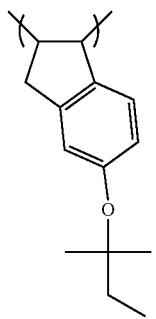
(VI-137) 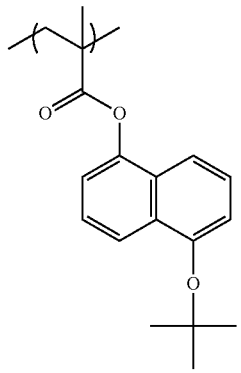
(VI-138) 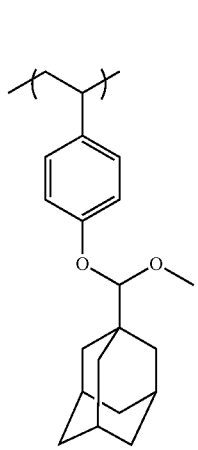
(VI-139) 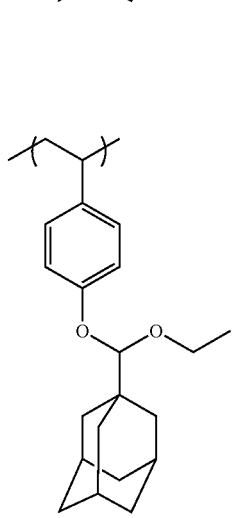

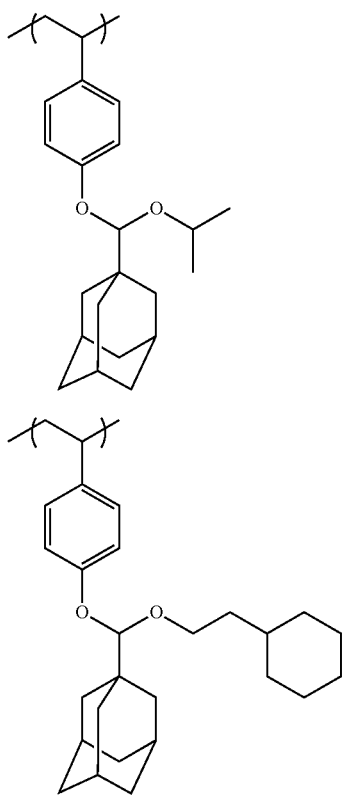

(VI-140)

(VI-141)

The repeating unit (a) is also preferably a repeating unit represented by the following formula (VI):

[Chem. 53]

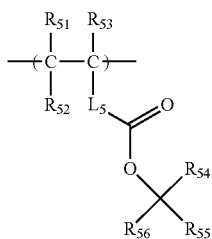

(VI)

In formula (VI), each of $R_{51}$, $R_{52}$ and $R_{53}$ independently represents a hydrogen atom, an alkyl group, a cycloalkyl group, a halogen atom, a cyano group or an alkoxycarbonyl group. $R_{52}$ may combine with $L_5$ to form a ring, and in this case, $R_{52}$ represents an alkylene group.

$L_5$ represents a single bond or a divalent linking group and in the case of forming a ring with $R_{52}$, represents a trivalent linking group.

$R_{54}$ represents an alkyl group, and each of $R_{55}$ and $R_{56}$ independently represents a hydrogen atom, an alkyl group, a cycloalkyl group, a monovalent aromatic ring group, or an aralkyl group. $R_{55}$ and $R_{56}$ may combine with each other to form a ring. However, $R_{55}$ and $R_{56}$ are not a hydrogen atom at the same time.

Formula (VI) is described in more detail below.

The alkyl group of $R_{51}$ to $R_{53}$ in formula (VI) is preferably an alkyl group having a carbon number of 20 or less, such as methyl group, ethyl group, propyl group, isopropyl group, n-butyl group, sec-butyl group, hexyl group, 2-ethylhexyl group, octyl group and dodecyl group, which may have a substituent, more preferably an alkyl group having a carbon number of 8 or less, still more preferably an alkyl group having a carbon number of 3 or less.

As the alkyl group contained in the alkoxycarbonyl group, the same alkyl group as that in $R_{51}$ to $R_{53}$ is preferred.

The cycloalkyl group may be either monocyclic or polycyclic and is preferably a monocyclic cycloalkyl group having a carbon number of 3 to 8, such as cyclopropyl group, cyclopentyl group and cyclohexyl group, which may have a substituent.

The halogen atom includes fluorine atom, chlorine atom, bromine atom and iodine atom, with fluorine atom being preferred.

Preferable substituents on each of the groups above include, for example, an alkyl group, a cycloalkyl group, an aryl group, an amino group, an amido group, a ureido group, a urethane group, a hydroxyl group, a carboxyl group, a halogen atom, an alkoxy group, a thioether group, an acyl group, an acyloxy group, an alkoxycarbonyl group, a cyano group, and a nitro group. The carbon number of the substituent is preferably 8 or less.

In the case where $R_{52}$ is an alkylene group and forms a ring with $L_5$, the alkylene group is preferably an alkylene group having a carbon number of 1 to 8, such as methylene group, ethylene group, propylene group, butylene group, hexylene group and octylene group, more preferably an alkylene group having a carbon number of 1 to 4, still more preferably an alkylene group having a carbon number of 1 or 2. The ring formed by combining $R_{52}$ and $L_5$ is preferably a 5- or 6-membered ring, among others.

In formula (VI), each of $R_{51}$ and $R_{53}$ is preferably a hydrogen atom, an alkyl group or a halogen atom, more preferably a hydrogen atom, a methyl group, an ethyl group, a trifluoromethyl group (—$CF_3$), a hydroxymethyl group (—$CH_2$—OH), a chloromethyl group (—$CH_2$—Cl) or a fluorine atom (—F). $R_{52}$ is preferably a hydrogen atom, an alkyl group, a halogen atom or an alkylene group (forming a ring with $L_5$), more preferably a hydrogen atom, a methyl group, an ethyl group, a trifluoromethyl group (—$CF_3$), a hydroxymethyl group (—$CH_2$—OH), a chloromethyl group (—$CH_2$—Cl), a fluorine atom (—F), a methylene group (forming a ring with $L_5$) or an ethylene group (forming a ring with $L_5$).

The divalent linking group represented by $L_5$ includes, for example, an alkylene group, a divalent aromatic ring group, —COO-$L_1$-, —O-$L_1$-, and a group formed by combining two or more of these groups. Here, $L_1$ represents an alkylene group, a cycloalkylene group, a divalent aromatic ring group, or a group formed by combining an alkylene group with a divalent aromatic ring group.

$L_5$ is preferably a single bond, a group represented by —COO-$L_1$-, or a divalent aromatic ring group. $L_1$ is preferably an alkylene group having a carbon number of 1 to 5, more preferably a methylene group or a propylene group. The divalent aromatic ring group is preferably a 1,4-phenylene group, a 1,3-phenylene group, a 1,2-phenylene group or a 1,4-naphthylene group, more preferably a 1,4-phenylene group.

As the trivalent linking group represented by $L_5$ when forming a ring by combining $L_5$ and $R_{52}$, groups formed by removing one arbitrary hydrogen atom from specific examples recited above of the divalent linking group represented by $L_5$ are preferred.

The alkyl group of $R_{54}$ to $R_{56}$ is preferably an alkyl group having a carbon number of 1 to 20, more preferably an alkyl group having a carbon number of 1 to 10, still more preferably an alkyl group having a carbon number of 1 to 4, such as methyl group, ethyl group, n-propyl group, isopropyl group, n-butyl group, isobutyl group and tert-butyl group.

The cycloalkyl group represented by $R_{55}$ and $R_{56}$ is preferably a cycloalkyl group having a carbon number of 3 to 20 and may be a monocyclic cycloalkyl group such as cyclopentyl group and cyclohexyl group or a polycyclic cycloalkyl group such as norbornyl group, adamantyl group, tetracyclodecanyl group and tetracyclododecanyl group.

The ring formed by combining $R_{55}$ and $R_{56}$ with each other is preferably a ring having a carbon number of 3 to 20 and may be a monocyclic ring such as cyclopentyl group and cyclohexyl group or a polycyclic ring such as norbornyl group, adamantyl group, tetracyclodecanyl group and tetracyclododecanyl group. In the case where $R_{55}$ and $R_{56}$ combine with each other to form a ring, $R_{54}$ is preferably an alkyl group having a carbon number of 1 to 3, more preferably a methyl group or an ethyl group.

The monovalent aromatic ring group represented by $R_{55}$ and $R_{56}$ is preferably an aromatic ring group having a carbon number of 6 to 20, and the aromatic ring group may be monocyclic or polycyclic or may have a substituent and includes, for example, a phenyl group, a 1-naphthyl group, a 2-naphthyl group, a 4-methylphenyl group, and a 4-methoxyphenyl group. In the case where either one of $R_{55}$ and $R_{56}$ is a hydrogen atom, the other one is preferably a monovalent aromatic ring group.

The aralkyl group represented by $R_{55}$ and $R_{56}$ may be monocyclic or polycyclic or may have a substituent. The aralkyl group is preferably an aralkyl group having a carbon number of 7 to 21 and includes a benzyl group, a 1-naphthylmethyl group, etc.

As the method for synthesizing a monomer corresponding to the repeating unit represented by formula (VI), a synthesis method for a general polymerizable group-containing ester may be applied, and the synthesis method is not particularly limited.

Specific examples of the repeating unit (a) represented by formula (VI) are illustrated below, but the present invention is not limited thereto.

In specific examples, each of Rx and $Xa_1$ represents a hydrogen atom, $CH_3$, $CF_3$ or $CH_2OH$, and each of Rxa and Rxb independently represents an alkyl group having a carbon number of 1 to 4, an aryl group having a carbon number of 6 to 18, or an aralkyl group having a carbon number of 7 to 19. Z represents a substituent. p represents 0 or a positive integer and is preferably 0 to 2, more preferably 0 or 1. When a plurality of Z are present, each Z may be the same as or different from every other Z. From the standpoint of increasing the dissolution contrast for an organic solvent-containing developer between before and after the acid-induced decomposition, Z is preferably a group composed of only a hydrogen atom and a carbon atom and, for example, preferably a linear or branched alkyl group or a cycloalkyl group.

[Chem. 54]

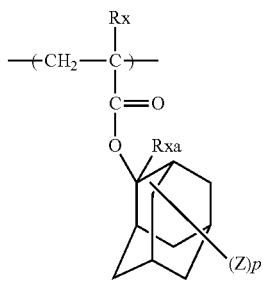

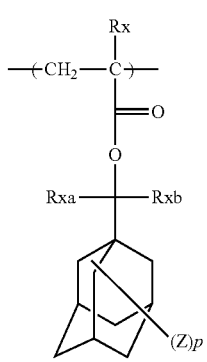

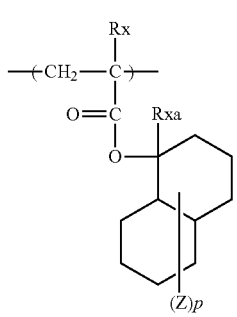

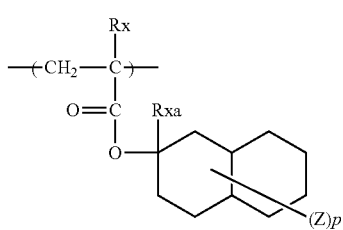

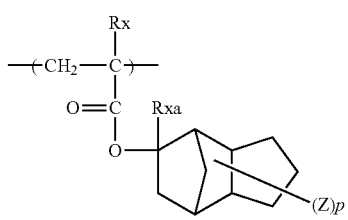

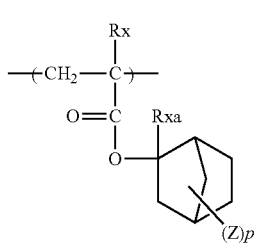

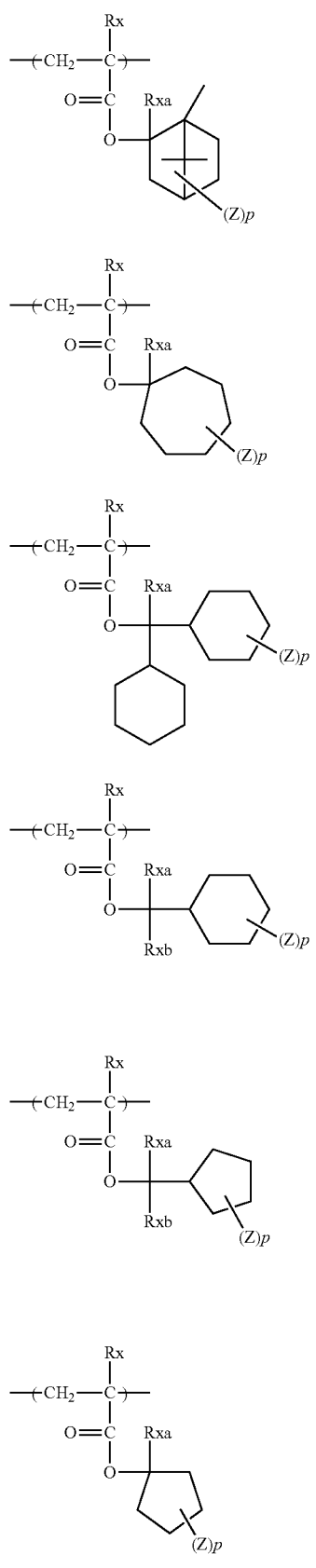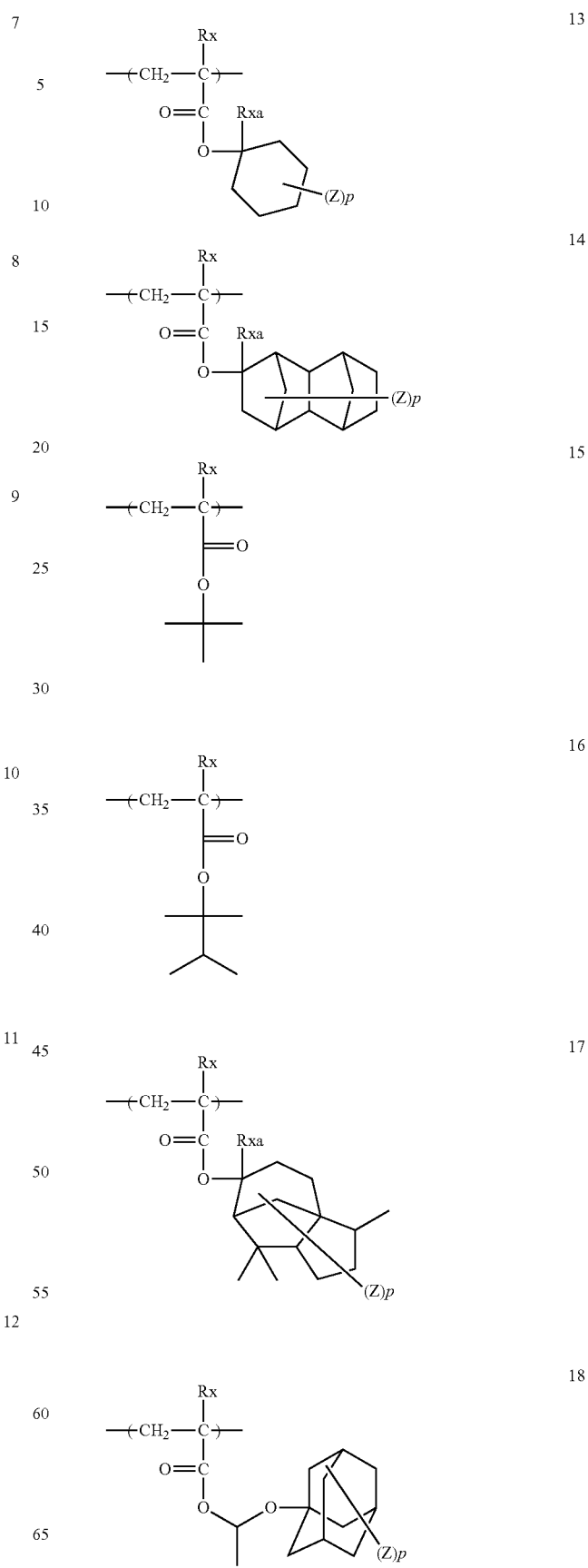

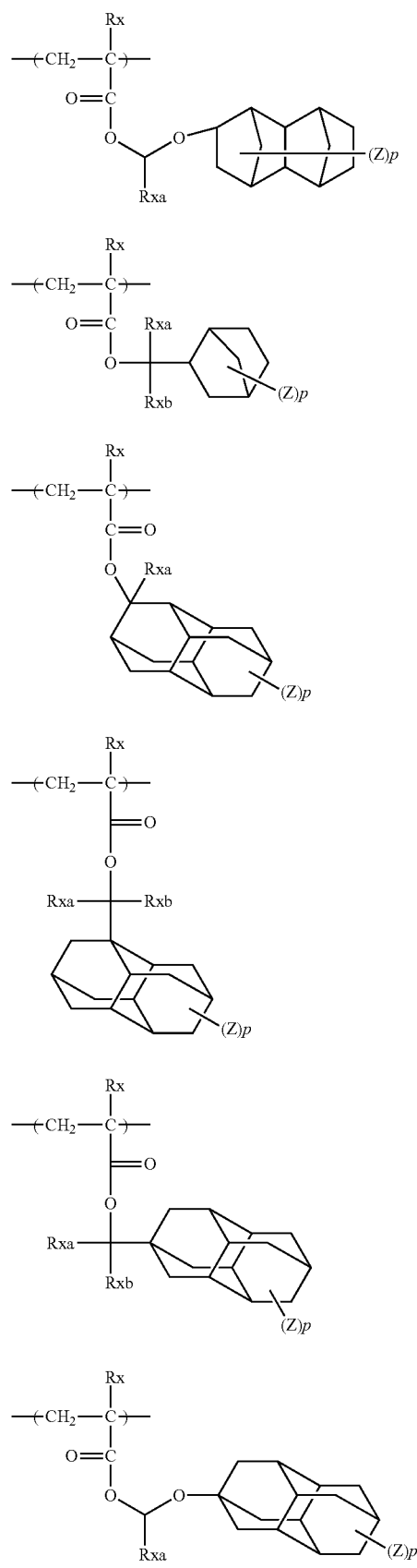
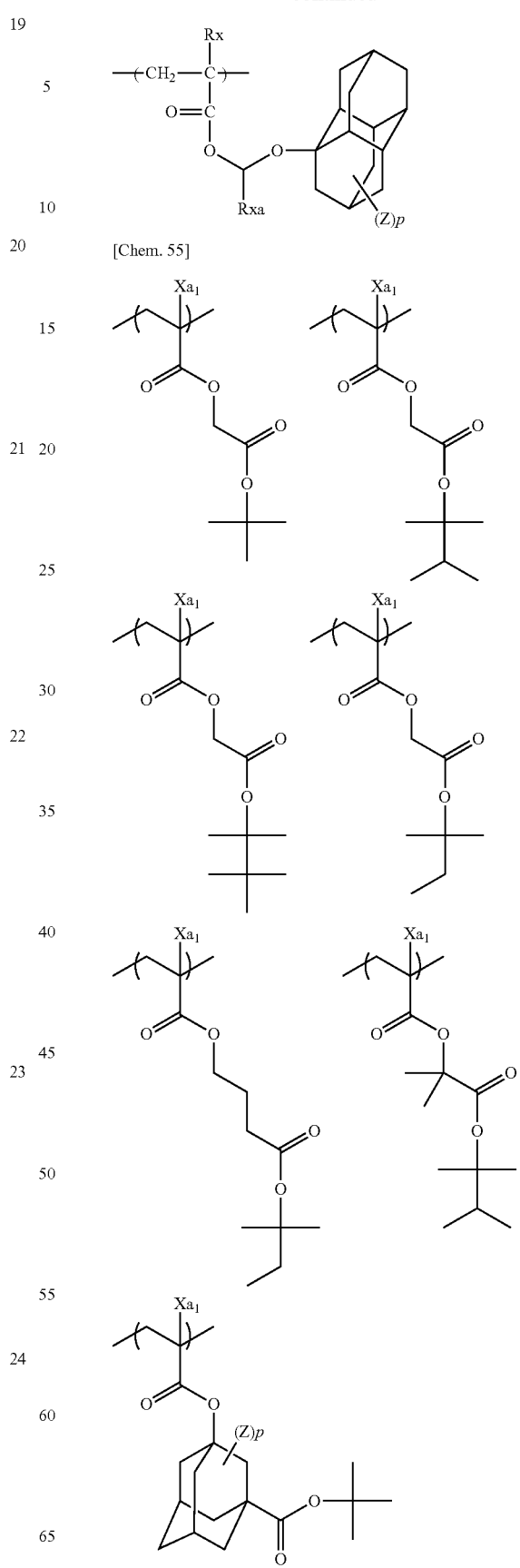

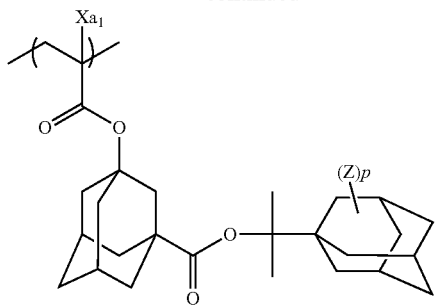
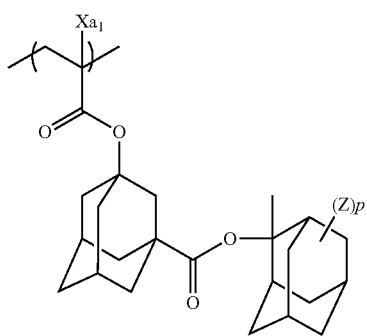
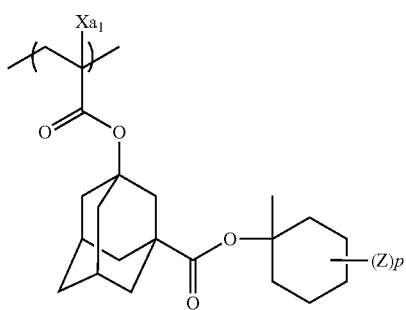
[Chem. 56]
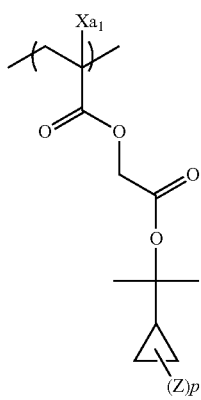
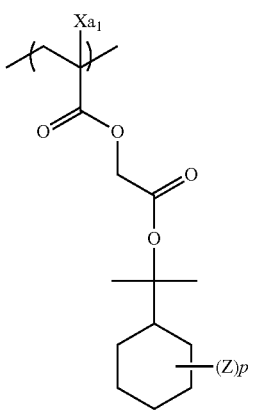
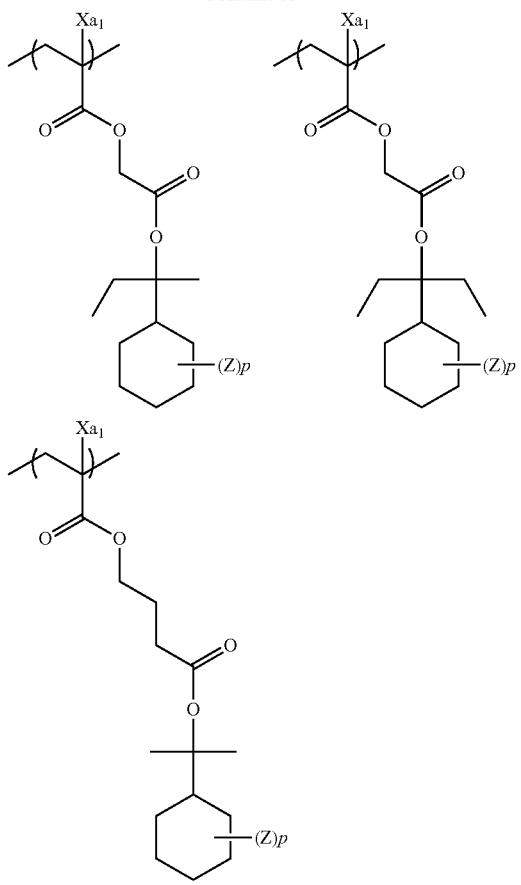
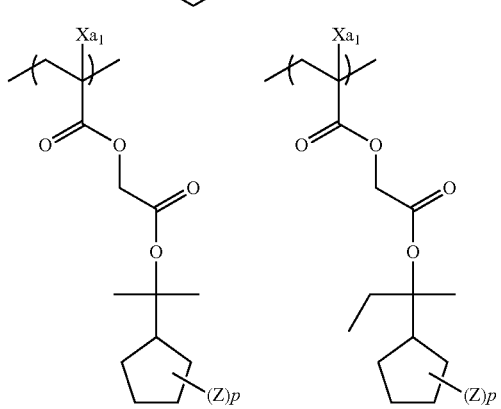
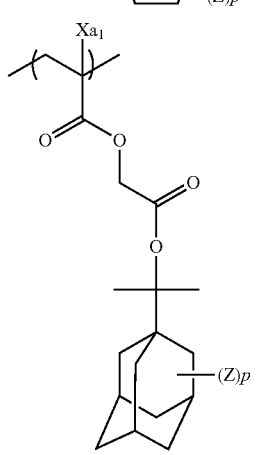

135
-continued
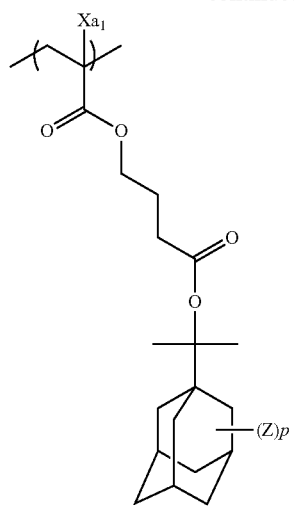
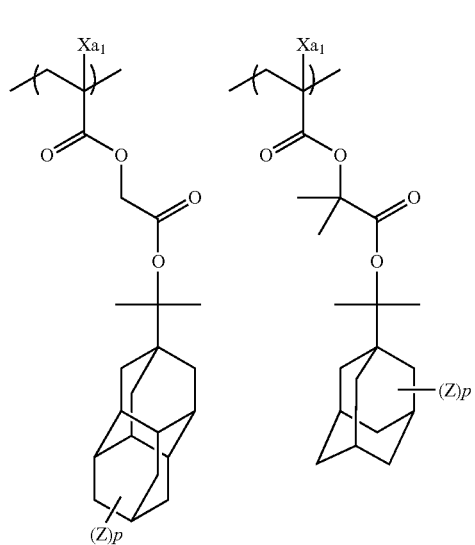
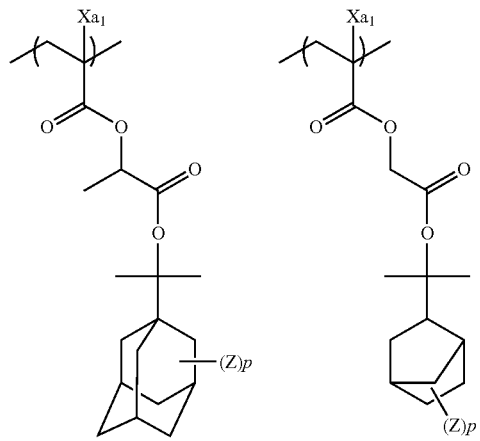
136
-continued
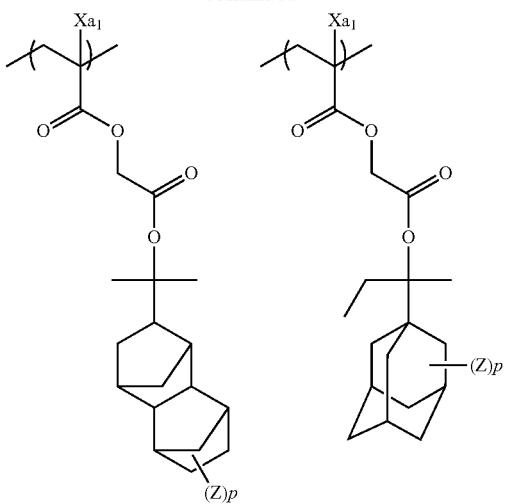
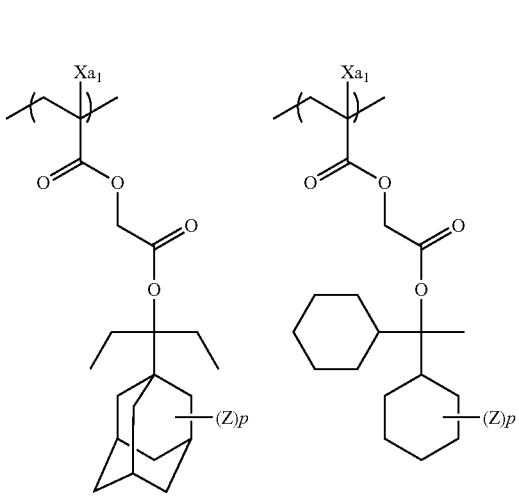
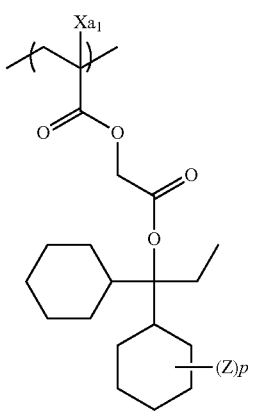

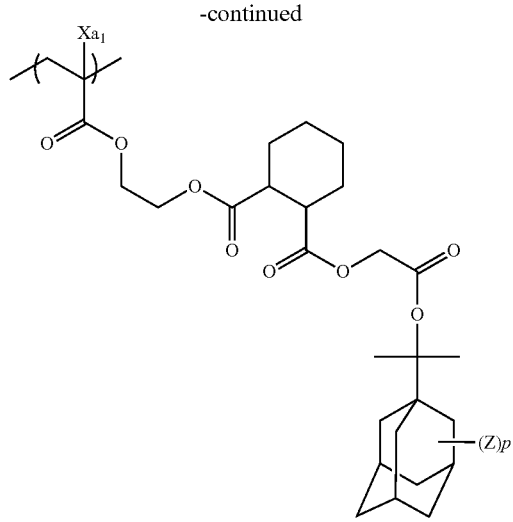
[Chem. 57]
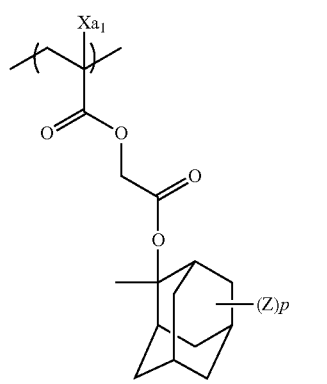
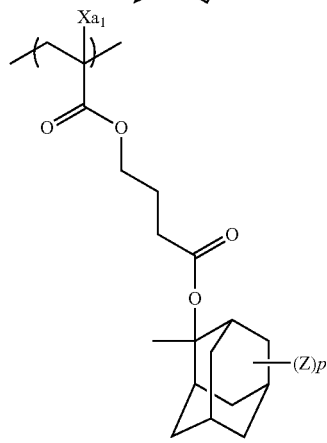
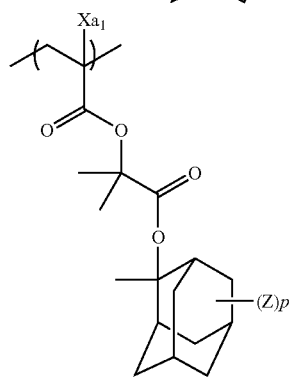
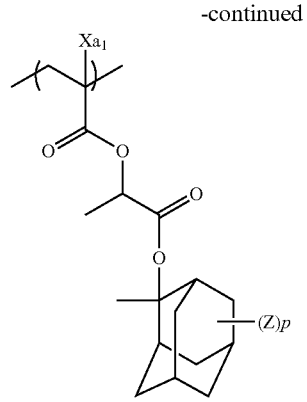
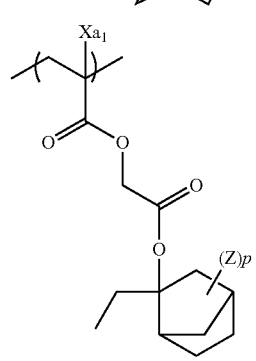
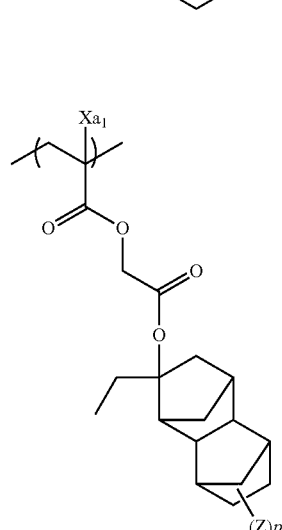
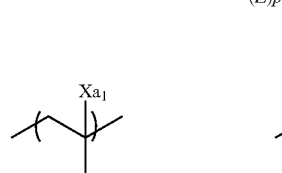
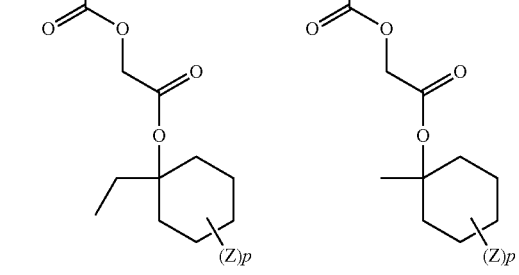

-continued
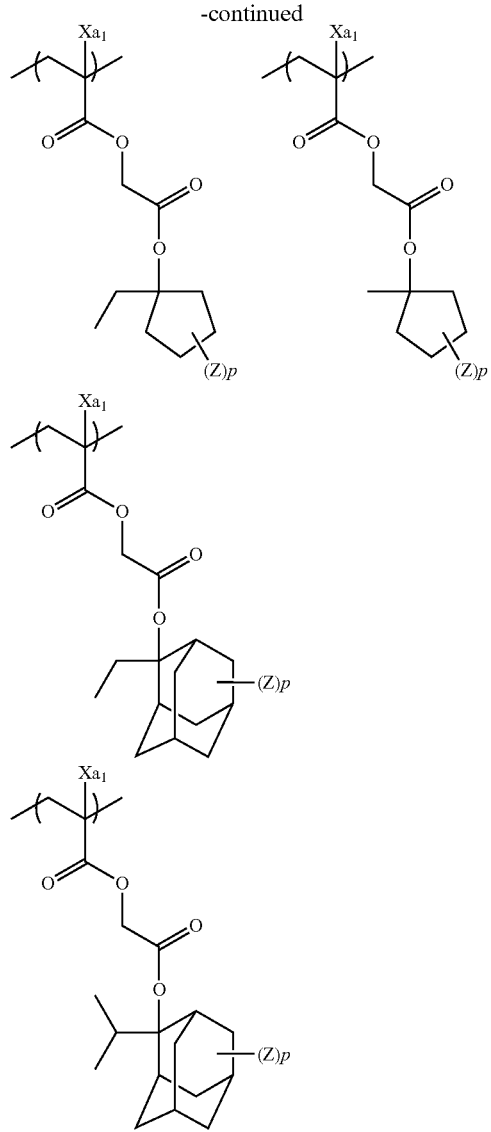
[Chem. 58]
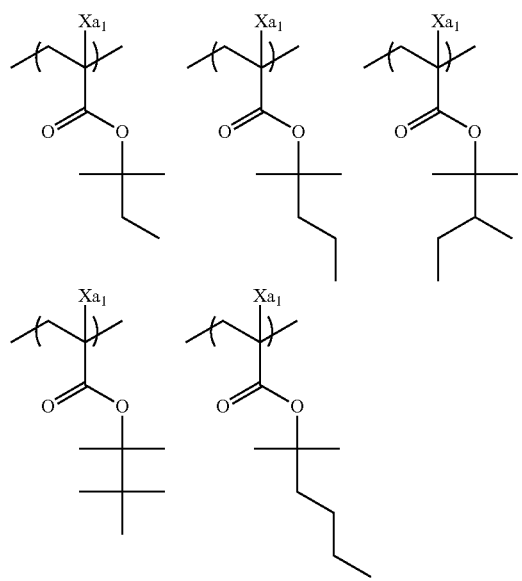
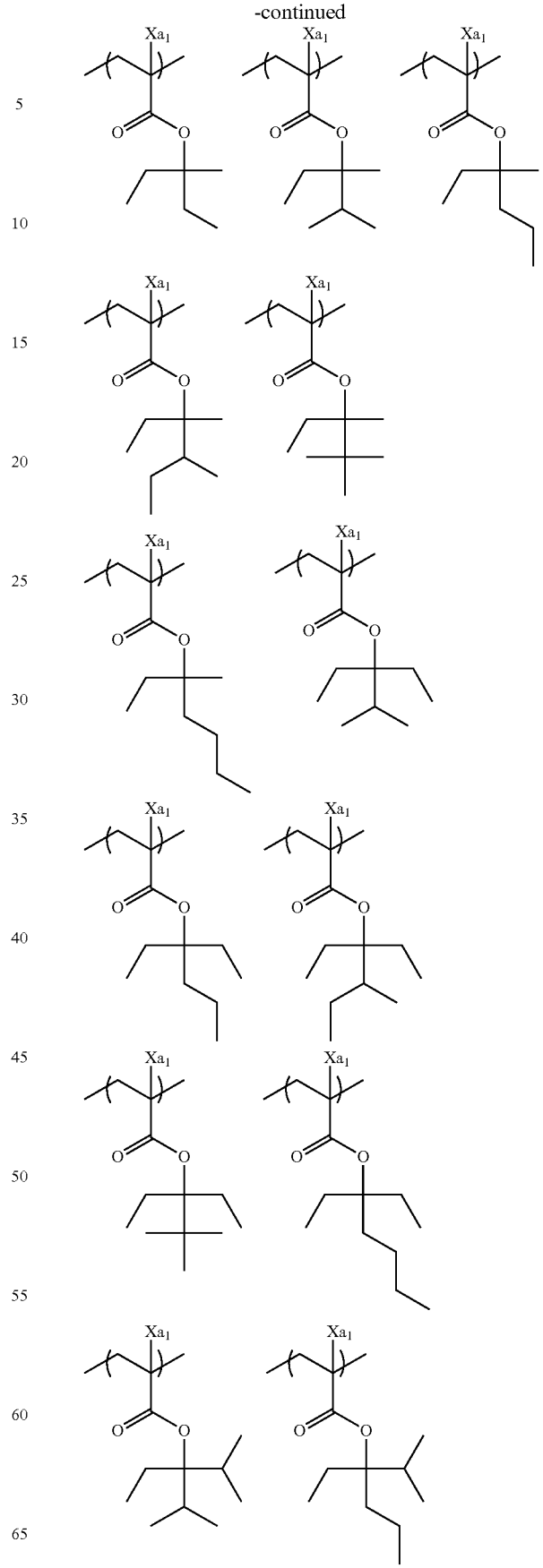

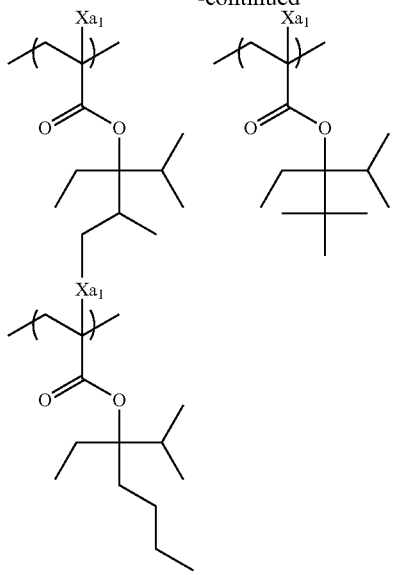
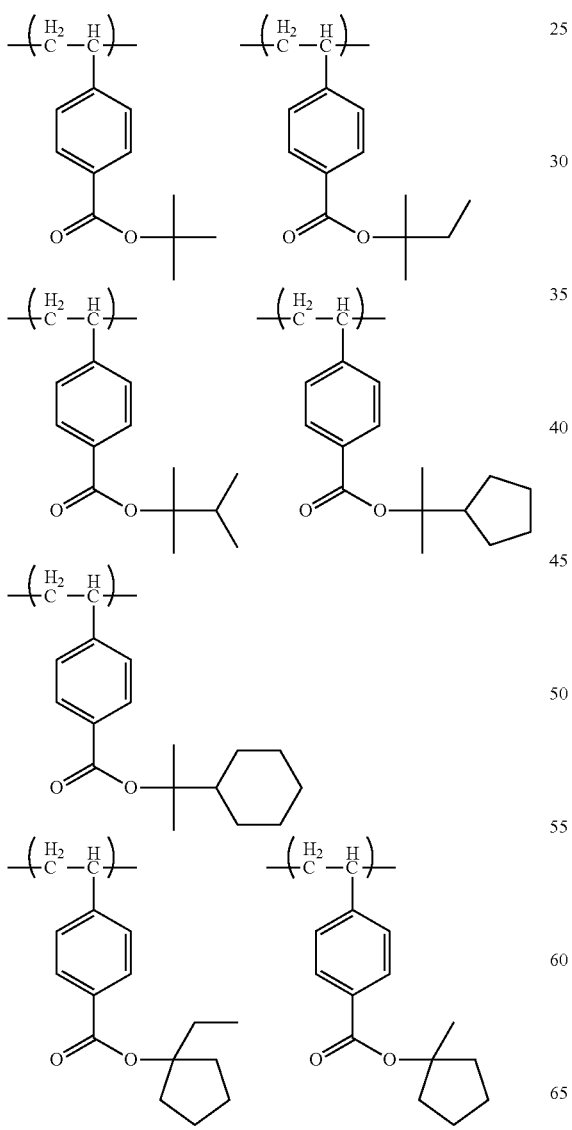
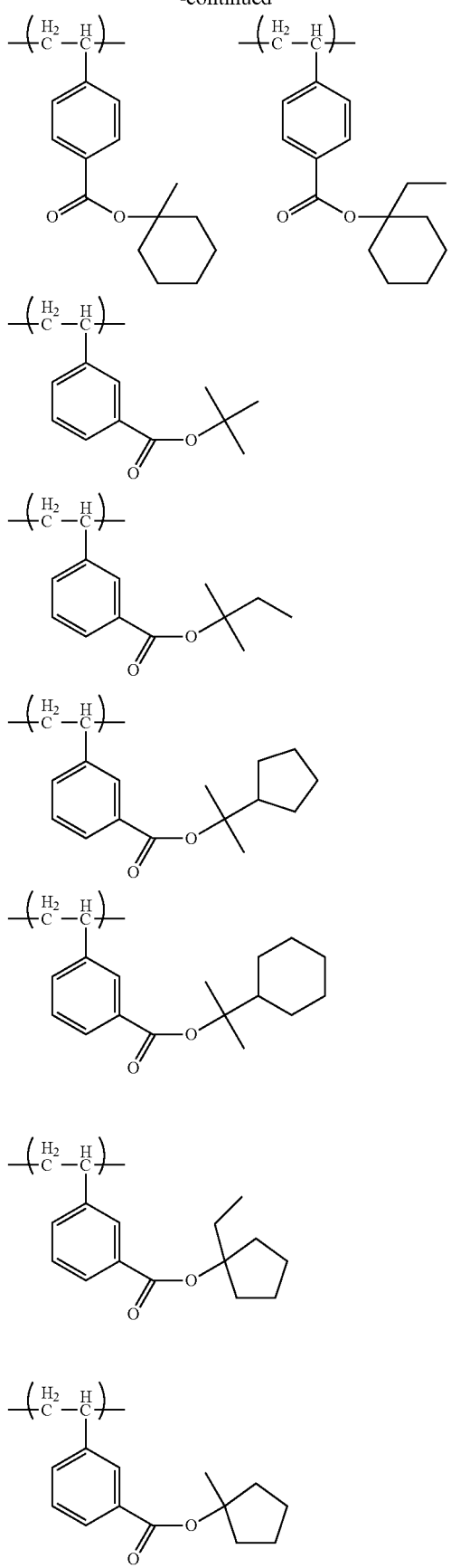

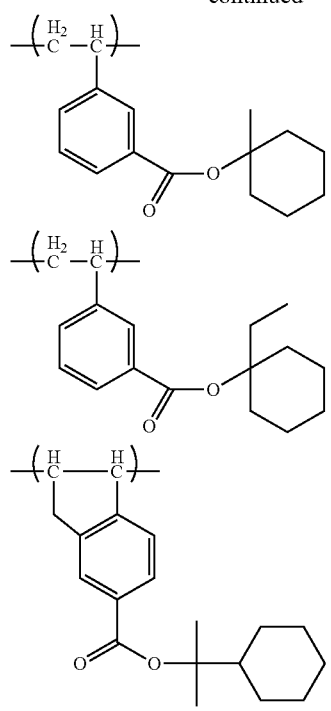
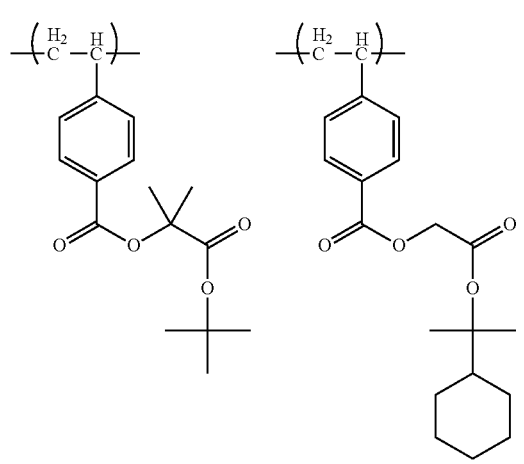
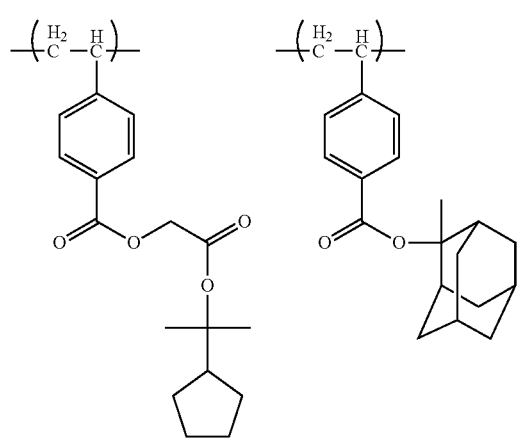
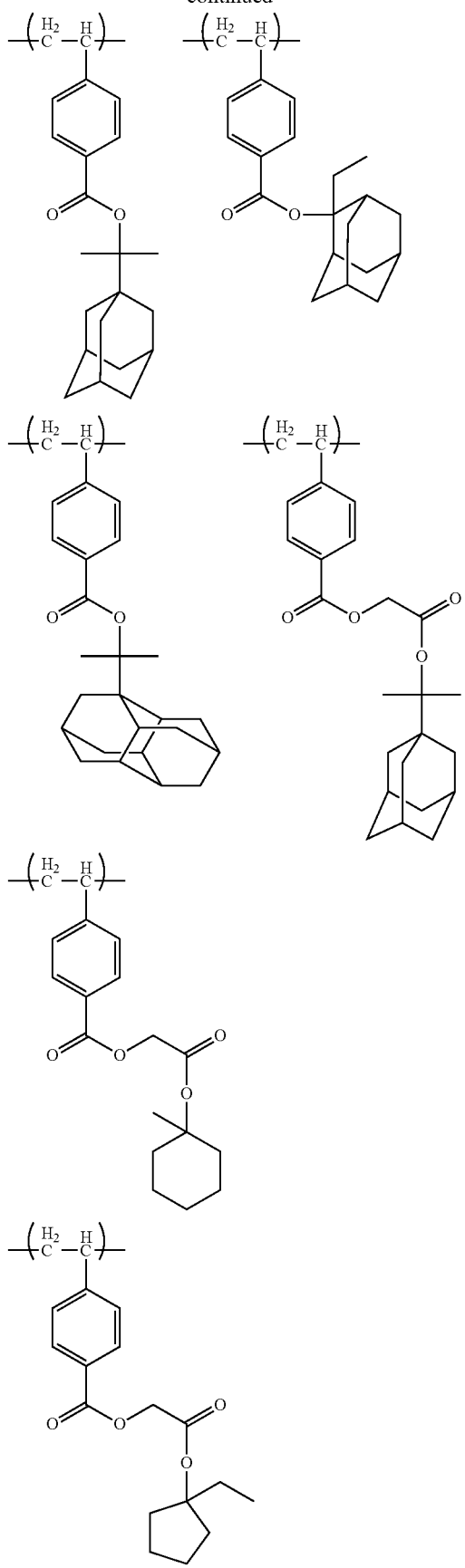

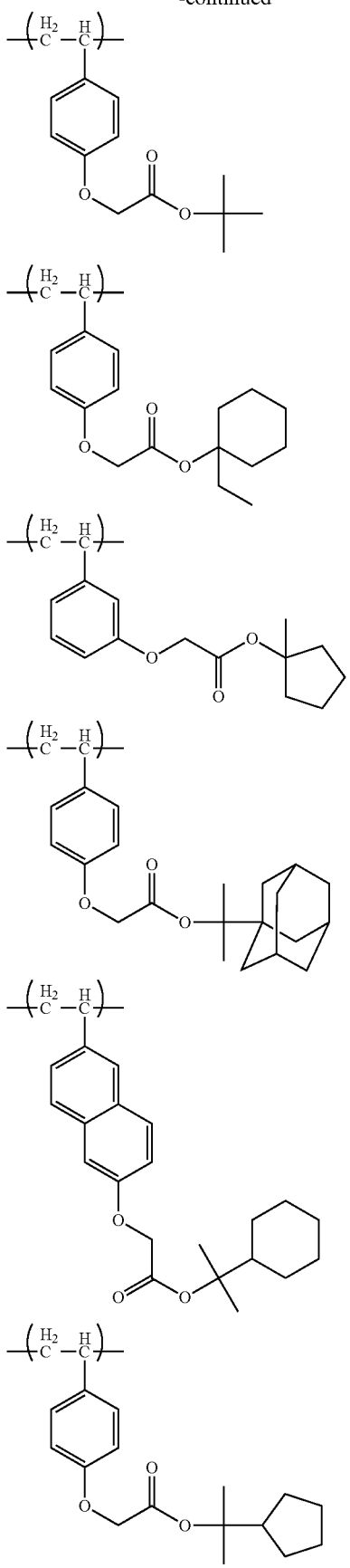

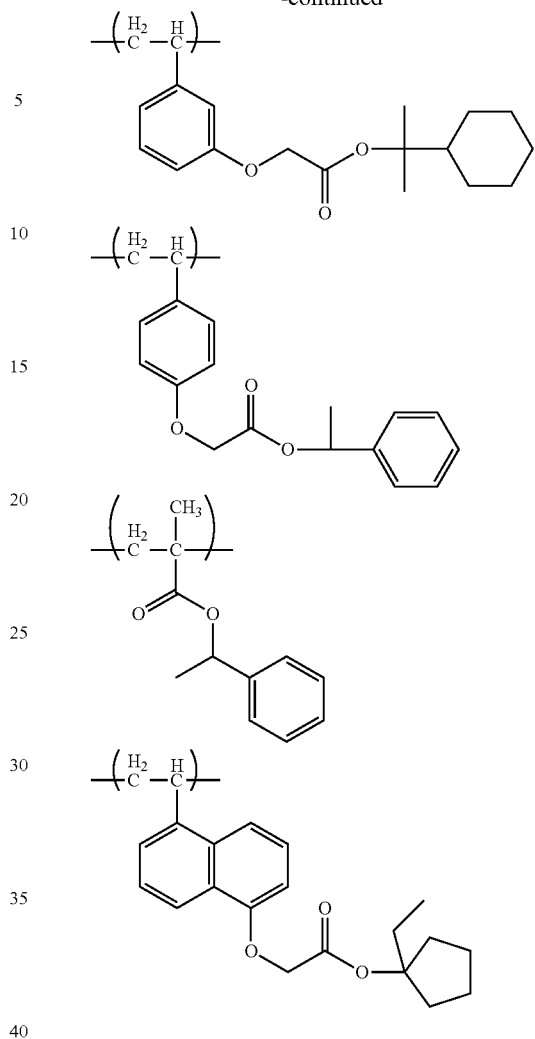

In addition, the resin (A) may contain, as the repeating unit (a), a repeating unit represented by the following formula (VII):

[Chem. 61]

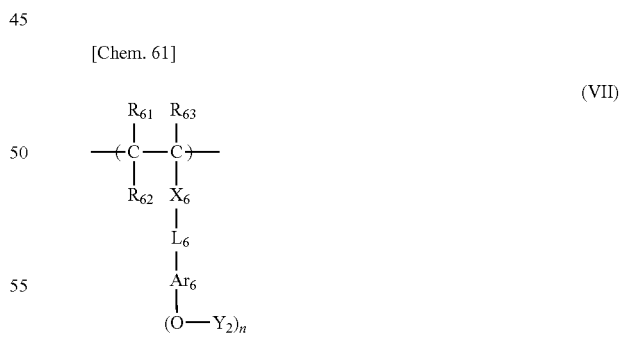

In formula (VII), each of $R_{61}$, $R_{62}$ and $R_{63}$ independently represents a hydrogen atom, an alkyl group, a cycloalkyl group, a halogen atom, a cyano group or an alkoxycarbonyl group. However, $R_{62}$ may combine with $Ar_6$ to form a ring and in this case, $R_{62}$ represents a single bond or an alkylene group.

$X_6$ represents a single bond, —COO— or —CONR$_{64}$—, wherein $R_{64}$ represents a hydrogen atom or an alkyl group.

$L_6$ represents a single bond or an alkylene group.

$Ar_6$ represents an (n+1)-valent aromatic ring group and in the case of combining with $R_{62}$ to form a ring, represents an (n+2)-valent aromatic ring group.

$Y_2$ represents, when n≥2, each independently represents, a hydrogen atom or a group capable of leaving by an action of an acid. However, at least one $Y_2$ represents a group capable of leaving by an action of an acid.

n represents an integer of 1 to 4.

Formula (VII) is described in more detail.

In formula (VII), the alkyl group of $R_{61}$ to $R_{63}$ is preferably an alkyl group having a carbon number of 20 or less, such as methyl group, ethyl group, propyl group, isopropyl group, n-butyl group, sec-butyl group, hexyl group, 2-ethylhexyl group, octyl group and dodecyl group, which may have a substituent, more preferably an alkyl group having a carbon number of 8 or less.

As the alkyl group contained in the alkoxycarbonyl group, the same alkyl group as that in $R_{61}$ to $R_{63}$ is preferred.

The cycloalkyl group may be either monocyclic or polycyclic and is preferably a monocyclic cycloalkyl group having a carbon number of 3 to 8, such as cyclopropyl group, cyclopentyl group and cyclohexyl group, which may have a substituent.

The halogen atom includes fluorine atom, chlorine atom, bromine atom and iodine atom, with fluorine atom being preferred.

In the case where $R_{62}$ represents an alkylene group, the alkylene group is preferably an alkylene group having a carbon atom of 1 to 8, such as methylene group, ethylene group, propylene group, butylene group, hexylene group and octylene group, which may have a substituent.

Examples of the alkyl group of $R_{64}$ in —CONR$_{64}$— ($R_{64}$ represents a hydrogen atom or an alkyl group) represented by $X_6$ are the same as those of the alkyl group of $R_{61}$ to $R_{63}$.

$X_6$ is preferably a single bond, —COO— or —CONH—, more preferably a single bond or —COO—.

The alkylene group of $L_6$ is preferably an alkylene group having a carbon number of 1 to 8, such as methylene group, ethylene group, propylene group, butylene group, hexylene group and octylene group, which may have a substituent. The ring formed by combining $R_{62}$ with $L_6$ is preferably a 5- or 6-membered ring.

$Ar_6$ represents an (n+1)-valent aromatic ring group. The divalent aromatic ring group when n is 1 may have a substituent, and preferable examples of the divalent aromatic ring group include an arylene group having a carbon number of 6 to 18, such as phenylene group, tolylene group and naphthylene group, and a divalent aromatic ring group containing a heterocyclic ring such as thiophene, furan, pyrrole, benzothiophene, benzofuran, benzopyrrole, triazine, imidazole, benzimidazole, triazole, thiadiazole and thiazole.

Specific examples of the (n+1)-valent aromatic ring group when n is an integer of 2 or more include the groups formed by removing arbitrary (n−1) hydrogen atoms from the above-described specific examples of the divalent aromatic ring group.

The (n+1)-valent aromatic ring group may further have a substituent.

Specific examples of the substituent that may be substituted on the above-described alkyl group, cycloalkyl group, alkoxycarbonyl group, alkylene group and (n+1)-valent aromatic ring group are the same as those of the substituent that may be substituted on each of the groups represented by $R_{51}$ to $R_{53}$ in formula (VI).

n is preferably 1 or 2, more preferably 1.

Each of n $Y_2$ independently represents a hydrogen atom or a group capable of leaving by an action of an acid. However, at least one of n $Y_2$ represents a group capable of leaving by an action of an acid.

The group $Y_2$ capable of leaving by an action of an acid includes, for example, —C($R_{36}$)($R_{37}$)($R_{38}$), —C(=O)—O—C($R_{36}$)($R_{37}$)($R_{38}$), —C($R_{01}$)($R_{02}$)(OR$_{39}$), —C($R_{01}$)($R_{02}$)—C(=O)—O—C($R_{36}$)($R_{37}$)($R_{38}$), and —CH($R_{36}$)(Ar).

In the formulae, each of $R_{36}$ to $R_{39}$ independently represents an alkyl group, a cycloalkyl group, a monovalent aromatic ring group, a group formed by combining an alkylene group with a monovalent aromatic ring group, or an alkenyl group. $R_{36}$ and $R_{37}$ may combine with each other to form a ring.

Each of $R_{01}$ and $R_{02}$ independently represents a hydrogen atom, an alkyl group, a cycloalkyl group, a monovalent aromatic ring group, a group formed by combining an alkylene group with a monovalent aromatic ring group, or an alkenyl group.

Ar represents a monovalent aromatic ring group.

The alkyl group of $R_{36}$ to $R_{39}$, $R_{01}$ and $R_{02}$ is preferably an alkyl group having a carbon number of 1 to 8, and examples thereof include a methyl group, an ethyl group, a propyl group, an n-butyl group, a sec-butyl group, a hexyl group, and an octyl group.

The cycloalkyl group of $R_{36}$ to $R_{39}$, $R_{01}$ and $R_{02}$ may be monocyclic or polycyclic. The monocyclic cycloalkyl group is preferably a cycloalkyl group having a carbon number of 3 to 8, and examples thereof include a cyclopropyl group, a cyclobutyl group, a cyclopentyl group, a cyclohexyl group, and a cyclooctyl group. The polycyclic cycloalkyl group is preferably a cycloalkyl group having a carbon number of 6 to 20, and examples thereof include an adamantyl group, a norbornyl group, an isoboronyl group, a camphanyl group, a dicyclopentyl group, an α-pinel group, a tricyclodecanyl group, a tetracyclododecyl group, and an androstanyl group. Incidentally, part of carbon atoms in the cycloalkyl group may be substituted with a heteroatom such as oxygen atom.

The monovalent aromatic ring group of $R_{36}$ to $R_{39}$, $R_{01}$, $R_{02}$ and Ar is preferably a monovalent aromatic ring group having a carbon number of 6 to 10, and examples thereof include an aryl group such as phenyl group, naphthyl group and anthryl group, and a divalent aromatic ring group containing a heterocyclic ring such as thiophene, furan, pyrrole, benzothiophene, benzofuran, benzopyrrole, triazine, imidazole, benzimidazole, triazole, thiadiazole and thiazole.

The group formed by combining an alkylene group with a monovalent aromatic ring group, represented by $R_{36}$ to $R_{39}$, $R_{01}$ and $R_{02}$, is preferably an aralkyl group having a carbon number of 7 to 12, and examples thereof include a benzyl group, a phenethyl group, and a naphthylmethyl group.

The alkenyl group of $R_{36}$ to $R_{39}$, $R_{01}$ and $R_{02}$ is preferably an alkenyl group having a carbon number of 2 to 8, and examples thereof include a vinyl group, an allyl group, a butenyl group, and a cyclohexenyl group.

The ring formed by combining $R_{36}$ and $R_{37}$ with each other may be either monocyclic or polycyclic. The monocyclic ring is preferably a cycloalkyl structure having a carbon number of 3 to 8, and examples thereof include a cyclopropane structure, a cyclobutane structure, a cyclopentane structure, a cyclohexane structure, a cycloheptane structure, and a cyclooctane structure. The polycyclic ring is preferably a cycloalkyl structure having a carbon number of 6 to 20, and examples thereof include an adamantane structure, a norbornane structure, a dicyclopentane structure, a tricyclodecane structure, and a tetracyclododecane structure. Incidentally, part of carbon atoms in the cycloalkyl structure may be substituted with a heteroatom such as oxygen atom.

Each of the groups above of $R_{36}$ to $R_{39}$, $R_{01}$, $R_{02}$ and Ar may have a substituent, and the substituent includes, for example, an alkyl group, a cycloalkyl group, an aryl group, an amino group, an amido group, a ureido group, a urethane group, a hydroxyl group, a carboxyl group, a halogen atom, an alkoxy group, a thioether group, an acyl group, an acyloxy group, an alkoxycarbonyl group, a cyano group, and a nitro group. The carbon number of the substituent is preferably 8 or less.

The resin (A) may also contain, as the repeating unit (a) a repeating unit represented by the following formula (BZ):

[Chem. 62]

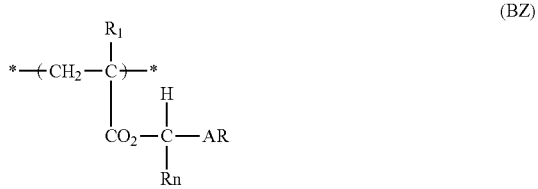

(BZ)

In formula (BZ), AR represents an aryl group, Rn represents an alkyl group, a cycloalkyl group or an aryl group, and Rn and AR may combine with each other to form a non-aromatic ring.

$R_1$ represents a hydrogen atom, an alkyl group, a cycloalkyl group, a halogen atom, a cyano group or an alkyloxycarbonyl group.

The aryl group of AR is preferably an aryl group having a carbon number of 6 to 20, such as phenyl group, naphthyl group, anthryl group and fluorene group, more preferably an aryl group having a carbon number of 6 to 15.

In the case where AR is a naphthyl group, an anthryl group or a fluorene group, the bonding site between AR and the carbon atom to which Rn is bonded is not particularly limited. For example, when AR is a naphthyl group, the carbon atom may be bonded to the α-position or the β-position of the naphthyl group, or when AR is an anthryl group, the carbon atom may be bonded to the 1-position, the 2-position or the 9-position of the anthryl group.

The aryl group of AR may have one or more substituents. Specific examples of the substituent include a linear or branched alky group having a carbon number of 1 to 20, such as methyl group, ethyl group, propyl group, isopropyl group, n-butyl group, isobutyl group, tert-butyl group, pentyl group, hexyl group, octyl group and dodecyl group, an alkoxy group containing such an alkyl group moiety, a cycloalkyl group such as cyclopentyl group and cyclohexyl group, a cycloalkyl group containing such a cycloalkyl group moiety, a hydroxyl group, a halogen atom, an aryl group, a cyano group, a nitro group, an acyl group, an acyloxy group, an acylamino group, a sulfonylamino group, an alkylthio group, an arylthio group, an aralkylthio group, a thiophenecarbonyloxy group, a thiophenemethylcarbonyloxy group, and a heterocyclic residue such as pyrrolidone residue. The substituent is preferably a linear or branched alkyl group having a carbon number of 1 to 5 or an alkoxy group containing such an alkyl group moiety, more preferably a para-methyl group or a para-methoxy group.

In the case where the aryl group of AR has a plurality of substituents, at least two members out of the plurality of substituents may combine with each other to form a ring. The ring is preferably a 5- to 8-membered ring, more preferably a 5- or 6-membered ring. The ring may be also a heterocyclic ring containing, in the ring member, a heteroatom such as oxygen atom, nitrogen atom and sulfur atom.

Furthermore, this ring may have a substituent. Examples of the substituent are the same as those described later for the further substituent that may be substituted on Rn.

In view of the roughness performance, the repeating unit (a) represented by formula (BZ) preferably contains two or more aromatic rings. Usually, the number of aromatic rings contained in this repeating unit is preferably 5 or less, more preferably 3 or less.

In addition, in view of the roughness performance, AR in the repeating unit (a) represented by formula (BZ) preferably contains two or more aromatic rings, and AR is more preferably a naphthyl group or a biphenyl group. Usually, the number of aromatic rings contained in AR is preferably 5 or less, more preferably 3 or less.

Rn represents an alkyl group, a cycloalkyl group or an aryl group as described above.

The alkyl group of Rn may be a linear alkyl group or a branched alkyl group. This alkyl group is preferably an alky group having a carbon number of 1 to 20, such as methyl group, ethyl group, propyl group, isopropyl group, n-butyl group, isobutyl group, tert-butyl group, pentyl group, hexyl group, cyclohexyl group, octyl group and dodecyl group. The alkyl group of Rn is preferably an alkyl group having a carbon number of 1 to 5, more preferably an alkyl group having a carbon number of 1 to 3.

The cycloalkyl group of Rn includes, for example, a cycloalkyl group having a carbon number of 3 to 15, such as cyclopentyl group and cyclohexyl group.

The aryl group of Rn is preferably, for example, an aryl group having a carbon number of 6 to 14, such as phenyl group, xylyl group, toluoyl group, cumenyl group, naphthyl group and anthryl group.

Each of the alkyl group, cycloalkyl group and aryl group as Rn may further have a substituent. The substituent includes, for example, an alkoxy group, a hydroxyl group, a halogen atom, a nitro group, an acyl group, an acyloxy group, an acylamino group, a sulfonylamino group, a dialkylamino group, an alkylthio group, an arylthio group, an aralkylthio group, a thiophenecarbonyloxy group, a thiophenemethylcarbonyloxy group, and a heterocyclic residue such as pyrrolidone residue. Among these, an alkoxy group, a hydroxyl group, a halogen atom, a nitro group, an acyl group, an acyloxy group, an acylamino group and a sulfonylamino group are preferred.

$R_1$ represents a hydrogen atom, an alkyl group, a cycloalkyl group, a halogen atom, a cyano group or an alkyloxycarbonyl group as described above.

Examples of the alkyl group and cycloalkyl group of $R_1$ are the same as those described above for Rn. Each of these alkyl group and cycloalkyl group may have a substituent. Examples of this substituent are the same as those described above for Rn.

In the case where $R_1$ is an alkyl or cycloalkyl group having a substituent, particularly preferable examples of $R_1$ include a trifluoromethyl group, an alkyloxycarbonylmethyl group, an alkylcarbonyloxymethyl group, a hydroxymethyl group, and an alkoxymethyl group.

The halogen atom of $R_1$ includes fluorine atom, chlorine atom, bromine atom and iodine atom, with fluorine atom being preferred.

As the alkyl group moiety contained in the alkyloxycarbonyl group of $R_1$, for example, the configuration recited above as the alkyl group of $R_1$ may be employed.

Rn and AR preferably combine with each other to form a non-aromatic ring and in this case, particularly the roughness performance can be more improved.

The non-aromatic ring that may be formed by combining Rn and AR with each other is preferably a 5- to 8-membered ring, more preferably a 5- or 6-membered ring.

The non-aromatic ring may be an aliphatic ring or a heterocyclic ring containing, as a ring member, a heteroatom such as oxygen atom, nitrogen atom and sulfur atom.

The non-aromatic ring may have a substituent. Examples of the substituent are the same as those described above for the further substituent that may be substituted on Rn.

Specific examples of the repeating unit (a) represented by formula (BZ) are illustrated below, but the present invention is not limited thereto.

[Chem. 63]

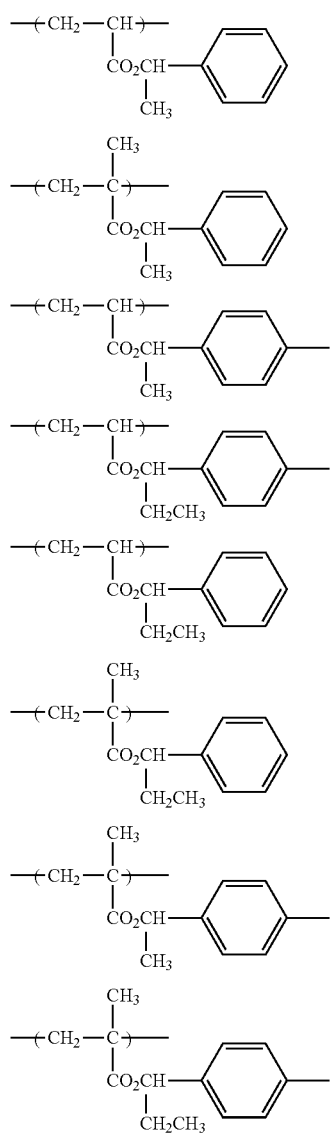

[Chem. 64]

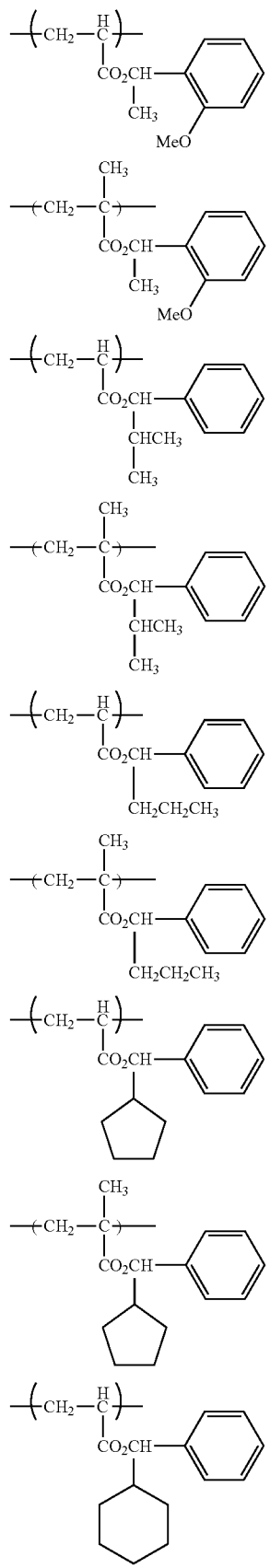

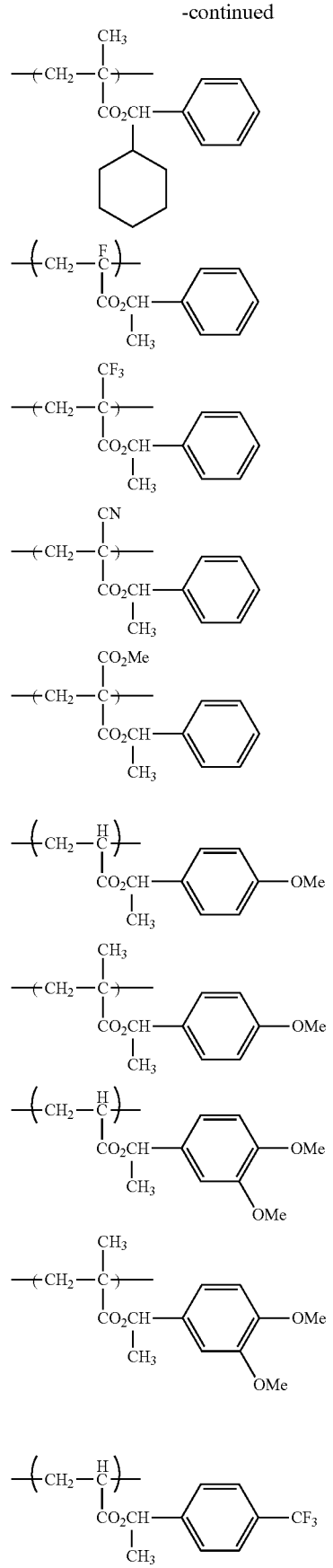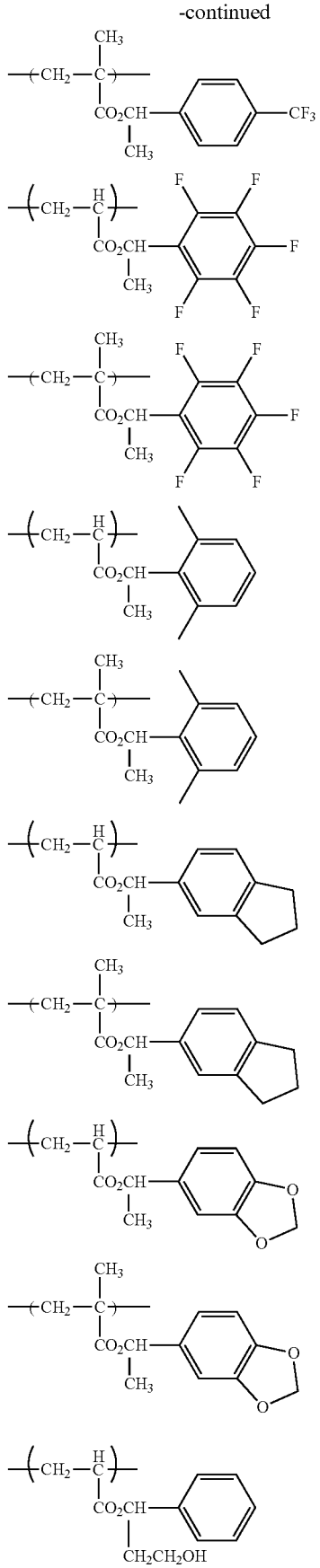

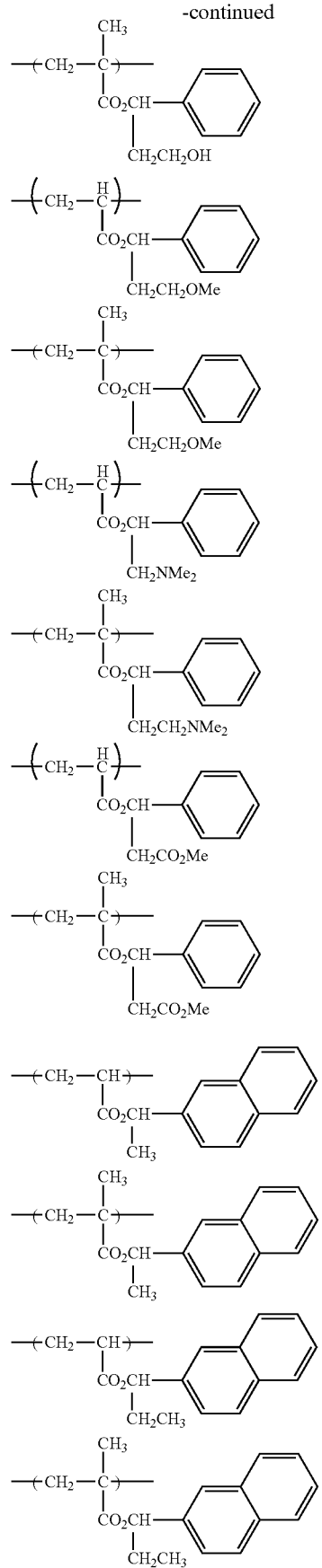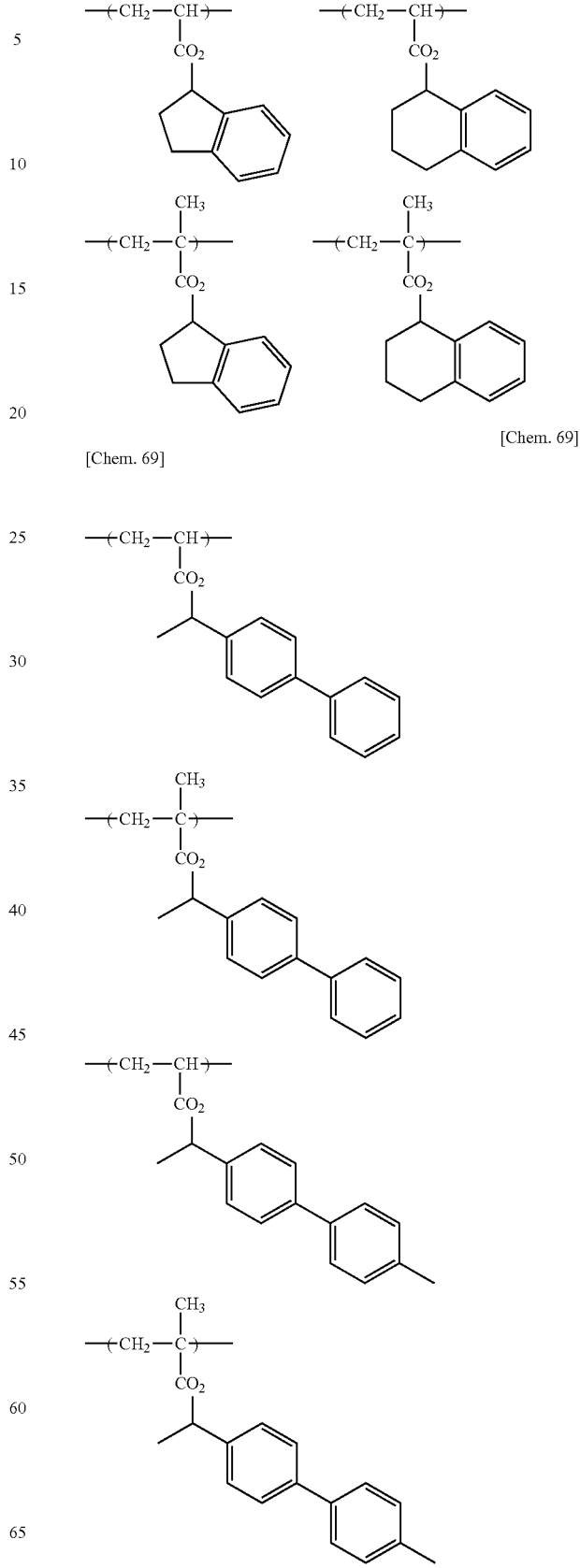

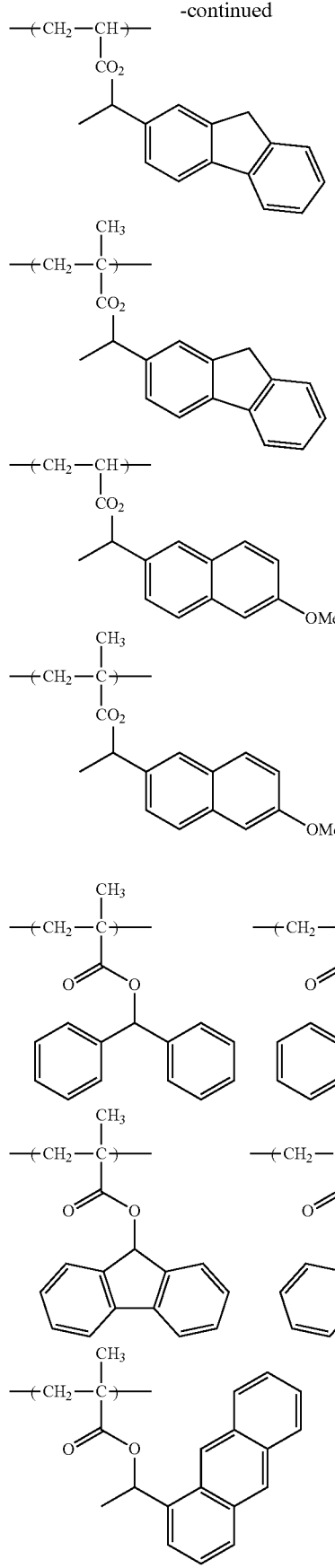
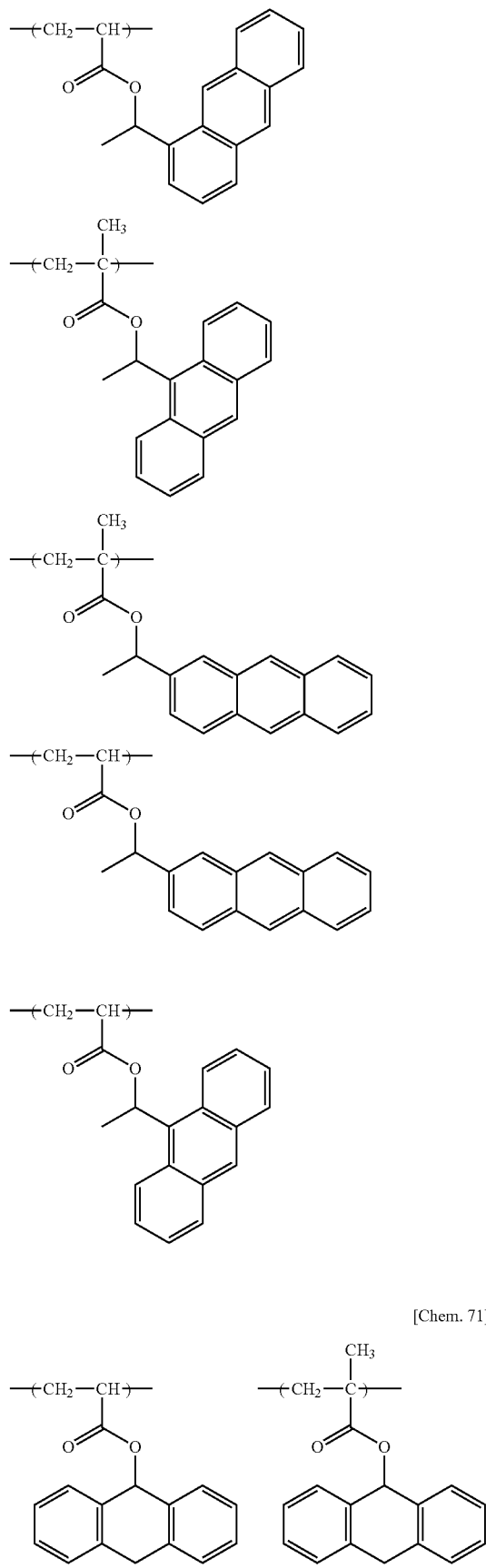

-continued

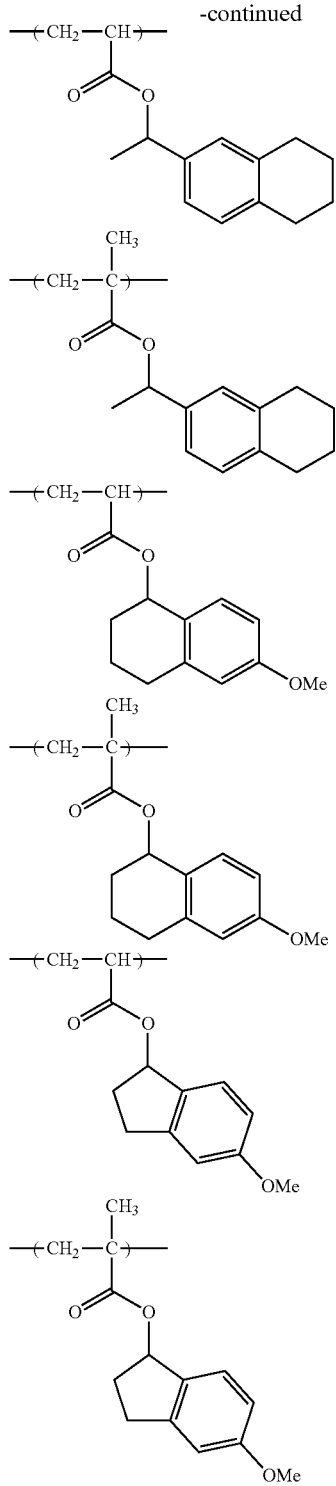

As an embodiment of the acid-decomposable group-containing repeating unit different from the repeating units exemplified above, the repeating unit may be in an embodiment of decomposing by an action of an acid to produce an alcoholic hydroxyl group. In this case, the repeating unit is preferably represented by any one of the following formulae (I-1) to (I-10). This repeating unit is more preferably represented by any one of the following formulae (I-1) to (I-3), still more preferably represented by the following formula (I-1).

[Chem. 72]

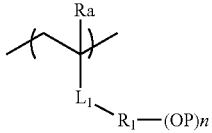   (I-1)

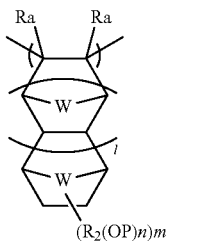   (I-2)

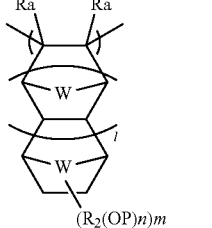   (I-3)

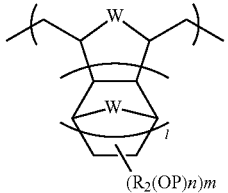   (I-4)

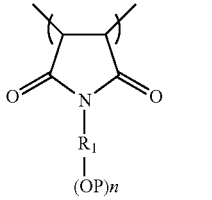   (I-5)

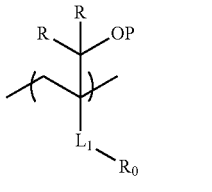   (I-6)

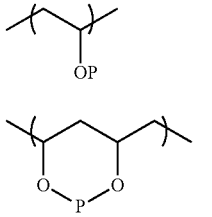   (I-7)

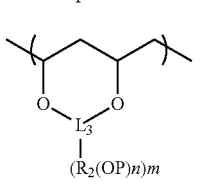   (I-8)

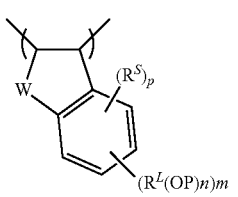   (I-9)

-continued

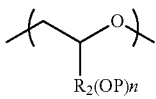
(I-10)

In the formulae, each Ra independently represents a hydrogen atom, an alkyl group or a group represented by —CH₂—O—Ra₂, wherein Ra₂ represents a hydrogen atom, an alkyl group or an acyl group.

$R_1$ represents an (n+1)-valent organic group.

$R_2$ represents, when m≥2, each independently represents, a single bond or an (n+1)-valent organic group.

Each OP independently represents the above-described group capable of decomposing by an action of an acid to produce an alcoholic hydroxy group, and when n≥2 and/or m≥2, two or more OP may combine with each other to form a ring.

W represents a methylene group, an oxygen atom or a sulfur atom.

Each of n and m represents an integer of 1 or more. Incidentally, in the case where $R_2$ in formula (I-2), (I-3) or (I-8) represents a single bond, n is 1.

l represents an integer of 0 or more.

$L_1$ represents a linking group represented by —COO—, —OCO—, —CONH—, —O—, —Ar—, —SO₃— or —SO₂NH—, wherein Ar represents a divalent aromatic ring group.

Each R independently represents a hydrogen atom or an alkyl group.

$R_0$ represents a hydrogen atom or an organic group.

$L_3$ represents an (m+2)-valent linking group.

$R^L$ represents, when m≥2, each independently represents, an (n+1)-valent linking group.

$R^S$ represents, when p≥2, each independently represents, a substituent, and when p≥2, the plurality of $R^S$ may combine with each other to form a ring.

p represents an integer of 0 to 3.

Ra represents a hydrogen atom, an alkyl group or a group represented by —CH₂—O—Ra₂. Ra is preferably a hydrogen atom or an alkyl group having a carbon number of 1 to 10, more preferably a hydrogen or a methyl group.

W represents a methylene group, an oxygen atom or a sulfur atom. W is preferably a methylene group or an oxygen atom.

$R_1$ represents an (n+1)-valent organic group. $R_1$ is preferably a non-aromatic hydrocarbon group. In this case, $R_1$ may be a chain hydrocarbon group or an alicyclic hydrocarbon group. $R_1$ is more preferably an alicyclic hydrocarbon group.

$R_2$ represents a single bond or an (n+1)-valent organic group. $R_2$ is preferably a single bond or a non-aromatic hydrocarbon group. In this case, $R_2$ may be a chain hydrocarbon group or an alicyclic hydrocarbon group.

In the case where $R_1$ and/or $R_2$ are a chain hydrocarbon group, this chain hydrocarbon group may be linear or branched. The carbon number of the chain hydrocarbon group is preferably from 1 to 8. For example, when $R_1$ and/or $R_2$ are an alkylene group, $R_1$ and/or $R_2$ are preferably a methylene group, an ethylene group, an n-propylene group, an isopropylene group, an n-butylene group, an isobutylene group or a sec-butylene group.

In the case where $R_1$ and/or $R_2$ are an alicyclic hydrocarbon group, this alicyclic hydrocarbon group may be monocyclic or polycyclic. The alicylcic hydrocarbon group has, for example, a monocyclo, bicyclo, tricyclo or tetracyclo structure. The carbon number of the alicyclic hydrocarbon group is usually 5 or more, preferably from 6 to 30, more preferably from 7 to 25.

The alicyclic hydrocarbon group includes, for example, those having partial structures recited below. Each of these partial structures may have a substituent. Furthermore, in each of these partial structures, the methylene group (—CH₂—) may be substituted with an oxygen atom (—O—), a sulfur atom (—S—), a carbonyl group [—C(=O)—], a sulfonyl group [—S(=O)₂—], a sulfinyl group [—S(=O)—] or an imino group [—N(R)—] (wherein R is a hydrogen atom or an alkyl group).

[Chem. 73]

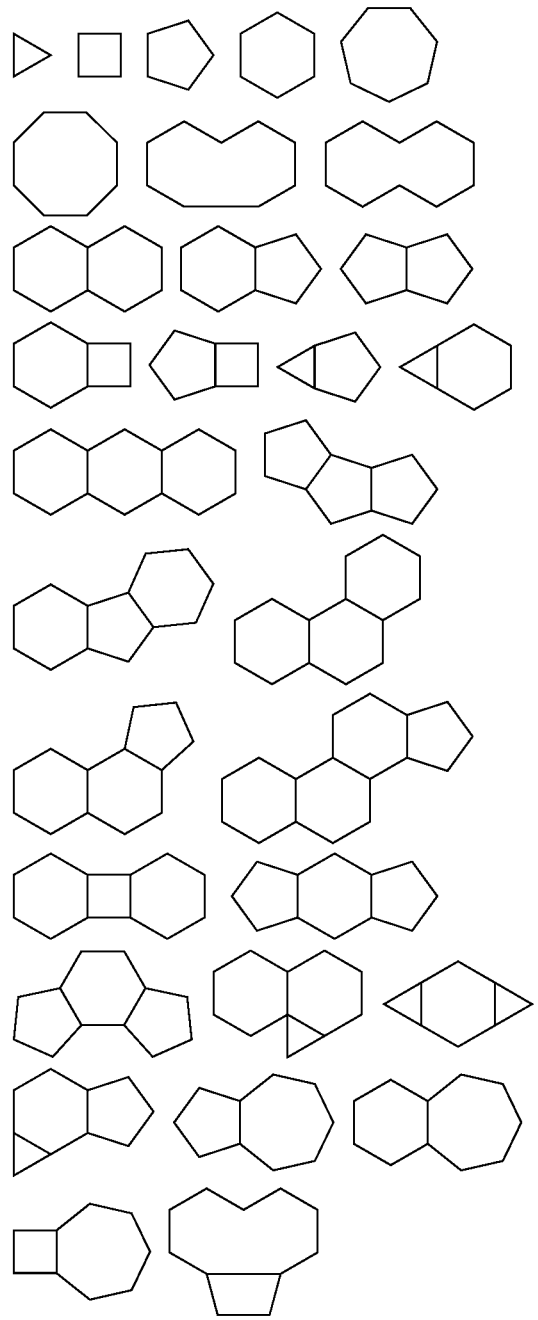

-continued

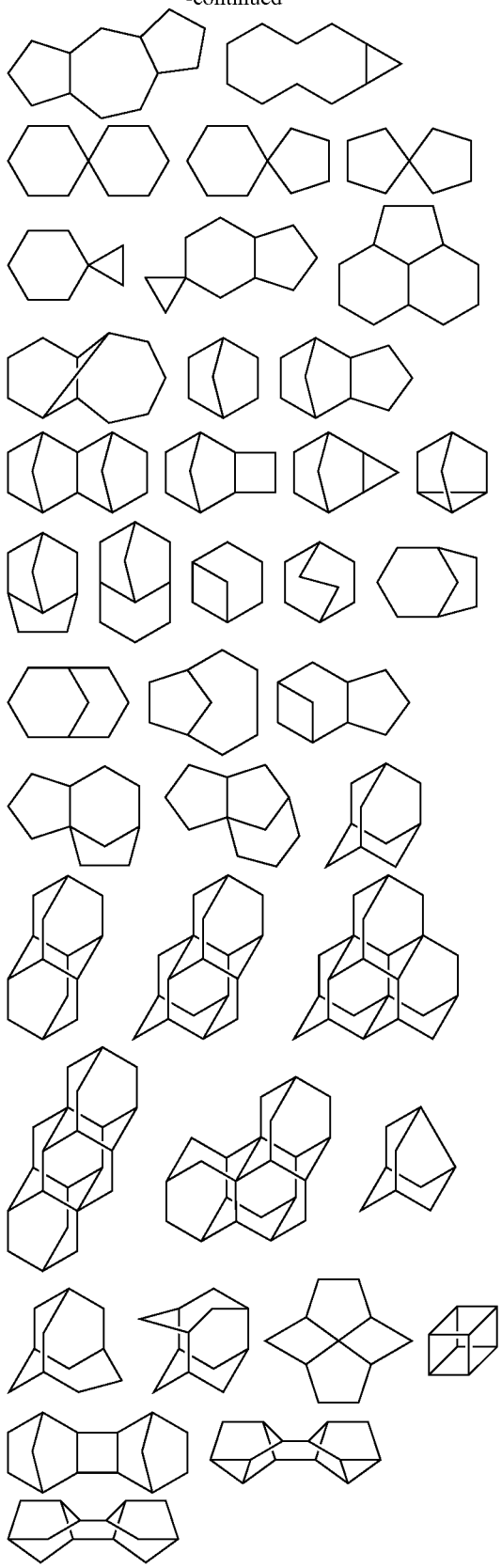

For example, when $R_1$ and/or $R_2$ are a cycloalkylene group, $R_1$ and/or $R_2$ are preferably an adamantylene group, a noradamantylene group, a decahydronaphthylene group, a tricyclodecanylene group, a tetracyclododecanylene group, a norbornylene group, a cyclopentylene group, a cyclohexylene group, a cycloheptylene group, a cyclooctylene group, a cyclodecanylene group or a cyclododecanylene group, more preferably an adamantylene group, a norbornylene group, a cyclohexylene group, a cyclopentylene group, a tetracyclododecanylene group or a tricyclodecanylene group.

The non-aromatic hydrocarbon group of $R_1$ and/or $R_2$ may have a substituent. This substituent includes, for example, an alkyl group having a carbon number of 1 to 4, a halogen atom, a hydroxy group, an alkoxy group having a carbon number of 1 to 4, a carboxy group, and an alkoxycarbonyl group having a carbon number of 2 to 6. These alkyl group, alkoxy group and alkoxycarbonyl group may further have a substituent, and the substituent includes, for example, a hydroxy group, a halogen atom and an alkoxy group.

$L_1$ represents a linking group represented by —COO—, —OCO—, —CONH—, —O—, —Ar—, —SO$_3$— or —SO$_2$NH—, wherein Ar represents a divalent aromatic ring group. $L_1$ is preferably a linking group represented by —COO—, —CONH— or —Ar—, more preferably a linking group represented by —COO— or —CONH—.

R represents a hydrogen atom or an alkyl group. The alkyl group may be linear or branched. The carbon number of this alkyl group is preferably from 1 to 6, more preferably from 1 to 3. R is preferably a hydrogen atom or a methyl group, more preferably a hydrogen atom.

$R_0$ represents a hydrogen atom or an organic group. The organic group includes, for example, an alkyl group, a cycloalkyl group, an aryl group, an alkynyl group, and an alkenyl group. $R_0$ is preferably a hydrogen atom or an alkyl group, more preferably a hydrogen atom or a methyl group.

$L_3$ represents an (m+2)-valent linking group. That is, $L_3$ represents a trivalent or higher valent linking group. Such a linking group includes, for example, corresponding groups in specific examples illustrated later.

$R^L$ represents an (n+1)-valent linking group. That is, $R^L$ represents a divalent or higher valent linking group. Such a linking group includes, for example, an alkylene group, a cycloalkylene group, and corresponding groups in specific examples illustrated later. $R^L$ may combine with another $R^L$ or $R^S$ to form a ring structure.

$R^S$ represents a substituent. The substituent includes, for example, an alkyl group, an alkenyl group, an alkynyl group, an aryl group, an alkoxy group, an acyloxy group, an alkoxycarbonyl group, and a halogen atom.

n is an integer of 1 or more. n is preferably an integer of 1 to 3, more preferably 1 or 2. In addition, when n is an integer of 2 or more, the dissolution contrast for an organic solvent-containing developer can be more enhanced and in turn, the limiting resolution and roughness characteristics can be more improved.

m is an integer of 1 or more. m is preferably an integer of 1 to 3, more preferably 1 or 2.

l is an integer of 0 or more. l is preferably 0 or 1.

p is an integer of 0 to 3.

Specific examples of the repeating unit having a group capable of decomposing by an action of an acid to produce an alcoholic hydroxy group are illustrated below. In specific examples, Ra and OP have the same meanings as respective members in formulae (I-1) to (I-3). In the case where a plurality of OP combine with each other to form a ring, the corresponding ring structure is conveniently denoted by "O—P—O".

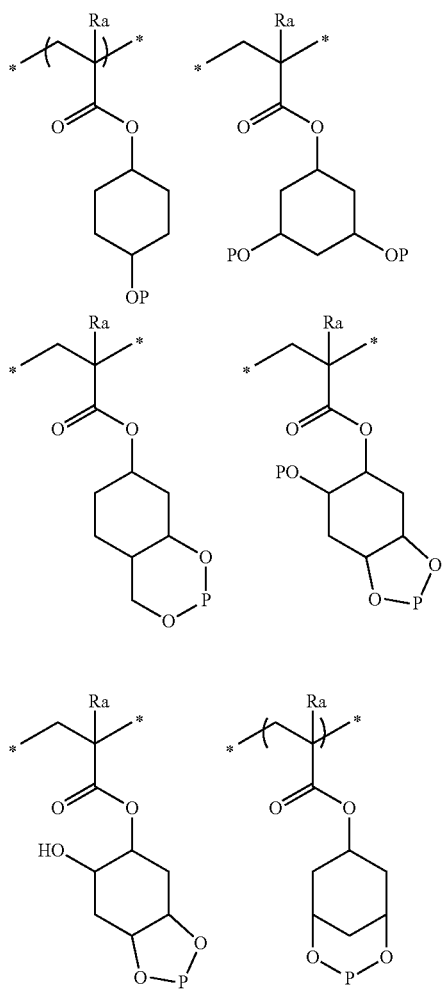
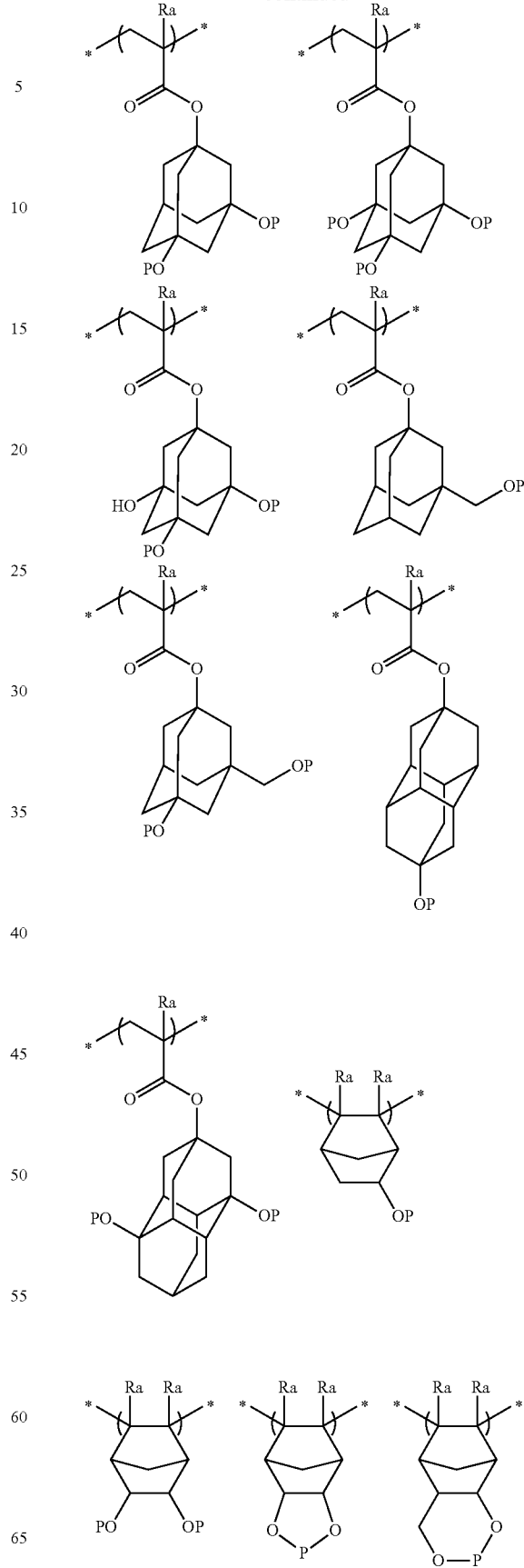

-continued

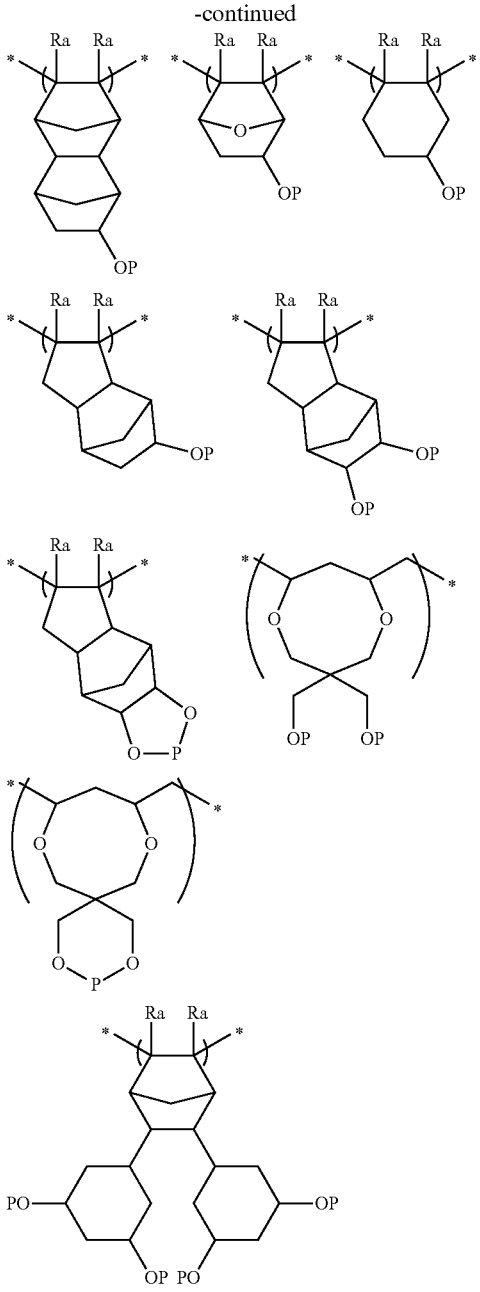

The group capable of decomposing by an action of an acid to produce an alcoholic hydroxy group is preferably represented by any one of the following formulae (II-1) to (II-4):

[Chem. 75]

(II-1)

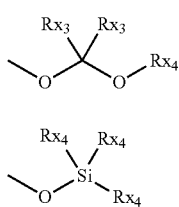

(II-2)

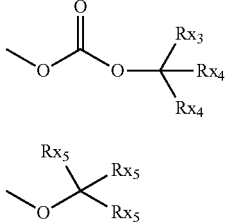

-continued (II-3)

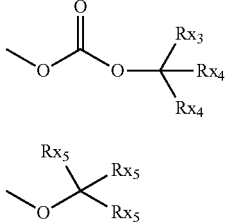

(II-4)

In the formulae, each $Rx_3$ independently represents a hydrogen atom or a monovalent organic group. $Rx_3$ may combine with each other to form a ring.

Each $Rx_4$ independently represents a monovalent organic group. $Rx_4$ may combine with each other to form a ring. $Rx_3$ and $Rx_4$ may combine with each other to form a ring.

Each $Rx_5$ independently represents a hydrogen atom, an alkyl group, a cycloalkyl group, an aryl group, an alkenyl group or an alkynyl group. At least two $Rx_5$ may combine with each other to form a ring, provided that when one or two of those three $Rx_5$ are a hydrogen atom, at least one of the remaining $Rx_5$ represents an aryl group, an alkenyl group or an alkynyl group.

It is also preferred that the group capable of decomposing by an action of an acid to produce an alcoholic hydroxy group is represented by any one of the following formulae (II-5) to (II-9):

[Chem. 76]

(II-5)

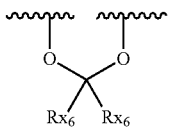

(II-6)

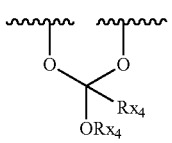

(II-7)

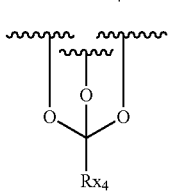

(II-8)

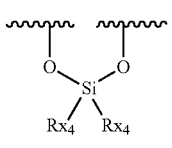

(II-9)

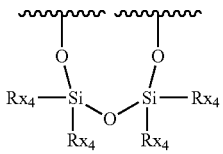

In the formulae, $Rx_4$ has the same meaning as in formulae (II-1) to (II-3).

Each $Rx_6$ independently represents a hydrogen atom or a monovalent organic group. $Rx_6$ may combine with each other to form a ring.

The group capable of decomposing by an action of an acid to produce an alcoholic hydroxy group is more preferably represented by any one of formulae (II-1) to (II-3), still more preferably represented by formula (II-1) or (II-3), yet still more preferably represented by formula (II-1).

$Rx_3$ represents a hydrogen atom or a monovalent organic group as described above. $Rx_3$ is preferably a hydrogen atom, an alkyl group or a cycloalkyl group, more preferably a hydrogen atom or an alkyl group.

The alkyl group of $Rx_3$ may be linear or branched. The carbon number of the alkyl group of $Rx_3$ is preferably from 1 to 10, more preferably from 1 to 3. The alkyl group of $Rx_3$ includes, for example, a methyl group, an ethyl group, an n-propyl group, an isopropyl group, and an n-butyl group.

The cycloalkyl group of $Rx_3$ may be monocyclic or polycyclic. The carbon number of the cycloalkyl group of $Rx_3$ is preferably from 3 to 10, more preferably from 4 to 8. The cycloalkyl group of $Rx_3$ includes, for example, a cyclopropyl group, a cyclobutyl group, a cyclopentyl group, a cyclohexyl group, a norbornyl group, and an adamantyl group.

In formula (II-1), at least either one $Rx_3$ is preferably a monovalent organic group. When such a configuration is employed, high sensitivity can be achieved, among others.

$Rx_4$ represents a monovalent organic group. $Rx_4$ is preferably an alkyl group or a cycloalkyl group, more preferably an alkyl group. These alkyl group and cycloalkyl group may have a substituent.

The alkyl group of $Rx_4$ preferably has no substituent or has one or more aryl groups and/or one or more silyl groups as the substituent. The carbon number of the unsubstituted alkyl group is preferably from 1 to 20. The carbon number of the alkyl group moiety in the alkyl group substituted with one or more aryl groups is preferably from 1 to 25. The carbon number of the alkyl group moiety in the alkyl group substituted with one or more silyl groups is preferably from 1 to 30. In the case where the cycloalkyl group of $Rx_4$ does not have a substituent, the carbon number thereof is preferably from 3 to 20.

$Rx_5$ represents a hydrogen atom, an alkyl group, a cycloalkyl group, an aryl group, an alkenyl group or an alkynyl group. However, when one or two of those three $Rx_5$ are a hydrogen atom, at least one of the remaining $Rx_5$ represents an aryl group, an alkenyl group or an alkynyl group. $Rx_5$ is preferably a hydrogen atom or an alkyl group. The alkyl group may or may not have a substituent. In the case where the alkyl group does not have a substituent, the carbon number thereof is preferably from 1 to 6, more preferably from 1 to 3.

$Rx_6$ represents a hydrogen atom or a monovalent organic group as described above. $Rx_6$ is preferably a hydrogen atom, an alkyl group or a cycloalkyl group, more preferably a hydrogen atom or an alkyl group, still more preferably a hydrogen atom or an alkyl group having no substituent. $Rx_6$ is preferably a hydrogen atom or an alkyl group having a carbon number of 1 to 10, more preferably a hydrogen atom or an alkyl group having a carbon number of 1 to 10 and having no substituent.

Examples of the alkyl group and cycloalkyl group of $Rx_4$, $Rx_5$ and $Rx_6$ are the same as those described above for $Rx_3$.

Specific examples of the group capable of decomposing by an action of an acid to produce an alcoholic hydroxyl group are illustrated below.

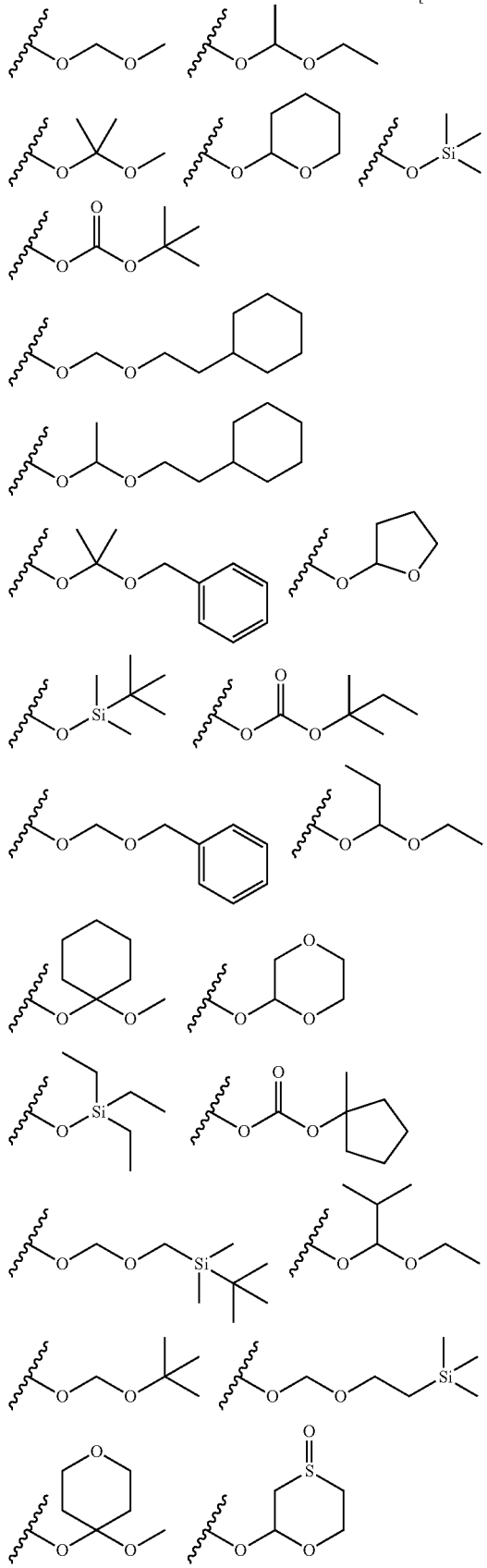

[Chem. 77]

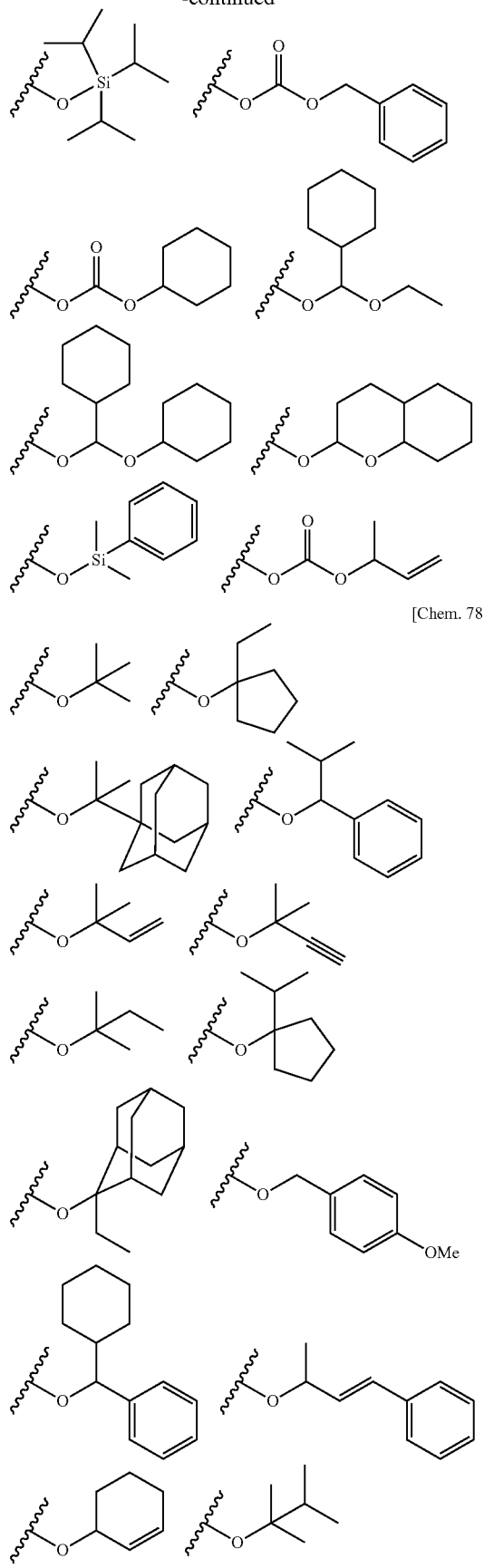
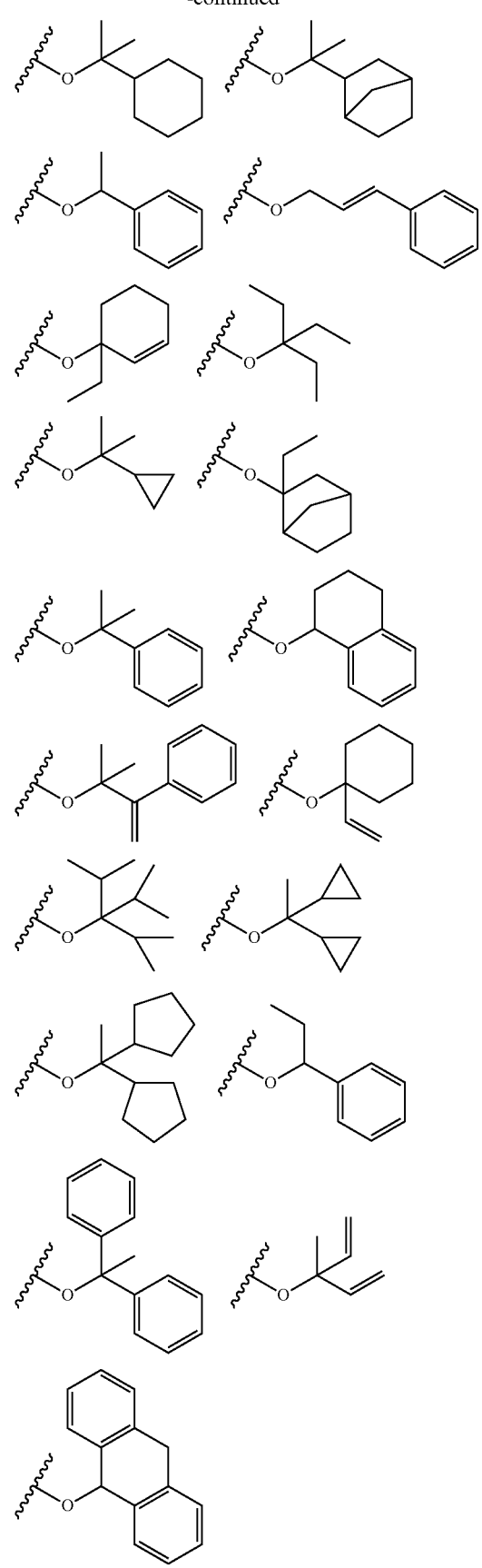

[Chem. 79]
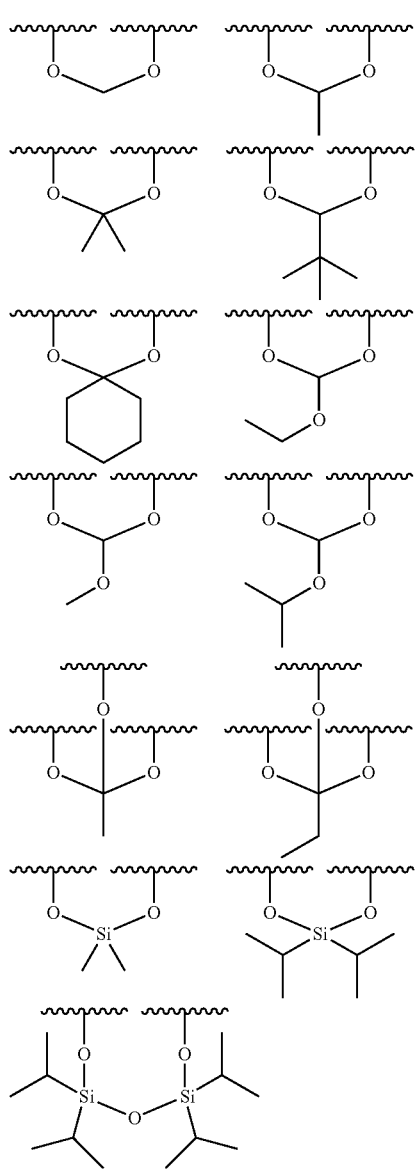
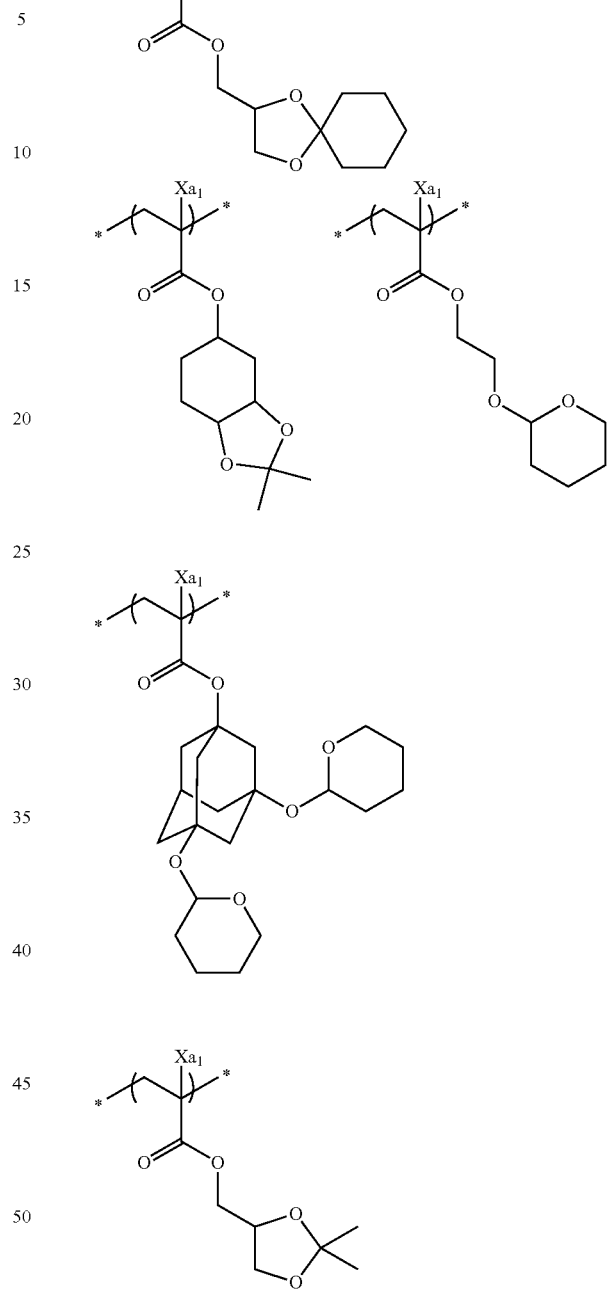
Specific examples of the repeating unit having a group capable of decomposing by an action of an acid to produce an alcoholic hydroxy group are illustrated below. In specific examples, $Xa_1$ represents a hydrogen atom, $CH_3$, $CF_3$ or $CH_2OH$.
[Chem. 80]
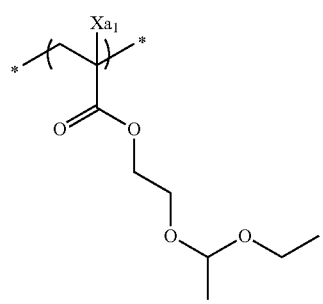
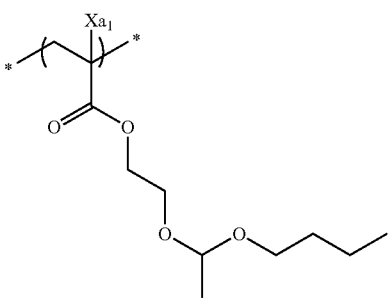

175
-continued

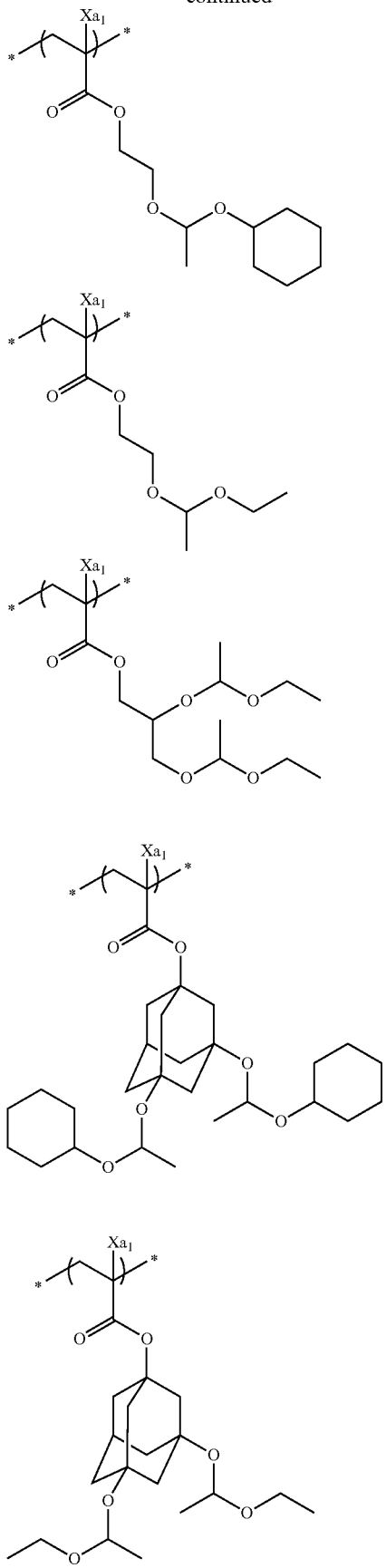

176
-continued

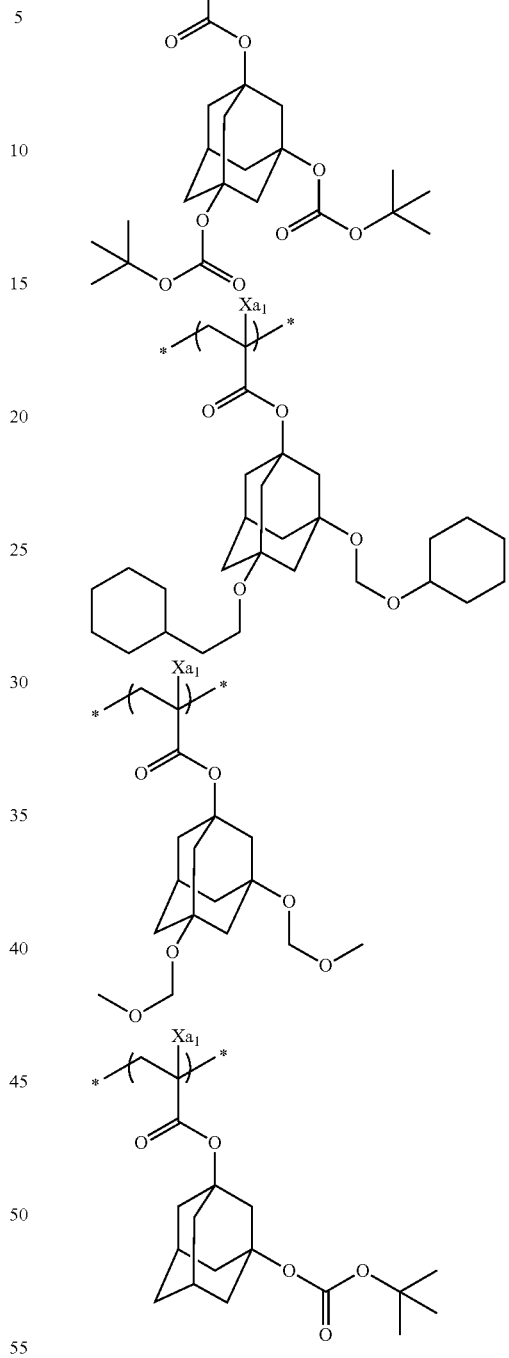

As for the repeating unit (a) having an acid-decomposable group, one kind may be used, or two more kinds may be used in combination.

The content of the repeating unit (a) having an acid-decomposable group (in the case of containing a plurality of kinds of repeating units, the total thereof) in the resin (A) is preferably from 5 to 90 mol %, more preferably from 5 to 80 mol %, still more preferably from 10 to 70 mol %, relative to all repeating units in the resin (A).

The resin (A) preferably contains (b) a repeating unit having a polar group. By containing the repeating unit (b), for example, the sensitivity of the composition containing the resin can be enhanced. The repeating unit (b) is preferably a non-acid-decomposable repeating unit (that is, preferably has no acid-decomposable group).

The "polar group" that can be contained in the repeating unit (b) includes, for example, the following (1) to (4). In the following, the "electronegativity" means a Pauling's value.

(1) Functional Group Containing a Structure where an Oxygen Atom and an Atom Having an Electronegativity Difference from Oxygen Atom of 1.1 or More are Bonded Through a Single Bond This polar group includes, for example, a group containing a structure represented by O—H such as hydroxy group.

(2) Functional Group Containing a Structure where a Nitrogen Atom and an Atom Having an Electronegativity Difference from Nitrogen Atom of 0.6 or More are Bonded Through a Single Bond This polar group includes, for example, a group containing a structure represented by N—H such as amino group.

(3) Functional Group Containing a Structure where Two Atoms Differing in the Electronegativity by 0.5 or More are Bonded Through a Double Bond or a Triple Bond This polar group includes, for example, a group containing a structure represented by C≡N, C═O, N═O, S═O or C═N.

(4) Functional Group Having an Ionic Moiety

This polar group includes, for example, a group having a moiety represented by $N^+$ or $S^+$.

Specific examples of the partial structure that can be contained in the "polar group" are illustrated below. In the following specific examples, $X^-$ represents a counter anion.

[Chem. 81]

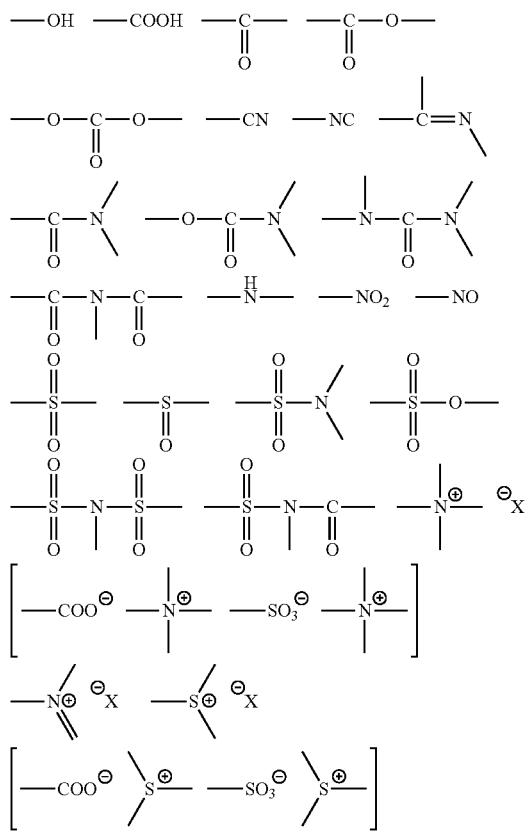

The "polar group" that can be contained in the repeating unit (b) is preferably, for example, at least one selected from the group consisting of (I) a hydroxy group, (II) a cyano group, (III) a lactone group, (IV) a carboxylic acid group or a sulfonic acid group, (V) an amide group, a sulfonamide group or a group corresponding to a derivative thereof, (VI) an ammonium group or a sulfonium group, and a group formed by combining two or more thereof.

The polar group is preferably selected from a hydroxyl group, a cyano group, a lactone group, a carboxylic acid group, a sulfonic acid group, an amide group, a sulfonamide group, an ammonium group, a sulfonium group, and a group formed by combining two or more thereof, more preferably an alcoholic hydroxy group, a cyano group, a lactone group, or a cyanolactone structure-containing group.

When a repeating unit having an alcoholic hydroxy group is further incorporated into the resin, the exposure latitude (EL) of a composition containing the resin can be more enhanced.

When a repeating unit having a cyano group is further incorporated into the resin, the sensitivity of a composition containing the resin can be more enhanced.

When a repeating unit having a lactone group is further incorporated into the resin, the dissolution contrast for an organic solvent-containing developer can be more enhanced. In addition, the composition containing the resin can also be more improved in the dry etching resistance, coatability and adherence to substrate.

When a repeating unit having a group containing a cyano group-containing lactone structure is further incorporated into the resin, the dissolution contrast for an organic solvent-containing developer can be more enhanced. In addition, the composition containing the resin can also be further improved in the sensitivity, dry etching resistance, coatability and adherence to substrate. Furthermore, a single repeating unit can play functions attributable to a cyano group and a lactone group, respectively, and the latitude in designing the resin can be more broadened.

In the case where the polar group contained in the repeating unit (b) is an alcoholic hydroxy group, the repeating unit is preferably represented by any one of the following formulae (I-1H) to (I-10H), more preferably represented by any one of the following formulae (I-1H) to (I-3H), still more preferably represented by the following formula (I-1H):

[Chem. 82]

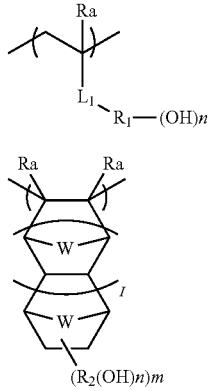

-continued (I-3H)
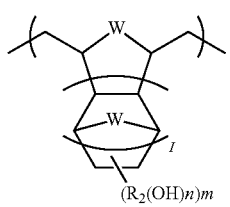

(I-4H)
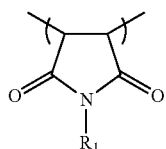

(I-5H)
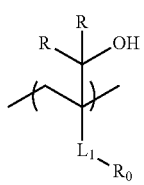

(I-6H)
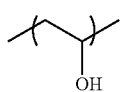

(I-7H)
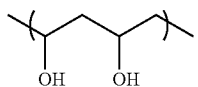

(I-8H)
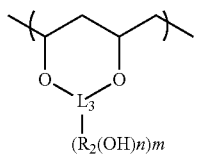

(I-9H)
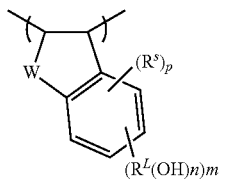

(I-10H)
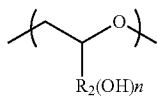

In the formulae, Ra, $R_1$, $R_2$, W, n, m, l, $L_1$, R, $R_0$, $L_3$, $R^L$, $R^S$ and p have the same meanings as respective members in formulae (I-1) to (I-10).

When a repeating unit having a group capable of decomposing by an action of an acid to produce an alcoholic hydroxy group and a repeating unit represented by any one of formulae (I-1H) to (I-10H) are used in combination, for example, acid diffusion is suppressed by the alcoholic hydroxy group, and the sensitivity is increased by the group capable of decomposing by an action of an acid to produce an alcoholic hydroxy group, so that the exposure latitude (EL) can be improved without deteriorating other performances.

The content percentage of the repeating unit having an alcoholic hydroxy group is preferably from 1 to 60 mol %, more preferably from 3 to 50 mol %, still more preferably from 5 to 40 mol %, relative to all repeating units in the resin (A).

Specific examples of the repeating unit represented by any one of formulae (I-1H) to (I-10H) are illustrated below. In specific examples, Ra has the same meaning as that in formulae (I-1H) to (I-10H).

[Chem. 83]

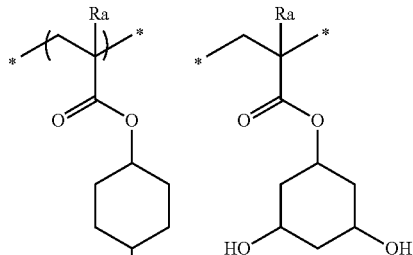
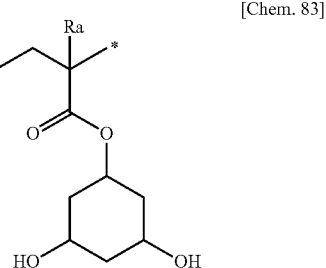
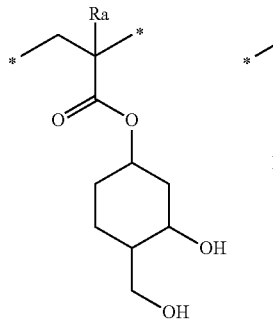
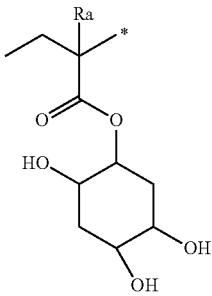
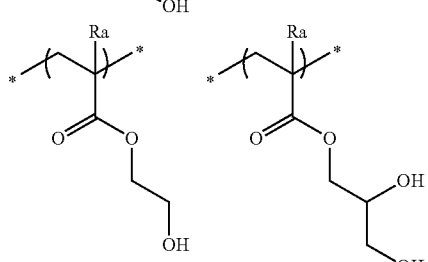
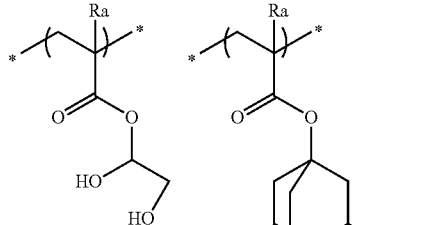
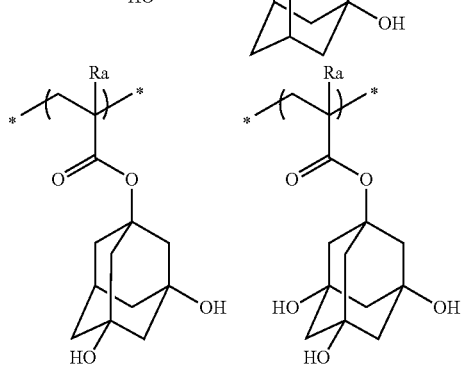

-continued

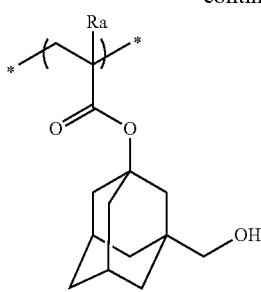
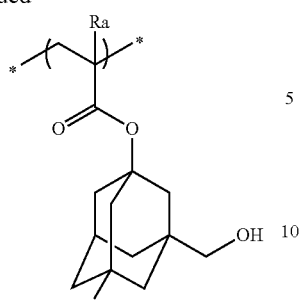
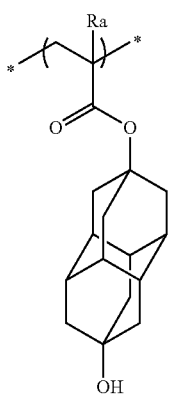
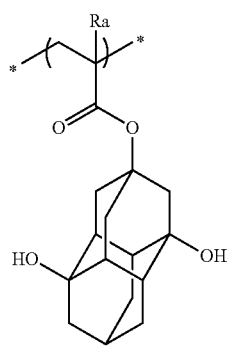
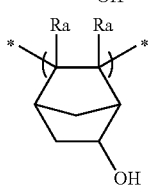
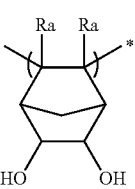
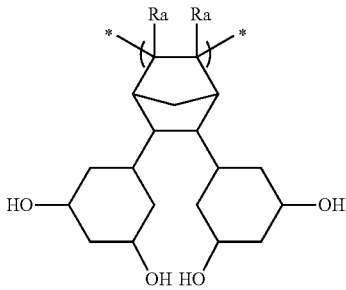
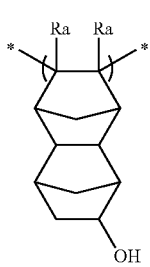
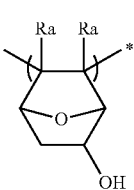
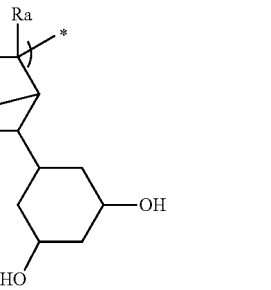

-continued

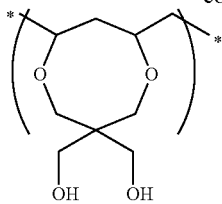

In the case where the polar group contained in the repeating unit (b) is an alcoholic hydroxy group or a cyano group, one preferred embodiment of the repeating unit is a repeating unit having an alicyclic hydrocarbon structure substituted with a hydroxyl group or a cyano group. At this time, the repeating unit preferably has no acid-decomposable group. The alicyclic hydrocarbon structure in the alicyclic hydrocarbon structure substituted with a hydroxyl group or a cyano group is preferably an adamantyl group, a diamantyl group or a norbornane group. The alicyclic hydrocarbon structure substituted with a hydroxyl group or a cyano group is preferably a partial structure represented by the following formulae (VIIa) to (VIIc). Thanks to this repeating unit, adherence to substrate and affinity for developer are enhanced.

[Chem. 84]

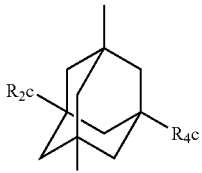
(VIIa)

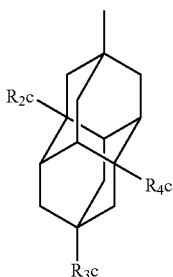
(VIIb)

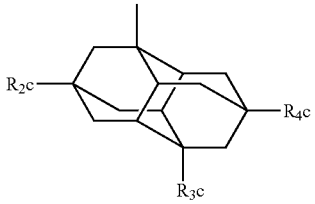
(VIIc)

In formulae (VIIa) to (VIIc), each of $R_2c$ to $R_4c$ independently represents a hydrogen atom, a hydroxyl group or a cyano group, provided that at least one of $R_2c$ to $R_4c$ represents a hydroxyl group. A structure where one or two members out of $R_2c$ to $R_4c$ are a hydroxyl group, with the remaining being a hydrogen atom, is preferred. In formula (VIIa), it is more preferred that two members out of $R_2c$ to $R_4c$ are a hydroxyl group and the remaining is a hydrogen atom.

The repeating unit having a partial structure represented by formulae (VIIa) to (VIIc) includes repeating units represented by the following formulae (AIIa) to (AIIc):

[Chem. 85]

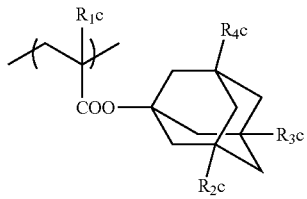

(AIIa)

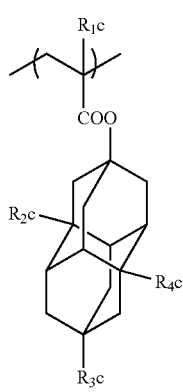

(AIIb)

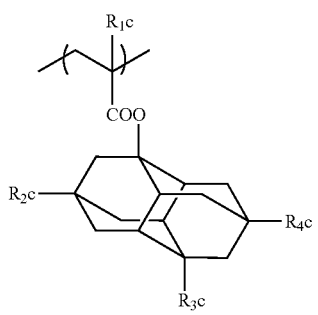

(AIIc)

In formulae (AIIa) to (AIIc), $R_1c$ represents a hydrogen atom, a methyl group, a trifluoromethyl group or a hydroxymethyl group.

$R_2c$ to $R_4c$ have the same meanings as $R_2c$ to $R_4c$ in formulae (VIIa) to (VIIc).

The resin (A) may or may not contain a repeating unit having a hydroxyl group or a cyano group, but in the case of containing a repeating unit having a hydroxyl group or a cyano group, the content thereof is preferably from 1 to 60 mol %, more preferably from 3 to 50 mol %, still more preferably from 5 to 40 mol %, relative to all repeating units in the resin (A).

Specific examples of the repeating unit having a hydroxyl group or a cyano group are illustrated below, but the present invention is not limited thereto.

[Chem. 86]

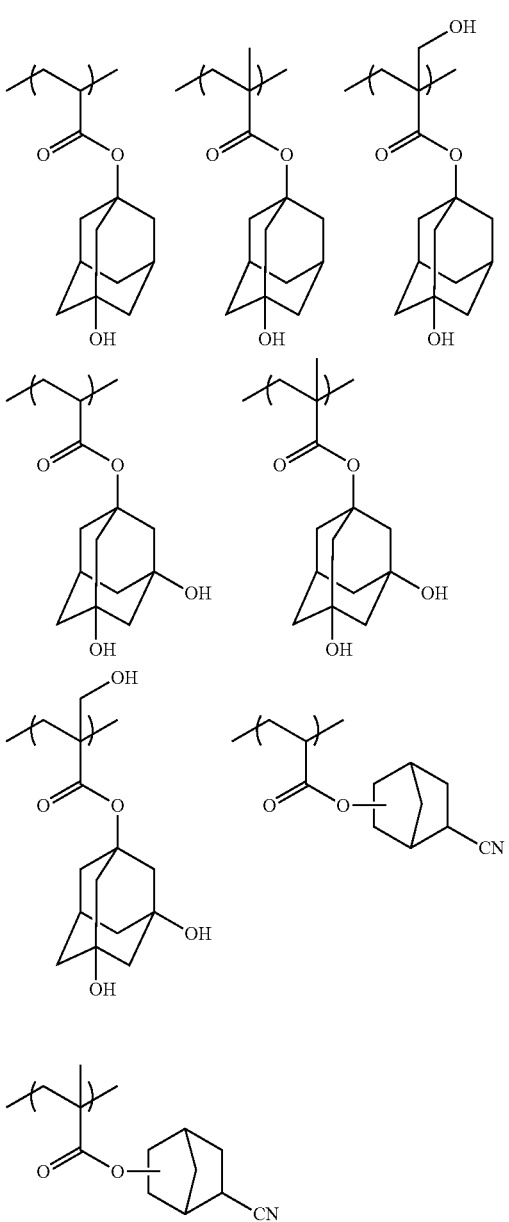

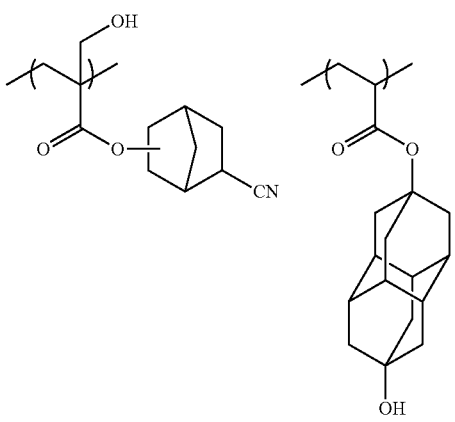

-continued

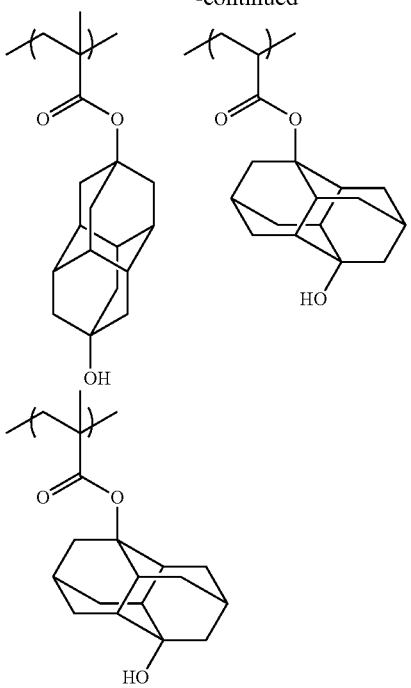

The repeating unit (b) may be a repeating unit having a lactone structure as the polar group.

The repeating unit having a lactone structure is preferably a repeating unit represented by the following formula (AII):

[Chem. 87]

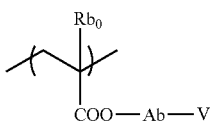

(AII)

In formula (AII), $Rb_0$ represents a hydrogen atom, a halogen atom or an alkyl group (preferably having a carbon number of 1 to 4) which may have a substituent.

Preferable substituents which may be substituted on the alkyl group of $Rb_0$ include a hydroxyl group and a halogen atom. The halogen atom of $Rb_0$ includes a fluorine atom, a chlorine atom, a bromine atom, and an iodine atom. $Rb_0$ is preferably a hydrogen atom, a methyl group, a hydroxymethyl group or a trifluoromethyl group, more preferably a hydrogen atom or a methyl group.

Ab represents a single bond, an alkylene group, a divalent linking group having a monocyclic or polycyclic cycloalkyl structure, an ether bond, an ester bond, a carbonyl group, or a divalent linking group formed by combining these. Ab is preferably a single bond or a divalent linking group represented by -$Ab_1$-$CO_2$—.

$Ab_1$ is a linear or branched alkylene group or a monocyclic or polycyclic cycloalkylene group and is preferably a methylene group, an ethylene group, a cyclohexylene group, an adamantylene group or a norbornylene group.

V represents a group having a lactone structure.

As the group having a lactone structure, any group may be used as long as it has a lactone structure, but a 5- to 7-membered ring lactone structure is preferred, and a 5- to 7-membered ring lactone structure to which another ring structure is fused to form a bicyclo or spiro structure is preferred. It is more preferred to contain a repeating unit having a lactone structure represented by any one of the following formulae (LC1-1) to (LC1-17). The lactone structure may be bonded directly to the main chain. Preferable lactone structures are (LC1-1), (LC1-4), (LC1-5), (LC1-6), (LC1-8), (LC1-13) and (LC1-14).

[Chem. 88]

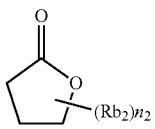

LC1-1

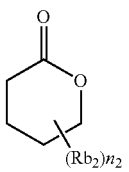

LC1-2

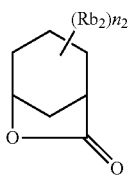

LC1-3

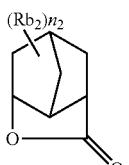

LC1-4

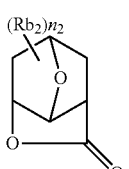

LC1-5

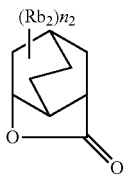

LC1-6

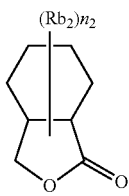

LC1-7

-continued

LC1-8 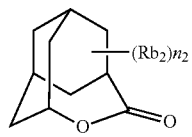

LC1-9

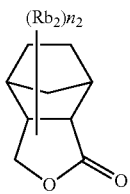

LC1-16 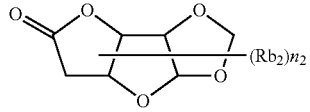

LC1-17

LC1-10

LC1-11

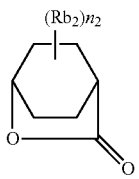

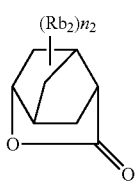

The lactone structure moiety may or may not have a substituent ($Rb_2$). Preferable substituents ($Rb_2$) include an alkyl group having a carbon number of 1 to 8, a monovalent cycloalkyl group having a carbon number of 4 to 7, an alkoxy group having a carbon number of 1 to 8, an alkoxycarbonyl group having a carbon number of 2 to 8, a carboxyl group, a halogen atom, a hydroxyl group, a cyano group, an acid-decomposable group, etc. An alkyl group having a carbon number of 1 to 4, a cyano group and an acid-decomposable group are more preferred. $n_2$ represents an integer of 0 to 4. When $n_2$ is 2 or more, each substituent ($Rb_2$) may be the same as or different from every other substituent ($Rb_2$) and in addition, the plurality of substituents ($Rb_2$) may combine with each other to form a ring.

The repeating unit having a lactone group usually has an optical isomer, and any optical isomer may be used. One optical isomer may be used alone, or a mixture of a plurality of optical isomers may be used. In the case of mainly using one optical isomer, the optical purity (ee) thereof is preferably 90% or more, more preferably 95% or more.

The resin (A) may or may not contain a repeating unit having a lactone structure, but in the case of containing a repeating unit having a lactone structure, the content of the repeating unit in the resin (A) is preferably from 1 to 70 mol %, more preferably from 3 to 65 mol %, still more preferably from 5 to 60 mol %, relative to all repeating units.

LC1-12

LC1-13

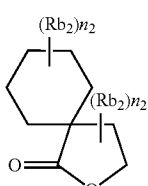

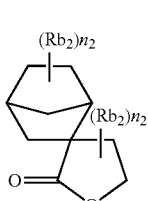

Specific examples of the lactone structure-containing repeating unit in the resin (A) are illustrated below, but the present invention is not limited thereto. In the formulae, Rx represents H, $CH_3$, $CH_2OH$ or $CF_3$.

[Chem. 89]

LC1-14

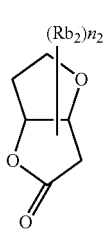

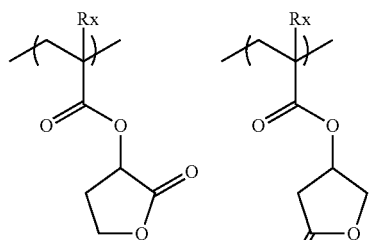

LC1-15

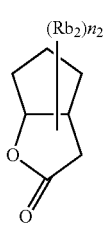

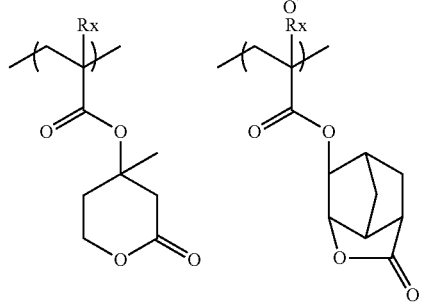

-continued

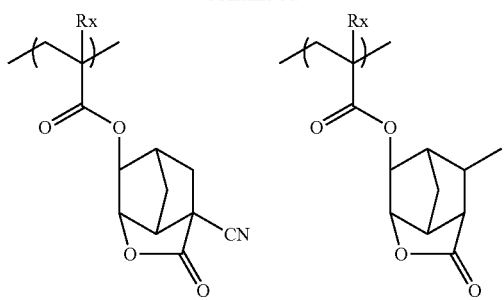
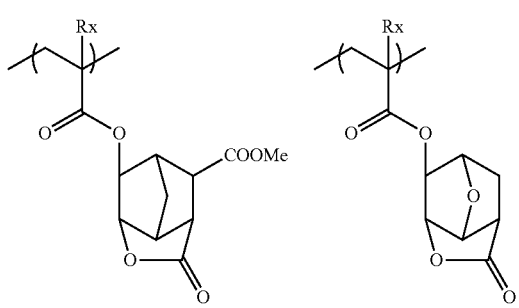
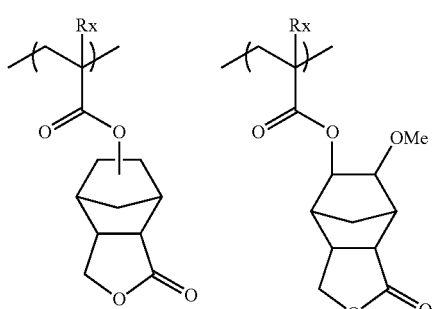

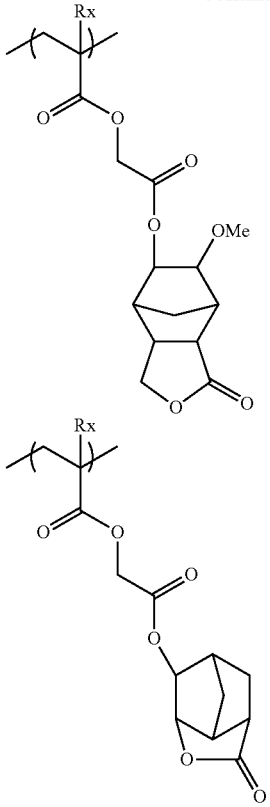

[Chem. 90]

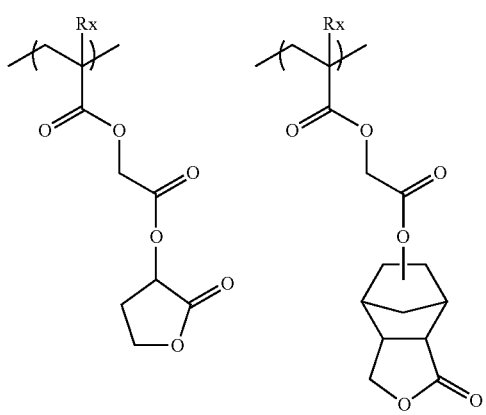

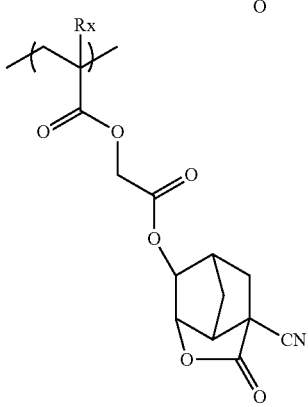

It is also one of particularly preferred embodiments that the polar group which can be contained in the repeating unit (b) is an acidic group. Preferable acidic groups include a phenolic hydroxyl group, a carboxylic acid group, a sulfonic acid group, a fluorinated alcohol group (such as hexafluoroisopropanol group), a sulfonamide group, a sulfonylimide group, an (alkylsulfonyl)(alkylcarbonyl)methylene group, an (alkylsulfonyl)(alkylcarbonyl)imide group, a bis(alkylcarbonyl)methylene group, a bis(alkylcarbonyl)imide group, a bis(alkylsulfonyl)methylene group, a bis(alkylsulfonyl)imide group, a tris(alkylcarbonyl)methylene group, and a tris(alkylsulfonyl)methylene group. Among others, the repeating unit (b) is preferably a repeating unit having a carboxyl group. By virtue of containing a repeating unit having an acidic group, the resolution increases in usage of forming contact holes. As the repeating unit having an acidic group, all of a repeating unit where an acidic group is directly bonded to the main chain of the resin, such as repeating unit by an acrylic acid or a methacrylic acid, a repeating unit where an acidic group is bonded to the main chain of the resin through a linking group, and a repeating unit where an acidic group is introduced into the polymer chain terminal by using an acidic group-containing polymerization initiator or chain transfer agent at the time of polymerization, are preferred. In particular, a repeating unit by an acrylic acid or a methacrylic acid is preferred.

The acidic group that can be contained in the repeating unit (b) may or may not contain an aromatic ring, but in the case of containing an aromatic ring, the acidic group is preferably selected from acidic groups except for a phenolic hydroxyl group. In the case where the repeating unit (b) contains an acidic group, the content of the repeating unit having an acidic group is preferably 30 mol % or less, more preferably 20 mol % or less, relative to all repeating units in the resin (A). In the case where the resin (A) contains a repeating unit having an acidic group, the content of the repeating unit having an acidic group in the resin (A) is usually 1 mol % or more.

Specific examples of the repeating unit having an acidic group are illustrated below, but the present invention is not limited thereto.

In specific examples, Rx represents H, $CH_3$, $CH_2OH$ or $CF_3$.

[Chem. 91]

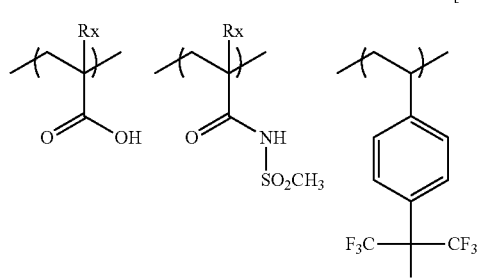
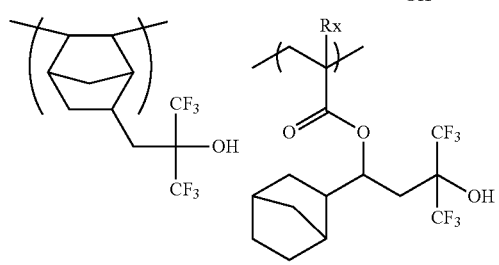
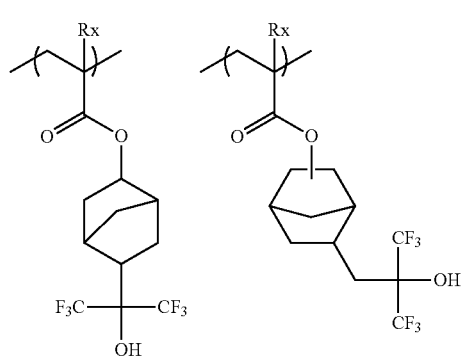

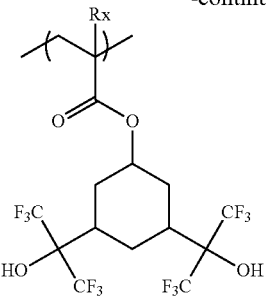

Among others, in the case of forming a pattern by exposure to an electron beam or an extreme-ultraviolet ray, the resin (A) of the present invention preferably contains (b) a non-acid-decomposable repeating unit having a phenolic hydroxyl group. The repeating unit (b) preferably has a structure represented by the following formula (1):

[Chem. 92]

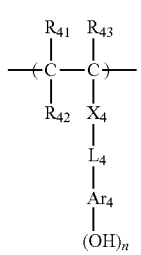

(I)

In the formula, each of $R_{41}$, $R_{42}$ and $R_{43}$ independently represents a hydrogen atom, an alkyl group, a halogen atom, a cyano group or an alkoxycarbonyl group. $R_{42}$ may combine with $Ar_4$ to form a ring and in this case, $R_{42}$ represents a single bond or an alkylene group.

$X_4$ represents a single bond, —COO— or —$CONR_{64}$—, and $R_{64}$ represents a hydrogen atom or an alkyl group.

$L_4$ represents a single bond or an alkylene group.

$Ar_4$ represents an (n+1)-valent aromatic ring group and in the case of combining with $R_{42}$ to form a ring, represents an (n+2)-valent aromatic ring group.

n represents an integer of 1 to 4.

Specific examples of the alkyl group, cycloalkyl group, halogen atom and alkoxycarbonyl group of $R_{41}$, $R_{42}$ and $R_{43}$ in formula (I) and the substituent that may be substituted on these groups are the same as specific examples described above for each of the groups represented by $R_{51}$, $R_{52}$ and $R_{53}$ in formula (VI).

$Ar_4$ represents an (n+1)-valent aromatic ring group. The divalent aromatic ring group when n is 1 may have a substituent, and preferable examples of the divalent aromatic ring group include an arylene group having a carbon number of 6 to 18, such as phenylene group, tolylene group, naphthylene group and anthracenylene group, and an aromatic ring group containing a heterocyclic ring such as thiophene, furan, pyrrole, benzothiophene, benzofuran, benzopyrrole, triazine, imidazole, benzimidazole, triazole, thiadiazole and thiazole.

Specific preferable examples of the (n+1)-valent aromatic ring group when n is an integer of 2 or more include groups formed by removing arbitrary (n−1) hydrogen atoms from the above-described specific examples of the divalent aromatic ring group.

The (n+1)-valent aromatic ring group may further have a substituent.

The substituent that may be substituted on the above-described alkyl group, cycloalkyl group, alkoxycarbonyl group, alkylene group and (n+1)-valent aromatic ring group includes the alkyl group recited for $R_{51}$ to $R_{53}$ in formula (VI), an alkoxy group such as methoxy group, ethoxy group, hydroxyethoxy group, propoxy group, hydroxypropoxy group and butoxy group, and an aryl group such as phenyl group.

Examples of the alkyl group of $R_4$ in —$CONR_{64}$— ($R_{64}$ represents a hydrogen atom or an alkyl group) represented by $X_4$ are the same as those of the alkyl group of $R_{61}$ to $R_{63}$.

$X_4$ is preferably a single bond, —COO— or —CONH—, more preferably a single bond or —COO—.

The alkylene group of $L_4$ is preferably an alkylene group having a carbon number of 1 to 8, such as methylene group, ethylene group, propylene group, butylene group, hexylene group and octylene group, which may have a substituent.

$Ar_4$ is preferably an aromatic ring group having a carbon number of 6 to 18, which may have a substituent, more preferably a benzene ring group, a naphthalene ring group or a biphenylene ring group.

The repeating unit (b) preferably has a hydroxystyrene structure, that is, $Ar_4$ is preferably a benzene ring group.

Specific examples of the repeating unit (b) represented by formula (I) are illustrated below, but the present invention is not limited thereto. In the formulae, a represents 1 or 2.

[Chem. 93]

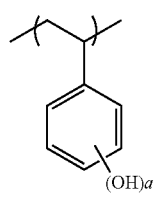
(B-1)

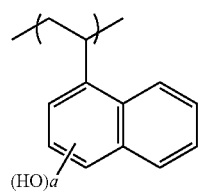
(B-2)

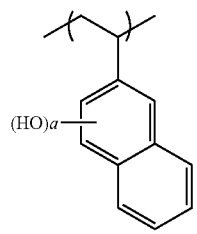
(B-3)

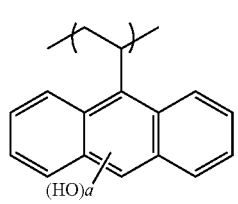
(B-4)

-continued

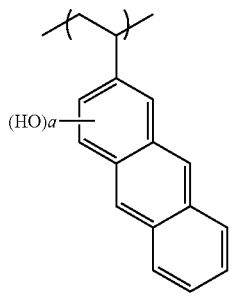
(B-5)

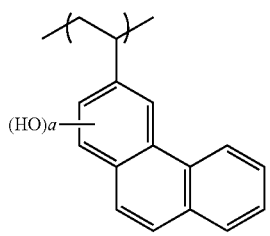
(B-6)

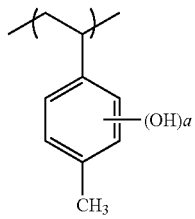
(B-7)

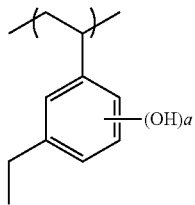
(B-8)

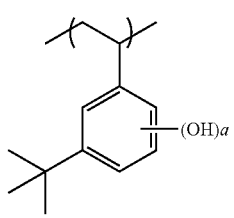
(B-9)

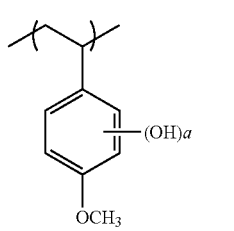
(B-10)

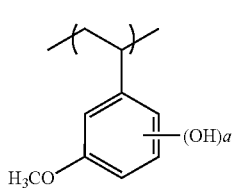
(B-11)

(B-12) 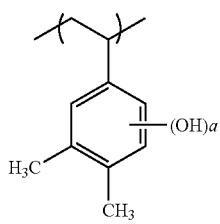
(B-13) 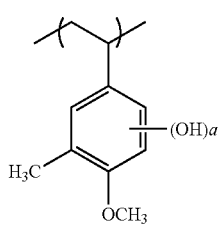
(B-14) 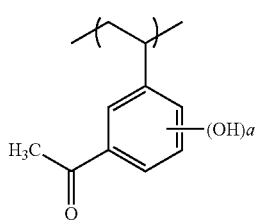
(B-15) 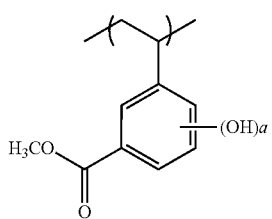
(B-16) 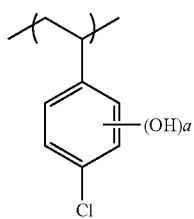
(B-17) 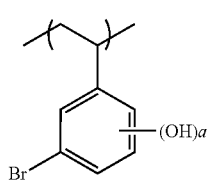
(B-18) 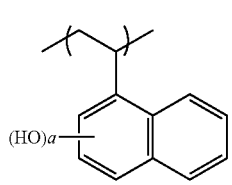
(B-19) 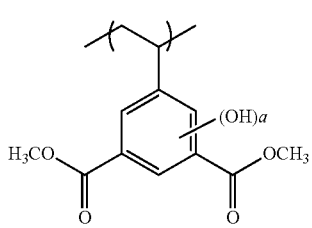
(B-20) 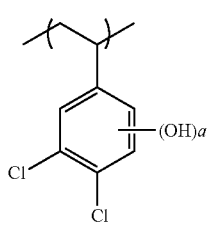
(B-21) 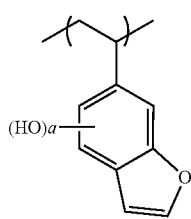
(B-22) 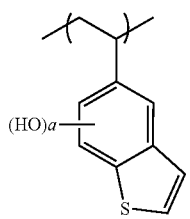
(B-23) 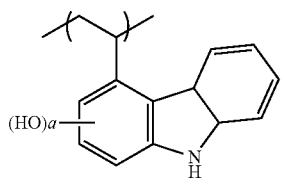
(B-24) 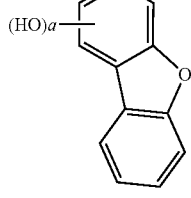
(B-25) 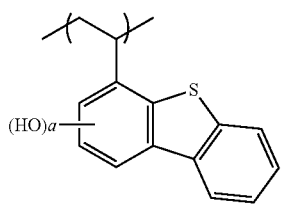

-continued (B-26)
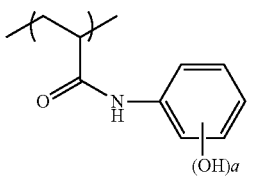

(B-27)
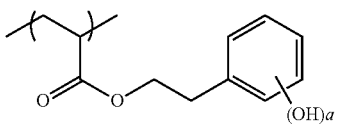

[Chem. 94]

(B-28)
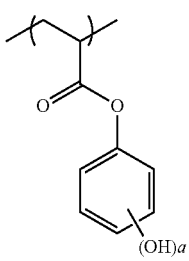

(B-29)
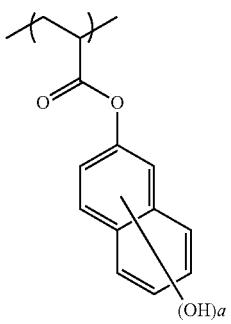

(B-30)
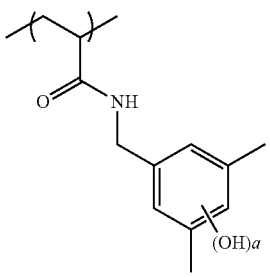

The resin (A) may contain two or more kinds of repeating units represented by formula (I).

The content of the repeating unit (b) is preferably from 5 to 90 mol %, more preferably from 10 to 80 mol %, still more preferably from 10 to 70 mol %, relative to all repeating units in the resin (A).

The resin (A) may contain (c) a repeating unit having a plurality of aromatic rings represented by the following formula (c1):

[Chem. 95]

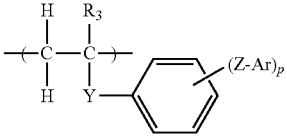

(c1)

In formula (c1), $R_3$ represents a hydrogen atom, an alkyl group, a halogen atom, a cyano group or a nitro group;

Y represents a single bond or a divalent linking group;

Z represents a single bond or a divalent linking group;

Ar represents an aromatic ring group; and p represents an integer of 1 or more.

The alkyl group as $R_3$ may be either linear or branched, and examples thereof include a methyl group, an ethyl group, an n-propyl group, an i-propyl group, an n-butyl group, a sec-butyl group, a tert-butyl group, an n-pentyl group, an n-hexyl group, an n-heptyl group, an n-octyl group, an n-nonyl group, an n-decanyl group, and an i-butyl group. The alkyl group may further have a substituent, and preferable substituents include an alkoxy group, a hydroxyl group, a halogen atom, a nitro group, etc. Among others, the alkyl group having a substituent is preferably a $CF_3$ group, an alkyloxycarbonylmethyl group, an alkylcarbonyloxymethyl group, a hydroxymethyl group, an alkoxymethyl group, etc.

The halogen atom as $R_3$ includes fluorine atom, chlorine atom, bromine atom and iodine atom, with fluorine atom being preferred.

Y represents a single bond or a divalent linking group, and the divalent linking group includes, for example, an ether group (oxygen atom), a thioether group (sulfur atom), an alkylene group, an arylene group, a carbonyl group, a sulfide group, a sulfone group, —COO—, —CONH—, —SO$_2$NH—, —CF$_2$—, —CF$_2$CF$_2$—, —OCF$_2$O—, —CF$_2$OCF$_2$—, —SS—, —CH$_2$SO$_2$CH$_2$—, —CH$_2$COCH$_2$—, —COCF$_2$CO—, —COCO—, —OCOO—, —OSO$_2$O—, an amino group (nitrogen atom), an acyl group, an alkylsulfonyl group, —CH=CH—, —C≡C—, an aminocarbonylamino group, an aminosulfonylamino group, and a group formed by a combination thereof. Y preferably has a carbon number of 15 or less, more preferably a carbon number of 10 or less.

Y is preferably a single bond, a —COO— group, a —COS— group or a —CONH— group, more preferably a —COO— group or a —CONH— group, still more preferably a —COO— group.

Z represents a single bond or a divalent linking group, and the divalent linking group includes, for example, an ether group (oxygen atom), a thioether group (sulfur atom), an alkylene group, an arylene group, a carbonyl group, a sulfide group, a sulfone group, —COO—, —CONH—, —SO$_2$NH—, an amino group (nitrogen atom), an acyl group, an alkylsulfonyl group, —CH=CH—, an aminocarbonylamino group, an aminosulfonylamino group, and a group formed by a combination thereof.

Z is preferably a single bond, an ether group, a carbonyl group or —COO—, more preferably a single bond or an ether group, still more preferably a single bond.

Ar represents an aromatic ring group, and specific examples thereof include a phenyl group, a naphthyl group, an anthracenyl group, a phenanthrenyl group, a quinolinyl group, a furanyl group, a thiophenyl group, a fluorenyl-9-on-yl group, an anthraquinonyl group, a phenanthraquinonyl group, and a pyrrole group, with a phenyl group being preferred. Such an aromatic ring group may further have a substituent, and preferable substituents include, for example, an alkyl group, an alkoxy group, a hydroxyl group, a halogen atom, a nitro group, an acyl group, an acyloxy group, an acylamino group, a sulfonylamino group, an aryl group such as phenyl group, an aryloxy group, an arylcarbonyl group, and a heterocyclic residue. Among these, a phenyl group is preferred from the standpoint of preventing deterioration of the exposure latitude or pattern profile due to out-of-band light.

p is an integer of 1 or more and is preferably an integer of 1 to 3.

The repeating unit (c) is more preferably a repeating unit represented by the following formula (c2):

[Chem. 96]

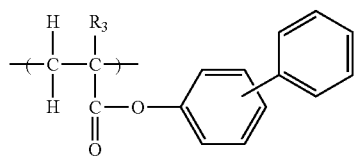

(c2)

In formula (c2), $R_3$ represents a hydrogen atom or an alkyl group. Preferable examples of the alkyl group of $R_3$ are the same as in formula (c1).

Here, as concerns the extreme-ultraviolet (EUV) exposure, leakage light (out-of-band light) generated in the ultraviolet region at a wavelength of 100 to 400 nm worsens the surface roughness, as a result, the resolution and LWR performance tend to be impaired due to bridge between patterns or disconnection of a pattern.

However, the aromatic ring in the repeating unit (c) functions as an internal filter capable of absorbing the above-described out-of-band light. Accordingly, in view of high resolution and low LWR, the resin (A) preferably contains the repeating unit (c).

In this connection, from the standpoint of obtaining high resolution, the repeating unit (c) is preferably free from a phenolic hydroxyl group (a hydroxyl group bonded directly on an aromatic ring).

Specific examples of the repeating unit (c) are illustrated below, but the present invention is not limited thereto.

[Chem. 97]

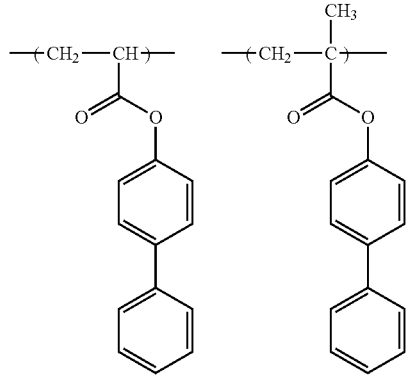

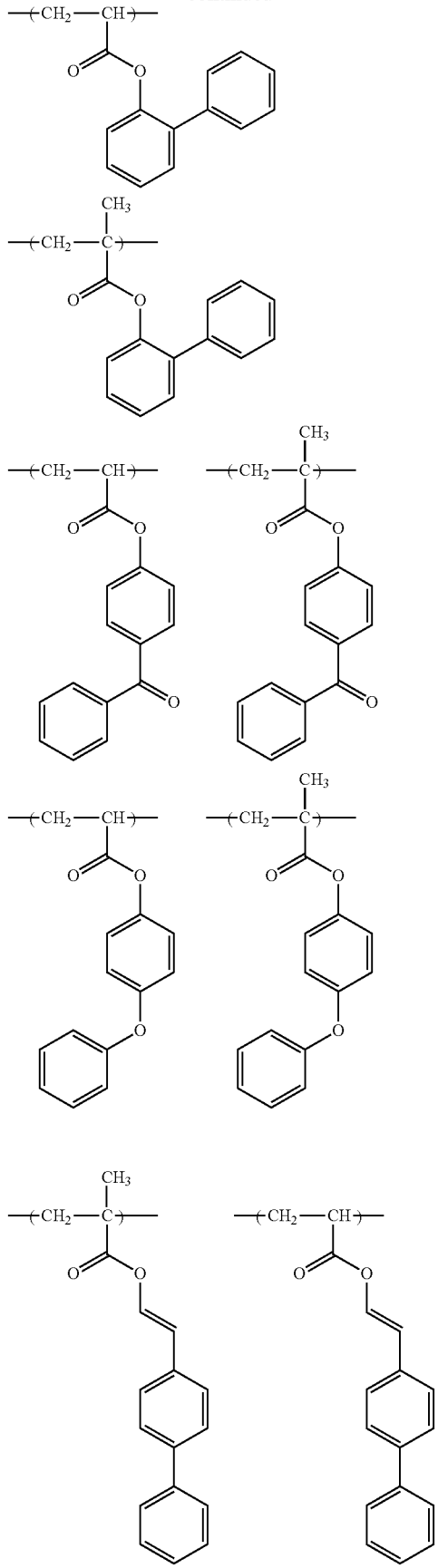

-continued

201
-continued
202
-continued
[Chem. 98]
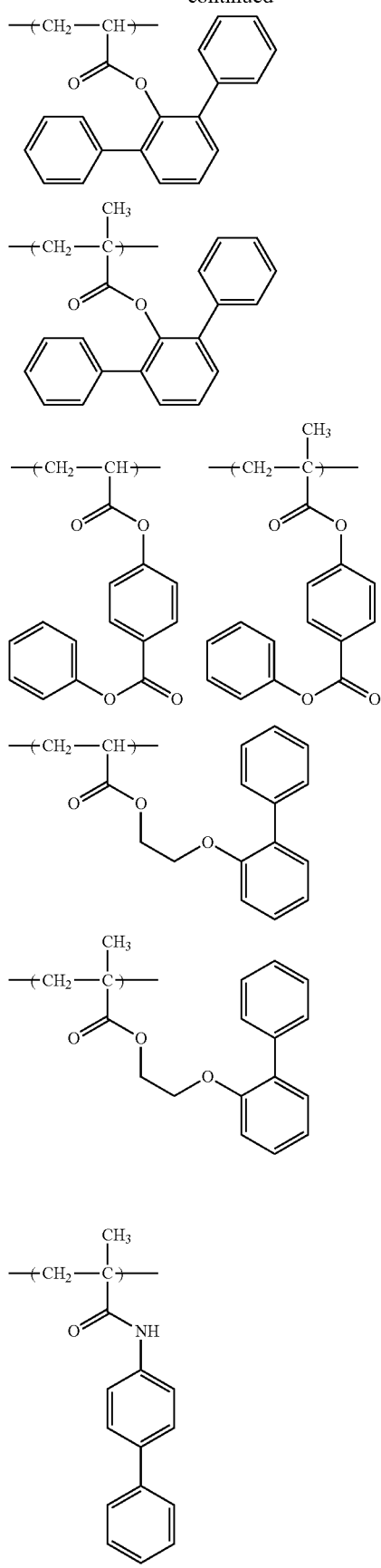
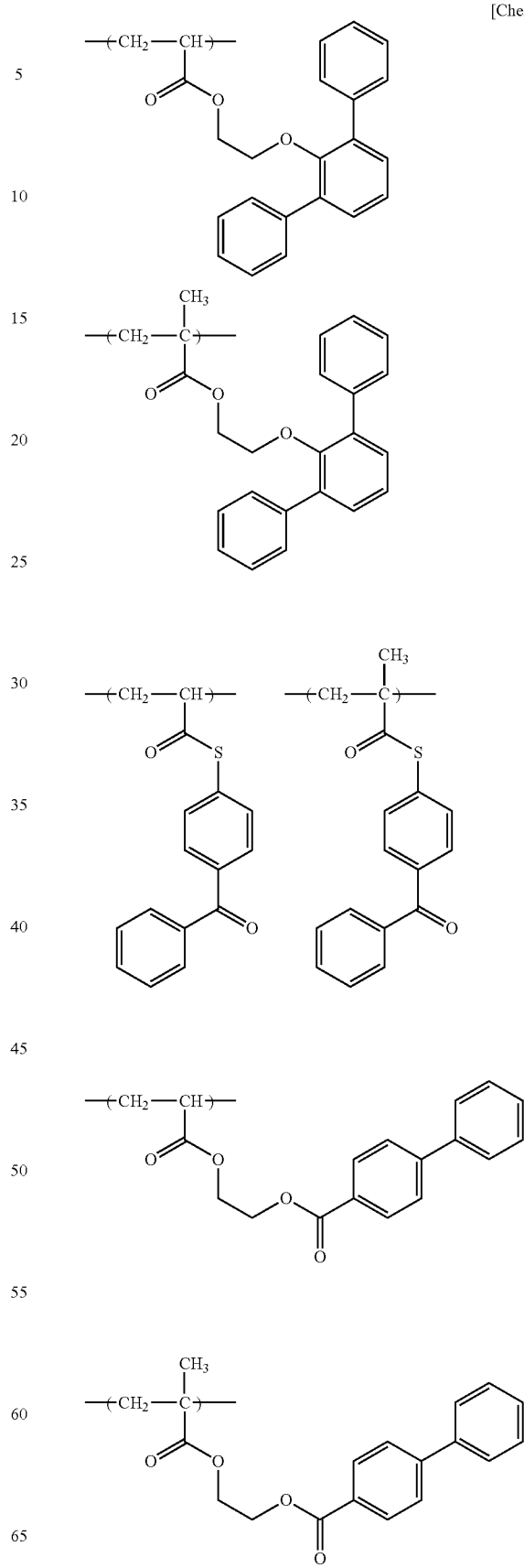

203
-continued
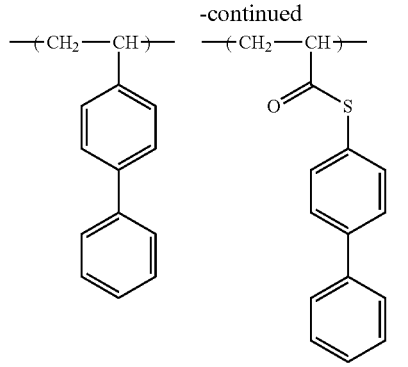
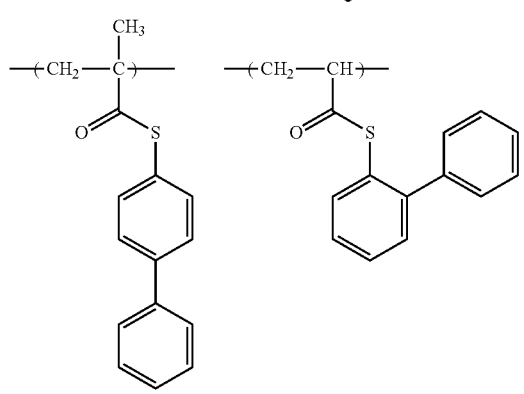
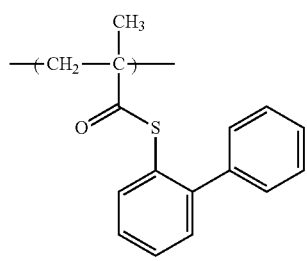
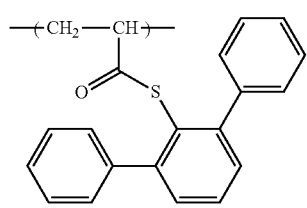
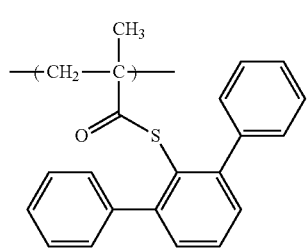
204
-continued
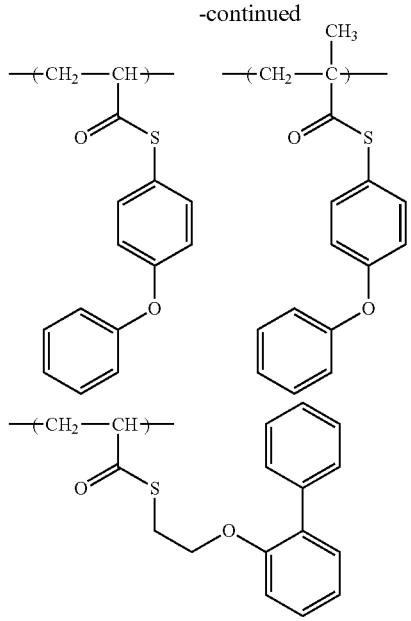
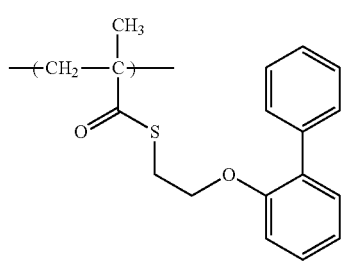
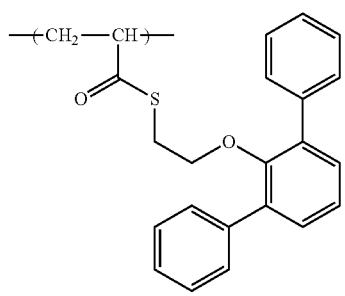
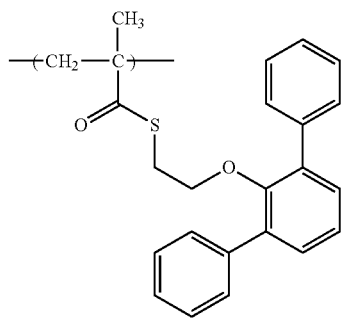

-continued

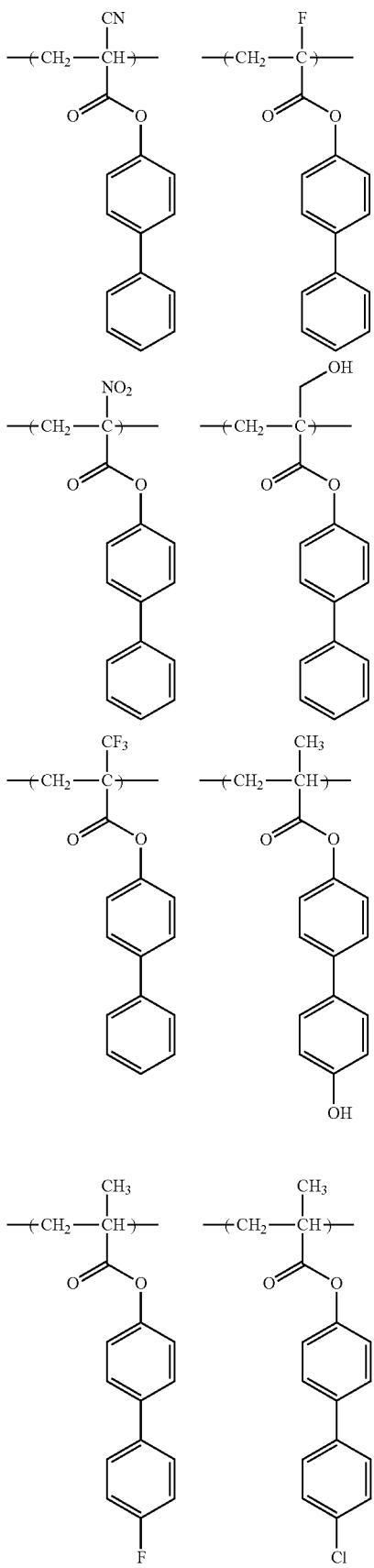

[Chem. 99]

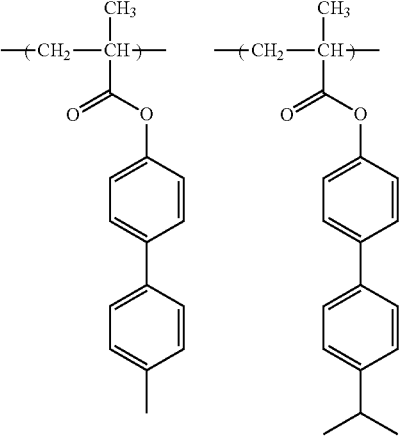

The resin (A) may or may not contain the repeating unit (c), but in the case containing the repeating unit (c), the content percentage thereof is preferably from 1 to 30 mol %, more preferably from 1 to 20 mol %, still more preferably from 1 to 15 mol %, relative to all repeating units in the resin (A). As for the repeating unit (c) contained in the resin (A), two or more kinds of repeating units may be contained in combination.

The resin (A) for use in the present invention may appropriately contain a repeating unit other than the above-described repeating units (a) to (c). As an example of such a repeating unit, the resin may contain a repeating unit having an alicyclic hydrocarbon structure free from a polar group (for example, the above-described acid group, a hydroxyl group or a cyano group) and not exhibiting acid decomposability. Thanks to this configuration, the solubility of the resin at the time of development using an organic solvent-containing developer can be appropriately adjusted. Such a repeating unit includes a repeating unit represented by formula (IV):

[Chem. 100]

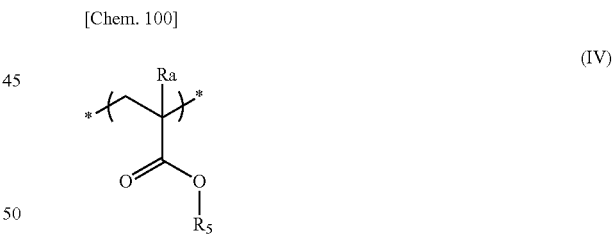

(IV)

In formula (IV), $R_5$ represents a hydrocarbon group having at least one cyclic structure and having no polar group. Ra represents a hydrogen atom, an alkyl group or a —$CH_2$—O—$Ra_2$ group, wherein $Ra_2$ represents a hydrogen atom, an alkyl group or an acyl group. Ra is preferably a hydrogen atom, a methyl group, a hydroxymethyl group or a trifluoromethyl group, more preferably a hydrogen atom or a methyl group.

The cyclic structure contained in $R_5$ includes a monocyclic hydrocarbon group and a polycyclic hydrocarbon group. The monocyclic hydrocarbon group includes, for example, a cycloalkyl group having a carbon number of 3 to 12, such as cyclopentyl group, cyclohexyl group, cycloheptyl group and cyclooctyl group, and a cycloalkenyl group having a carbon number of 3 to 12, such as cyclohexenyl group. The monocyclic hydrocarbon group is preferably a monocyclic hydrocarbon group having a carbon number of 3 to 7, more preferably a cyclopentyl group or a cyclohexyl group.

The polycyclic hydrocarbon group includes a ring assembly hydrocarbon group and a crosslinked cyclic hydrocarbon group. Examples of the ring assembly hydrocarbon group include a bicyclohexyl group and a perhydronaphthalenyl group. The crosslinked cyclic hydrocarbon ring includes, for example, a bicyclic hydrocarbon ring such as pinane ring, bornane ring, norpinane ring, norbornane ring and bicyclooctane ring (e.g., bicyclo[2.2.2]octane ring, bicyclo[3.2.1]octane ring), a tricyclic hydrocarbon ring such as homobledane ring, adamantane ring, tricyclo[5.2.1.0$^{2,6}$]decane ring and tricyclo[4.3.1.1$^{2,5}$]undecane ring, and a tetracyclic hydrocarbon ring such as tetracyclo[4.4.0.1$^{2,5}$.1$^{7,10}$] dodecane ring and perhydro-1,4-methano-5,8-methanonaphthalene ring. In addition, the crosslinked cyclic hydrocarbon ring also includes a condensed cyclic hydrocarbon ring, for example, a condensed ring formed by fusing a plurality of 5- to 8-membered cycloalkane rings, such as perhydronaphthalene (decalin) ring, perhydroanthracene ring, perhydrophenathrene ring, perhydroacenaphthene ring, perhydrofluorene ring, perhydroindene ring and perhydrophenalene ring.

Preferable crosslinked cyclic hydrocarbon rings include a norbornyl group, an adamantyl group, a bicyclooctanyl group, a tricyclo[5.2.1.0$^{2,6}$]decanyl group, etc., and more preferable crosslinked cyclic hydrocarbon rings include a norbornyl group and an adamantyl group.

Such an alicyclic hydrocarbon group may have a substituent, and preferable substituents include, for example, a halogen atom, an alkyl group, a hydroxyl group with a hydrogen atom being substituted for, and an amino group with a hydrogen atom being substituted for. Preferable halogen atoms include bromine atom, chlorine atom and fluorine atom, and preferable alkyl groups include a methyl group, an ethyl group, a butyl group and a tert-butyl group. This alkyl group may further have a substituent, and the substituent which may be further substituted on the alkyl group includes a halogen atom, an alkyl group, a hydroxyl group with a hydrogen atom being substituted for, and an amino group with a hydrogen atom being substituted for.

The substituent for the hydrogen atom includes, for example, an alkyl group, a cycloalkyl group, an aralkyl group, a substituted methyl group, a substituted ethyl group, an alkoxycarbonyl group, and an aralkyloxycarbonyl group. The alkyl group is preferably an alkyl group having a carbon number of 1 to 4; the substituted methyl group is preferably a methoxymethyl group, a methoxythiomethyl group, a benzyloxymethyl group, a tert-butoxymethyl group or a 2-methoxyethoxymethyl group; the substituted ethyl group is preferably a 1-ethoxyethyl group or a 1-methyl-1-methoxyethyl group; the acyl group is preferably an aliphatic acyl group having a carbon number of 1 to 6, such as formyl group, acetyl group, propionyl group, butyryl group, isobutyryl group, valeryl group and pivaloyl group; and the alkoxycarbonyl group includes, for example, an alkoxycarbonyl group having a carbon number of 1 to 4.

The resin (A) may or may not contain a repeating unit having an alicyclic hydrocarbon structure free from a polar group and not exhibiting acid decomposability, but in the case of containing this repeating unit, the content thereof is preferably from 1 to 20 mol %, more preferably from 5 to 15 mol %, relative to all repeating units in the resin (A).

Specific examples of the repeating unit having an alicyclic hydrocarbon structure free from a polar group and not exhibiting acid decomposability are illustrated below, but the present invention is not limited thereto. In the formulae, Ra represents H, $CH_3$, $CH_2OH$ or $CF_3$.

[Chem. 101]

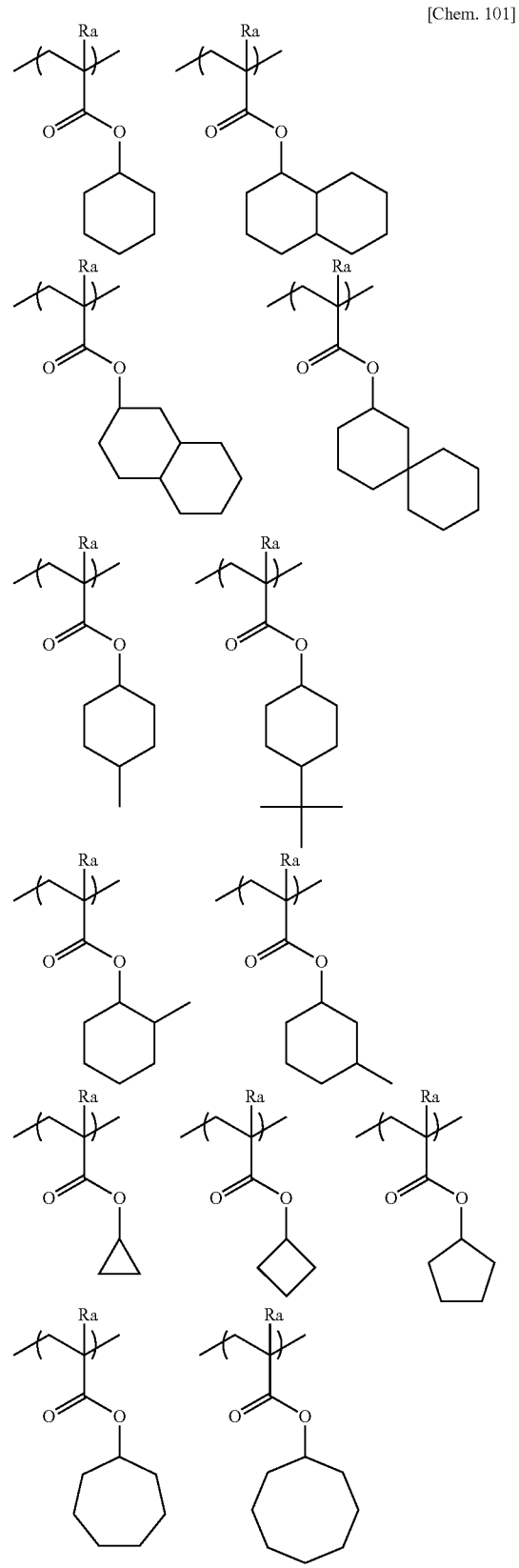

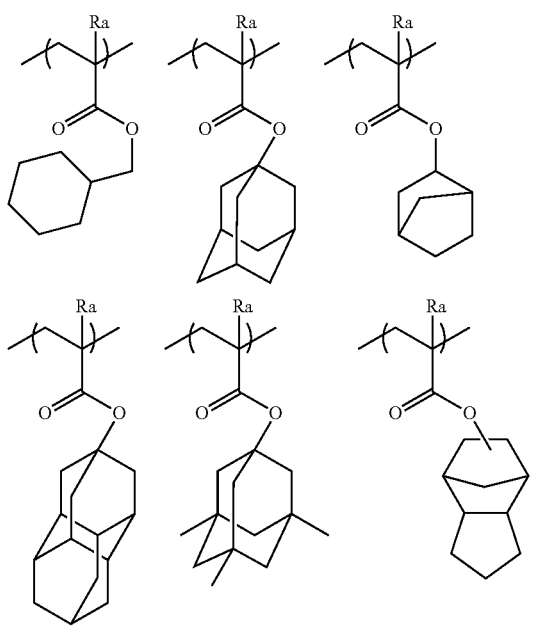

In addition, from the standpoint of elevating Tg, increasing the dry etching resistance or producing an effect such as internal filer for the out-of-band light described above, the resin (A) may contain the following monomer component:

[Chem. 102]

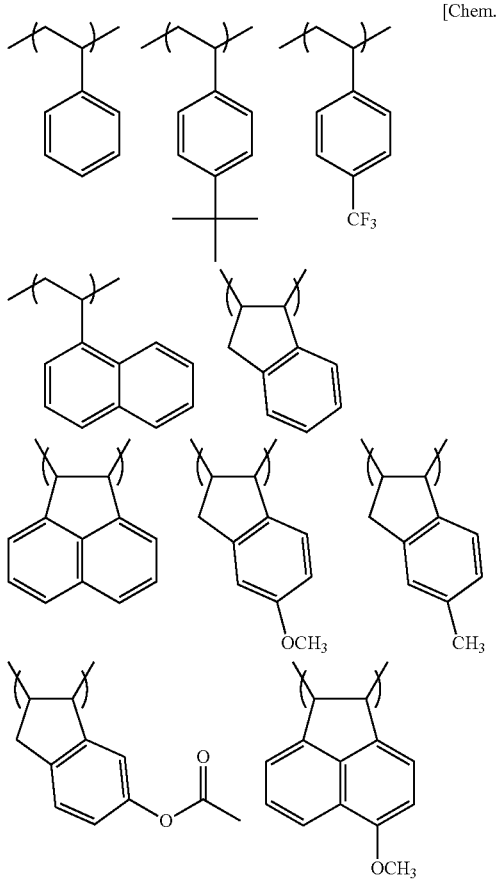

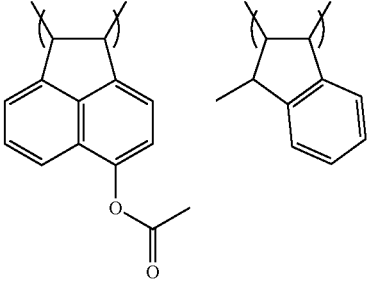

In the resin (A) for use in the composition of the present invention, the molar ratio of respective repeating structural units contained is appropriately set to control the dry etching resistance of resist, suitability for standard developer, adherence to substrate, resist profile and performances generally required of a resist, such as resolution, heat resistance and sensitivity.

The form of the resin (A) for use in the present invention may be any of random type, block type, comb type and star type.

The resin (A) can be synthesized, for example, by radical, cationic or anionic polymerization of unsaturated monomers corresponding to respective structures. It is also possible to obtain the target resin by polymerizing unsaturated monomers corresponding to precursors of respective structures and then performing a polymer reaction.

The general synthesis method includes, for example, a batch polymerization method of dissolving unsaturated monomers and a polymerization initiator in a solvent and heating the solution, thereby effecting the polymerization, and a dropping polymerization method of adding dropwise a solution containing unsaturated monomers and a polymerization initiator to a heated solvent over 1 to 10 hours. A dropping polymerization method is preferred.

The solvent used for the polymerization includes, for example, a solvent which can be used when preparing the later-described actinic ray-sensitive or radiation-sensitive resin composition, and it is more preferable to perform the polymerization by using the same solvent as the solvent used in the composition of the present invention. By the use of this solvent, production of particles during storage can be suppressed.

The polymerization reaction is preferably performed in an inert gas atmosphere such as nitrogen or argon. As for the polymerization initiator, the polymerization is started using a commercially available radical initiator (e.g., azo-based initiator, peroxide). The radical initiator is preferably an azo-based initiator, and an azo-based initiator having an ester group, a cyano group or a carboxyl group is preferred. Preferable initiators include azobisisobutyronitrile, azobisdimethylvaleronitrile, dimethyl 2,2'-azobis(2-methylpropionate), etc. If desired, the polymerization may be performed in the presence of a chain transfer agent (e.g., alkylmercaptan).

The concentration during the reaction is from 5 to 70 mass %, preferably from 10 to 50 mass %, and the reaction temperature is usually from 10 to 150° C., preferably from 30 to 120° C., more preferably from 40 to 100° C.

The reaction time is usually from 1 to 48 hours, preferably from 1 to 24 hours, more preferably from 1 to 12 hours.

After the completion of reaction, the reaction solution is allowed to cool to room temperature and purified. In the purification, a conventional method, for example, a liquid-liquid extraction method of applying water washing or combining an appropriate solvent to remove residual monomers or oligomer components, a purification method in a solution sate, such as ultrafiltration of removing by extraction only polymers having a molecular weight not more than a specific molecular weight, a reprecipitation method of adding dropwise the resin solution to a poor solvent to solidify the resin in the poor solvent and thereby remove residual monomers, etc., or a purification method in a solid state, such as washing of the resin slurry with a poor solvent after separation of the slurry by filtration, may be applied. For example, the resin is precipitated as a solid by contacting the reaction solution with a solvent in which the resin is sparingly soluble or insoluble (poor solvent) and which is in a volumetric amount of 10 times or less, preferably from 10 to 5 times, the reaction solution.

The solvent used at the operation of precipitation or reprecipitation from the polymer solution (precipitation or reprecipitation solvent) may be sufficient if it is a poor solvent to the polymer, and the solvent which can be used may be appropriately selected from a hydrocarbon, a halogenated hydrocarbon, a nitro compound, an ether, a ketone, an ester, a carbonate, an alcohol, a carboxylic acid, water, a mixed solvent containing such a solvent, and the like, according to the kind of the polymer. Among these solvents, a solvent containing at least an alcohol (particularly, methanol, etc.) or water is preferred as the precipitation or reprecipitation solvent.

The amount of the precipitation or reprecipitation solvent used may be appropriately selected by taking into consideration the efficiency, yield, etc., but in general, the amount used is from 100 to 10,000 parts by mass, preferably from 200 to 2,000 parts by mass, more preferably from 300 to 1,000 parts by mass, per 100 parts by mass of the polymer solution.

The temperature at the time of precipitation or reprecipitation may be appropriately selected by taking into consideration the efficiency or operability but is usually on the order of 0 to 50° C., preferably in the vicinity of room temperature (for example, approximately from 20 to 35° C.). The precipitation or reprecipitation operation may be performed using a commonly employed mixing vessel such as stirring tank, by a known method such as batch system and continuous system.

The precipitated or reprecipitated polymer is usually subjected to commonly employed solid-liquid separation such as filtration and centrifugation, then dried and used. The filtration is performed using a solvent-resistant filter element preferably under pressure. The drying is performed under atmospheric pressure or reduced pressure (preferably under reduced pressure) at a temperature of approximately from 30 to 100° C., preferably on the order of 30 to 50° C.

Incidentally, after the resin is once precipitated and separated, the resin may be again dissolved in a solvent and then put into contact with a solvent in which the resin is sparingly soluble or insoluble. That is, there may be used a method including, after the completion of radical polymerization reaction, bringing the polymer into contact with a solvent in which the polymer is sparingly soluble or insoluble, to precipitate a resin (step a), separating the resin from the solution (step b), anew dissolving the resin in a solvent to prepare a resin solution A (step c), bringing the resin solution A into contact with a solvent in which the resin is sparingly soluble or insoluble and which is in a volumetric amount of less than 10 times (preferably 5 times or less) the resin solution A, to precipitate a resin solid (step d), and separating the precipitated resin (step e).

The polymerization reaction is preferably performed in an inert gas atmosphere such as nitrogen or argon. As for the polymerization initiator, the polymerization is started using a commercially available radical initiator (e.g., azo-based initiator, peroxide). The radical initiator is preferably an azo-based initiator, and an azo-based initiator having an ester group, a cyano group or a carboxyl group is preferred. Preferable initiators include azobisisobutyronitrile, azobisdimethylvaleronitrile, dimethyl 2,2'-azobis(2-methylpropionate), etc. The initiator is added additionally or in parts, if desired. After the completion of reaction, the reaction product is poured in a solvent, and the desired polymer is collected, for example, by a method for powder or solid recovery. The concentration during the reaction is from 5 to 50 mass %, preferably from 10 to 30 mass %, and the reaction temperature is usually from 10 to 150° C., preferably from 30 to 120° C., more preferably from 60 to 100° C.

The molecular weight of the resin (A) according to the present invention is not particularly limited, but the weight average molecular weight is preferably from 1,000 to 100,000, more preferably from 1,500 to 60,000, still more preferably from 2,000 to 30,000. When the weight average molecular weight is from 1,000 to 100,000, the heat resistance and dry etching resistance can be kept from deterioration and at the same time, the film-forming property can be prevented from becoming poor due to impairment of developability or increase in the viscosity. Here, the weight average molecular weight of the resin indicates a molecular weight in terms of polystyrene measured by GPC (carrier: THF or N-methyl-2-pyrrolidone (NMP)).

The polydispersity (Mw/Mn) is preferably from 1.00 to 5.00, more preferably from 1.03 to 3.50, still more preferably from 1.05 to 2.50. As the molecular weight distribution is narrower, the resolution and resist profile are more excellent, the side wall of the resist pattern is smoother, and the roughness is more improved.

As for the resin (A) used in the present invention, one kind of a resin may be used alone, or two or more kinds of resins may be used in combination. The actinic ray-sensitive or radiation-sensitive resin composition of the present invention preferably contains (A) a resin having a group represented by any one of formulae (1) to (IV) and formula (V), more preferably contains a resin having a group represented by formula (I) or (II). The content percentage of the resin (A) is preferably from 20 to 99 mass %, more preferably from 30 to 89 mass %, still more preferably from 40 to 79 mass %, based on the total solid content in the actinic ray-sensitive or radiation-sensitive resin composition of the present invention.

[4] Basic Compound

The actinic ray-sensitive or radiation-sensitive resin composition of the present invention preferably contains a basic compound.

The basic compound is preferably a nitrogen-containing basic compound.

The compound that can be used is not particularly limited, but, for example, a compound classified into the following (1) to (4) is preferably used.

(1) Compound Represented by the Following Formula (BS-1)

[Chem. 103]

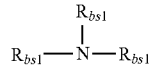

(Bs-1)

In formula (BS-1), each $R_{bs1}$ independently represents any one of a hydrogen atom, an alkyl group (linear or branched), a cycloalkyl group (monocyclic or polycyclic), an aryl group, and an aralkyl group. However, all of three $R_{bs1}$ are not a hydrogen atom.

The carbon number of the alkyl group as $R_{bs1}$ is not particularly limited but is usually from 1 to 20, preferably from 1 to 12.

The carbon number of the cycloalkyl group as $R_{bs1}$ is not particularly limited but is usually from 3 to 20, preferably from 5 to 15.

The carbon number of the aryl group as $R_{bs1}$ is not particularly limited but is usually from 6 to 20, preferably from 6 to 10. Specific examples thereof include a phenyl group and a naphthyl group.

The carbon number of the aralkyl group as $R_{bs1}$ is not particularly limited but is usually from 7 to 20, preferably from 7 to 11. Specific examples thereof include a benzyl group.

In the alkyl group, cycloalkyl group, aryl group and aralkyl group as $R_{bs1}$, a hydrogen atom may be substituted for by a substituent. This substituent includes, for example, an alkyl group, a cycloalkyl group, an aryl group, an aralkyl group, a hydroxyl group, a carboxyl group, an alkoxy group, an aryloxy group, an alkylcarbonyloxy group, and an alkyloxycarbonyl group.

In the compound represented by formula (BS-1), only one of three $R_{bs1}$ is preferably a hydrogen atom, and it is more preferred that all $R_{bs1}$ are not a hydrogen atom.

Specific examples of the compound represented by formula (BS-1) include tri-n-butylamine, tri-n-pentylamine, tri-n-octylamine, tri-n-decylamine, tri-n-dodecylamine, triisodecylamine, dicyclohexylmethylamine, tetradecylamine, pentadecylamine, hexadecylamine, octadecylamine, didecylamine, methyloctadecylamine, dimethylundecylamine, N,N-dimethyldodecylamine, methyldioctadecylamine, N,N-dibutylaniline, and N,N-dihexylaniline.

In addition, one preferred embodiment is a compound where in formula (BS-1), at least one $R_{bs1}$ is an alkyl group substituted with a hydroxy group. Specific compounds include triethanolamine, N,N-dihydroxyethylaniline, etc.

The alkyl group as $R_{bs1}$ may have an oxygen atom in the alkyl chain to form an oxyalkylene chain. The oxyalkylene chain is preferably —CH$_2$CH$_2$O—. Specific examples thereof include tris(methoxyethoxyethyl)amine and compounds illustrated in column 3, line 60 et seq. of U.S. Pat. No. 6,040,112.

(2) Compound Having a Nitrogen-Containing Heterocyclic Structure

The heterocyclic structure may or may not have aromaticity, may contain a plurality of nitrogen atoms, and may further contain a heteroatom other than nitrogen. Specifically, the compound includes a compound having an imidazole structure (e.g., 2-phenylbenzimidazole, 2,4,5-triphenylimidazole), a compound having a piperidine structure (e.g., N-hydroxyethylpiperidine, bis(1,2,2,6,6-pentamethyl-4-piperidyl)sebacate), a compound having a pyridine structure (e.g., 4-dimethylaminopyridine), and a compound having an antipyrine structure (e.g., antipyrine, hydroxyantipyrine).

A compound having two or more ring structures is also suitably used. Specific examples thereof include 1,5-diazabicyclo[4.3.0]non-5-ene and 1,8-diazabicyclo[5.4.0]undec-7-ene.

(3) Phenoxy Group-Containing Amine Compound

The phenoxy group-containing amine compound is an amine compound having a phenoxy group at the terminal of an alkyl group, opposite nitrogen atom. The phenoxy group may have, for example, a substituent such as alkyl group, alkoxy group, halogen atom, cyano group, nitro group, carboxyl group, carboxylic acid ester group, sulfonic acid ester group, aryl group, aralkyl group, acyloxy group and aryloxy group.

The compound is preferably a compound having at least one oxyalkylene chain between the phenoxy group and the nitrogen atom. The number of oxyalkylene chains per molecule is preferably from 3 to 9, more preferably from 4 to 6. Among oxyalkylene chains, —CH$_2$CH$_2$O— is preferred.

Specific examples of the compound include 2-[2-{2-(2,2-dimethoxy-phenoxyethoxy)ethyl}-bis-(2-methoxyethyl)]-amine and Compounds (C1-1) to (C3-3) illustrated in paragraph [0066] of U.S. Patent Application Publication No. 2007/0224539A1.

(4) Ammonium Salt

An ammonium salt is also appropriately used. The salt is preferably a hydroxide or a carboxylate. More specifically, a tetraalkylammonium hydroxide typified by tetrabutylammonium hydroxide is preferred. In addition, ammonium salts derived from amines in (1) to (3) above can be used.

As other usable basic compounds, for example, compounds described in JP-A-2011-85926, compounds synthesized in Examples of JP-A-2002-363146, and compounds described in paragraph 0108 of JP-A-2007-298569 can also be used.

The composition according to the present invention may contain, as the basic compound, a low molecular compound having a nitrogen atom and having a group capable of leaving by an action of an acid (hereinafter, sometimes referred to as "low molecular compound (D)" or "compound (D)").

The group capable of leaving by an action of an acid is not particularly limited but is preferably an acetal group, a carbonate group, a carbamate group, a tertiary ester group, a tertiary hydroxyl group or a hemiaminal ether group, more preferably a carbamate group or a hemiaminal ether group.

The molecular weight of the compound (D) is preferably from 100 to 1,000, more preferably from 100 to 700, still more preferably from 100 to 500.

The compound (D) is preferably an amine derivative having, on the nitrogen atom, a group capable of leaving by an action of an acid.

The compound (D) may have a protective group-containing carbamate group on the nitrogen atom. The protective group constituting the carbamate group can be represented, for example, by the following formula (d-1):

[Chem. 104]

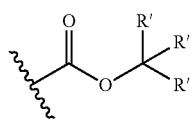

(d-1)

In formula (d-1), each R' independently represents a hydrogen atom, a linear or branched alkyl group, a cycloalkyl group, an aryl group, an aralkyl group or an alkoxyalkyl group. R' may combine with each other to form a ring.

R' is preferably a linear or branched alkyl group, a cycloalkyl group or an aryl group, more preferably a linear or branched alkyl group or a cycloalkyl group.

Specific examples of the group above are illustrated below.
[Chem. 105]
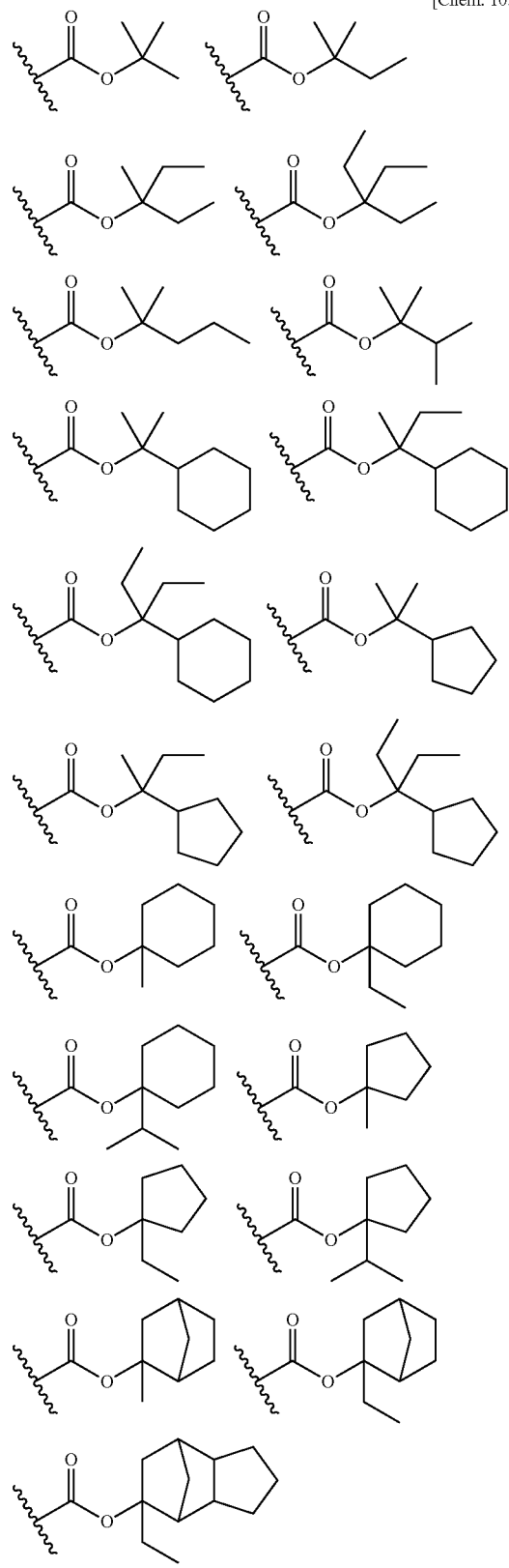
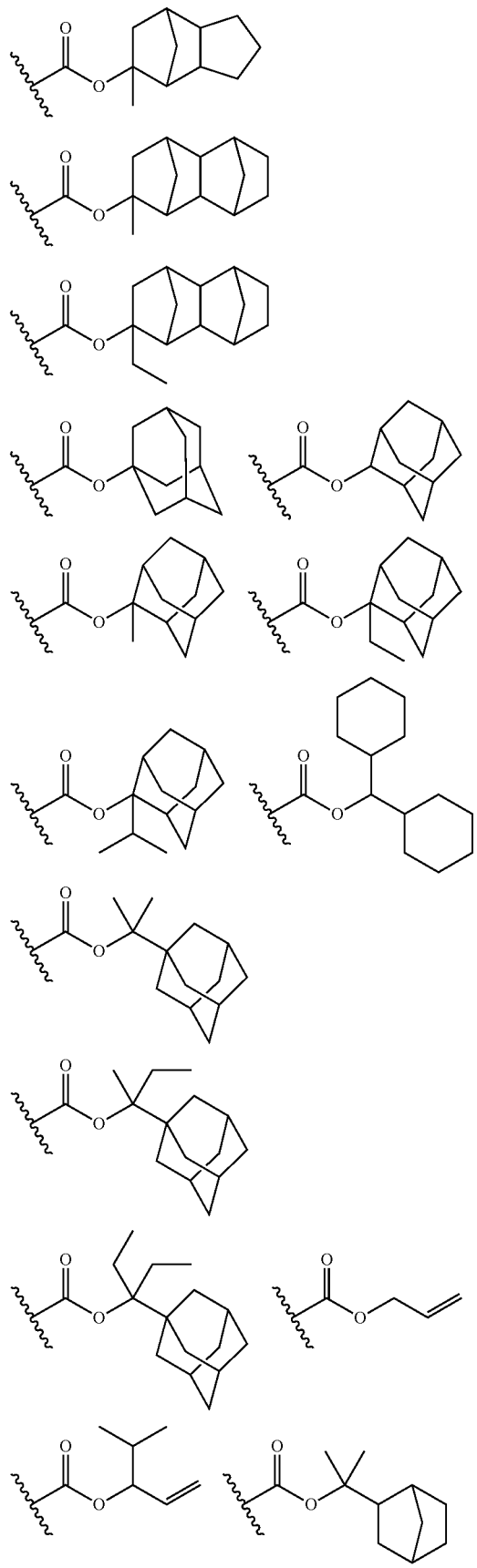

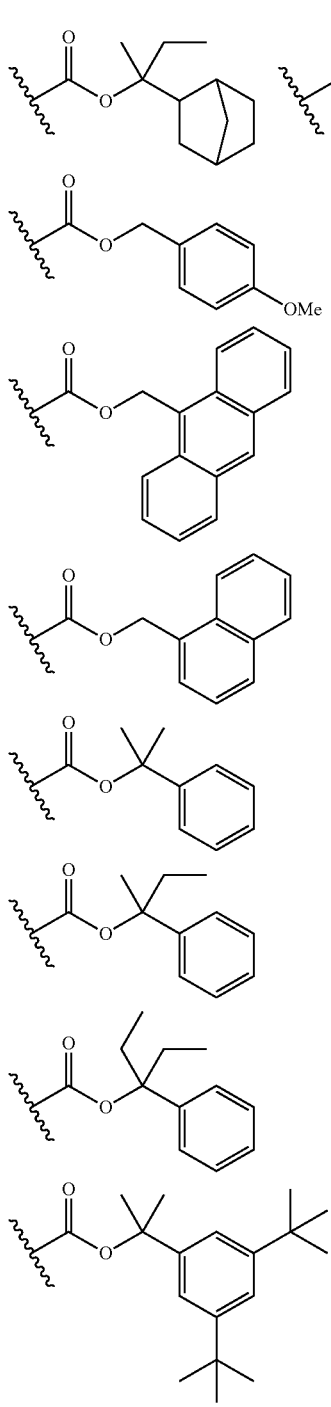

The compound (D) may also be composed by arbitrarily combining various basic compounds described above with the structure represented by formula (d-1).

Among others, the compound (D) is preferably a compound having a structure represented by the following formula (F).

Incidentally, the compound (D) may be a compound corresponding to the above-described various basic compounds as long as it is a low molecular compound having a group capable of leaving by an action of an acid.

[Chem. 106]

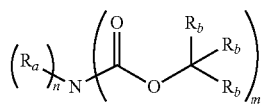

(F)

In formula (F), Ra represents a hydrogen atom, an alkyl group, a cycloalkyl group, an aryl group or an aralkyl group. In addition, when n=2, two Ra may be the same or different, and two Ra may combine with each other to form a divalent heterocyclic hydrocarbon group (preferably having a carbon number of 20 or less) or a derivative thereof.

Each Rb independently represents a hydrogen atom, an alkyl group, a cycloalkyl group, an aryl group, an aralkyl group or an alkoxyalkyl group. However, when one or more Rb in —C(Rb)(Rb)(Rb) are a hydrogen atom, at least one of the remaining Rb is a cyclopropyl group, a 1-alkoxyalkyl group or an aryl group.

At least two Rb may combine to form an alicyclic hydrocarbon group, an aromatic hydrocarbon group, a heterocyclic hydrocarbon group, or a derivative thereof.

n represents an integer of 0 to 2, m represents an integer of 1 to 3, and n+m=3.

In formula (F), the alkyl group, cycloalkyl group, aryl group and aralkyl group represented by Ra and Rb may be substituted with a functional group such as hydroxyl group, cyano group, amino group, pyrrolidino group, piperidino group, morpholino group and oxo group, an alkoxy group, or a halogen atom. The same applies to the alkoxyalkyl group represented by Rb.

The alkyl group, cycloalkyl group, aryl group and aralkyl group (these alkyl, cycloalkyl, aryl and aralkyl groups may be substituted with the above-described functional group, an alkoxy group or a halogen atom) of Ra and/or Rb include:

a group derived from a linear or branched alkane such as methane, ethane, propane, butane, pentane, hexane, heptane, octane, nonane, decane, undecane and dodecane, or a group where the group derived from an alkane is substituted with one or more kinds of or one or more groups of cycloalkyl groups such as cyclobutyl group, cyclopentyl group and cyclohexyl group;

a group derived from a cycloalkane such as cyclobutane, cyclopentane, cyclohexane, cycloheptane, cyclooctane, norbornane, adamantane and noradamantane, or a group where the group derived from a cycloalkane is substituted with one or more kinds of or one or more groups of linear or branched alkyl groups such as methyl group, ethyl group, n-propyl group, i-propyl group, n-butyl group, 2-methylpropyl group, 1-methylpropyl group and tert-butyl group;

a group derived from an aromatic compound such as benzene, naphthalene and anthracene, or a group where the group derived from an aromatic compound is substituted with one or more kinds of or one or more groups of linear or branched alkyl groups such as methyl group, ethyl group, n-propyl group, i-propyl group, n-butyl group, 2-methylpropyl group, 1-methylpropyl group and tert-butyl group;

a group derived from a heterocyclic compound such as pyrrolidine, piperidine, morpholine, tetrahydrofuran, tetrahydropyran, indole, indoline, quinoline, perhydroquinoline, indazole and benzimidazole, or a group where the group derived from a heterocyclic compound is substituted with one or more kinds of or one or more groups of linear or branched alkyl groups or aromatic compound-derived groups; a group where the group derived from a linear or branched alkane or the group derived from a cycloalkane is substituted with one or more kinds of or one or more groups of aromatic compound-derived groups such as phenyl group, naphthyl group and anthracenyl group; a group where the substituent above is substituted with a functional group such as hydroxyl group, cyano group, amino group, pyrrolidino group, piperidino group, morpholino group and oxo group; etc.

The divalent heterocyclic hydrocarbon group (preferably having a carbon number of 1 to 20) formed by combining Ra with each other or a derivative thereof includes, for example, a group derived from a heterocyclic compound such as pyrrolidine, piperidine, morpholine, 1,4,5,6-tetrahydropyrimidine, 1,2,3,4-tetrahydroquinoline, 1,2,3,6-tetrahydropyridine, homopiperazine, 4-azabenzimidazole, benzotriazole, 5-azabenzotriazole, 1H-1,2,3-triazole, 1,4,7-triazacyclononane, tetrazole, 7-azaindole, indazole, benzimidazole, imidazo[1,2-a]pyridine, (1S,4S)-(+)-2,5-diazabicyclo[2.2.1]heptane, 1,5,7-triazabicyclo[4.4.0]dec-5-ene, indole, indoline, 1,2,3,4-tetrahydroquinoxaline, perhydroquinoline and 1,5,9-triazacyclododecane, and a group where the group derived from a heterocyclic compound is substituted with one or more kinds of or one or more groups of linear or branched alkane-derived groups, cycloalkane-derived groups, aromatic compound-derived groups, heterocyclic compound-derived groups, and functional groups such as hydroxyl group, cyano group, amino group, pyrrolidino group, piperidino group, morpholino group and oxo group.

Particularly preferable compounds (D) in the present invention are specifically illustrated below, but the present invention is not limited thereto.

[Chem. 107]

(D-1)

(D-2)

(D-3)

(D-4)

(D-5)

(D-6)

(D-7)

(D-8)

(D-9)

(D-10)

(D-11)

(D-12)

(D-13)

(D-14)

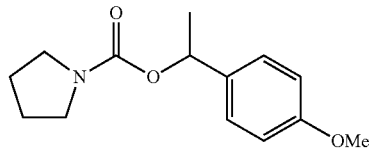
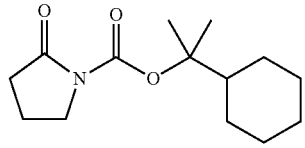
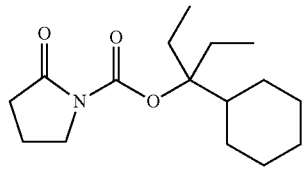
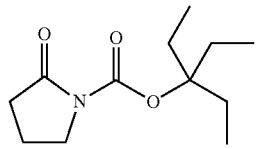
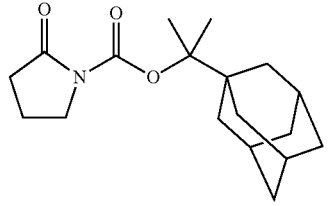
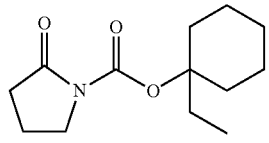
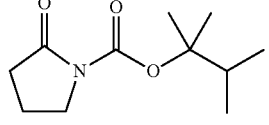
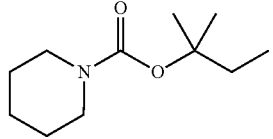
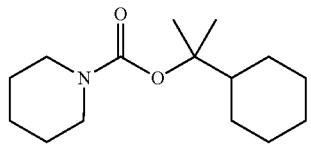
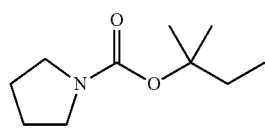
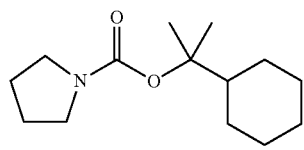
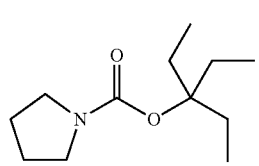
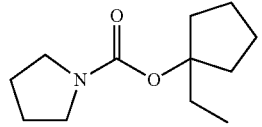
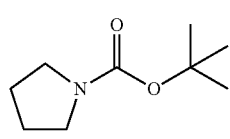

(D-15) 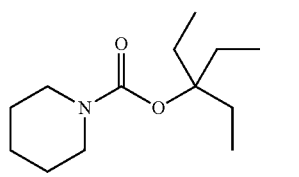
(D-16) 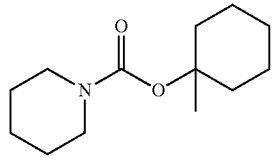
(D-17) 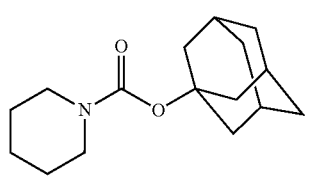
(D-18) 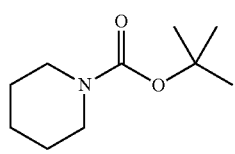
(D-19) 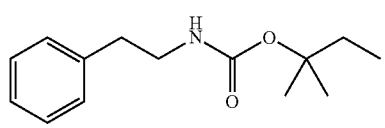
(D-20) 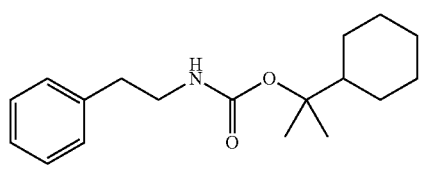
(D-21) 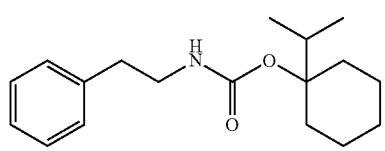
(D-22) 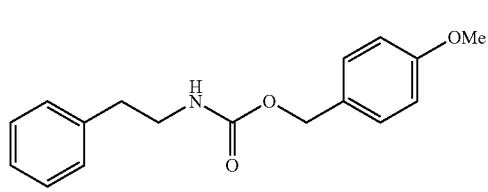
(D-23) 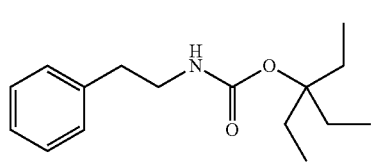
(D-24) 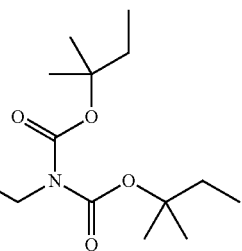
(D-25) 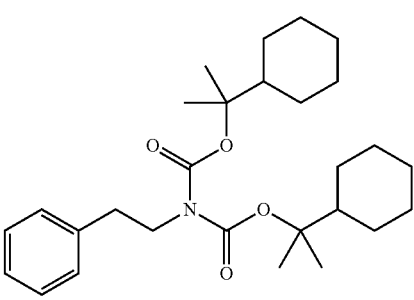
(D-26) 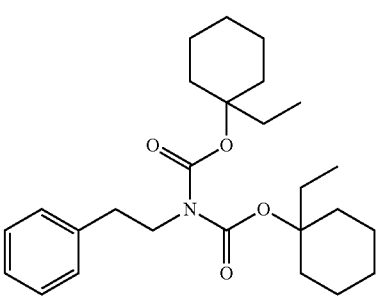
(D-27) 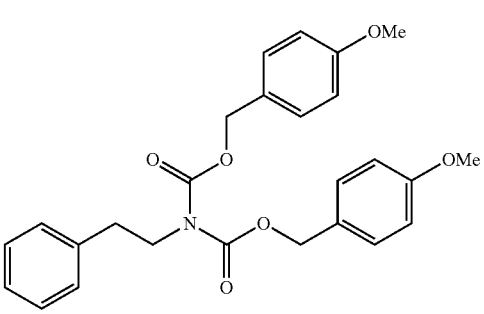
(D-28) 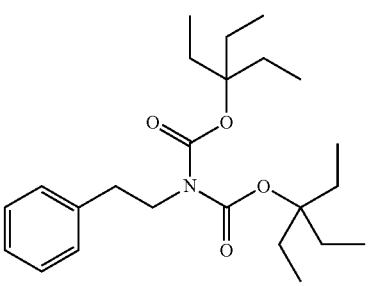

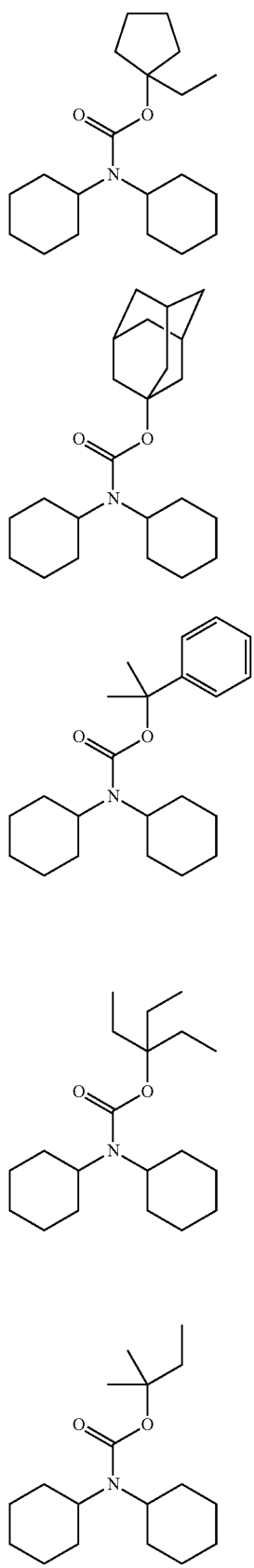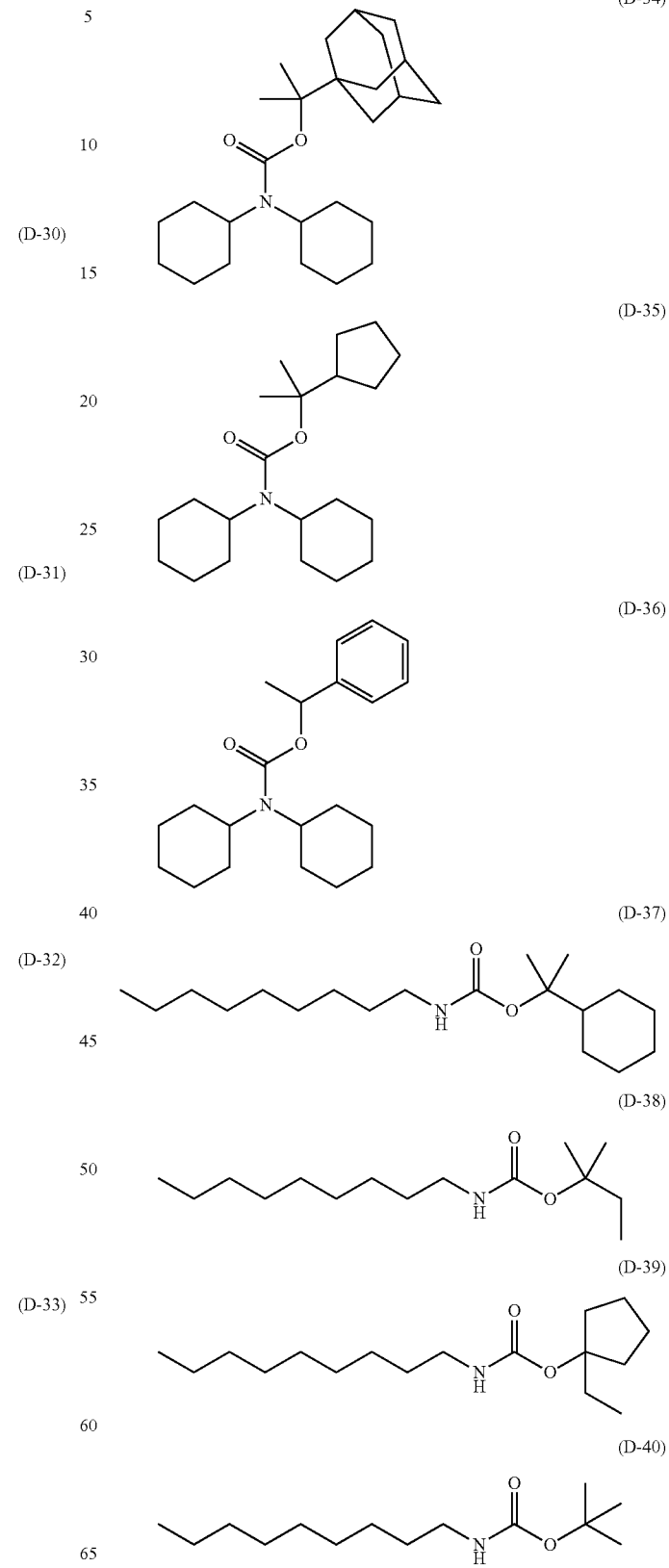

(D-41)
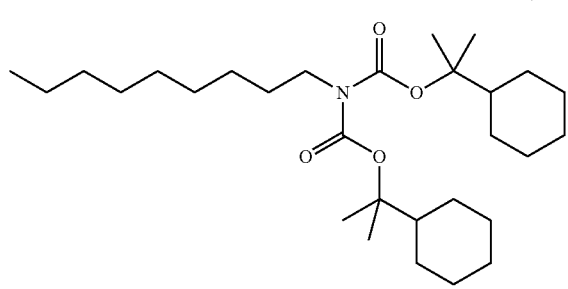
(D-42)
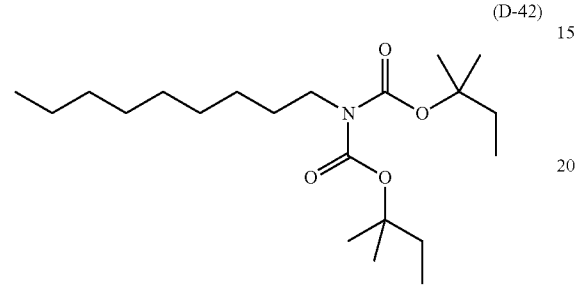
(D-43)
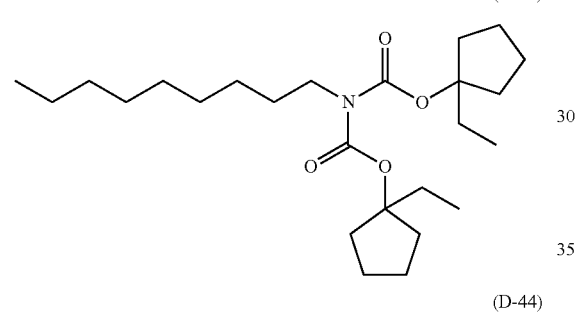
(D-44)
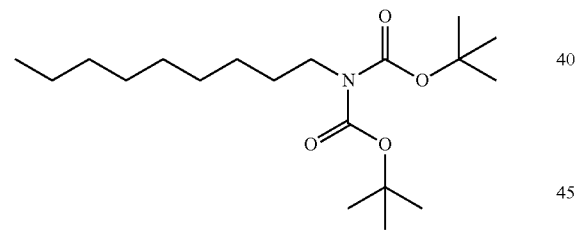
(D-45)
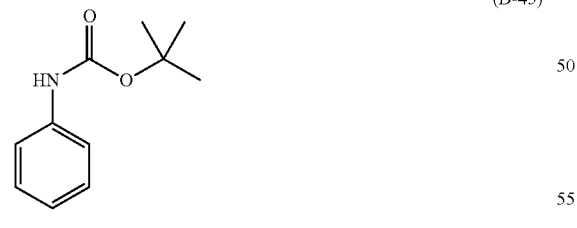
(D-46)
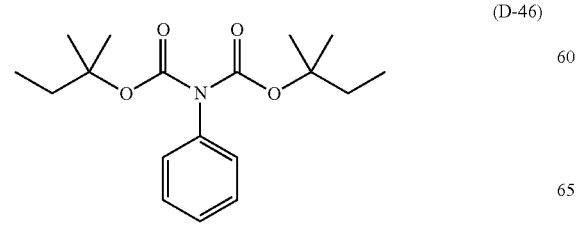
(D-47)
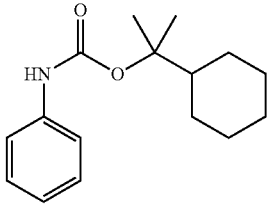
(D-48)
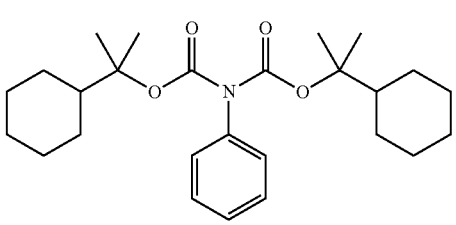
(D-49)
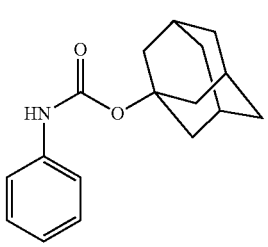
(D-50)
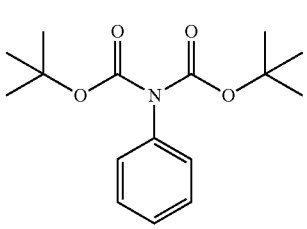
(D-51)
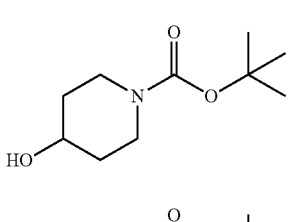
(D-52)
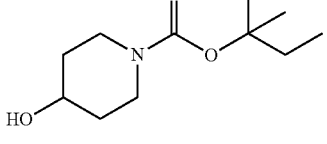
(D-53)
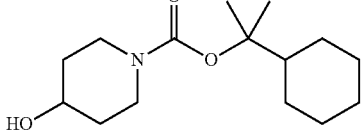
(D-54)
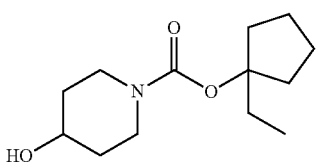

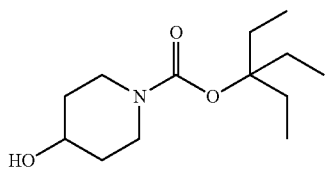
(D-55)

The compound represented by formula (F) can be easily synthesized from a commercially available amine by the method described, for example, in *Protective Groups in Organic Synthesis*, 4th edition. A most general method is a method of causing a dicarbonic acid ester or a haloformic acid ester to act on a commercially available amine to obtain the compound. In the formulae, X represents a halogen atom, and definitions and specific examples of Ra and Rb are the same as those described in formula (F).

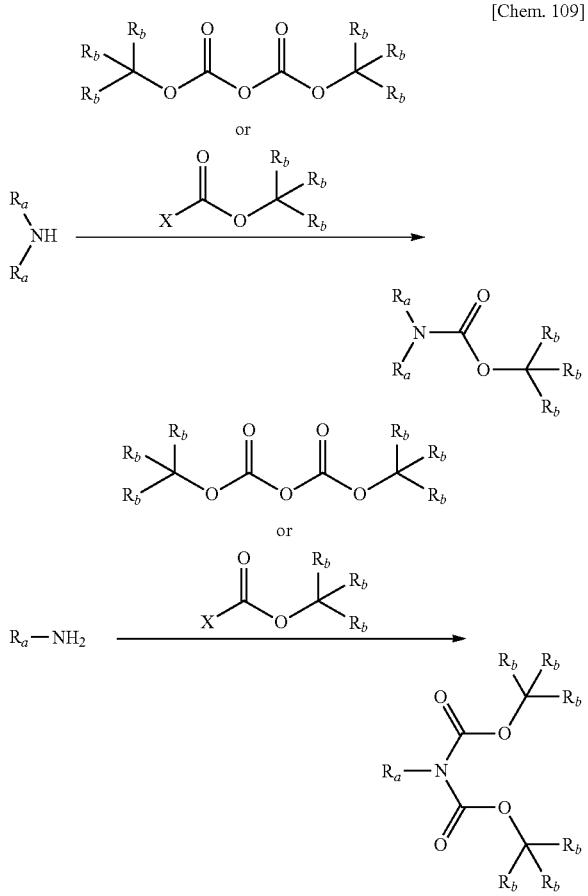

[Chem. 109]

In addition, a photodecomposable basic compound (a compound which initially exhibits basicity due to the action of a basic nitrogen atom as a base but decomposes upon irradiation with an actinic ray or radiation to generate a zwitterionic compound having a basic nitrogen atom and an organic acid moiety and resulting from their neutralization in the molecule, is reduced in or deprived of the basicity; for example, onium salts described in Japanese Patent No. 3,577,743, JP-A-2001-215689, JP-A-2001-166476 and JP-A-2008-102383), and a photobase generator (for example, compounds described in JP-A-2010-243773) may also be appropriately used.

As for the basic compound (including the compound (D), one compound is used alone, or two or more compounds are used in combination.

The amount of the basic compound used is usually from 0.001 to 10 mass %, preferably from 0.01 to 5 mass %, based on the solid content of the composition.

The molar ratio of acid generator/basic compound is preferably from 2.5 to 300. That is, the molar ratio is preferably 2.5 or more in view of sensitivity and resolution and preferably 300 or less from the standpoint of suppressing the reduction in resolution due to thickening of the pattern with aging after exposure until heat treatment. The molar ratio is more preferably from 5.0 to 200, still more preferably from 7.0 to 150.

[5] Surfactant

The composition according to the present invention may further contain a surfactant. By virtue of containing a surfactant, when an exposure light source having a wavelength of 250 nm or less, particularly 220 nm or less is used, a pattern with good sensitivity and resolution as well as little adherence or development defect can be formed.

Among others, fluorine-containing and/or silicon-containing surfactants are preferably used as the surfactant.

The fluorine-containing and/or silicon-containing surfactants include, for example, surfactants described in paragraph [0276] of U.S. Patent Application Publication No. 2008/0248425. There may also be used EFtop EF301 or EF303 (produced by Shin-Akita Kasei K.K.); Florad FC430, 431 or 4430 (produced by Sumitomo 3M Inc.); Megaface F171, F173, F176, F189, F113, F110, F177, F120 or R08 (produced by DIC Corporation); Surflon S-382, SC101, 102, 103, 104, 105 or 106 (produced by Asahi Glass Co., Ltd.); Troysol S-366 (produced by Troy Chemical Corp.); GF-300 or GF-150 (produced by Toagosei Chemical Industry Co., Ltd.); Surflon S-393 (produced by Seimi Chemical Co., Ltd.); EFtop EF121, EF122A, EF122B, RF122C, EF125M, EF135M, EF351, EF352, EF801, EF802 or EF601 (produced by JEMCO Inc.); PF636, PF656, PF6320 or PF6520 (produced by OMNOVA); or FTX-204G, 208G, 218G, 230G, 204D, 208D, 212D, 218D or 222D (produced by NEOS Co., Ltd.). Incidentally, Polysiloxane Polymer KP-341 (produced by Shin-Etsu Chemical Co., Ltd.) may also be used as the silicon-containing surfactant.

In addition to these known surfactants, the surfactant may also be synthesized using a fluoro-aliphatic compound produced by a telomerization process (also called a telomer process) or an oligomerization process (also called an oligomer process). Specifically, a polymer having a fluoro-aliphatic group derived from the fluoro-aliphatic compound may be used as the surfactant. The fluoro-aliphatic compound can be synthesized by the method described in JP-A-2002-90991.

The polymer having a fluoro-aliphatic group is preferably a copolymer of a fluoro-aliphatic group-containing monomer with a (poly(oxyalkylene)) acrylate or methacrylate and/or a (poly(oxyalkylene)) methacrylate, and the polymer may have an irregular distribution or may be a block copolymer.

The poly(oxyalkylene) group includes, for example, a poly(oxyethylene) group, a poly(oxypropylene) group, and a poly(oxybutylene) group. This group may also be a unit having, within the same chain, alkylenes differing in the chain length, such as block-linked poly(oxyethylene, oxypropylene and oxyethylene) and block-linked poly(oxyethylene and oxypropylene).

Furthermore, the copolymer of a fluoro-aliphatic group-containing monomer and a (poly(oxyalkylene)) acrylate or methacrylate may be a ternary or higher copolymer obtained by simultaneously copolymerizing, for example, two or more different fluoro-aliphatic group-containing monomers and two or more different (poly(oxyalkylene)) acrylates or methacrylates.

The copolymer includes, for example, as the commercially available surfactant, Megaface F178, F-470, F-473, F-475, F-476 and F-472 (produced by DIC Corporation) and further includes a copolymer of a $C_6F_{13}$ group-containing acrylate or methacrylate with a (poly(oxyalkylene)) acrylate or methacrylate, a copolymer of a $C_6F_{13}$ group-containing acrylate or methacrylate with a (poly(oxyethylene)) acrylate or methacrylate and a (poly(oxypropylene))acrylate or methacrylate, a copolymer of a $C_8F_{17}$ group-containing acrylate or methacrylate with a (poly(oxyalkylene)) acrylate or methacrylate, and a copolymer of a $C_8F_{17}$ group-containing acrylate or methacrylate with a (poly(oxyethylene)) acrylate or methacrylate and a (poly(oxypropylene)) acrylate or methacrylate.

Surfactants other than the fluorine-containing and/or silicon-containing surfactants, described in paragraph [0280] of U.S. Patent Application Publication No. 2008/0248425, may also be used.

As for these surfactants, one kind may be used alone, or two or more kinds may be used in combination.

In the case where the composition according to the present invention contains a surfactant, the content of the surfactant is preferably from 0 to 2 mass %, more preferably from 0.0001 to 2 mass %, still more preferably from 0.0005 to 1 mass %, based on the total solid content of the composition.

[6] Other Additives

The composition of the present invention may appropriately contain, in addition to the components described above, a carboxylic acid, an onium carboxylate, a dissolution inhibiting compound having a molecular weight of 3,000 or less described, for example, in *Proceeding of SPIE*, 2724, 355 (1996), a dye, a plasticizer, a photosensitizer, a light absorber, an antioxidant, etc.

In particular, a carboxylic acid is suitably used for enhancing the performance. The carboxylic acid is preferably an aromatic carboxylic acid such as benzoic acid and naphthoic acid.

The content of the carboxylic acid is preferably from 0.01 to 10 mass %, more preferably from 0.01 to 5 mass %, still more preferably from 0.01 to 3 mass %, relative to the total solid content concentration of the composition.

From the standpoint of enhancing the resolution, the actinic ray-sensitive or radiation-sensitive resin composition of the present invention is preferably used in a film thickness of 10 to 250 nm, more preferably from 20 to 200 nm, still more preferably from 30 to 100 nm. Such a film thickness can be achieved by setting the solid content concentration in the composition to an appropriate range, thereby imparting an appropriate viscosity and enhancing the coatability and film-forming property.

The solid content concentration in the actinic ray-sensitive or radiation-sensitive resin composition of the present invention is usually from 1.0 to 10 mass %, preferably from 1.0 to 5.7 mass %, more preferably from 1.0 to 3.0 mass %. By setting the solid content concentration to the range above, the resist solution can be uniformly coated on a substrate and furthermore, a resist pattern improved in the line width roughness can be formed. The reason therefor is not clearly known, but it is considered that probably thanks to a solid content concentration of 10 mass % or less, preferably 5.7 mass % or less, aggregation of materials, particularly, a photoacid generator, in the resist solution is suppressed, as a result, a uniform resist film can be formed.

The solid content concentration is a weight percentage of the weight of resist components excluding the solvent, relative to the total weight of the actinic ray-sensitive or radiation-sensitive resin composition.

The actinic ray-sensitive or radiation-sensitive resin composition of the present invention is used by dissolving the components above in a predetermined organic solvent, preferably in the above-described mixed solvent, filtering the solution through a filter, and applying the filtrate onto a predetermined support (substrate). The filter used for filtration is preferably a polytetrafluoroethylene-, polyethylene- or nylon-made filter having a pore size of 0.1 μm or less, more preferably 0.05 μm or less, still more preferably 0.03 μm or less. In the filtration through a filter, as described, for example, in JP-A-2002-62667, circulating filtration may be performed, or the filtration may be performed by connecting a plurality of kinds of filters in series or in parallel. In addition, the composition may be filtered a plurality of times. Furthermore, a deaeration treatment, etc. may be applied to the composition before and after filtration through a filter.

[7] Pattern Forming Method

The present invention relates to an actinic ray-sensitive or radiation-sensitive film (hereinafter, sometimes referred to as "resist film") formed using the above-described composition of the present invention.

The pattern forming method of the present invention includes at least:

(i) a step of forming a film (resist film) from the actinic ray-sensitive or radiation-sensitive resin composition, (ii) a step of exposing the film, and (iii) a step of developing the exposed film by using a developer to form a pattern.

The developer in the step (iii) may be an organic solvent-containing developer or an alkali developer but is preferably an organic solvent-containing developer, because the effects of the present invention are more successfully achieved.

Specifically, the pattern forming method of the present invention preferably includes at least:

(i) a step of forming a film (resist film) from the actinic ray-sensitive or radiation-sensitive resin composition, (ii) a step of exposing the film, and (iii') a step of developing the exposed film by using an organic solvent-containing developer to form a negative pattern.

The exposure in the step (ii) may be immersion exposure.

The pattern forming method of the present invention preferably includes (iv) a heating step after the exposure step (ii).

The pattern forming method of the present invention may further include (v) a step of performing development by using an alkali developer when the developer in the step (iii) is an organic solvent-containing developer, and on the other hand, may further include (v) a step of performing development by using an organic solvent-containing developer when the developer in the step (iii) is an alkali developer.

In the pattern forming method of the present invention, the exposure step (ii) may be performed a plurality of times.

In the pattern forming method of the present invention, the heating step (v) may be performed a plurality of times.

The resist film is formed of the above-described actinic ray-sensitive or radiation-sensitive resin composition of the present invention and, more specifically, is preferably formed on a substrate. In the pattern forming method of the present invention, the step of forming a film on a substrate by using the actinic ray-sensitive or radiation-sensitive resin composition, the step of exposing the film, and the development step can be performed by generally known methods.

For example, the composition is coated on a substrate (e.g., silicon/silicon dioxide-coated substrate, silicon nitride and chromium-deposited quartz substrate) used in the production of a precision integrated circuit device, an imprint mold, etc. by using a spinner, a coater, etc. Thereafter, the coating is dried, whereby an actinic ray-sensitive or radiation-sensitive film can be formed.

Before forming the resist film, an antireflection film may be previously provided by coating on the substrate.

The antireflection film used may be either an inorganic film type such as titanium, titanium dioxide, titanium nitride, chromium oxide, carbon and amorphous silicon, or an organic film type composed of a light absorber and a polymer material. A commercially available organic antireflection film such as DUV30 Series and DUV-40 Series produced by Brewer Science, Inc. and AR-2, AR-3 and AR-5 produced by Shipley Co., Ltd. may also be used as the organic antireflection film.

The pattern forming method also preferably includes, after film formation, a pre-baking step. (PB) before entering the exposure step.

It is also preferable to include a post-exposure baking step (PEB) after the exposure step but before the development step.

As for the heating temperature, both PB and PEB are preferably performed at 70 to 120° C., more preferably at 80 to 110° C.

The heating time is preferably from 30 to 300 seconds, more preferably from 30 to 180 seconds, still more preferably from 30 to 90 seconds.

The heating can be performed using a device attached to an ordinary exposure/developing machine or may be performed using a hot plate, etc.

The reaction in the exposed area is accelerated by the baking and in turn, the sensitivity or pattern profile is improved.

It is also preferable to include a heating step (Post Bake) after the rinsing step. By the baking, the developer and rinsing solution remaining between patterns as well as in the inside of the pattern are removed.

The actinic ray or radiation includes, for example, infrared light, visible light, ultraviolet light, far ultraviolet light, X-ray, and electron beam. An actinic ray or radiation having, for example, a wavelength of 250 nm or less, particularly 220 nm or less, is preferred. Such an actinic ray or radiation includes, for example, KrF excimer laser (248 nm), ArF excimer laser (193 nm), $F_2$ excimer laser (157 nm), X-ray, and electron beam. The actinic ray or radiation is preferably, for example, KrF excimer laser, ArF excimer laser, electron beam, X-ray or EUV light, more preferably electron beam, X-ray or EUV light, still more preferably electron beam or EUV light.

From the standpoint of suppressing outgassing or development defect or more improving the pattern profile, the actinic ray-sensitive or radiation-sensitive resin composition used in the pattern forming method of the present invention may contain a hydrophobic resin. Alternatively, a coating layer (so-called "topcoat") may be formed using the hydrophobic resin on the resist film formed of the above-described actinic ray-sensitive or radiation-sensitive resin composition.

The hydrophobic resin includes a fluorine atom-containing resin, etc., and specific examples and preferable examples thereof include those described in paragraphs [0308] to [0361] of JP-A-2012-137698.

The content of the hydrophobic resin is preferably from 0.01 to 10 mass %, more preferably from 0.1 to 5 mass %, relative to the total solid content in the actinic ray-sensitive or radiation-sensitive resin composition.

In the present invention, the substrate on which the film is formed is not particularly limited, and a substrate generally used in the process of producing a semiconductor such as IC or producing a liquid crystal device or a circuit board such as thermal head or in the lithography of other photofabrication processes, for example, an inorganic substrate such as silicon, SiN, $SiO_2$ and SiN, or a coating-type inorganic substrate such as SOG, can be used. If desired, an organic antireflection film may be formed between the film and the substrate.

In the case where the pattern forming method of the present invention includes a step of performing development by using an alkali developer, the alkali developer which can be used includes, for example, an alkaline aqueous solution of inorganic alkalis such as sodium hydroxide, potassium hydroxide, sodium carbonate, sodium silicate, sodium metasilicate and aqueous ammonia, primary amines such as ethylamine and n-propylamine, secondary amines such as diethylamine and di-n-butylamine, tertiary amines such as triethylamine and methyldiethylamine, alcohol amines such as dimethylethanolamine and triethanolamine, quaternary ammonium salts such as tetramethylammonium hydroxide and tetraethylammonium hydroxide, or cyclic amines such as pyrrole and piperidine.

The alkaline aqueous solution above may also be used after adding thereto alcohols and a surfactant each in an appropriate amount.

The alkali concentration of the alkali developer is usually from 0.1 to 20 mass %.

The pH of the alkali developer is usually from 10.0 to 15.0.

In particular, an aqueous solution of 2.38 mass % tetramethylammonium hydroxide is preferred.

As the rinsing solution in the rinsing treatment performed after the alkali development, pure water is used, and the pure water may also be used after adding thereto an appropriate amount of a surfactant.

After the development or rinsing, a treatment of removing the developer or rinsing solution adhering on the pattern by a supercritical fluid may be performed.

In the case where the pattern forming method of the present invention includes a step of performing development by using an organic solvent-containing developer, a polar solvent such as ketone-based solvent, ester-based solvent, alcohol-based solvent, amide-based solvent and ether-based solvent, or a hydrocarbon-based solvent can be used as the developer used in the step (hereinafter, sometimes referred to as an "organic developer").

The ketone-based solvent includes, for example, 1-octanone, 2-octanone, 1-nonanone, 2-nonanone, acetone, 2-heptanone (methyl amyl ketone), 4-heptanone 1-hexanone, 2-hexanone, diisobutyl ketone, cyclohexanone, methylcyclohexanone, phenylacetone, methyl ethyl ketone, methyl isobutyl ketone, acetyl acetone, acetonyl acetone, ionone, diacetonyl alcohol, acetyl carbinol, acetophenone, methyl naphthyl ketone, isophorone, and propylene carbonate.

The ester-based solvent includes, for example, methyl acetate, butyl acetate, ethyl acetate, isopropyl acetate, pentyl acetate, isopentyl acetate, amyl acetate, propylene glycol monomethyl ether acetate, ethylene glycol monoethyl ether acetate, diethylene glycol monobutyl ether acetate, diethylene glycol monoethyl ether acetate, ethyl-3-ethoxypropionate, 3-methoxybutyl acetate, 3-methyl-3-methoxybutyl acetate, methyl formate, ethyl formate, butyl formate, propyl formate, ethyl lactate, butyl lactate, and propyl lactate.

The alcohol-based solvent includes, for example, an alcohol such as methyl alcohol, ethyl alcohol, n-propyl alcohol, isopropyl alcohol, n-butyl alcohol, sec-butyl alcohol, tert-butyl alcohol, isobutyl alcohol, n-hexyl alcohol, n-heptyl alcohol, n-octyl alcohol and n-decanol; a glycol-based solvent such as ethylene glycol, diethylene glycol and triethylene glycol; and a glycol ether-based solvent such as ethylene glycol monomethyl ether, propylene glycol monomethyl ether, ethylene glycol monoethyl ether, propylene glycol monoethyl ether, diethylene glycol monomethyl ether, triethylene glycol monoethyl ether and methoxymethyl butanol.

The ether-based solvent includes, for example, in addition to the glycol ether-based solvents above, anisole, dioxane and tetrahydrofuran.

As the amide-based solvent, for example, N-methyl-2-pyrrolidone, N,N-dimethylacetamide, N,N-dimethylformamide, hexamethylphosphoric triamide, and 1,3-dimethyl-2-imidazolidinone can be used.

The hydrocarbon-based solvent includes, for example, an aromatic hydrocarbon-based solvent such as toluene and xylene, and an aliphatic hydrocarbon-based solvent such as pentane, hexane, octane and decane.

A plurality of these solvents may be mixed, or the solvent may be used by mixing it with a solvent other than those described above or with water. However, in order to sufficiently bring out the effects of the present invention, the percentage water content in the entire developer is preferably less than 10 mass %, and it is more preferable to contain substantially no water.

That is, the amount of the organic solvent used in the organic developer is preferably from 90 to 100 mass %, more preferably from 95 to 100 mass %, relative to the total amount of the developer.

In particular, the organic developer is preferably a developer containing at least one kind of an organic solvent selected from the group consisting of a ketone-based solvent, an ester-based solvent, an alcohol-based solvent, an amide-based solvent and an ether-based solvent.

The vapor pressure at 20° C. of the organic developer is preferably 5 kPa or less, more preferably 3 kPa or less, still more preferably 2 kPa or less. By setting the vapor pressure of the organic developer to 5 kPa or less, evaporation of the developer on a substrate or in a development cup is suppressed and the temperature uniformity in the wafer plane is enhanced, as a result, the dimensional uniformity in the wafer plane is improved.

Specific examples of the solvent having a vapor pressure of 5 kPa or less include a ketone-based solvent such as 1-octanone, 2-octanone, 1-nonanone, 2-nonanone, 2-heptanone (methyl amyl ketone), 4-heptanone, 2-hexanone, diisobutyl ketone, cyclohexanone, methylcyclohexanone, phenylacetone and methyl isobutyl ketone; an ester-based solvent such as butyl acetate, pentyl acetate, isopentyl acetate, amyl acetate, propylene glycol monomethyl ether acetate, ethylene glycol monoethyl ether acetate, diethylene glycol monobutyl ether acetate, diethylene glycol monoethyl ether acetate, ethyl-3-ethoxypropionate, 3-methoxybutyl acetate, 3-methyl-3-methoxybutyl acetate, butyl formate, propyl formate, ethyl lactate, butyl lactate and propyl lactate; an alcohol-based solvent such as n-propyl alcohol, isopropyl alcohol, n-butyl alcohol, sec-butyl alcohol, tert-butyl alcohol, isobutyl alcohol, n-hexyl alcohol, n-heptyl alcohol, n-octyl alcohol and n-decanol; a glycol-based solvent such as ethylene glycol, diethylene glycol and triethylene glycol; a glycol ether-based solvent such as ethylene glycol monomethyl ether, propylene glycol monomethyl ether, ethylene glycol monoethyl ether, propylene glycol monoethyl ether, diethylene glycol monomethyl ether, triethylene glycol monoethyl ether and methoxymethylbutanol; an ether-based solvent such as anisole and tetrahydrofuran; an amide-based solvent such as N-methyl-2-pyrrolidone, N,N-dimethylacetamide and N,N-dimethylformamide; an aromatic hydrocarbon-based solvent such as toluene and xylene; and an aliphatic hydrocarbon-based solvent such as octane and decane.

Specific examples of the solvent having a vapor pressure of 2 kPa or less that is a particularly preferable range include a ketone-based solvent such as 1-octanone, 2-octanone, 1-nonanone, 2-nonanone, 2-heptanone, 4-heptanone, 2-hexanone, diisobutyl ketone, cyclohexanone, methylcyclohexanone and phenylacetone; an ester-based solvent such as butyl acetate, amyl acetate, propylene glycol monomethyl ether acetate, ethylene glycol monoethyl ether acetate, diethylene glycol monobutyl ether acetate, diethylene glycol monoethyl ether acetate, ethyl-3-ethoxypropionate, 3-methoxybutyl acetate, 3-methyl-3-methoxybutyl acetate, ethyl lactate, butyl lactate and propyl lactate; an alcohol-based solvent such as n-butyl alcohol, sec-butyl alcohol, tert-butyl alcohol, isobutyl alcohol, n-hexyl alcohol, n-heptyl alcohol, n-octyl alcohol and n-decanol; a glycol-based solvent such as ethylene glycol, diethylene glycol and triethylene glycol; a glycol ether-based solvent such as ethylene glycol monomethyl ether, propylene glycol monomethyl ether, ethylene glycol monoethyl ether, propylene glycol monoethyl ether, diethylene glycol monomethyl ether, triethylene glycol monoethyl ether and methoxymethylbutanol; an amide-based solvent such as N-methyl-2-pyrrolidone, N,N-dimethylacetamide and N,N-dimethylformamide; an aromatic hydrocarbon-based solvent such as xylene; and an aliphatic hydrocarbon-based solvent such as octane and decane.

Above all, it is more preferable to contain one or more solvents selected from the group consisting of 2-heptanone, butyl acetate, pentyl acetate, isopentyl acetate, propylene glycol monomethyl ether acetate and anisole.

In the organic developer, a surfactant can be added in an appropriate amount, if desired.

The surfactant is not particularly limited but, for example, ionic or nonionic fluorine-containing and/or silicon-containing surfactants can be used. The fluorine-containing and/or silicon-containing surfactants include surfactants described in JP-A-62-36663, JP-A-61-226746, JP-A-61-226745, JP-A-62-170950, JP-A-63-34540, JP-A-7-230165, JP-A-8-62834, JP-A-9-54432, JP-A-9-5988 and U.S. Pat. Nos. 5,405,720, 5,360,692, 5,529,881, 5,296,330, 5,436,098, 5,576,143, 5,294,511 and 5,824,451. A nonionic surfactant is preferred. The nonionic surfactant is not particularly limited, but use of a fluorine-containing surfactant or a silicon-containing surfactant is more preferred.

The amount of the surfactant used is usually from 0.001 to 5 mass %, preferably from 0.005 to 2 mass %, still more preferably from 0.01 to 0.5 mass %, relative to the total amount of the developer.

The developer for use in the present invention may contain a basic compound. Specific examples and preferable examples of the basic compound that can be contained in the developer for use in the present invention are the same as those of the basic compound described above which can be contained in the actinic ray-sensitive or radiation-sensitive resin composition.

As regards the developing method, for example, a method of dipping the substrate in a bath filled with the developer for a fixed time (dipping method), a method of raising the developer on the substrate surface by the effect of a surface tension and keeping it still for a fixed time, thereby performing the development (puddling method), a method of spraying the developer on the substrate surface (spraying method), and a method of continuously ejecting the developer on the substrate spinning at a constant speed while scanning a developer ejecting nozzle at a constant rate (dynamic dispense method) may be applied.

In the case where the above-described various developing methods include a step of ejecting the developer toward the resist film from a development nozzle of a developing apparatus, the ejection pressure of the developer ejected (the flow velocity per unit area of the developer ejected) is preferably 2 mL/sec/mm$^2$ or less, more preferably 1.5 mL/sec/mm$^2$ or less, still more preferably 1 mL/sec/mm$^2$ or less. The flow velocity has no particular lower limit but in view of throughput, is preferably 0.2 mL/sec/mm$^2$ or more.

By setting the ejection pressure of the ejected developer to the range above, pattern defects attributable to the resist scum after development can be greatly reduced.

Details of this mechanism are not clearly known, but it is considered that thanks to the ejection pressure in the above-described range, the pressure imposed on the resist film by the developer becomes small and the resist film or resist pattern is kept from inadvertent chipping or collapse.

Here, the ejection pressure (mL/sec/mm$^2$) of the developer is a value at the outlet of a development nozzle in a developing apparatus.

The method for adjusting the ejection pressure of the developer includes, for example, a method of adjusting the ejection pressure by a pump, etc., and a method of supplying the developer from a pressurized tank and adjusting the pressure to change the ejection pressure.

The pattern forming method of the present invention preferably includes a step of performing development by using an organic solvent-containing developer.

In addition, after the step of performing development by using an organic solvent-containing developer, a step of stopping the development by replacing the solvent with another solvent may be practiced.

In the pattern forming method of the present invention, in addition to a step of performing development by using an organic solvent-containing developer (organic solvent development step), a step of performing development by using an aqueous alkali solution (alkali development step) may be used in combination. By this combination use, a finer pattern can be formed.

In the present invention, a portion of low exposure intensity is removed in the organic solvent development step, and by further performing an alkali development step, a portion of high exposure intensity is also removed. By virtue of a multiple development process of performing development a plurality of times in this way, a pattern can be formed by keeping only the region of intermediate exposure intensity from being dissolved, so that a finer pattern than usual can be formed (the same mechanism as in [0077] of JP-A-2008-292975).

In the pattern forming method of the present invention, the order of the alkali development step and the organic solvent development step is not particularly limited, but it is more preferable to perform the alkali development before the organic solvent development step.

The pattern forming method may include a step of rinsing the film with a rinsing solution after the step of performing development by using an organic solvent-containing developer, but in view of, for example, throughput (productivity) and the amount of rinsing solution used, it is preferable not to include a step of rinsing the film with a rinsing solution.

The rinsing solution used in the rinsing step after the step of performing development by using an organic solvent-containing developer is not particularly limited as long as it does not dissolve the resist pattern, and a solution containing a general organic solvent may be used. As the rinsing solution, a rinsing solution containing at least one kind of an organic solvent selected from the group consisting of a hydrocarbon-based solvent, a ketone-based solvent, an ester-based solvent, an alcohol-based solvent, an amide-based solvent and an ether-based solvent is preferably used.

Specific examples of the hydrocarbon-based solvent, ketone-based solvent, ester-based solvent, alcohol-based solvent, amide-based solvent and ether-based solvent are the same as those described above for the organic solvent-containing developer.

After the step of performing development by using an organic solvent-containing developer, more preferably, a step of rinsing the film by using a rinsing solution containing at least one kind of an organic solvent selected from the group consisting of a ketone-based solvent, an ester-based solvent, an alcohol-based solvent and an amide-based solvent is preformed; still more preferably, a step of rinsing the film by using a rinsing solution containing an alcohol-based solvent or an ester-based solvent is performed; yet still more preferably, a step of rinsing the film by using a rinsing solution containing a monohydric alcohol is performed; and most preferably, a step of rinsing the film by using a rinsing solution containing a monohydric alcohol having a carbon number of 5 or more is performed.

The monohydric alcohol used in the rinsing step includes a linear, branched or cyclic monohydric alcohol, and specifically, 1-butanol, 2-butanol, 3-methyl-1-butanol, tert-butyl alcohol, 1-pentanol, 2-pentanol, 1-hexanol, 4-methyl-2-pentanol, 1-heptanol, I-octanol, 2-hexanol, cyclopentanol, 2-heptanol, 2-octanol, 3-hexanol, 3-heptanol, 3-octanol, 4-octanol, etc. may be used. As the particularly preferable monohydric alcohol having a carbon number of 5 or more, 1-hexanol, 2-hexanol, 4-methyl-2-pentanol, 1-pentanol, 3-methyl-1-butanol, etc. may be used.

A plurality of these components may be mixed, or the solvent may be used by mixing it with an organic solvent other than those described above.

The percentage water content in the rinsing solution is preferably 10 mass % or less, more preferably 5 mass % or less, still more preferably 3 mass % or less. By setting the percentage water content to 10 mass % or less, good development characteristics can be obtained.

The vapor pressure at 20° C. of the rinsing solution used after the step of performing development by using an organic solvent-containing developer is preferably from 0.05 to 5 kPa, more preferably from 0.1 to 5 kPa, and most preferably from 0.12 to 3 kPa. By setting the vapor pressure of the rinsing solution to the range from 0.05 to 5 kPa, the temperature uniformity in the wafer plane is enhanced and moreover, swelling due to permeation of the rinsing solution is suppressed, as a result, the dimensional uniformity in the wafer plane is improved.

The rinsing solution may also be used after adding thereto a surfactant in an appropriate amount.

In the rinsing step, the wafer after development using an organic solvent-containing developer is rinsed using a rinsing solution containing the above-described organic solvent. The method for rinsing treatment is not particularly limited, but, for example, a method of continuously ejecting the rinsing solution on the substrate spinning at a constant speed (spin coating method), a method of dipping the substrate in a bath filled with the rinsing solution for a fixed time (dipping method), and a method of spraying the rinsing solution on the substrate surface (spraying method) may be applied. Above all, it is preferable to perform the rinsing treatment by the spin coating method and after the rinsing, remove the rinsing solution from the substrate surface by spinning the substrate at a rotation speed of 2,000 to 4,000 rpm. It is also preferable to include a heating step (Post Bake) after the rinsing step. By the baking, the developer and rinsing solution remaining between patterns as well as in the inside of the pattern are removed. The heating step after the rinsing step is performed at usually from 40 to 160° C., preferably from 70 to 95° C., for usually from 10 seconds to 3 minutes, preferably from 30 to 90 seconds.

In addition, an imprint mold may also be produced using the composition according to the present invention. For details, refer to, for example, Japanese Patent 4,109,085, JP-A-2008-162101, and Yoshihiko Hirai (compiler), *Nanoimprint no Kiso to Gijutsu Kaihatsu/Oyo Tenkai—Nanoimprint no Kiban Gijutsu to Saishin no Gijutsu Tenkai* (*Basic and Technology Expansion/Application Development of Nanoimprint—Substrate Technology of Nanoimprint and Latest Technology Expansion*), Frontier Shuppan.

The present invention also relates to a method for manufacturing an electronic device, including the pattern forming method of the present invention, and an electronic device manufactured by this manufacturing method.

The electronic device of the present invention is suitably mounted on electric electronic equipment (such as home electronic device, OA/media-related device, optical device and communication device).

EXAMPLES

The present invention is described in greater detail below by referring to Examples, but the present invention should not be construed as being limited to these Examples.

Synthesis Example of Acid Generator

Synthesis Example 1

Synthesis of Compound b-1

Compound b-1 was synthesized according to the following synthesis scheme.

[Chem. 110]

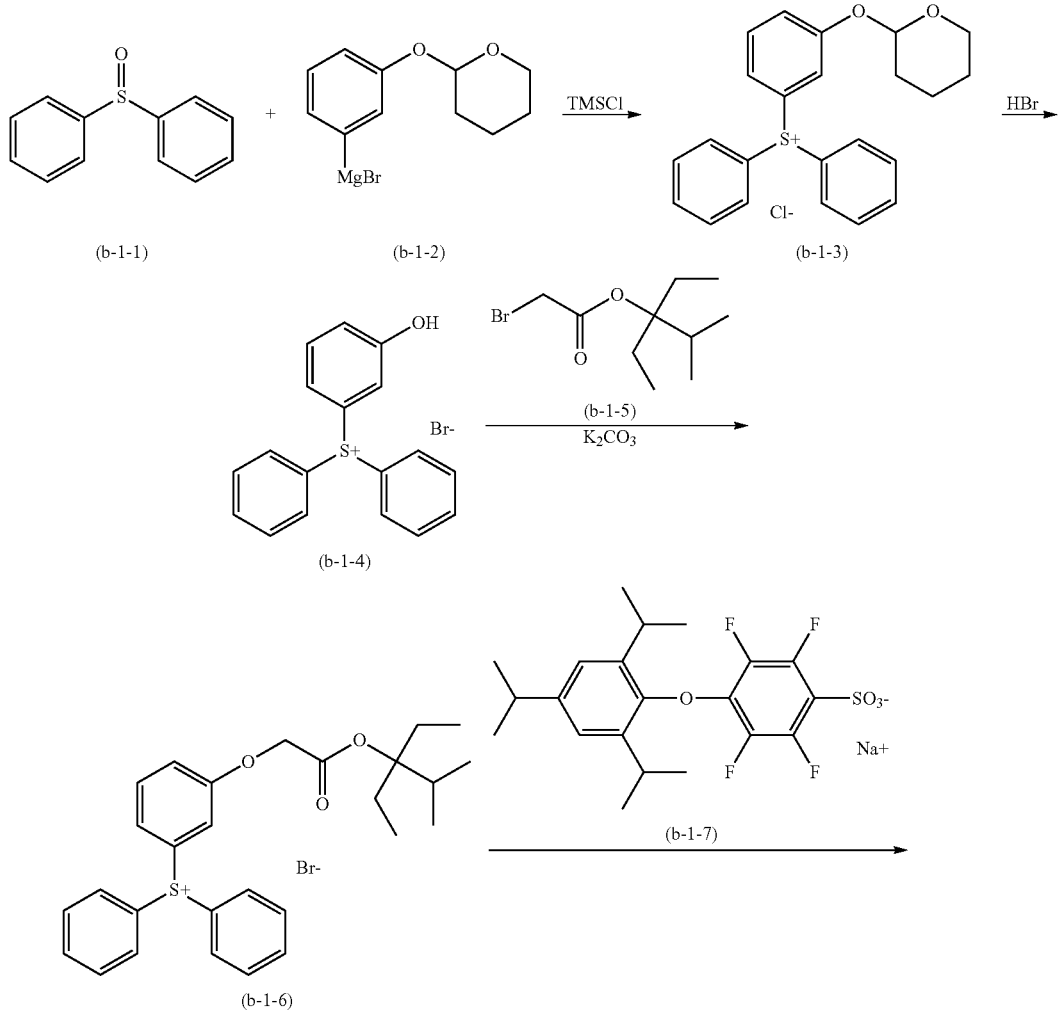

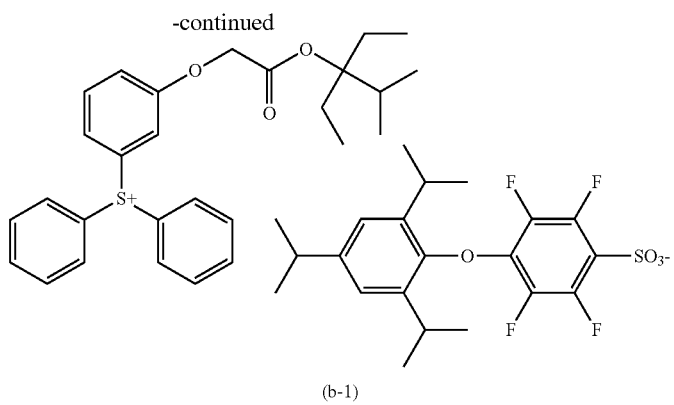

(b-1)

101 g (500 mmol) of diphenyl sulfoxide (b-1-1) was dissolved in 600 mL of tetrahydrofuran (abbrev.: THF), and 350 g of Compound (b-1-2) (a 50 Wt % THF solution) was added dropwise thereto over 30 minutes. After ice cooling to 0° C., 92 g of trimethylsilyl chloride was added dropwise over 2 hours, and 1 L of water was added. THF was removed by distillation on an evaporator, and the aqueous layer was washed with 500 mL of toluene twice and with 500 mL of hexane once. The washed aqueous layer was extracted with 500 mL of chloroform four times, and the solvent in the combined organic layer was removed by distillation on an evaporator to obtain 100 g of Compound (b-1-3) (yield: 50%).

500 mL of MeOH (methanol) and 78 g of hydrobromic acid (26 Wt %) were added to 100 g of Compound (b-1-3) obtained, and the mixture was stirred for 1 hour. MeOH was removed by distillation on an evaporator, and the obtained oily compound was reslurried in tertiary-butyl methyl ether and then filtered to obtain 90 g of Compound (b-1-4) (yield: 100%, white solid).

After 90 g of Compound (b-1-4), 52 g of potassium carbonate, 4.1 g of potassium iodide and 630 mL of acetone were added and stirred, 75 g of Compound (1-b-5) was added dropwise over 30 minutes, and 500 mL of an aqueous ammonium chloride solution was added. Acetone was removed by distillation on an evaporator to obtain a mixture containing Compound (b-1-6), and the aqueous layer was washed with 300 mL of hexane three times. To the obtained aqueous layer, 300 mL of chloroform and 94 g of Compound (b-1-7) were added and stirred for 1 hour. The chloroform layer was subjected to a liquid-separation operation, and obtained aqueous layer was washed with 300 mL of chloroform four times. The organic layers were combined, and the solvent was removed by distillation on an evaporator to obtain 179 g of Compound (b–1) (yield: 80%, white solid).

$^1$H-NMR (400 MHz in CDCl$_3$): (ppm)=7.76-7.50 (m, 12H), 7.38-7.20 (m, 2H), 6.88 (s, 2H), 4.62 (s, 2H), 3.10 (m, 3H), 2.31 (hep, 1H), 2.92-1.72 (m, 4H), 1.33 (d, 6H), 1.28 (d, 12H), 0.91-0.79 (m, 12H).

Synthesis Example 2

Synthesis of Compounds (b-2) to (b-4)

Compounds were synthesized in the same manner as in Synthesis Example 1 except for changing Compound (b-1-5) to Compounds (b-2-1) to (b-4-1) shown below.

[Chem. 111]

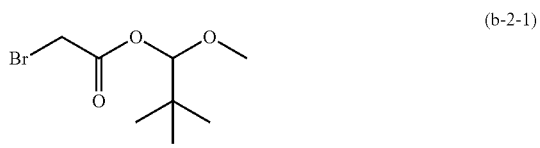

(b-2-1)

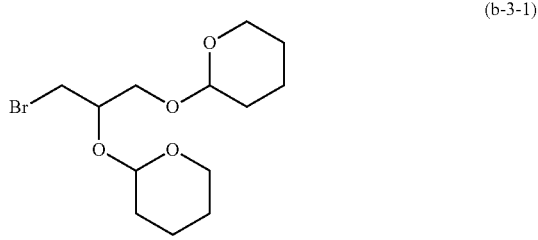

(b-3-1)

(b-4-1)

The acid generator used was appropriately selected from Compounds (b–1) to (b-137). Compounds (b–1) to (b–4) were synthesized based on the compounds above. In addition, the synthesis method of other acid generators was the same as the above-described synthesis method.

Figure 2:
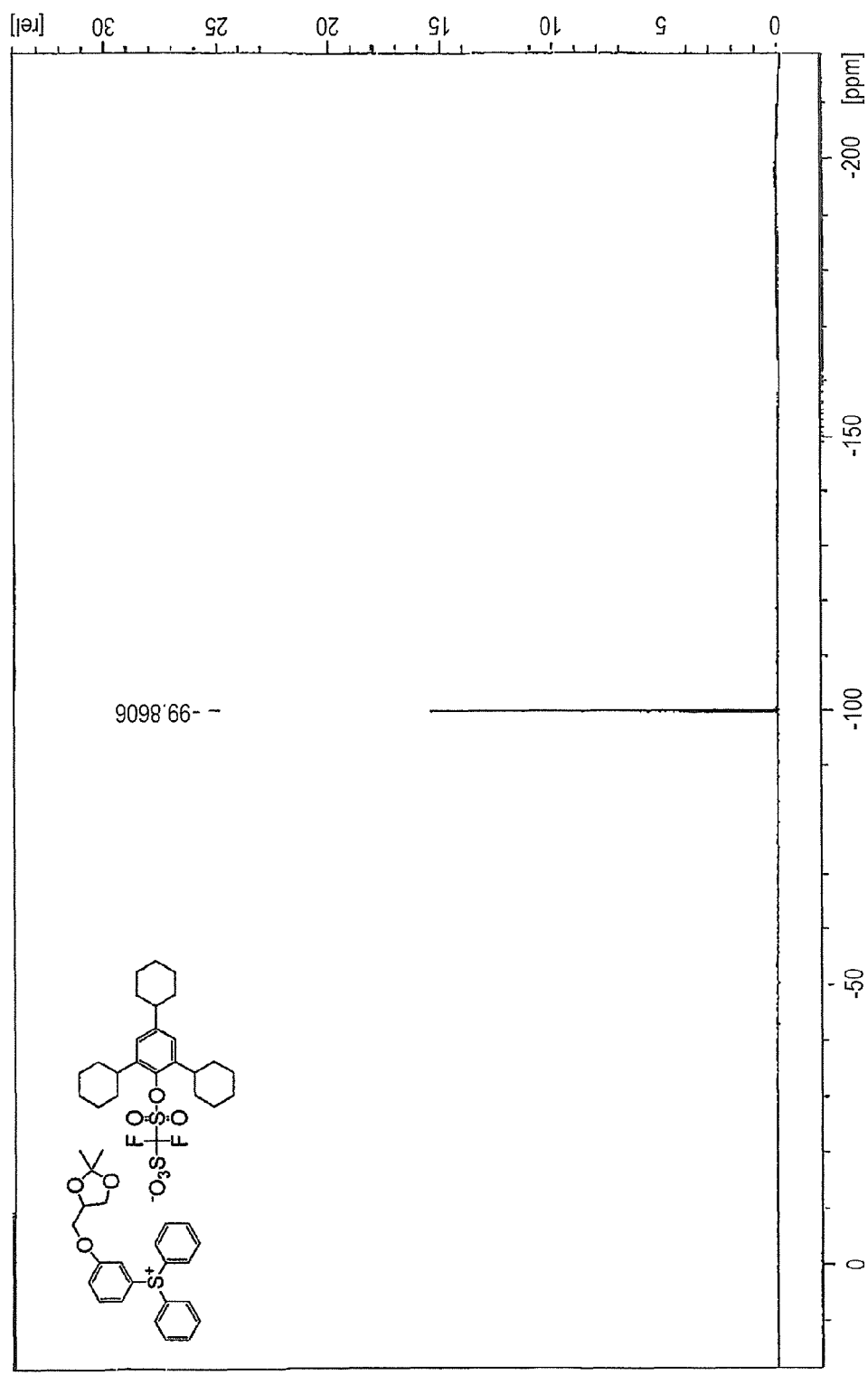
FIG. 2 is a view illustrating $^{19}$F-NMR chart of Compound (b-47).
Figure 3:
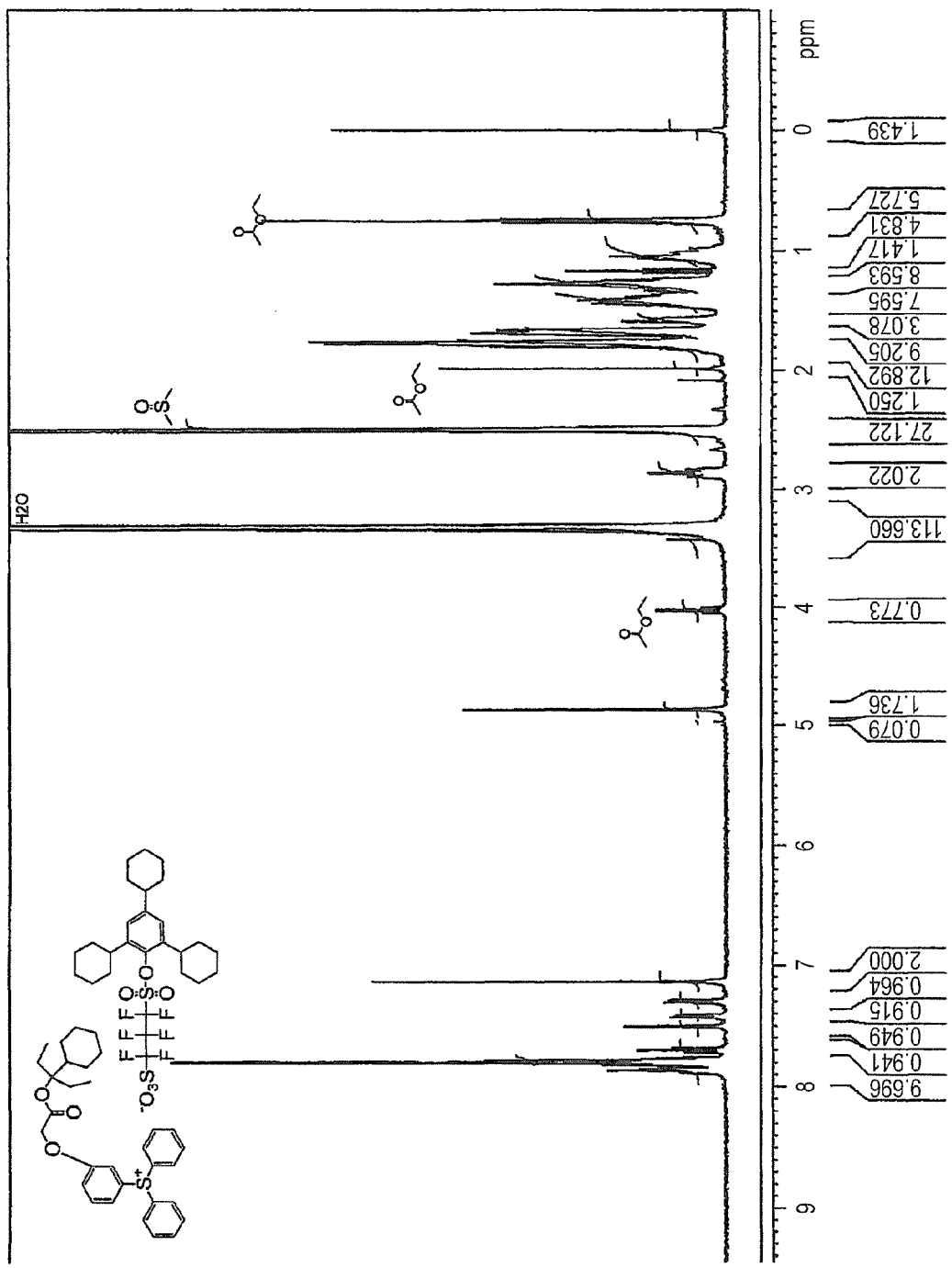
FIG. 3 is a view illustrating $^1$H-NMR chart of Compound (b-66).
Figure 4:
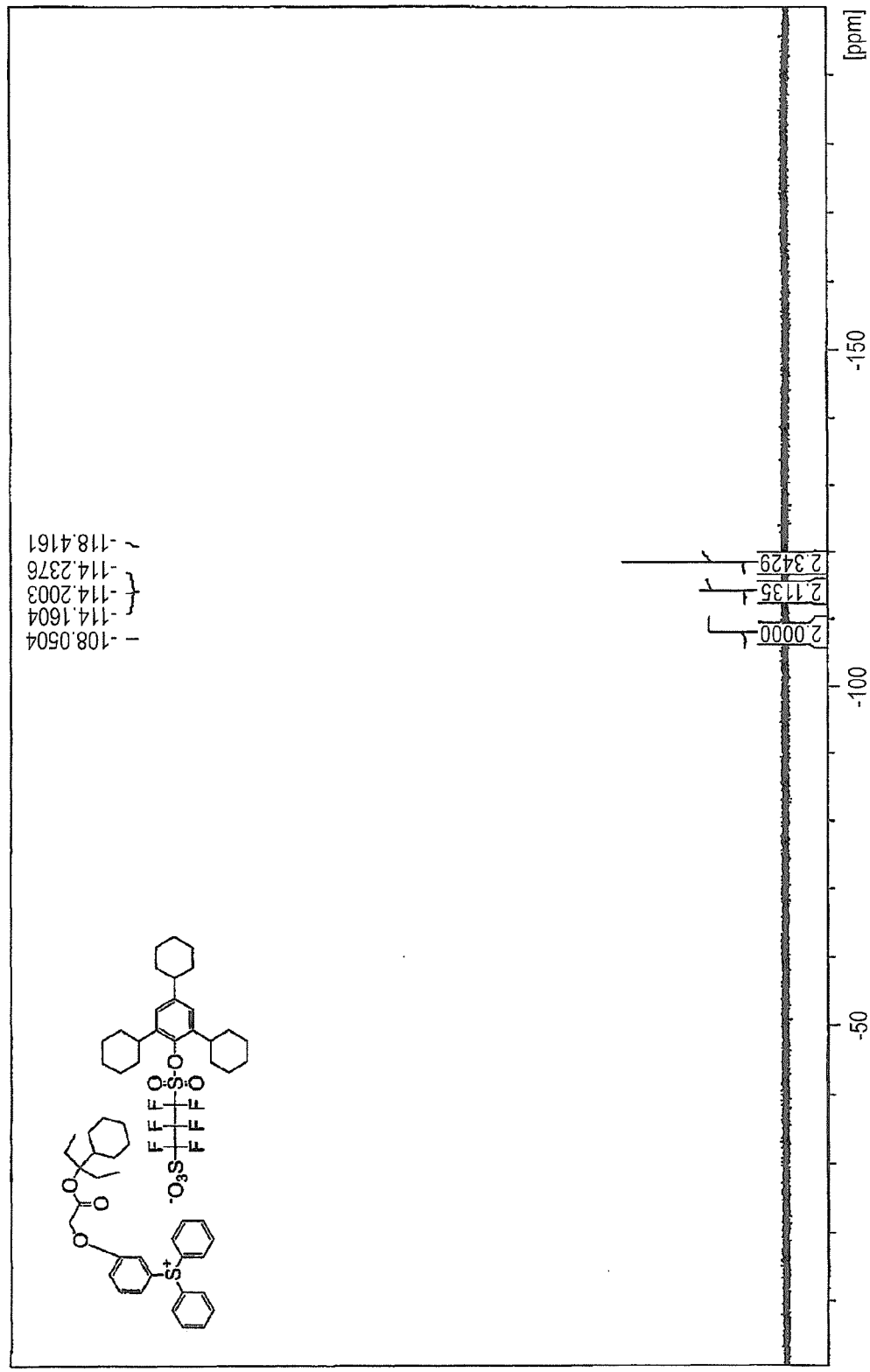
FIG. 4 is a view illustrating $^{19}$F-NMR chart of Compound (b-66).

FIGS. 1 and 2 show $^1$H-NMR chart and $^{19}$F-NMR chart, respectively, of Compound (b-47), and FIGS. 3 and 4 show $^1$H-NMR chart and $^{19}$F-NMR chart, respectively, of Compound (b-66).

As Comparative Examples, Compounds (r-1) to (r-4) shown below were used.

[Chem. 112]
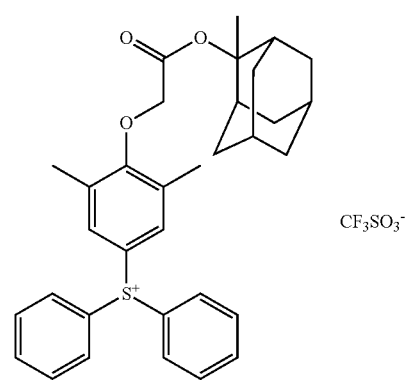
r-1
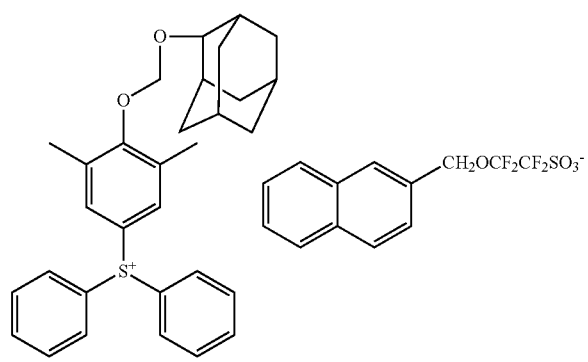
r-2
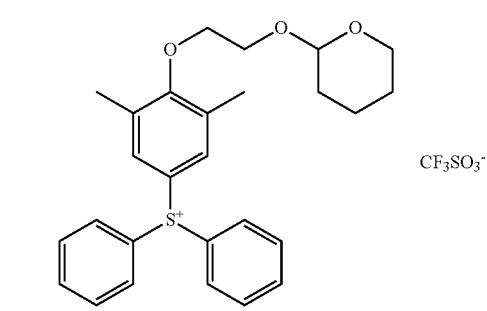
r-3
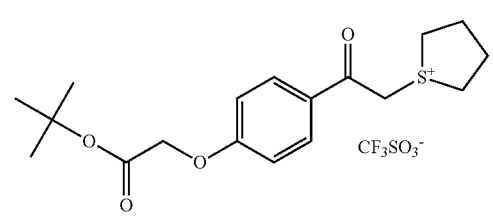
r-4
[Chem. 113]
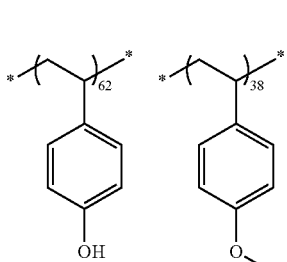
P-1
Mw = 6500
Mw/Mn = 1.23
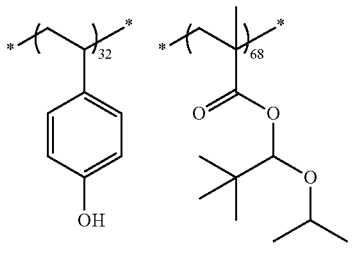
P-2
Mw = 12500
Mw/Mn = 1.65
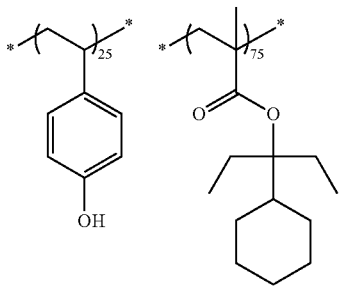
P-3
Mw = 13500
Mw/Mn = 1.60
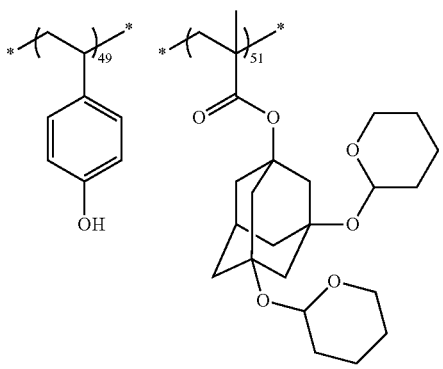
P-4
Mw = 12000
Mw/Mn = 1.66
The structural formula, the ratio (molar ratio) of repeating units, the weight average molecular weight and the polydispersity, of the resin (A) used in Examples, are shown below.

-continued
P-5
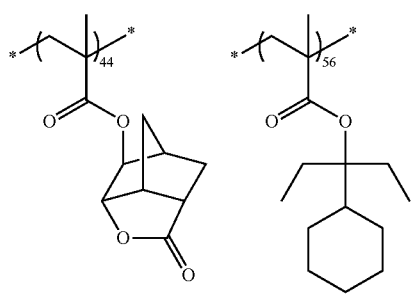
Mw = 18000
Mw/Mn = 1.43
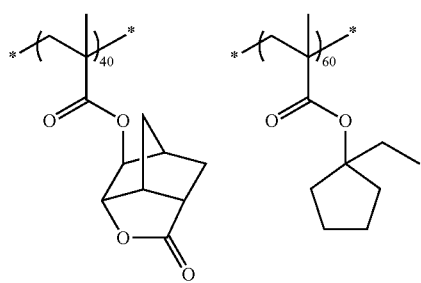
Mw = 15000
Mw/Mn = 1.85
P-7
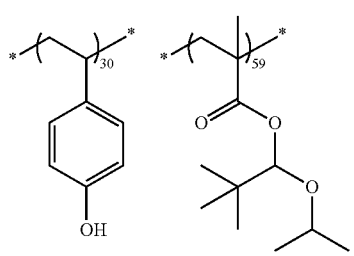
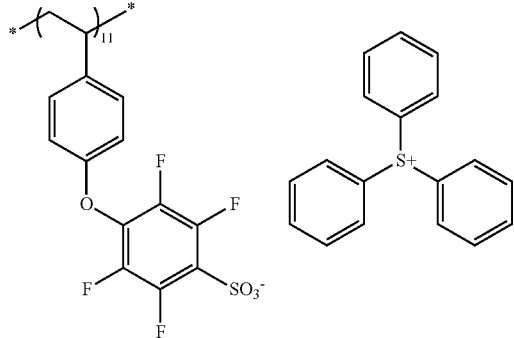
Mw = 18000
Mw/Mn = 1.56
P-8
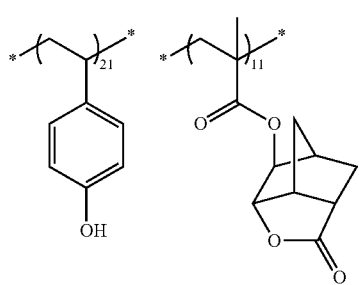
-continued
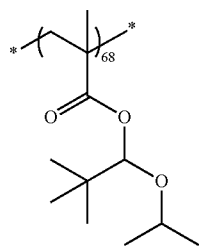
Mw = 11200
Mw/Mn = 1.32
P-6
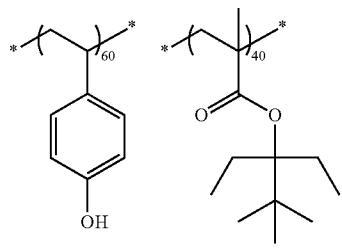
Mw 18000
Mw/Mn 1.76
[Chem. 114]
b-138
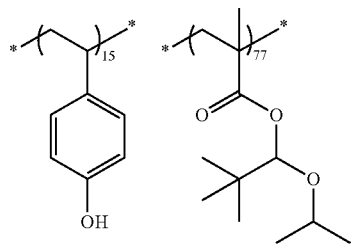
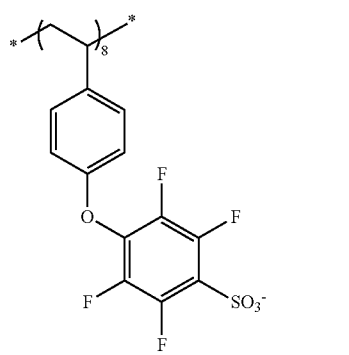
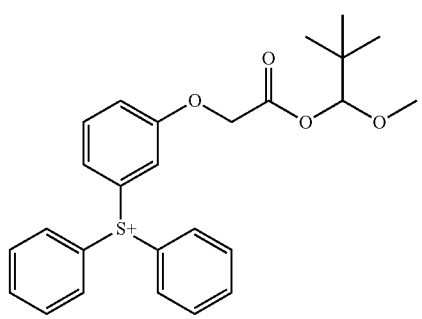
Mw 15600
Mw/Mn 1.56
P-9

245
-continued
b-141
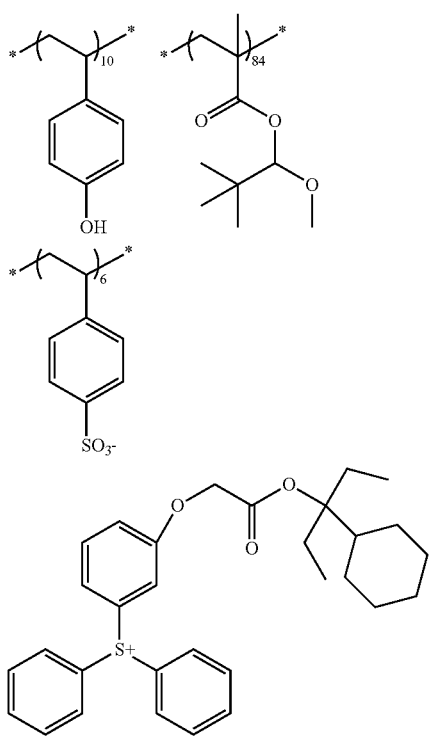
Mw 12400
Mw/Mn 1.34
As the basic compound, any one of Compounds (N-1) to (N-10) shown below was used.
[Chem. 115]
246
-continued
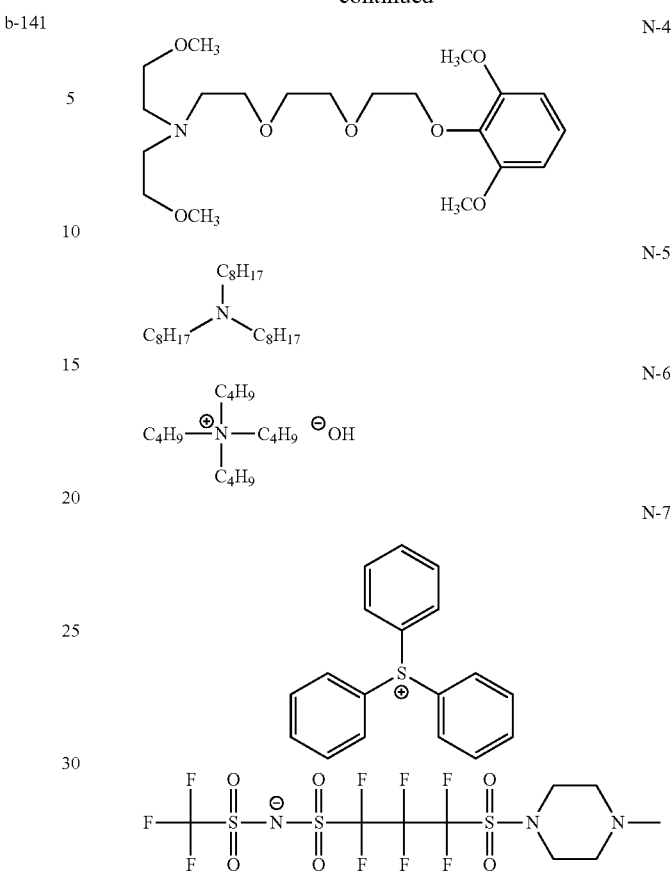
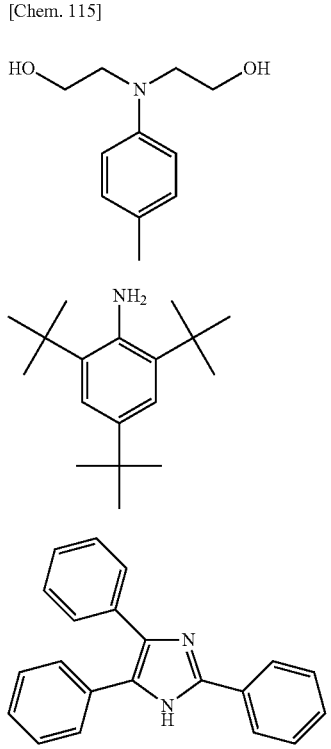
Here, Compound (N-7) comes under the compound (PA) and was synthesized based on the description in paragraph [0354] of JP-A-2006-330098.
As the jointly-used acid generator, the following compounds were used.

[Chem. 116]

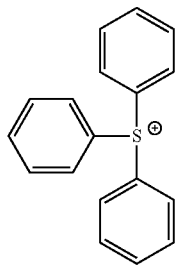
PAG-5

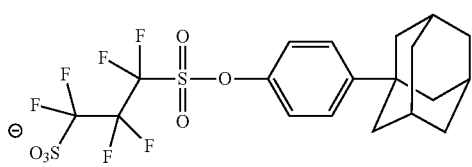
PAG-12

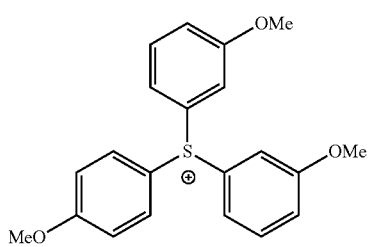

As the hydrophobic resin, the followings were used. The structural formula, the ratio (molar ratio) of repeating units, the weight average molecular weight, and the polydispersity, of the hydrophobic resin used in Examples, are shown.

[Chem. 117]

P-10

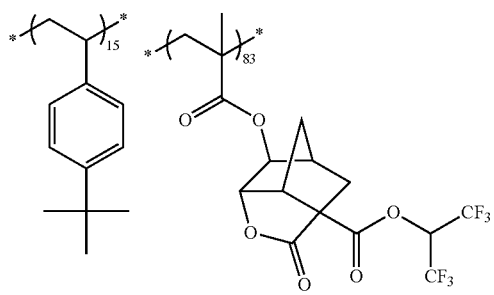

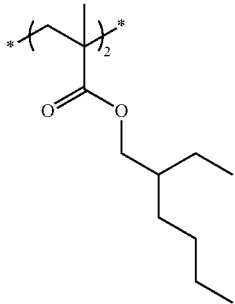

Mw 15000
Mw/Mn 1.23

P-11

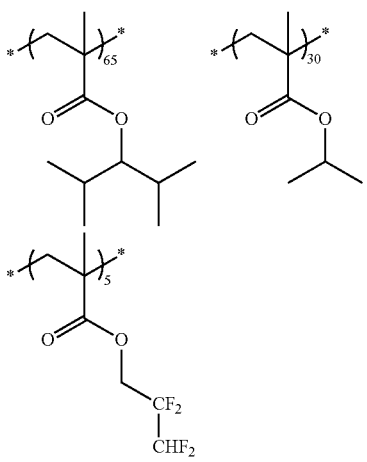

Mw 18000
Mw/Mn 1.56

As the surfactants, the following W-1 to W-3 were used.

W-1: Megaface R08 (produced by DIC Corporation; containing fluorine and silicone)

W-2: Polysiloxane Polymer KP-341 (produced by Shin-Etsu Chemical Co., Ltd.; silicon-containing)

W-3: Troysol S-366 (produced by Troy Chemical Corp.; fluorine-containing)

As the solvent, the following S1 to S-4 were appropriately mixed and used.

S1: Propylene glycol monomethyl ether acetate (PGMEA; b.p.=146° C.)

S2: Propylene glycol monomethyl ether (PGME; b.p.=120° C.)

S3: Methyl lactate (b.p.=145° C.)

S4: Cyclohexanone (b.p.=157° C.)

As the developer, the followings were used.

SG-1: 2-Nonane

SG-2: Methyl amyl ketone

SG-3: Butyl acetate

As the rinsing solution, the followings were used.

SR-1: 4-Methyl-2-pentanol

SR-2: 1-Hexanol

SR-3: Methyl isobutyl carbinol

Examples 1-1 to 1-24 and Comparative Examples 1-1 to 1-3

(Electron Beam (EB) Exposure)

(1) Preparation and Coating of Coating Solution of Actinic Ray-Sensitive or Radiation-Sensitive Resin Composition A coating solution composition having a solid content concentration of 2.5 mass % according to the formulation shown in the Table below was microfiltered through a membrane filter having a pore size of 0.1 μm to obtain an actinic ray-sensitive or radiation-sensitive resin composition (resist composition) solution.

This actinic ray-sensitive or radiation-sensitive resin composition solution was applied onto a 6-inch Si wafer previously subjected to a hexamethyldisilazane (HMDS) treatment, by using a spin coater, Mark 8, manufactured by Tokyo Electron Ltd. and dried on a hot plate at 100° C. for 60 seconds to obtain a resist film having a thickness of 50 nm.

(2) EB Exposure and Development

The resist film-coated wafer obtained in (1) above was patternwise irradiated by using an electron beam lithography apparatus (HL750, manufactured by Hitachi, Ltd., accelerating voltage: 50 KeV). At this time, the lithography was performed to form a 1:1 line-and-space pattern having a line width of 50 nm. After the electron beam lithography, the wafer was heated on a hot plate at 110° C. for 60 seconds, then developed for 30 seconds by puddling the organic developer shown in the Table below, rinsed using the rinsing solution shown in the Table below, thereafter, rotated for 30 seconds at a rotation speed of 4,000 rpm, and heated at 90° C. for 60 seconds to obtain a resist pattern of 1:1 line-and-space pattern having a line width of 50 nm.

(3) Evaluation of Resist Pattern

The obtained resist pattern was evaluated for the isolated space resolution, exposure latitude (EL) and pattern profile by the following methods.

(3-1) Isolated Space Resolution

The isolated space pattern (line:space=5:1) above was formed at an irradiation dose for reproducing a 1:1 line-and-space pattern having a line width of 50 nm, and the limiting resolution (the minimum space width below which the line and space are not separated/resolved) was determined. The value obtained was defined as the "isolated space resolution (nm)".

(3-2) Exposure Latitude (EL)

The exposure dose when reproducing a 1:1 line-and-space pattern having a line width of 50 nm was taken as an optimum exposure dose. The exposure dose range allowing for a pattern size of 50 nm±10% when changing the exposure dose was determined, and this value was divided by the optimum exposure dose and expressed in percentage. As the value is larger, the performance change due to change in the exposure dose is smaller, and the exposure latitude is better.

(3-3) Pattern Profile

The obtained resist pattern was observed using a scanning electron microscope (S4800, manufacture by Hitachi Ltd.), and the profile was expressed by the ratio (L2/L1) between middle-part length L1 and topmost length L2 of the resist pattern. As L2/L1 is closer to 1, the profile is better.

The evaluation results are shown in the Table below.

TABLE 2

| | Resin Compound (mass %) | Photoacid Generator (mass %) | Basic Compound (mass %) | Solvent (mass ratio) | Surfactant (mass %) | Developer | Rinsing Solution | Isolated Space Resolution (nm) | EL (%) | Profile (L2/L1) |
|---|---|---|---|---|---|---|---|---|---|---|
| Example 1-1 | P-2 (62.95) | b-1 (35) | N-1 (2) | S1/S2 (80/20) | W-1 (0.05) | SG-3 | SR-3 | 44 | 21.8 | 0.90 |
| Example 1-2 | P-3 (60.95) | b-2 (35) | N-1 (4) | S1/S2 (80/20) | W-3 (0.05) | SG-3 | SR-1 | 40 | 22.1 | 0.91 |
| Example 1-3 | P-4 (62.95) | b-3 (35) | N-1 (2) | S1/S2 (80/20) | W-3 (0.05) | SG-3 | — | 46 | 20.2 | 0.89 |
| Example 1-4 | P-2/P-4 (42/20.95) | b-4 (35) | N-2 (2) | S1/S2 (80/20) | W-3 (0.05) | SG-2 | — | 50 | 19.8 | 0.90 |
| Example 1-5 | P-8 (62.95) | b-5 (35) | N-1 (2) | S1/S2/S3 (70/20/10) | W-3 (0.05) | SG-3 | — | 44 | 21.6 | 0.92 |
| Example 1-6 | P-3 (62.95) | b-6 (35) | N-1 (2) | S1/S2 (80/20) | W-3 (0.05) | SG-3 | — | 40 | 22.3 | 0.93 |
| Example 1-7 | P-4 (62.95) | b-18 (35) | N-9 (2) | S1/S2 (80/20) | W-3 (0.05) | SG-3 | — | 42 | 22.1 | 1.26 |
| Example 1-8 | P-8 (62.95) | b-26 (35) | N-1 (2) | S1/S2 (80/20) | W-3 (0.05) | SG-3 | — | 44 | 16.0 | 0.90 |
| Example 1-9 | P-2 (62.95) | b-48 (35) | N-8 (2) | S1/S2 (80/20) | W-3 (0.05) | SG-3 | — | 44 | 21.0 | 1.23 |
| Example 1-10 | P-3 (77.95) | b-54 (20) | N-3 (2) | S1/S2 (80/20) | W-2 (0.05) | SG-3 | — | 42 | 21.9 | 1.28 |
| Example 1-11 | P-4 (62.95) | b-59 (35) | N-1 (2) | S1/S2 (80/20) | W-3 (0.05) | SG-3 | — | 40 | 21.5 | 1.10 |
| Example 1-12 | P-8 (63) | b-61 (35) | N-5 (2) | S1/S2/S3 (70/20/10) | — | SG-1 | — | 48 | 20.5 | 1.11 |
| Example 1-13 | P-2 (62.95) | b-62 (35) | N-6 (2) | S1/S2 (80/20) | W-3 (0.05) | SG-3 | — | 44 | 21.1 | 1.07 |
| Example 1-14 | P-3 (62.95) | b-64 (35) | N-3 (2) | S1/S2 (80/20) | W-2 (0.05) | SG-3 | — | 46 | 20.8 | 1.09 |
| Example 1-15 | P-4 (62.95) | b-74 (35) | N-8 (2) | S1/S2 (80/20) | W-3 (0.05) | SG-3 | — | 44 | 19.4 | 1.11 |
| Example 1-16 | P-8 (63.95) | b-75 (35) | N-3 (1) | S1/S2 (80/20) | W-2 (0.05) | SG-3 | — | 44 | 18.9 | 1.05 |
| Example 1-17 | P-2 (62.95) | b-85 (35) | N-3 (2) | S1/S2 (80/20) | W-3 (0.05) | SG-3 | — | 44 | 20.6 | 1.16 |
| Example 1-18 | P-3 (62.95) | b-86 (35) | N-3 (2) | S1/S2/S3 (70/20/10) | W-3 (0.05) | SG-3 | — | 44 | 20.0 | 1.14 |
| Example 1-19 | P-4 (62.95) | b-114 (35) | N-3 (2) | S1/S2 (80/20) | W-3 (0.05) | SG-3 | SR-2 | 42 | 21.8 | 1.12 |
| Example 1-20 | P-7 (85.95) | b-119 (10) | N-10 (4) | S1/S2 (80/20) | W-3 (0.05) | SG-3 | — | 44 | 21.0 | 1.09 |
| Example 1-21 | P-2 (62.95) | b-1/PAG12 (20/15) | N-4 (2) | S1/S2/S3 (70/20/10) | W-3 (0.05) | SG-3 | — | 44 | 21.1 | 0.91 |
| Example 1-22 | — | b-138 (97.95) | N-3 (2) | S1/S2/S3 (70/20/10) | W-2 (0.05) | SG-3 | — | 42 | 22.6 | 1.06 |
| Example 1-23 | — | b-141 (97.95) | N-3 (2) | S1/S2/S3 (70/20/10) | W-2 (0.05) | SG-3 | — | 44 | 22.7 | 0.92 |
| Example 1-24 | P-3 (87.95) | b-6 (10) | N-1 (2) | S1/S2 (80/20) | W-3 (0.05) | SG-3 | — | 42 | 21.6 | 0.92 |
| Comparative Example 1-1 | P-4 (62.95) | r-1 (35) | N-6 (2) | S1/S2 (80/20) | W-3 (0.05) | SG-3 | — | 88 | 89 | 1.42 |
| Comparative Example 1-2 | P-9 (62.95) | r-2 (35) | N-6 (2) | S1/S2 (80/20) | W-3 (0.05) | SG-3 | — | 80 | 63 | 1.48 |
| Comparative Example 1-3 | P-4 (62.5) | r-3 (35) | N-6 (2) | S1/S2 (80/20) | W-3 (0.05) | SG-3 | — | 90 | 80 | 1.47 |

It is apparent from the results in the Table above that in the negative pattern formation by EB exposure, the actinic ray-sensitive or radiation-sensitive resin composition used in Examples realizes high isolated space resolution, excellent exposure latitude and good pattern profile, compared with the actinic ray-sensitive or radiation-sensitive resin composition used in Comparative Examples, which does not contain a compound represented by formula (1) or (2).

Examples 2-1 to 2-25 and Comparative Examples 2-1 to 2-3

Extreme-Ultraviolet (EUV) Exposure (1) Preparation and Coating of Coating Solution of Actinic Ray-Sensitive or Radiation-Sensitive Resin Composition A coating solution composition having a solid content concentration of 1.5 mass % according to the formulation shown in the Table below was microfiltered through a membrane filter having a pore size of 0.05 m to obtain an actinic ray-sensitive or radiation-sensitive resin composition (resist composition) solution.

This actinic ray-sensitive or radiation-sensitive resin composition solution was applied onto a 6-inch Si wafer previously subjected to a hexamethyldisilazane (HMDS) treatment, by using a spin coater, Mark 8, manufactured by Tokyo Electron Ltd. and dried on a hot plate at 100° C. for 60 seconds to obtain a resist film having a thickness of 50 nm.

(2) EUV Exposure and Development

The resist film-coated wafer obtained in (1) above was patternwise exposed through an exposure mask (line/space=1/1) by using an EUV exposure apparatus (Micro Exposure Tool, manufactured by Exitech, NA: 0.3, Quadrupole, outer sigma: 0.68, inner sigma: 0.36). After the irradiation, the wafer was heated on a hot plate at 110° C. for 60 seconds, then developed for 30 seconds by puddling the organic developer shown in the Table below, rinsed using the rinsing solution shown in the Table below, thereafter, rotated for 30 seconds at a rotation speed of 4,000 rpm, and baked at 90° C. for 60 seconds to obtain a resist pattern of 1:1 line-and-space pattern having a line width of 50 nm.

(3) Evaluation of Resist Pattern

The obtained resist pattern was evaluated for the isolated space resolution, exposure latitude (EL) and pattern profile by the following methods.

(3-1) Isolated Space Resolution

The isolated space pattern (line:space=100:1) above was formed at an exposure dose for reproducing a 1:1 line-and-space pattern having a line width of 50 nm, and the limiting resolution (the minimum space width below which the line and space are not separated/resolved) was determined. The value obtained was defined as the "isolated space resolution (nm)".

(3-2) Exposure Latitude (EL)

The exposure dose when reproducing a resist pattern of 1:1 line-and-space pattern having a line width of 50 nm was taken as an optimum exposure dose. The exposure dose range allowing for a pattern size of 50 nm±10% when changing the exposure dose was determined, and this value was divided by the optimum exposure dose and expressed in percentage. As the value is larger, the performance change due to change in the exposure dose is smaller, and the exposure latitude is better.

(3-3) Pattern Profile

The obtained resist pattern was observed using a scanning electron microscope (S4800, manufacture by Hitachi Ltd.), and the profile was expressed by the ratio (L2/L1) between middle-part length L1 and topmost length L2 of the resist pattern. As L2/L1 is closer to 1, the profile is better.

The evaluation results are shown in the Table below.

TABLE 3

| | Resin Compound (mass %) | Photoacid Generator (mass %) | Basic Compound (mass %) | Solvent (mass ratio) | Surfactant (mass %) | Developer | Rinsing Solution | Isolated Space Resolution (nm) | EL (%) | Profile (L2/L1) |
|---|---|---|---|---|---|---|---|---|---|---|
| Example 2-1 | P-2 (62.95) | b-1 (35) | N-1 (2) | S1/S2 (80/20) | W-1 (0.05) | SG-3 | SR-3 | 26 | 20.8 | 0.93 |
| Example 2-2 | P-3 (60.95) | b-2 (35) | N-1 (4) | S1/S2 (80/20) | W-3 (0.05) | SG-3 | SR-1 | 24 | 21.0 | 0.92 |
| Example 2-3 | P-4 (62.95) | b-3 (35) | N-1 (2) | S1/S2 (80/20) | W-3 (0.05) | SG-3 | — | 28 | 19.2 | 0.90 |
| Example 2-4 | P-2/P-4 (42/20.95) | b-4 (35) | N-5 (2) | S1/S2 (80/20) | W-3 (0.05) | SG-2 | — | 30 | 18.9 | 0.95 |
| Example 2-5 | P-8 (62.95) | b-5 (35) | N-1 (2) | S1/S2/S3 (70/20/10) | W-3 (0.05) | SG-3 | — | 26 | 20.6 | 0.90 |
| Example 2-6 | P-3/P-11 (59.95/3) | b-6 (35) | N-1 (2) | S1/S2 (80/20) | W-3 (0.05) | SG-3 | — | 24 | 21.2 | 0.89 |
| Example 2-7 | P-4 (62.95) | b-18 (35) | N-9 (2) | S1/S2 (80/20) | W-3 (0.05) | SG-3 | — | 24 | 21.0 | 1.15 |
| Example 2-8 | P-8 (62.95) | b-26 (35) | N-1 (2) | S1/S2 (80/20) | W-3 (0.05) | SG-3 | — | 26 | 15.2 | 0.90 |
| Example 2-9 | P-2 (62.95) | b-47 (35) | N-8 (2) | S1/S2 (80/20) | W-3 (0.05) | SG-3 | — | 26 | 20.0 | 1.21 |
| Example 2-10 | P-3 (77.95) | b-54 (20) | N-3 (2) | S1/S2 (80/20) | W-2 (0.05) | SG-3 | — | 24 | 20.9 | 1.22 |
| Example 2-11 | P-4 (62.95) | b-59 (35) | N-1 (2) | S1/S2 (80/20) | W-3 (0.05) | SG-3 | — | 24 | 20.5 | 1.05 |
| Example 2-12 | P-8 (63) | b-66 (35) | N-2 (2) | S1/S2/83 (70/20/10) | — | SG-1 | — | 30 | 19.5 | 1.06 |
| Example 2-13 | P-2 (62.95) | b-62 (35) | N-6 (2) | S1/S2 (80/20) | W-3 (0.05) | SG-3 | — | 26 | 20.1 | 1.02 |
| Example 2-14 | P-3 (62.95) | b-64 (35) | N-3 (2) | S1/S2 (80/20) | W-2 (0.05) | SG-3 | — | 28 | 19.8 | 1.04 |
| Example 2-15 | P-4 (62.95) | b-74 (35) | N-8 (2) | S1/S2 (80/20) | W-3 (0.05) | SG-3 | — | 26 | 18.5 | 1.06 |
| Example 2-16 | P-8 (63.95) | b-75 (35) | N-3 (1) | S1/S2 (80/20) | W-2 (0.05) | SG-3 | — | 26 | 18.0 | 1.00 |
| Example 2-17 | P-2 (62.95) | b-85 (35) | N-3 (2) | S1/S2 (80/20) | W-3 (0.05) | SG-3 | — | 26 | 19.6 | 1.10 |
| Example 2-18 | P-3 (62.95) | b-86 (35) | N-3 (2) | S1/S2/S3 (70/20/10) | W-3 (0.05) | SG-3 | — | 26 | 19.0 | 1.09 |
| Example 2-19 | P-3 (62.95) | b-114 (35) | N-3 (2) | S1/S2 (80/20) | W-3 (0.05) | SG-3 | — | 28 | 19.2 | 1.15 |
| Example 2-20 | P-4 (62.95) | b-117 (35) | N-3 (2) | S1/S2 (80/20) | W-3 (0.05) | SG-3 | SR-2 | 24 | 20.8 | 0.87 |
| Example 2-21 | P-7 (85.95) | b-119 (10) | N-10 (4) | S1/S2 (80/20) | W-3 (0.05) | SG-3 | — | 26 | 20.0 | 1.04 |
| Example 2-22 | P-2 (62.95) | b-1/PAG12 (20/15) | N-4 (2) | S1/S2/S3 (70/20/10) | W-3 (0.05) | SG-3 | — | 26 | 20.1 | 0.92 |
| Example 2-23 | — | b-138 (97.95) | N-3 (2) | S1/S2/S3 (70/20/10) | W-2 (0.05) | SG-3 | — | 24 | 21.5 | 1.01 |
| Example 2-24 | — | b-141 (97.95) | N-3 (2) | S1/S2/S3 (70/20/10) | W-2 (0.05) | SG-3 | — | 26 | 21.6 | 0.93 |
| Example 2-25 | P-3 (87.95) | b-6 (10) | N-1 (2) | S1/S2 (80/20) | W-3 (0.05) | SG-3 | — | 24 | 20.6 | 0.90 |
| Comparative Example 2-1 | P-4 (62.95) | r-1 (35) | N-6 (2) | S1/S2 (80/20) | W-3 (0.05) | SG-3 | — | 90 | 8.5 | 1.35 |

TABLE 3-continued

|  | Resin Compound (mass %) | Photoacid Generator (mass %) | Basic Compound (mass %) | Solvent (mass ratio) | Surfactant (mass %) | Developer | Rinsing Solution | Isolated Space Resolution (nm) | EL (%) | Profile (L2/L1) |
|---|---|---|---|---|---|---|---|---|---|---|
| Comparative Example 2-2 | P-9 (62.95) | r-2 (35) | N-6 (2) | S1/S2 (80/20) | W-3 (0.05) | SG-3 | — | 70 | 6.0 | 1.50 |
| Comparative Example 2-3 | P-4 (62.5) | r-3 (35) | N-6 (2) | S1/S2 (80/20) | W-3 (0.05) | SG-3 | — | 86 | 7.6 | 1.52 |

It is apparent from the results in the Table above that in the negative pattern formation by EUV exposure, the actinic ray-sensitive or radiation-sensitive resin composition used in Examples realizes high isolated space resolution, excellent exposure latitude and good pattern profile, compared with the actinic ray-sensitive or radiation-sensitive resin composition used in Comparative Examples, which does not contain a compound represented by formula (1) or (2).

Examples 3-1 to 3-7 and Comparative Examples 3-1 and 3-2

ArF Exposure (1) Preparation of Coating Solution of Actinic Ray-Sensitive or Radiation-Sensitive Resin Composition The components shown in the Table below were dissolved in the solvent shown in the same Table to a solid content of 3.5 mass %, and the solution was filtered through a polyethylene filter having a pore size of 0.03 m to prepare an actinic ray-sensitive or radiation-sensitive resin composition.

(2) Exposure Condition: ArF Immersion Exposure

An organic antireflection film, ARC29SR (produced by Nissan Chemical Industries, Ltd.), was applied onto a silicon wafer and baked at 205° C. for 60 seconds to form a 95 nm-thick antireflection film, and the actinic ray-sensitive or radiation-sensitive resin composition was applied thereon and baked (PB) at 100° C. for 60 seconds to form a resist film having a thickness of 100 nm.

The obtained wafer was patternwise exposed through an exposure mask (binary mask, line/space=60 nm/60 nm) by using an ArF excimer laser immersion scanner (XT1700i, manufactured by ASML, NA: 1.20, C-Quad, outer sigma: 0.981, inner sigma: 0.895, XY deflection). As the immersion liquid, ultrapure water was used. Subsequently, the wafer was heated (PEB) at 100° C. for 60 seconds, then developed for 30 seconds by puddling the developer shown in the Table below, rinsed for 30 seconds by puddling the rising solution shown in the Table below while shaking off the developer, thereafter, rotated for 30 seconds at a rotation speed of 4,000 rpm, and baked at 90° C. for 60 seconds. In this way, a 1:1 line-and-space resist pattern having a line width of 50 n was obtained.

(3) Evaluation of Resist Pattern

The obtained resist pattern was evaluated for the isolated space resolution, exposure latitude (EL) and pattern profile by the following methods.

(3-1) Isolated Space Resolution

The isolated space pattern (line:space=100:1) above was formed at an exposure dose for reproducing a 1:1 line-and-space pattern having a line width of 50 nm and an isolated space pattern (line:space=100:1), and the limiting resolution (the minimum space width below which the line and space are not separated/resolved) was determined. The value obtained was defined as the "isolated space resolution (nm)".

(3-2) Exposure Latitude (EL)

The exposure dose when reproducing a resist pattern of 1:1 line-and-space pattern having a line width of 50 nm was taken as an optimum exposure dose. The exposure dose range allowing for a pattern size of 50 nm±10% when changing the exposure dose was determined, and this value was divided by the optimum exposure dose and expressed in percentage. As the value is larger, the performance change due to change in the exposure dose is smaller, and the exposure latitude is better.

(3-3) Pattern Profile

The obtained resist pattern was observed using a scanning electron microscope (S4800, manufacture by Hitachi Ltd.), and the profile was expressed by the ratio (L2/L1) between middle-part length L1 and topmost length L2 of the resist pattern. As L2/L1 is closer to 1, the profile is better.

The evaluation results are shown in the Table below.

TABLE 4

|  | Resin Compound (mass %) | Photoacid Generator (mass %) | Basic Compound (mass %) | Solvent (mass ratio) | Surfactant (mass %) | Developer | Rinsing Solution | Isolated Space Resolution (nm) | EL (%) | Profile (L2/L1) |
|---|---|---|---|---|---|---|---|---|---|---|
| Example 3-1 | P-5/P-11 (76.95/3) | b-19 (15) | N-1 (5) | S1/S2 (80/20) | W-3 (0.05) | SG-3 | SR-3 | 42 | 19.1 | 1.10 |
| Example 3-2 | P-6/P-11 (76.95/3) | b-21 (15) | N-1 (5) | S1/S2 (80/20) | W-3 (0.05) | SG-3 | SR-3 | 38 | 19.4 | 1.09 |
| Example 3-3 | P-5/P-11 (76.95/3) | b-39 (15) | N-3 (5) | S1/S2 (80/20) | W-3 (0.05) | SG-3 | SR-2 | 40 | 20.2 | 1.10 |
| Example 3-4 | P-6/P-11 (76.95/3) | b-50 (15) | N-6 (5) | S1/S2 (50/50) | W-3 (0.05) | SG-3 | SR-3 | 40 | 19.8 | 1.11 |
| Example 3-5 | P-5/P-11 (76.95/3) | b-110 (15) | N-4 (5) | S3/S4 (80/20) | W-3 (0.05) | SG-3 | SR-3 | 40 | 22.1 | 1.08 |
| Example 3-6 | P-6/P-11 (84.45/3) | b-137 (7.5) | N-6 (5) | S3/S4 (80/20) | W-3 (0.05) | SG-3 | SR-2 | 38 | 19.2 | 0.99 |
| Example 3-7 | P-5/P-11 (76.95/3) | b-21/PAG-5 (10/5) | N-6 (5) | S1/S2 (50/50) | W-3 (0.05) | SG-3 | SR-3 | 38 | 19.4 | 1.09 |
| Comparative Example 3-1 | P-5/P-11 (76.95/3) | r-3 (15) | N-6 (5) | S1/S2 (80/20) | W-3 (0.05) | SG-3 | — | 92 | 5.8 | 1.16 |
| Comparative Example 3-2 | P-5/P-11 (76.95/3) | r-4 (15) | N-6 (5) | S1/S2 (80/20) | W-3 (0.05) | SG-3 | — | 92 | 7.2 | 1.15 |

It is apparent from the results in the Table above that in the negative pattern formation by ArF exposure, the actinic ray-sensitive or radiation-sensitive resin composition used in Examples realizes high isolated space resolution, excellent exposure latitude and good pattern profile, compared with the actinic ray-sensitive or radiation-sensitive resin composition used in Comparative Examples, which does not contain a compound represented by formula (1) or (2).

Examples 4-1 to 4-22 and Comparative Examples 4-1 to 4-3

Electron Beam (EB) Exposure (1) Preparation and Coating of Coating Solution of Actinic Ray-Sensitive or Radiation-Sensitive Resin Composition The components shown in the Table below were dissolved in the solvent to prepare solutions each having a solid content concentration of 4 mass %, and the solution was filtered through a polytetrafluoroethylene filter having a pore size of 0.10 μm to prepare an actinic ray-sensitive or radiation-sensitive resin composition (resist composition). The actinic ray-sensitive or radiation-sensitive resin composition was evaluated by the following methods, and the results are shown in the Table below.

With respect to each component in the Table below, the ratio when using a plurality of kinds is the mass ratio.

(2) EB Exposure and Development

The actinic ray-sensitive or radiation-sensitive resin composition prepared was uniformly applied onto a silicon substrate subjected to a hexamethyldisilazane treatment, by using a spin coater, and heated/dried on a hot plate at 120° C. for 90 seconds to form an actinic ray-sensitive or radiation-sensitive film (resist film) having a thickness of 100 nm. This actinic ray-sensitive or radiation-sensitive film was irradiated with an electron beam by using an electron beam irradiation apparatus (HL750, manufactured by Hitachi, Ltd., accelerating voltage: 50 KeV). Immediately after the irradiation, the resist film was baked on a hot plate at 110° C. for 90 seconds. Furthermore, the resist film was developed at 23° C. for 60 seconds by using an aqueous tetramethylammonium hydroxide solution having a concentration of 2.38 mass %, rinsed with pure water for 30 seconds, and spin-dried to obtain a 1:1 line-and-space resist pattern having a line width of 50 nm.

(3) Evaluation of Resist Pattern

The obtained resist pattern was evaluated for the isolated space resolution, exposure latitude (EL) and pattern profile by the same methods as in Example I-1.

The evaluation results are shown in the Table below.

TABLE 5

| | Resin Compound (mass %) | Photoacid Generator (mass %) | Basic Compound (mass %) | Solvent (mass ratio) | Surfactant (mass %) | Isolated Space Resolution (nm) | EL (%) | Profile (L2/L1) |
|---|---|---|---|---|---|---|---|---|
| Example 4-1 | P-2 (77.95) | b-1 (20) | N-1 (2) | S1/S2 (80/20) | W-1 (0.05) | 48 | 17.8 | 1.15 |
| Example 4-2 | P-3 (75.95) | b-2 (20) | N-1 (4) | S1/S2 (80/20) | W-3 (0.05) | 46 | 17.2 | 1.10 |
| Example 4-3 | P-1 (77.95) | b-3 (20) | N-2 (2) | S1/S2 (80/20) | W-3 (0.05) | 50 | 16.0 | 1.09 |
| Example 4-4 | P-8 (77.95) | b-5 (20) | N-7 (2) | S1/S2/S3 (70/20/10) | W-3 (0.05) | 48 | 17.6 | 1.09 |
| Example 4-5 | P-3 (77.95) | b-6 (20) | N-1 (2) | S1/S2 (80/20) | W-3 (0.05) | 46 | 17.8 | 1.13 |
| Example 4-6 | P-1 (77.95) | b-18 (20) | N-9 (2) | S1/S2 (80/20) | W-3 (0.05) | 46 | 17.7 | 0.79 |
| Example 4-7 | P-8 (77.95) | b-26 (20) | N-1 (2) | S1/S2 (80/20) | W-3 (0.05) | 48 | 12.4 | 1.18 |
| Example 4-8 | P-2 (77.95) | b-48 (20) | N-8 (2) | S1/S2 (80/20) | W-3 (0.05) | 48 | 16.4 | 0.76 |
| Example 4-9 | P-3 (87.95) | b-54 (10) | N-3 (2) | S1/S2 (80/20) | W-2 (0.05) | 46 | 17.5 | 0.75 |
| Example 4-10 | P-1 (77.95) | b-59 (20) | N-1 (2) | S1/S2 (80/20) | W-3 (0.05) | 46 | 17.0 | 0.90 |
| Example 4-11 | P-2 (77.95) | b-62 (20) | N-6 (2) | S1/S2 (80/20) | W-3 (0.05) | 48 | 16.7 | 1.01 |
| Example 4-12 | P-3 (77.95) | b-64 (20) | N-5 (2) | S1/S2 (80/20) | W-2 (0.05) | 50 | 16.6 | 1.08 |
| Example 4-13 | P-1 (77.95) | b-74 (20) | N-8 (2) | S1/S2 (80/20) | W-3 (0.05) | 48 | 15.4 | 1.03 |
| Example 4-14 | P-8 (78.95) | b-75 (20) | N-3 (1) | S1/S2 (80/20) | W-2 (0.05) | 48 | 14.9 | 1.04 |
| Example 4-15 | P-2 (77.95) | b-85 (20) | N-3 (2) | S1/S2 (80/20) | W-3 (0.05) | 48 | 16.9 | 0.90 |
| Example 4-16 | P-3 (77.95) | b-86 (20) | N-3 (2) | S1/S2/S3 (70/20/10) | W-3 (0.05) | 48 | 15.9 | 0.84 |
| Example 4-17 | P-1 (77.95) | b-117 (20) | N-3 (2) | S1/S2 (80/20) | W-3 (0.05) | 46 | 17.9 | 1.20 |
| Example 4-18 | P-7 (90.95) | b-119 (5) | N-10 (4) | S1/S2 (80/20) | W-3 (0.05) | 48 | 16.8 | 0.85 |
| Example 4-19 | P-2 (82.95) | b-1/PAG12 (10/5) | N-4 (2) | S1/S2/S3 (70/20/10) | W-3 (0.05) | 48 | 16.9 | 1.19 |
| Example 4-20 | — | b-138 (97.95) | N-3 (2) | S1/S2/S3 (70/20/10) | W-2 (0.05) | 46 | 18.2 | 0.91 |
| Example 4-21 | — | b-141 (97.95) | N-3 (2) | S1/S2/S3 (70/20/10) | W-2 (0.05) | 48 | 18.3 | 1.15 |
| Example 4-22 | P-3 (87.95) | b-6 (10) | N-1 (2) | S1/S2 (80/20) | W-3 (0.05) | 46 | 17.4 | 1.15 |
| Comparative Example 4-1 | P-9 (77.95) | r-1 (20) | N-6 (2) | S1/S2 (80/20) | W-3 (0.05) | 88 | 9.5 | 0.50 |
| Comparative Example 4-2 | P-1 (77.95) | r-2 (20) | N-6 (2) | S1/S2 (80/20) | W-3 (0.05) | 96 | 8.2 | 0.55 |
| Comparative Example 4-3 | P-1 (77.95) | r-3 (20) | N-6 (2) | S1/S2 (80/20) | W-3 (0.05) | 98 | 7.3 | 0.51 |

It is apparent from the results in the Table above that in the positive pattern formation by EB exposure, the actinic ray-sensitive or radiation-sensitive resin composition used in Examples realizes high isolated space resolution, excellent exposure latitude and good pattern profile, compared with the actinic ray-sensitive or radiation-sensitive resin composition used in Comparative Examples, which does not contain a compound represented by formula (1) or (2).

Examples 5-1 to 5-22 and Comparative Examples 5-1 to 5-3

EUV (Extreme-Ultraviolet) Exposure (1) Preparation and Coating of Coating Solution of Actinic Ray-Sensitive or Radiation-Sensitive Resin Composition The components shown in the Table below were dissolved in the solvent to prepare solutions each having a solid content concentration of 4 mass %, and the solution was filtered through a polytetrafluoroethylene filter having a pore size of 0.10 μm to prepare an actinic ray-sensitive or radiation-sensitive resin composition (resist composition). The actinic ray-sensitive or radiation-sensitive resin composition was evaluated by the following methods, and the results are shown in the Table below.

With respect to each component in the Table below, the ratio when using a plurality of kinds is the mass ratio.

(2) EUV Exposure and Development

The actinic ray-sensitive or radiation-sensitive resin composition prepared was uniformly applied onto a silicon substrate subjected to a hexamethyldisilazane treatment, by using a spin coater, and heated/dried on a hot plate at 120° C. for 90 seconds to form an actinic ray-sensitive or radiation-sensitive film (resist film) having a thickness of 100 nm. The wafer coated with this resist film was patternwise exposed through an exposure mask (line/space=1/1) by using an EUV exposure apparatus (Micro Exposure Tool, manufactured by Exitech, NA: 0.3, Quadrupole, outer sigma: 0.68, inner sigma: 0.36). Immediately after the exposure, the substrate was heated on a hot plate at 110° C. for 90 seconds. Furthermore, the resist film was developed at 23° C. for 60 seconds by using an aqueous tetramethylammonium hydroxide solution having a concentration of 2.38 mass %, rinsed with pure water for 30 seconds, and spin-dried to obtain a 1:1 line-and-space resist pattern having a line width of 50 nm.

(3) Evaluation of Resist Pattern

The obtained resist pattern was evaluated for the isolated space resolution, exposure latitude (EL) and pattern profile by the same methods as in Example 2-1.

The evaluation results are shown in the Table below.

TABLE 6

|  | Resin Compound (mass %) | Photoacid Generator (mass %) | Basic Compound (mass %) | Solvent (mass ratio) | Surfactant (mass %) | Isolated Space Resolution (nm) | EL (%) | Profile (L2/L1) |
|---|---|---|---|---|---|---|---|---|
| Example 5-1 | P-2 (62.95) | b-1 (35) | N-2 (2) | S1/S2 (80/20) | W-1 (0.05) | 30 | 19.8 | 1.10 |
| Example 5-2 | P-3 (60.95) | b-2 (35) | N-1 (4) | S1/S2 (80/20) | W-3 (0.05) | 28 | 20.0 | 1.12 |
| Example 5-3 | P-1 (62.95) | b-3 (35) | N-1 (2) | S1/S2 (80/20) | W-3 (0.05) | 32 | 18.2 | 1.10 |
| Example 5-4 | P-8 (62.95) | b-5 (35) | N-1 (2) | S1/S2/S3 (70/20/10) | W-3 (0.05) | 30 | 19.6 | 1.14 |
| Example 5-5 | P-3 (62.95) | b-6 (35) | N-1 (2) | S1/S2 (80/20) | W-3 (0.05) | 28 | 20.1 | 1.13 |
| Example 5-6 | P-1 (62.95) | b-18 (35) | N-9 (2) | S1/S2 (80/20) | W-3 (0.05) | 28 | 20.0 | 0.73 |
| Example 5-7 | P-8/P-10 (59.95/3) | b-26 (35) | N-5 (2) | S1/S2 (80/20) | — | 30 | 14.4 | 1.15 |
| Example 5-8 | P-2 (62.95) | b-48 (35) | N-8 (2) | S1/S2 (80/20) | W-3 (0.05) | 30 | 19.0 | 0.76 |
| Example 5-9 | P-3 (77.95) | b-54 (20) | N-3 (2) | S1/S2 (80/20) | W-2 (0.05) | 28 | 199 | 0.75 |
| Example 5-10 | P-1 (62.95) | b-59 (35) | N-1 (2) | S1/S2 (80/20) | W-3 (0.05) | 28 | 19.5 | 0.88 |
| Example 5-11 | P-2 (62.95) | b-62 (35) | N-6 (2) | S1/S2 (80/20) | W-3 (0.05) | 30 | 19.1 | 0.90 |
| Example 5-12 | P-3 (62.95) | b-64 (35) | N-7 (2) | S1/S2 (80/20) | W-2 (0.05) | 32 | 18.8 | 1.02 |
| Example 5-13 | P-1 (62.95) | b-74 (35) | N-8 (2) | S1/S2 (80/20) | W-3 (0.05) | 30 | 17.6 | 1.05 |
| Example 5-14 | P-8 (63.95) | b-75 (35) | N-3 (1) | S1/S2 (80/20) | W-2 (0.05) | 30 | 17.1 | 0.92 |
| Example 5-15 | P-2 (62.95) | b-85 (35) | N-3 (2) | S1/S2 (80/20) | W-3 (0.05) | 30 | 18.6 | 0.84 |
| Example 5-16 | P-3 (62.95) | b-86 (35) | N-3 (2) | S1/S2/S3 (70/20/10) | W-3 (0.05) | 30 | 18.1 | 0.84 |
| Example 5-17 | P-1 (62.95) | b-117 (35) | N-3 (2) | S1/S2 (80/20) | W-3 (0.05) | 28 | 19.8 | 1.09 |
| Example 5-18 | P-7 (85.95) | b-119 (10) | N-10 (4) | S1/S2 (80/20) | W-3 (0.05) | 30 | 19.0 | 0.90 |
| Example 5-19 | P-2 (62.95) | b-1/PAG12 (20/15) | N-4 (2) | S1/S2/S3 (70/20/10) | W-3 (0.05) | 30 | 19.1 | 1.10 |
| Example 5-20 | — | b-138 (97.95) | N-3 (2) | S1/S2/S3 (70/20/10) | W-2 (0.05) | 28 | 20.4 | 0.91 |
| Example 5-21 | — | b-141 (97.95) | N-3 (2) | S1/S2/S3 (70/20/10) | W-2 (0.05) | 30 | 20.5 | 1.19 |
| Example 5-22 | P-3 (87.95) | b-6 (10) | N-1 (2) | S1/S2 (80/20) | W-3 (0.05) | 28 | 19.6 | 1.17 |
| Comparative Example 5-1 | P-9 (62.95) | r-1 (35) | N-6 (2) | S1/S2 (80/20) | W-3 (0.05) | 86 | 8.1 | 0.50 |
| Comparative Example 5-2 | P-1 (62.95) | r-2 (35) | N-6 (2) | S1/S2 (80/20) | W-3 (0.05) | 92 | 5.9 | 0.55 |
| Comparative Example 5-3 | P-1 (62.5) | r-3 (35) | N-6 (2) | S1/S2 (80/20) | W-3 (0.05) | 92 | 6.1 | 0.51 |

It is apparent from the results in the Table above that in the positive pattern formation by EUV exposure, the actinic ray-sensitive or radiation-sensitive resin composition used in Examples realizes high isolated space resolution, excellent exposure latitude and good pattern profile, compared with the actinic ray-sensitive or radiation-sensitive resin composition used in Comparative Examples, which does not contain a compound represented by formula (1) or (2).

Examples 6-1 to 6-7 and Comparative Examples 6-1 and 6-2

ArF Exposure (1) Preparation of Coating Solution of Actinic Ray-Sensitive or Radiation-Sensitive Resin Composition A coating solution composition having a solid content concentration of 3.8 mass % according to the formulation shown in the Table below was microfiltered through a membrane filter having a pore size of 0.03 μm to obtain an actinic ray-sensitive or radiation-sensitive resin composition (resist composition) solution.

(2) Exposure Condition: ArF Immersion Exposure

An organic antireflection film, ARC29A (produced by Nissan Chemical Industries, Ltd.), was applied onto a 12-inch silicon wafer and baked at 205° C. for 60 seconds to form a 75 nm-thick antireflection film, and the actinic ray-sensitive or radiation-sensitive resin composition prepared was applied thereon and baked at 130° C. for 60 seconds to form a resist film having a thickness of 120 nm. This resist film was exposed through a mask by using an ArF excimer laser immersion scanner (XT1700i, manufactured by ASML, NA: 1.20, C-Quad, outer sigma: 0.981, inner sigma: 0.895, XY deflection). Subsequently, the resist film was heated at 100° C. for 60 seconds, then developed with an aqueous tetramethylammonium hydroxide solution (2.38 mass %) for 30 seconds, rinsed with pure water, and then spin-dried to obtain a 1:1 line-and-space resist pattern having a line width of 50 nm.

(3) Evaluation of Resist Pattern

The obtained resist pattern was evaluated for the isolated space resolution, exposure latitude (EL) and pattern profile by the same methods as in Example 3-1.

The evaluation results are shown in the Table below.

lent exposure latitude and good pattern profile, compared with the actinic ray-sensitive or radiation-sensitive resin composition used in Comparative Examples, which does not contain a compound represented by formula (1) or (2).

INDUSTRIAL APPLICABILITY

According to the present invention, a compound, an actinic ray-sensitive or radiation-sensitive resin composition, a resist film, a pattern forming method, which are capable of realizing high resolution, high exposure latitude and good pattern profile in the region of fine (for example, a line width or space width of 50 nm or less) pattern formation, a manufacturing method of an electronic device using the same, and an electronic device, can be provided.

While the invention has been described in detail and with reference to specific embodiments thereof, it will be apparent to one skilled in the art that various changes and modifications can be made therein without departing from the spirit and scope of the invention.

This application is based on Japanese Patent Application (Patent Application No. 2013-075196) filed on Mar. 29, 2013, the contents of which are incorporated herein by way of reference.

The invention claimed is:

1. An actinic ray-sensitive or radiation-sensitive resin composition comprising:
   a resin;
   a solvent; and
   a compound represented by the following formula (1) or (2):

wherein
each of $R_1$ to $R_5$ independently represents an organic group having a carbon number of 30 or less, at least two members out of $R_1$ to $R_3$ may combine with each other to form a ring,

TABLE 7

| | Resin Compound (mass %) | Photoacid Generator (mass %) | Basic Compound (mass %) | Solvent (mass ratio) | Surfactant (mass %) | Isolated Space Resolution (nm) | EL (%) | Profile (L2/L1) |
|---|---|---|---|---|---|---|---|---|
| Example 6-1 | P-5/P-10 (76.95/3) | b-19 (15) | N-1 (5) | S1/S2 (80/20) | W-3 (0.05) | 48 | 18.2 | 0.91 |
| Example 6-2 | P-6/P-10 (76.95/3) | b-21 (15) | N-1 (5) | S1/S2 (80/20) | W-3 (0.05) | 44 | 18.5 | 0.92 |
| Example 6-3 | P-5/P-10 (76.95/3) | b-39 (15) | N-3 (5) | S1/S2 (80/20) | W-3 (0.05) | 40 | 19.2 | 0.91 |
| Example 6-4 | P-6/P-10 (76.95/3) | b-50 (15) | N-6 (5) | S1/S2 (50/50) | W-3 (0.05) | 42 | 18.9 | 0.90 |
| Example 6-5 | P-5/P-10 (76.95/3) | b-110 (15) | N-4(5) | S3/S4 (80/20) | W-3 (0.05) | 44 | 21.0 | 0.93 |
| Example 6-6 | P-6/P-10 (84.45/3) | b-137 (75) | N-6 (5) | S3/S4 (80/20) | W-3 (0.05) | 44 | 18.3 | 1.01 |
| Example 6-7 | P-5/P-10 (76.95/3) | b-21/PAG-5 (10/5) | N-6 (5) | S1/S2 (50/50) | W-3 (0.05) | 44 | 18.5 | 0.92 |
| Comparative Example 6-1 | P-5/P-10 (76.95/3) | r-3 (15) | N-6 (5) | S1/S2 (80/20) | W-3 (0.05) | 96 | 5.5 | 0.70 |
| Comparative Example 6-2 | P-5/P-10 (76.95/3) | r-4 (15) | N-6 (5) | S1/S2 (80/20) | W-3 (0.05) | 96 | 7.6 | 0.75 |

It is apparent from the results in the Table above that in the positive pattern formation by ArF exposure, the actinic ray-sensitive or radiation-sensitive resin composition used in Examples realizes high isolated space resolution, exceleach of at least one of $R_1$ to $R_3$ and at least one of $R_4$ and $R_5$ has at least one group selected from the group consisting of groups represented by the following formulae (I), (III) to (IV), and $Z^-$ represents a non-nucleophilic anion:

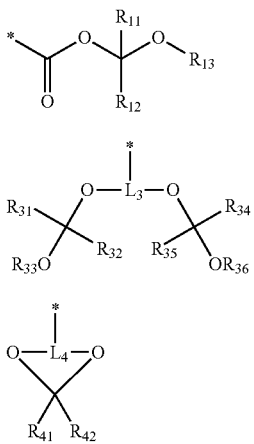

(I)

(III)

(IV)

wherein in formulae (I), (III) to (IV),
$R_{11}$ represents a hydrogen atom or an alkyl group,
$R_{12}$ represents a hydrogen atom, an alkyl group, a cycloalkyl group or an aryl group,
$R_{13}$ represents an alkyl group, a cycloalkyl group or an aryl group,
$R_{12}$ and $R_{13}$ may combine with each other to form a ring,
$L_3$ represents a trivalent linking group,
each of $R_{31}$ and $R_{34}$ independently represents a hydrogen atom or an alkyl group,
each of $R_{32}$ and $R_{35}$ independently represents a hydrogen atom, an alkyl group, a cycloalkyl group or an aryl group,
each of $R_{33}$ and $R_{36}$ independently represents an alkyl group, a cycloalkyl group or an aryl group,
$R_{32}$ and $R_{33}$ may combine with each other to form a ring,
$R_{35}$ and $R_{36}$ may combine with each other to form a ring,
$L_4$ represents a trivalent linking group,
each of $R_{41}$ and $R_{42}$ independently represents a hydrogen atom or an alkyl group,
$R_{41}$ and $R_{42}$ may combine with each other to form a ring, and
* represents a bond.

2. The actinic ray-sensitive or radiation-sensitive resin composition as claimed in claim 1,
wherein in formulae (1) and (2), $Z^-$ represents a sulfonate anion.

3. The actinic ray-sensitive or radiation-sensitive resin composition as claimed in claim 2,
wherein in formulae (1) and (2), $Z^-$ represents a benzenesulfonate anion.

4. The actinic ray-sensitive or radiation-sensitive resin composition as claimed in claim 1, wherein the resin has a group represented by any one of formulae (I), (III) to (IV) and the following formulae (II) and (V):

(II)

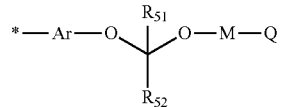

(V)

wherein in formula (II) and formula (V),
each of $R_{21}$ to $R_{24}$ independently represents an alkyl group,
$R_{25}$ represents a hydrogen atom or an alkyl group, at least two members out of $R_{23}$ to $R_{25}$ may combine with each other to form a ring, provided that $R_{21}$ and $R_{22}$ do not combine with each other to form a ring and at least one of $R_{21}$ and $R_{22}$ does not combine with at least one of $R_{23}$ to $R_{25}$ to form a ring,
Ar represents a divalent aromatic ring group,
each of $R_{51}$ and $R_{52}$ independently represents a hydrogen atom, an alkyl group, a cycloalkyl group, a monovalent aromatic ring group, or a group formed by combining an alkylene group and a monovalent aromatic ring group,
M represents a single bond or a divalent linking group,
Q represents an alkyl group, a cycloalkyl group that may contain a heteroatom, a monovalent aromatic ring group that may contain a heteroatom, an amino group, an ammonium group, a mercapto group, a cyano group or an aldehyde group,
two members out of Q, M and $R_{51}$ may combine to form a ring, and
* represents a bond.

5. The actinic ray-sensitive or radiation-sensitive resin composition as claimed in claim 4,
wherein the resin is a resin having a group represented by formula (I) or (II).

6. The actinic ray-sensitive or radiation-sensitive resin composition as claimed in claim 1, containing a compound represented by formula (1).

7. A resist film comprising the actinic ray-sensitive or radiation-sensitive resin composition claimed in claim 1.

8. A pattern forming method comprising:
a step of forming the resist film of claim 7 on a substrate;
a step of exposing the resist film;
a step of developing the exposed film.

9. The pattern forming method as claimed in claim 8,
wherein the exposure is performed using an electron beam or an extreme-ultraviolet ray.

10. The pattern forming method as claimed in claim 8,
wherein the development is performed using a developer containing an organic solvent.

11. A method for manufacturing an electronic device, comprising employing the pattern forming method claimed in claim 8 to form a pattern on an inorganic substrate or a coating-type inorganic substrate suitable for use in process of producing a semiconductor, a liquid crystal device or a circuit board.

12. A compound represented by formula (1):

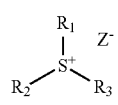

(1)

wherein each of $R_1$ to $R_3$ independently represents an aryl group having a carbon number of 30 to less, at least two members out of $R_1$ to $R_3$ may combine with each other to form a ring, at least one of $R_1$ to $R_3$ has at least one group selected from the group consisting of groups represented by the following formula (I), (III) to (IV), $Z^-$ represents a sulfonate anion:

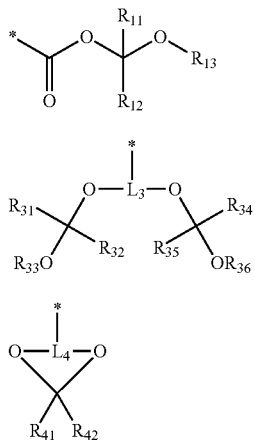

wherein in formulae (I), (III) to (IV), $R_{11}$ represents a hydrogen atom or an alkyl group, $R_{12}$ represents a hydrogen atom, an alkyl group, a cycloalkyl group or an aryl group, $R_{13}$ represents an alkyl group, a cycloalkyl group or an aryl group, $R_{12}$ and $R_{13}$ may combine with each other to form a ring, $L_3$ represents a trivalent linking group, each of $R_{31}$ and $R_{34}$ independently represents a hydrogen atom or an alkyl group, each of $R_{32}$ and $R_{35}$ independently represents a hydrogen atom, an alkyl group, a cycloalkyl group or an aryl group, each of $R_{33}$ and $R_{36}$ independently represents an alkyl group, a cycloalkyl group or an aryl group, $R_{32}$ and $R_{33}$ may combine with each other to form a ring, $R_{35}$ and $R_{36}$ may combine with each other to form a ring, $L_4$ represents a trivalent linking group, each of $R_{41}$ and $R_{42}$ independently represents a hydrogen atom or an alkyl group, $R_{41}$ and $R_{42}$ may combine with each other to form a ring, and \* represents a bond.

\* \* \* \* \*